United States Patent
Späth et al.

(10) Patent No.: US 11,938,233 B2
(45) Date of Patent: *Mar. 26, 2024

(54) 1,7-DIARYL-1,6-HEPTADIENE-3,5-DIONE DERIVATIVES, METHODS FOR THE PRODUCTION AND USE THEREOF

(71) Applicants: UNIVERSITÄTSKLINIKUM REGENSBURG, Regensburg (DE); UNIVERSITÄT SALZBURG, Salzburg (AT)

(72) Inventors: Andreas Späth, Regensburg (DE); Kristjan Plätzer, Salzburg (AT); Tim Maisch, Nuremberg (DE); Anja Eichner, Regensburg (DE)

(73) Assignees: UNIVERSITÄTSKLINIKUM REGENSBURG (DE); UNIVERSITÄT SALZBURG (AT)

(*) Notice: Subject to any disclaimer, the term of this patent is extended or adjusted under 35 U.S.C. 154(b) by 0 days.

This patent is subject to a terminal disclaimer.

(21) Appl. No.: 17/517,846

(22) Filed: Nov. 3, 2021

(65) Prior Publication Data

US 2022/0054671 A1 Feb. 24, 2022

Related U.S. Application Data

(62) Division of application No. 15/755,166, filed as application No. PCT/EP2016/070234 on Aug. 26, 2016, now Pat. No. 11,191,855.

(30) Foreign Application Priority Data

Aug. 26, 2015 (EP) .................... 15182597

(51) Int. Cl.
*A61L 2/08* (2006.01)
*A01N 35/02* (2006.01)
*A01N 47/44* (2006.01)
*A01N 55/02* (2006.01)
*A01N 55/08* (2006.01)
*A01N 57/34* (2006.01)
*A61L 2/18* (2006.01)
*C07C 217/08* (2006.01)
*C07C 217/18* (2006.01)
*C07C 217/20* (2006.01)
*C07C 217/22* (2006.01)
*C07C 217/24* (2006.01)
*C07C 225/06* (2006.01)
*C07C 279/08* (2006.01)
*C07F 3/06* (2006.01)
*C07F 5/02* (2006.01)
*C07F 9/54* (2006.01)

(52) U.S. Cl.
CPC .............. *A61L 2/08* (2013.01); *A01N 35/02* (2013.01); *A01N 47/44* (2013.01); *A01N 55/02* (2013.01); *A01N 55/08* (2013.01); *A01N 57/34* (2013.01); *A61L 2/18* (2013.01); *C07C 217/08* (2013.01); *C07C 217/18* (2013.01); *C07C 217/20* (2013.01); *C07C 217/22* (2013.01); *C07C 217/24* (2013.01); *C07C 225/06* (2013.01); *C07C 279/08* (2013.01); *C07F 3/06* (2013.01); *C07F 5/022* (2013.01); *C07F 9/5407* (2013.01); *C07F 9/5442* (2013.01)

(58) Field of Classification Search
None
See application file for complete search history.

(56) References Cited

U.S. PATENT DOCUMENTS

| 5,219,346 A | 6/1993 | Wagnières et al. |
| 8,962,674 B2 | 2/2015 | Takahashi et al. |
| 11,191,855 B2 * | 12/2021 | Späth .................... C07C 217/24 |
| 2009/0010806 A1 | 1/2009 | Hlavinka et al. .......... 422/82.05 |

FOREIGN PATENT DOCUMENTS

| CA | 2 888 140 A1 | 4/2014 |
| CN | 101570496 A | 11/2009 |
| CN | 103952008 A | 7/2014 |
| EP | 0 437 183 A1 | 7/1991 |
| EP | 2 698 368 A1 | 2/2014 |
| RU | 2 550 132 C1 | 5/2015 |
| WO | WO 96/29943 A1 | 10/1996 |
| WO | WO 99/43790 A1 | 9/1999 |
| WO | WO 2007/051314 A1 | 5/2007 |
| WO | WO 2008/066151 A1 | 3/2010 |
| WO | WO 2010/141564 A2 | 12/2010 |
| WO | WO 2013/172977 A1 | 11/2013 |

OTHER PUBLICATIONS

Fernando Luis Esteban Florez, et al., "Viability Study of Antimicrobial Photodynamic Therapy Using Curcumin, Hypericin and Photogem Photosensitizers in Planktonic Cells of *Streptococcus Mutans*," Scientific Journal of Dentistry, vol. 2, Jan. 1, 2015, pp. 22-27.

Mark Wainwright, "Photodynamic Antimicrobial Chemotherapy (PACT)," Journal of Antimicrobial Chemotherapy, Oxford University Press, GB, vol. 42, Jan. 1, 1998, pp. 13-28.

Tyler G. St. Denis, et al., "An Introduction to Photoantimicrobials: Photodynamic Therapy as a Novel Method of Microbial Pathogen Eradication," Science against microbial pathogens: communicating current research and technological advances, Jan. 1, 2011, pp. 675-683, URL:http://www.formatex.info/microbiology3/book/675-683.pdf.

(Continued)

*Primary Examiner* — Joseph R Kosack
(74) *Attorney, Agent, or Firm* — OSTROLENK FABER LLP

(57) ABSTRACT

1,7-diaryl-1,6-heptadiene-3,5-dione derivatives, methods for the production and use thereof.

9 Claims, 19 Drawing Sheets

(56) References Cited

OTHER PUBLICATIONS

Ludmila M. Baltazar, et al., "Antimicrobial Photodynamic Therapy: an Effective Alternative Approach to Control Fungal Infections," Frontiers in Microbiology, vol. 6, Article 202, Mar. 13, 2015, pp. 1-11.

J. R. Manjunatha, et al., "Synthesis of Amino Acid Conjugates of Tetrahydrocurcumin and Evaluation of Their Antibacterial and Anti-mutagenic Properties," Food Chemistry, vol. 139, Nos. 1-4, Aug. 1, 2013, pp. 332-338.

Abdellah Felouat, et al., "Synthesis and Photophysical Properties of Difluoroboron Complexes of Curcuminoid Derivatives Bearing Different Terminal Aromatic Units and a Meso-aryl Ring," The Journal of Organic Chemistry, vol. 78, No. 9, May 3, 2013, pp. 4446-4455.

Xubin Fang, et al., "Design and Synthesis of Dimethylaminomethyl-substituted Curcumin Derivatives/analogues: Potent Antitumor and Antioxidant Activity, Improved Stability and Aqueous Solubility Compared with Curcumin," Bioorganic & Medicinal Chemistry Letters, Pergamon, Amsterdam, NL, vol. 23, No. 5, Jan. 9, 2013, pp. 1297-1301.

James A. Lenhart, et al., "Clicked" Bivalent Ligands Containing Curcumin and Cholesterol as Multifunctional Aβ Oligomerization Inhibitors: Design, Synthesis, and Biological Characterization, Journal of Medicinal Chemistry, vol. 53, No. 16, Aug. 26, 2010, pp. 6198-6209.

Saiharish Raghavan, et al. "Synthesis and Anticancer Activity of Novel Curcumin-quinolone Hybrids," Bioorganic & Medicinal Chemistry Letters, vol. 25, No. 17, Jun. 26, 2015, pp. 3601-3605.

Xueli Zhang, et al., "Near-infrared Fluorescence Molecular Imaging of Amyloid Beta Species and Monitoring Therapy in Animal Models of Alzheimer's Disease," Proceedings of the National Academy of Sciences, vol. 112, No. 31, Jul. 21, 2015, pp. 9734-9739.

Lei Fang, et al., "Design, Synthesis and Anti-Alzheimer Properties of Dimethylaminomethyl-substituted Curcumin Derivatives," Bioorganic & Medicinal Chemistry Letters, vol. 24, No. 1, Jan. 1, 2014, pp. 40-43.

Cheruku Apoorva Reddy, et al., "Mitochondrial-targeted Curcuminoids: a Strategy to Enhance Bioavailability and Anticancer Efficacy of Curcumin," PLOS One, vol. 9, No. 3, Mar. 12, 2014, p. e89351.

Examination Report dated Oct. 25, 2017 in corresponding European Patent Application No. 15 182 597.3.

European Search Report dated Feb. 1, 2016 in corresponding European Patent Application No. 15 182 597.3.

Thanachai Taka, et al., "Curcuminoid Derivatives Enhance Telomerase Activity in an In Vitro TRAP Assay," Bioorganic & Medicinal Chemistry Letters, 24, 2014, pp. 5242-5246.

John M. Boyce, M.D., et al., "Guideline for Hand Hygiene in Health-Care Settings. Recommendations of the Healthcare Infection Control Practices Advisory Committee and the HICPAC/SHEA/APIC/IDSA Hand Hygiene Task Force," American Journal of Infection Control 30(8), 2002, pp. 1-46.

DIN EN 14885:Jan. 2007, "Chemische Desinfektionsmittel und Antiseptika—Anwendung Europäischer Normen für Chemische Desinfektionsmittel und Antiseptika," with English version—"Chemical Disinfectants and Antiseptics—Application of European Standards for Chemical Disinfectants and Antiseptics," Nov. 2015, 95 total pages.

Prof. Dr. Holger F. Rabenau, et al., "Leitlinie der Deutschen Vereinigung zur Bekämpfung der Viruskrankheiten (DVV) e.V. und des Robert Koch-Instituts (RKI) zur Prüfung von chemischen Desinfektionsmitteln auf Wirksamkeit gegen Viren in der Humanmedizin," Bundesgesundheitsblatt, Gesundheitsforschung, Gesundheitsschutz, 51(8), 2008, pp. 937-945 with English version.

Sandra Winter, et al., "Back to the Roots: Photodynamic Inactivation of Bacteria Based on Water-Soluble Curcumin Bound to Polyvinylpyrrolidone as a Photosensitizer," Photochemical & Photobiological Sciences, 2013, 12, pp. 1795-1802.

Salvatore D. Lepore, et al., "Use of Sonication for the Coupling of Sterically Hindered Substrates in the Phenolic Mitsunobu Reaction," J. Org. Chem., 68, 2003, pp. 8261-8263.

A. A. Miles, et al., "The Estimation of the Bactericidal Power of the Blood," The Journal of Hygiene, 38(6), Nov. 1938, pp. 732-749.

Luís G. Arnaut, et al., "Excited-state Proton Transfer Reactions. I. Fundamentals and Intermolecular Reactions," J. Photochem. Photobiol. A: Chem., 75, 1993, pp. 1-20.

CAS Registry Entry 1402547-14-1 (Year: 2012).

International Search Report dated Oct. 7, 2016 in corresponding PCT International Application No. PCT/EP2016/070234.

Written Opinion dated Oct. 7, 2016 in corresponding PCT International Application No. PCT/EP2016/070234.

* cited by examiner

PDI of E. coli using 10 and 50 μM of SA-CUR 0 and 33.8 J.cm$^{-2}$ @ 435 nm.

PDI of E. coli using 10, 25 and 50 μM of SACUR-1a and 33.8 J.cm$^{-2}$ @ 435 nm.

PDI of E. coli using 10 and 50 μM of SA-CUR 1b and 33.8 J.cm$^{-2}$ @ 435 nm.

PDI of E. coli using 10 and 50 μM of SA-CUR 1c and 33.8 J.cm$^{-2}$ @ 435 nm.

PDI of E. coli using 10 and 50 µM of SA-CUR 1e and 33.8 J.cm$^{-2}$ @ 435 nm.

PDI of E. coli using 10 and 50 µM of SA-CUR 2 and 33.8 J.cm$^{-2}$ @ 435 nm.

PDI of E. coli using 10 and 50 μM of SA-CUR 3 and 33.8 J.cm$^{-2}$ @ 435 nm.

PDI of E. coli using 1, 5 and 7.5 μM of SACUR-03 and 33.8 J.cm$^{-2}$ @ 435 nm.

PDI of E. coli using 10 and 50 μM of SA-CUR 4 and 33.8 J.cm$^{-2}$ @ 435 nm.

PDI of E. coli using 10 and 50 μM of SA-CUR 5 and 33.8 J.cm$^{-2}$ @ 435 nm.

PDI of E. coli using SA-CUR-08.

PDI of E. coli using SA-CUR-09b.

PDI of E. coli using 10 and 50 μM of SA-CUR-10a.

PDI of E. coli using 10 and 50 μM GUA-SA-CUR-10b, 5 and 25 min incubation.

PDI of E. coli using 10 and 50 μM of SA-CUR-10c.

PDI of E. coli using SA-CUR-11b.

PDI of E. coli using 10 and 50 µM of SA-CUR-12a.

PDI of E. coli using SA-CUR-13b.

PDI of E. coli using Zn-SA-CUR-1a.

PDI of E. coli using RO-SA-CUR-1a.

PDI of E. coli using 10, 25 and 50 µM of SACUR-14b, and 33.8 J.cm$^{-2}$ @ 435 nm.

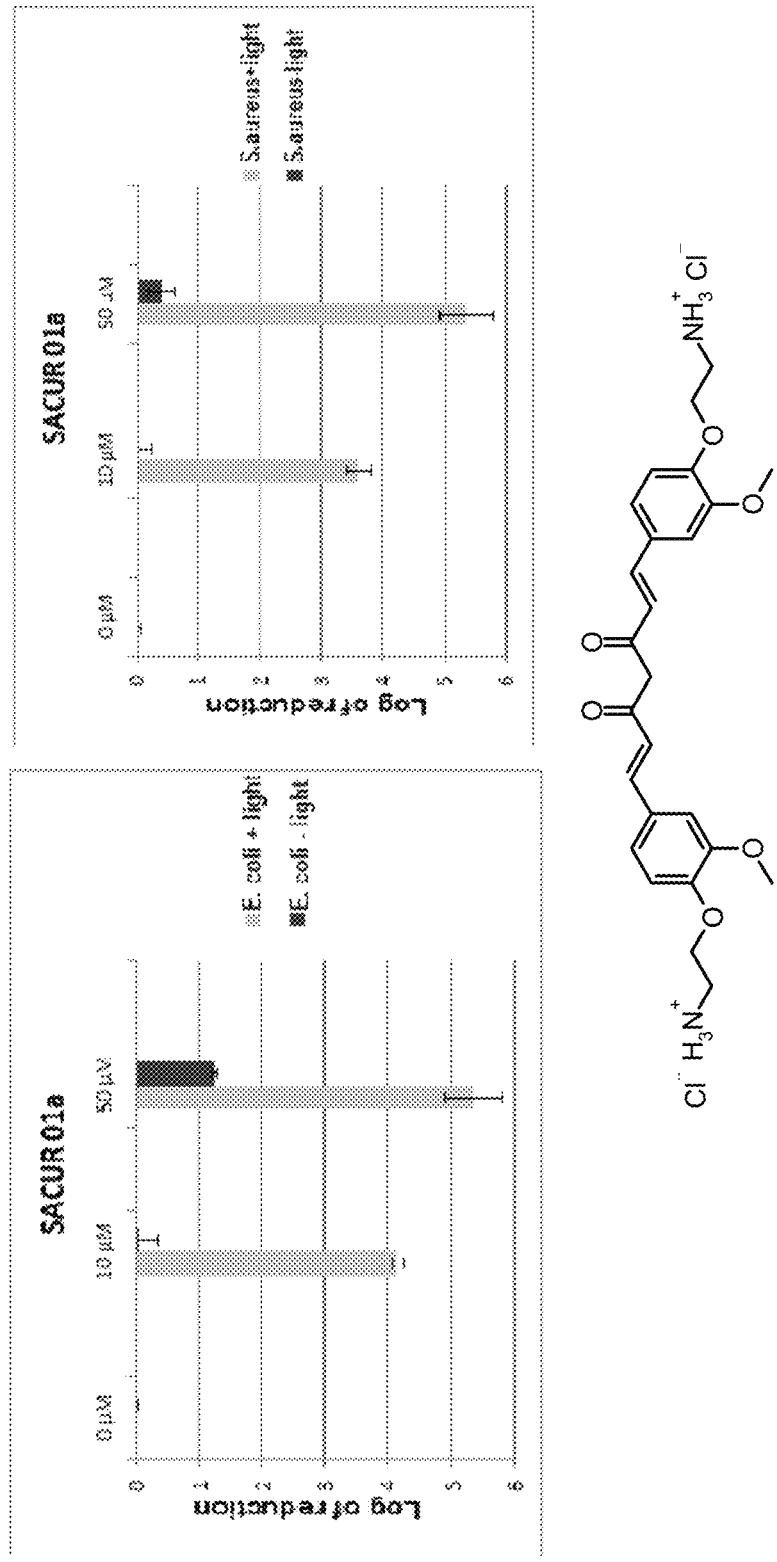
Fig. 21: Phototoxicity test for SACUR-01a against *E. coli* ATCC 25922 (left) and against *S. aureus* ATCC 25923 (right).

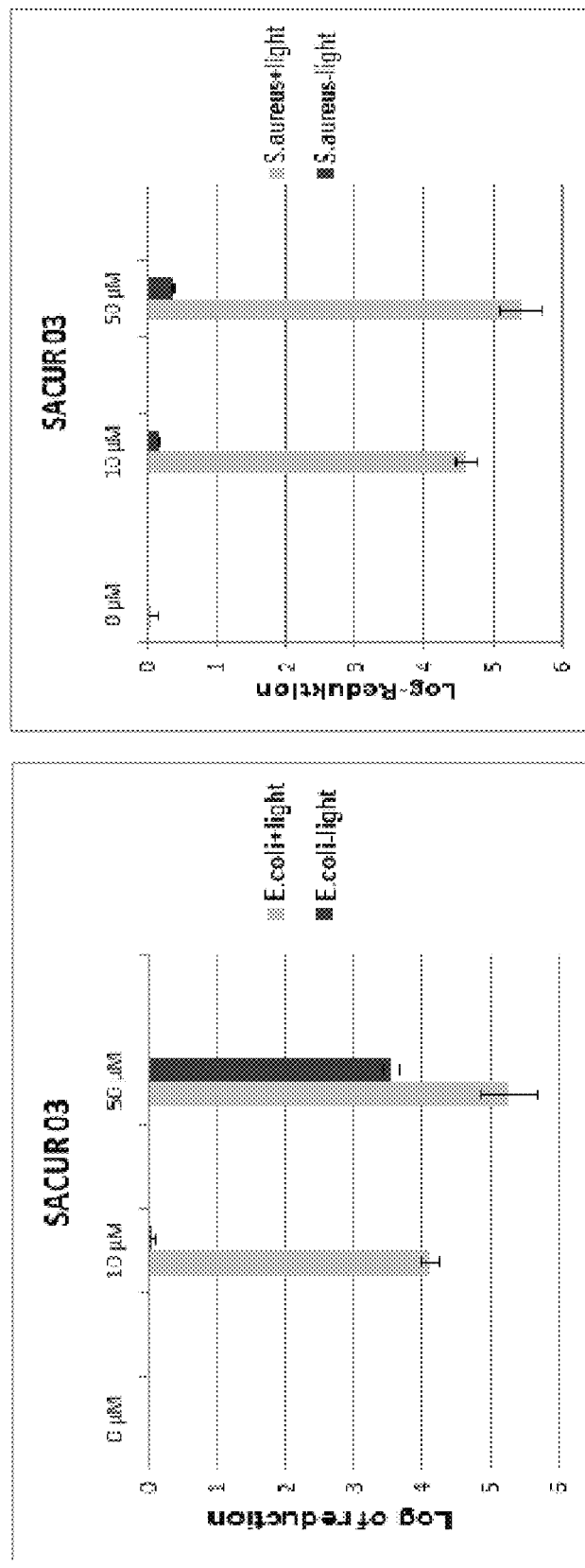
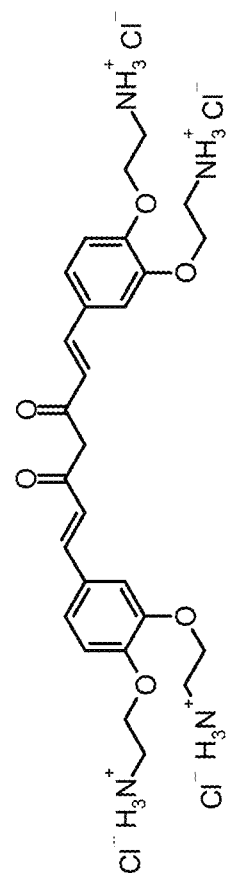
Fig. 22: Phototoxicity test for SACUR-03 against *E. coli* ATCC 25922 (left) and against *S. aureus* ATCC 25923 (right).

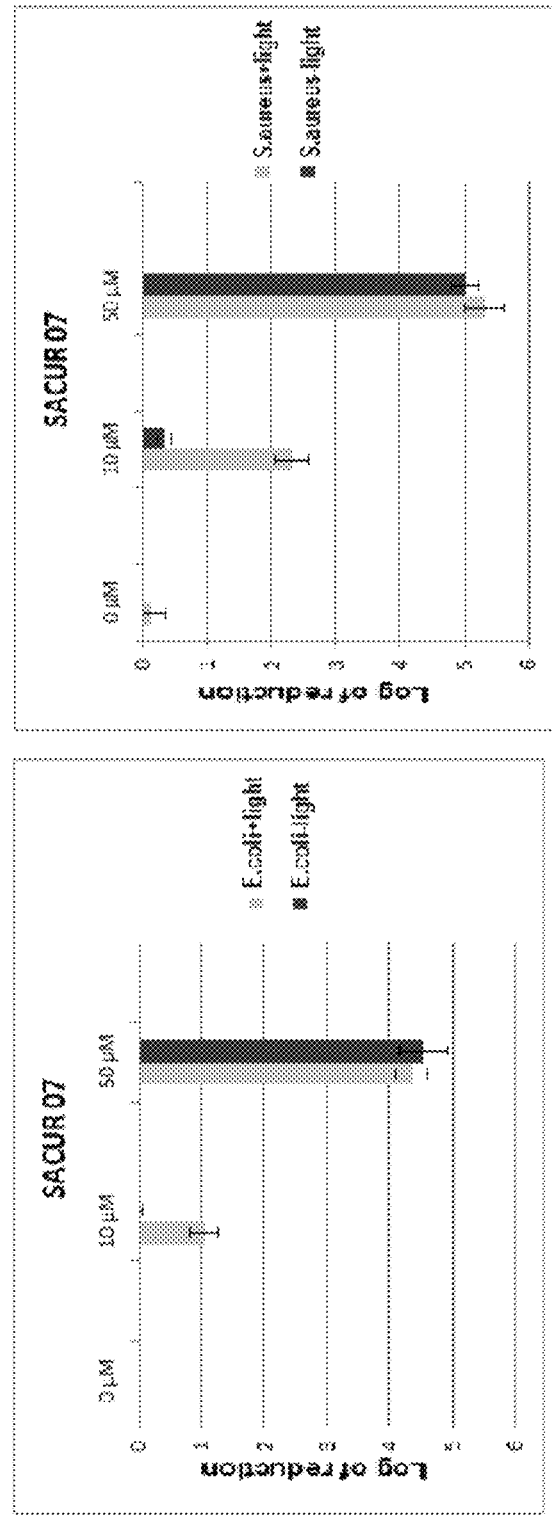
Fig. 23: Phototoxicity test for SACUR-07 against *E. coli* ATCC 25922 (left) and against *S. aureus* ATCC 25923 (right).

Fig. 24: Phototoxicity test for SACUR-01a BF2 against *S. aureus* ATCC 25923
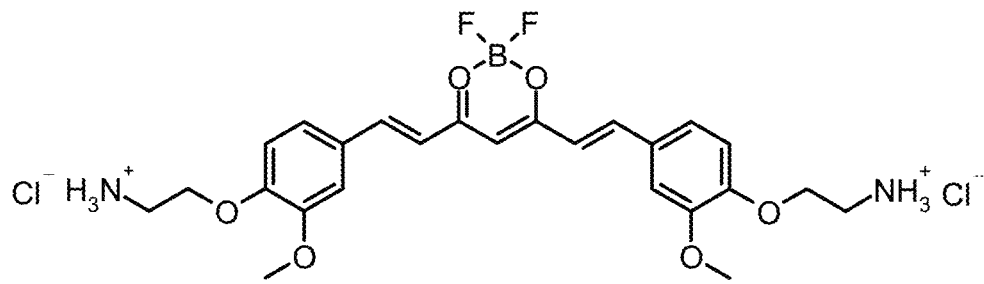
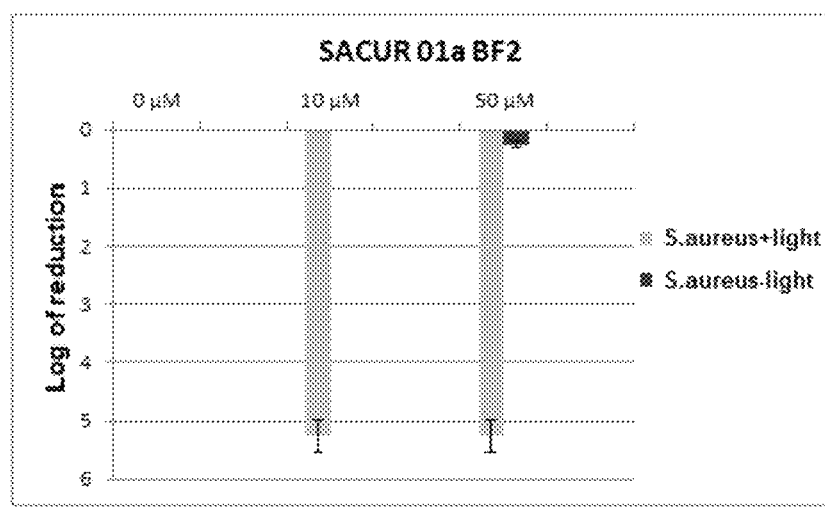
Fig. 25: Phototoxicity test for SACUR-09a against *S. aureus* ATCC 25923.
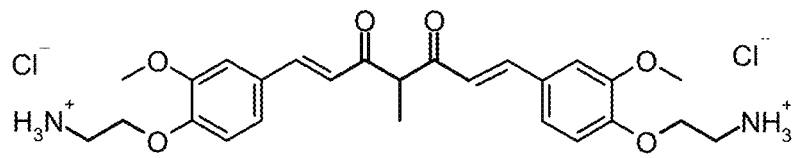
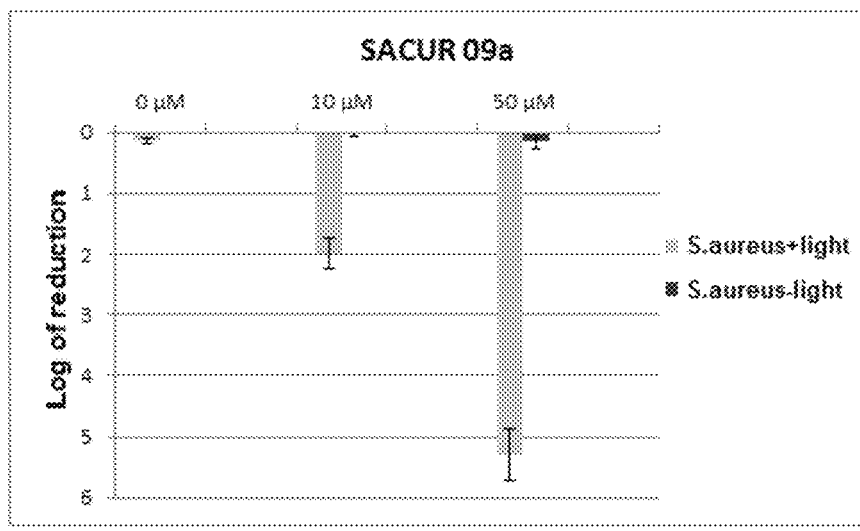

Fig. 26: Phototoxicity test for SACUR-11a against *S. aureus* ATCC 25923
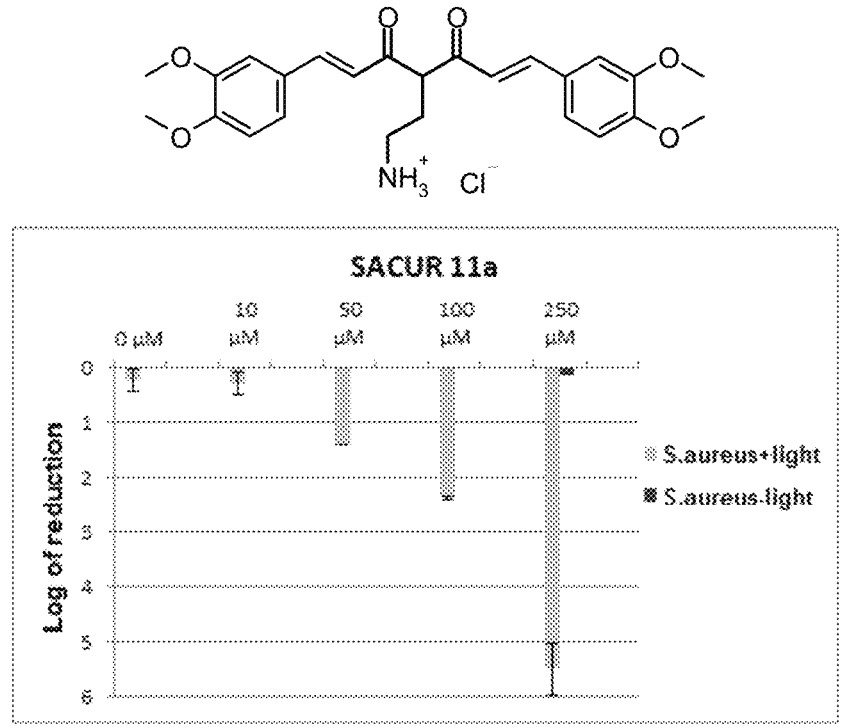
Fig. 27: Phototoxicity test for SACUR-11c against *S. aureus* ATCC 25923
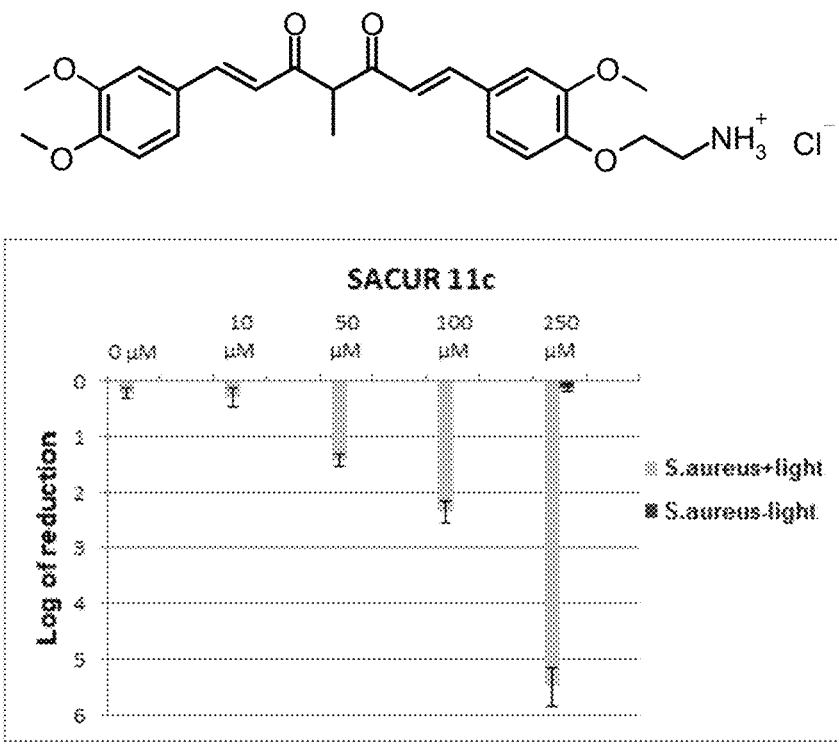

Fig. 28: Phototoxicity test for SACUR-12b against *S. aureus* ATCC 25923
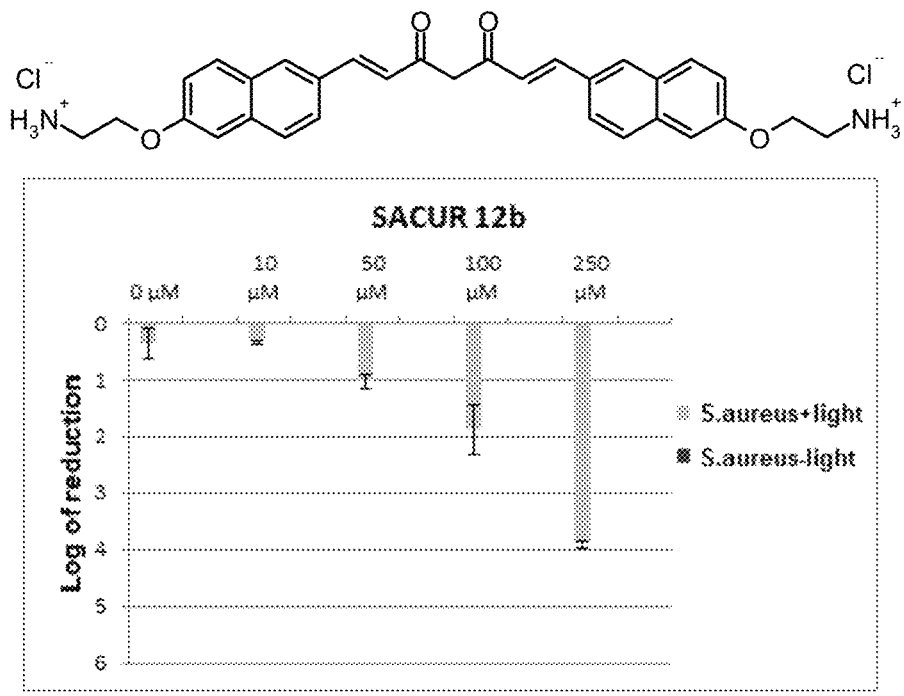
Fig. 29: Phototoxicity test for SACUR-13a against *S. aureus* ATCC 25923
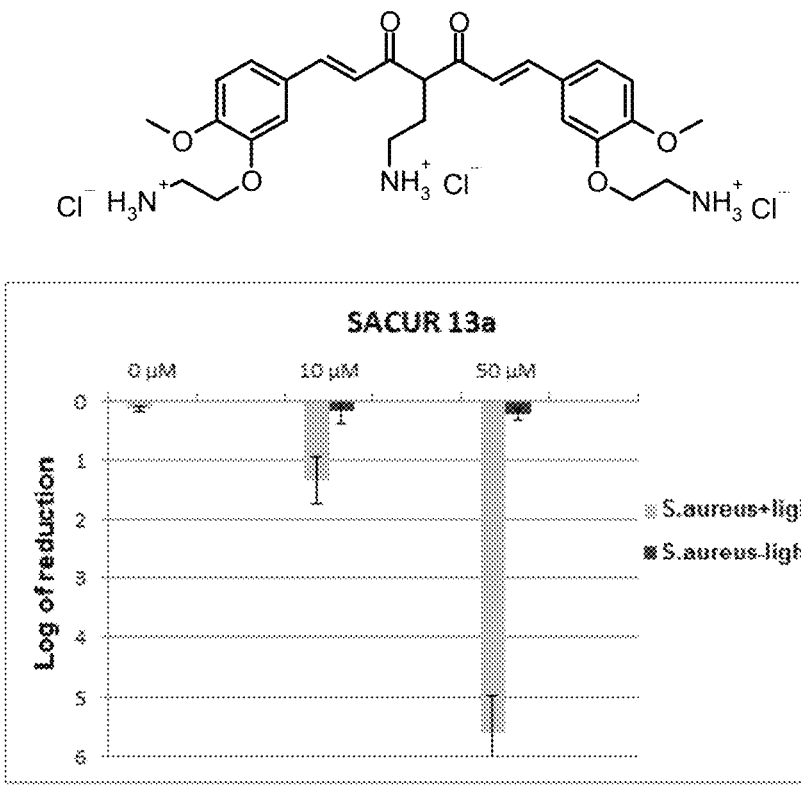

Fig. 30: Phototoxicity test for SACUR-13c against *S. aureus* ATCC 25923
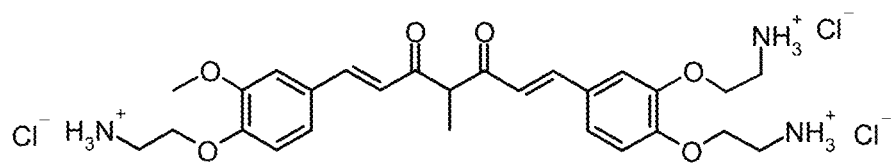
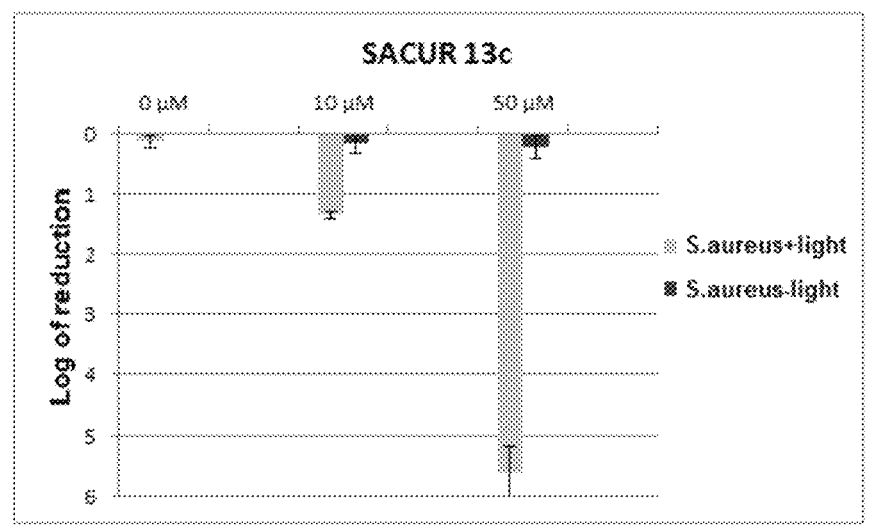
Fig. 31: Phototoxicity test for SACUR-14a against *S. aureus* ATCC 25923
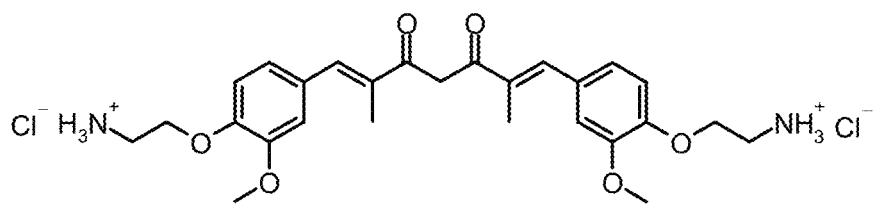
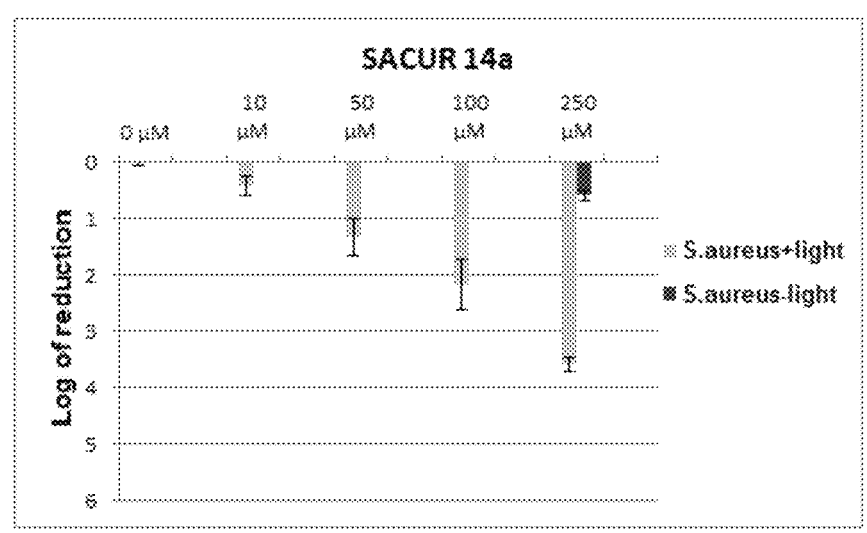

Fig. 32: Phototoxicity test for SACUR-15a against *S. aureus* ATCC 25923
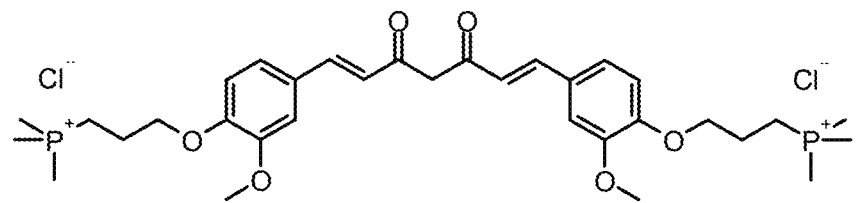
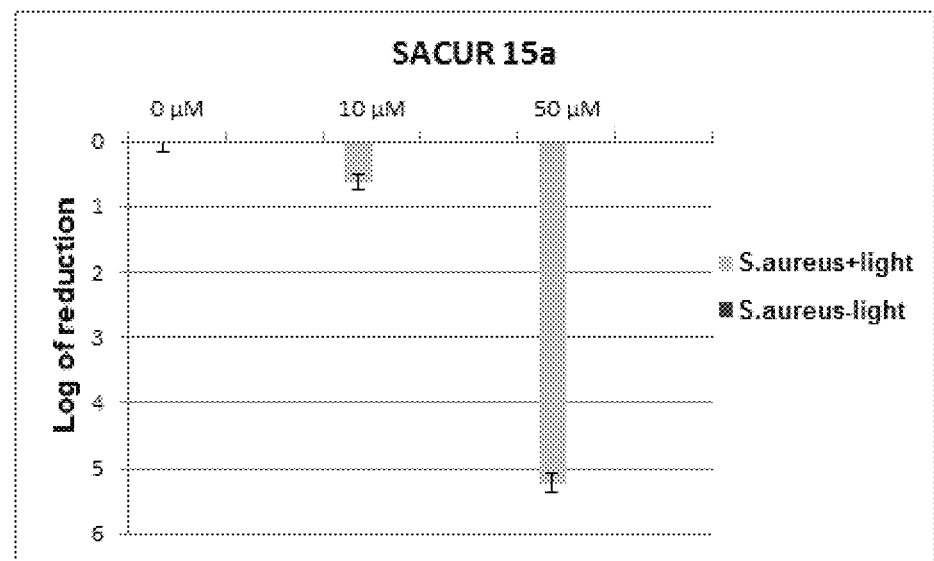
Fig. 33: Phototoxicity test for SACUR-15b against *S. aureus* ATCC 25923
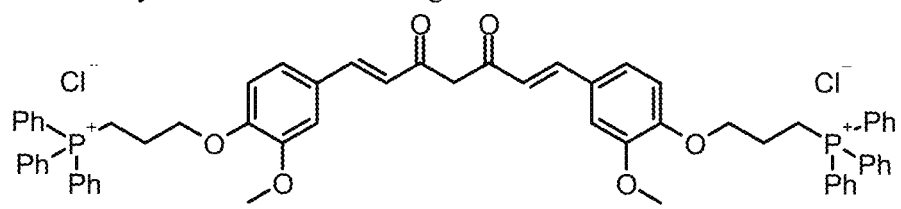
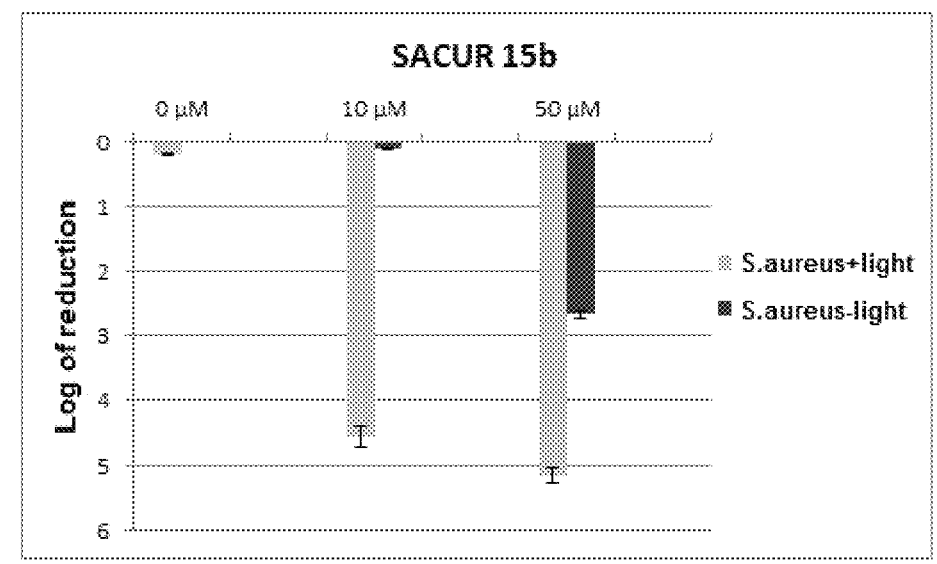

1,7-DIARYL-1,6-HEPTADIENE-3,5-DIONE DERIVATIVES, METHODS FOR THE PRODUCTION AND USE THEREOF

CROSS-REFERENCE TO RELATED APPLICATIONS

The present application is a divisional of prior U.S. patent application Ser. No. 15/755,166, filed Feb. 26, 2018, by Andreas SPÄTH. Kristjan PLÄTZER, Tim MAISCH and Anja EICHNER, entitled "1,7-DIARYL-1,6-HEPTADIENE-3,5-DIONE DERIVATIVES, METHODS FOR THE PRODUCTION AND USE THEREOF," which is a 35 U.S.C. §§ 371 national phase conversion of PCT/EP2016/070234, filed Aug. 26, 2016, which claims priority to European Patent Application No. 15182597.3, filed Aug. 26, 2015. The PCT International Application was published in the German language. The contents of each of the patent applications listed above are incorporated in full herein by reference.

TECHNICAL FIELD

The present invention relates to 1,7-diaryl-1,6-heptadiene-3,5-dione derivatives, to their manufacture and to their use.

BACKGROUND OF THE INVENTION

The occurrence of more and more multi-resistant bacterial isolates has meant that treating bacterial diseases has become more difficult. Increasingly strict hygiene standards and a global proliferation of nosocomial infections have sparked an interest in novel preparations, methods and applications which could inhibit the proliferation of multi-resistant germs.

The search for alternatives to antibiotic therapies is of vital importance to the treatment of infections which are caused by bacteria, for example, in particular as a result of the identification and increasing occurrences of vancomycin-resistant bacterial strains (VRSA), in 2002 in Japan and in the USA. In Europe, the first VRSA isolate from a patient was recorded in Portugal in 2013.

The increase in resistance to fungal infections as regards antifungal preparations further heightens the problem in the treatment of superficial infections. The clinical consequence of resistance to antifungal preparations is exhibited by failure of the treatment, most particularly in immunosuppressed patients.

New approaches to controlling resistant or multi-resistant disease-causing pathogens are thus on the one hand the search for novel antidotes, for example antibiotics or antimycotics, and on the other hand the search for alternative possibilities for inactivation.

The photodynamic inactivation of microorganisms has proved to be an alternative method. Two photooxidative processes play a decisive role in the photodynamic inactivation of microorganisms.

A photosensitizer is excited with light of a specific wavelength. The excited photosensitizer can cause the formation of reactive oxygen species (ROS), whereupon on the one hand radicals, for example superoxide anions, hydrogen peroxide or hydroxyl radicals, and/or on the other hand excited molecular oxygen, for example singlet oxygen, may be formed.

In both reactions, the photooxidation of specific biomolecules which are in the direct vicinity of the reactive oxygen species (ROS) is predominant. In this regard, in particular, lipids and proteins which, for example, are components of the cell membrane of microorganisms, are oxidized. The destruction of the cell membrane again brings about the inactivation of the relevant microorganisms. A similar elimination process occurs in viruses and fungi.

As an example, singlet oxygen preferentially attacks oxidation-sensitive molecules. Examples of oxidation-sensitive molecules are molecules which contain double bonds or oxidation-sensitive groups such as phenols, sulphides or thiols. Unsaturated fatty acids in the membranes of bacteria are particularly prone to damage.

Many photosensitizers are known in the prior art which, for example, derive from the group of porphyrins and their derivatives, or phthalocyanins and their derivatives, or fullerenes and their derivatives, or derivatives with a phenolthiazinium structure such as methylene blue or toluidine blue for example, or representatives from the phenoxazinium series, such as Nile blue. The photodynamics of methylene blue or toluidine blue as regards bacteria is already used in dentistry.

Most photosensitizers which are known in the prior art are substances with a relatively complex molecular structure, which therefore have a complicated production process.

Curcumin (1,7-bis-(4-hydroxy-3-methoxyphenyl)-1,6-heptadiene-3,5-dione) is one of the most important curcuminoids in turmeric. Turmeric (*Curcuma longa*) is a plant species in the ginger family. The rhizome has an intense yellow colour. The yellow coloration arises primarily because of the curcumin, demethoxycurcumin and bis-demethoxycurcumin.

Natural curcumin has low photostability. Bleaching of a curcumin solution occurs within 30 min in daylight, for example.

Natural curcumin also has a low solubility in water. In many cases, it is necessary to use solubilizing agents such as DMSO or other non-biocompatible substances in order to enable it to be used in an aqueous medium. Furthermore, it has limited effectiveness as regards gram-negative bacteria, because the structure of the cell wall of such microorganisms prevents efficient uptake of the curcumin.

SUMMARY OF THE INVENTION

One aim of the present invention is thus to provide novel photosensitizers which inactivate microorganisms more efficiently.

A further aim of the present invention is to provide novel photosensitizers which enable articles and/or fluids and/or patients to be contaminated during therapy and/or prophylaxis.

DESCRIPTION OF PREFERRED EMBODIMENTS

The aim of the invention is achieved by means of the provision of a method for inactivating microorganisms, which preferably include viruses, archaea, bacteria, bacterial spores, fungi, fungal spores, protozoa, algae, blood-borne parasites or combinations thereof, wherein the method comprises the following steps:
(A) bringing the microorganisms into contact with at least one photosensitizer, wherein the photosensitizer is at least one 1,7-diaryl-1,6-heptadiene-3,5-dione derivative with formula (100):

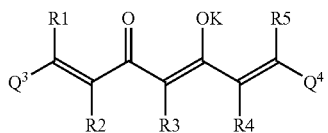
(100)

and/or at least one 1,7-diaryl-1,6-heptadiene-3,5-dione derivative with formula (101):

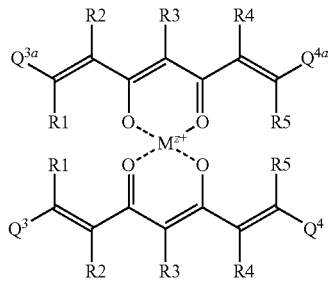

or respectively a pharmacologically acceptable salt and/or ester and/or complex thereof, wherein $Q^3$, $Q^{3a}$, $Q^4$ and $Q^{4a}$, respectively independently of each other, represent one substituted or unsubstituted, monocyclic or polycyclic aromatic residue or one substituted or unsubstituted, monocyclic or polycyclic heteroaromatic residue, wherein K represents hydrogen or a cation, and wherein $M^{z+}$ represents a cation of a metal, wherein z is the formal oxidation number of the metal M and z represents a whole number from 1 to 7, preferably from 2 to 5, and wherein (a1) at least one of the residues $Q^3$, $Q^{3a}$, $Q^4$ and $Q^{4a}$, respectively independently of each other, is an unsubstituted, monocyclic or polycyclic heteroaromatic residue, which has at least 5 ring atoms, wherein the ring atoms contain at least one carbon atom and at least one nitrogen atom which preferably can be protonated, or (a2) at least one of the residues $Q^3$, $Q^{3a}$, $Q^4$ and $Q^{4a}$, preferably each of the residues $Q^3$ and $Q^4$, preferably each of the residues $Q^3$ and $Q^{3a}$, preferably each of the residues $Q^3$, $Q^{3a}$ and $Q^4$, preferably each of the residues $Q^3$, $Q^{3a}$, $Q^4$ and $Q^{4a}$, respectively independently of each other, is substituted with at least one, preferably 1 to 9, more preferably 1 to 7, more preferably 1 to 5, more preferably 1 to 4, more preferably 2 to 3, organic residue(s) W1, which has the general formula (4), (5), (6), (7), (8), or (9), preferably (5), (7), or (9):

—(C(D)(E))$_h$-X, (4)

-A-(C(D)(E))$_h$-X, (5)

—(C(D)(E))$_k$-aryl-(C(D)(E))$_l$-X, (6)

-A-(C(D)(E))$_k$-aryl-(C(D)(E))$_l$-X, (7)

—((C(D)(E))$_m$-A)$_p$-(C(D)(E))$_n$-X, (8)

-A-((C(D)(E))$_m$-A)$_p$-(C(D)(E))$_n$-X, (9), wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n and p, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, G-$R^{(I)}$, or G-C(=G)-$R^{(II)}$, wherein G, respectively independently of each other, represents oxygen or sulphur, preferably oxygen, and wherein the residues $R^{(I)}$ and $R^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X, respectively independently of each other, is an organic residue which (i) contains at least one neutral nitrogen atom which can be protonated, or (ii) contains at least one positively charged, preferably quaternary, nitrogen atom, or (iii) contains at least one positively charged, preferably quaternary, phosphorus atom, and wherein the residues R1, R2, R3, R4 and R5, respectively independently of each other, represent hydrogen, halogen, alkyl containing 1 to 12 C atoms, cycloalkyl containing 1 to 12 C atoms, alkylaryl containing 1 to 12 C atoms, aryl containing 5 to 20 C atoms, ether containing 2 to 12 C atoms or glycol containing 2 to 12 C atoms, or wherein (b) the residue R3 is an organic residue W2, which has the general formula (4), (5), (6), (7), (8), (9), or (10), preferably (4):

—(C(D)(E))$_h$-X, (4)

-A-(C(D)(E))$_h$-X, (5)

—(C(D)(E))$_k$-aryl-(C(D)(E))$_l$-X, (6)

-A-(C(D)(E))$_k$-aryl-(C(D)(E))$_l$-X, (7)

—[(C(D)(E))$_m$-A]$_p$—(C(D)(E))$_n$-X, (8)

-A-[(C(D)(E))$_m$-A]$_p$—(C(D)(E))$_n$-X, (9)

—(—C(D)=C(E)-)$_r$-X, (10), and wherein, optionally, at least one of the residues $Q^3$, $Q^{3a}$, $Q^4$ and $Q^{4a}$, preferably each of the residues $Q^3$ and $Q^4$, preferably each of the residues $Q^3$ and $Q^{3a}$, preferably each of the residues $Q^3$, $Q^{3a}$ and $Q^4$, preferably each of the residues $Q^3$, $Q^{3a}$, $Q^4$ and $Q^{4a}$, respectively independently of each other, is substituted with at least one, preferably 1 to 9, more preferably 1 to 7, more preferably 1 to 5, more preferably 1 to 4, more preferably 2 to 3, organic residue(s) W1 which has the general formula (4), (5), (6), (7), (8), or (9), preferably (5), (7), or (9), wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n, p, and r, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, G-R$^{(I)}$, or G-C(=G)-R$^{(II)}$, wherein G, respectively independently of each other, represents oxygen or sulphur, preferably oxygen, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X, respectively independently of each other, is an organic residue which (i) contains at least one neutral nitrogen atom which can be protonated, (ii) contains at least one positively charged, preferably quaternary, nitrogen atom, or (iii) contains at least one positively charged, preferably quaternary, phosphorus atom, and wherein the residues R1, R2, R4 and R5, respectively independently of each other, represent hydrogen, halogen, alkyl containing 1 to 12 C atoms, alkylaryl containing 1 to 12 C atoms, aryl containing 5 to 20 C atoms, ether containing 2 to 12 C atoms or glycol containing 2 to 12 C atoms, and (B) irradiating the microorganisms and the at least one photosensitizer with electromagnetic radiation of a suitable wavelength and energy density.

Preferably, the method in accordance with the invention is carried out in order to inactivate microorganisms by the photodynamic therapy of a patient or by the photodynamic decontamination of a surface of an article or a fluid, preferably by the photodynamic decontamination of a surface of an article or a fluid.

The aim of the present invention is also achieved by providing at least one 1,7-diaryl-1,6-heptadiene-3,5-dione derivative with formula (100)

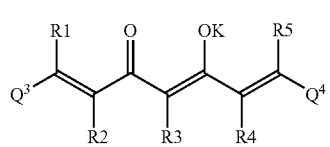

(100)

and/or at least one 1,7-diaryl-1,6-heptadiene-3,5-dione derivative with formula (101):

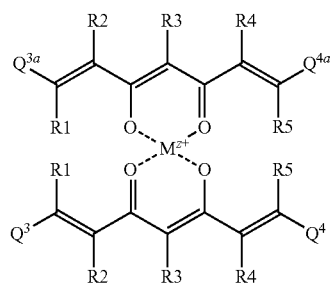

(101)

or respectively a pharmacologically acceptable salt and/or ester and/or complex thereof, for use as a photosensitizer in the medical treatment for the inactivation of microorganisms, which are preferably selected from the group formed by viruses, archaea, bacteria, bacterial spores, fungi, fungal spores, protozoa, algae and blood-borne parasites, wherein $Q^3$, $Q^{3a}$, $Q^4$ and $Q^{4a}$, respectively independently of each other, represent one substituted or unsubstituted, monocyclic or polycyclic aromatic residue or one substituted or unsubstituted, monocyclic or polycyclic heteroaromatic residue, wherein K represents hydrogen or a cation, and wherein $M^{z+}$ represents a cation of a metal, wherein z is the formal oxidation number of the metal M and z represents a whole number from 1 to 7, preferably from 2 to 5, and wherein (a1) at least one of the residues $Q^3$, $Q^{3a}$, $Q^4$ and $Q^{4a}$, respectively independently of each other, is an unsubstituted, monocyclic or polycyclic heteroaromatic residue, which has at least 5 ring atoms, wherein the ring atoms contain at least one carbon atom and at least one nitrogen atom which preferably can be protonated, or (a2) at least one of the residues $Q^3$, $Q^{3a}$, $Q^4$ and $Q^{4a}$, preferably each of the residues $Q^3$ and $Q^4$, preferably each of the residues $Q^3$ and $Q^{3a}$, preferably each of the residues $Q^3$, $Q^{3a}$ and $Q^4$, preferably each of the residues $Q^3$, $Q^{3a}$, $Q^4$ and $Q^{4a}$, respectively independently of each other, is substituted with at least one, preferably 1 to 9, more preferably 1 to 7, more preferably 1 to 5, more preferably 1 to 4, more preferably 2 to 3, organic residue(s) W1 with general formula (4), (5), (6), (7), (8), or (9); preferably (5), (7), or (9):

$$—(C(D)(E))_h\text{-}X, \qquad (4)$$

$$\text{-}A\text{-}(C(D)(E))_h\text{-}X, \qquad (5)$$

$$—(C(D)(E))_k\text{-aryl-}(C(D)(E))_l\text{-}X, \qquad (6)$$

$$\text{-}A\text{-}(C(D)(E))_k\text{-aryl-}(C(D)(E))_l\text{-}X, \qquad (7)$$

$$—((C(D)(E))_m\text{-}A)_p\text{-}(C(D)(E))_n\text{-}X, \qquad (8)$$

$$\text{-}A\text{-}((C(D)(E))_m\text{-}A)_p\text{-}(C(D)(E))_n\text{-}X, \qquad (9),$$

wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n and p, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, G-R$^{(I)}$, or G-C(=G)-R$^{(II)}$, wherein G, respectively independently of each other, represents oxygen or sulphur, preferably oxygen, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X, respectively independently of each other, is an organic residue which (i) contains at least one neutral nitrogen atom which can be protonated, or (ii) contains at least one positively charged, preferably quaternary, nitrogen atom, or (iii) contains at least one positively charged, preferably quaternary, phosphorus atom, and wherein the residues R1, R2, R3, R4 and R5, respectively independently of each other, represent hydrogen, halogen, alkyl containing 1 to 12 C atoms, cycloalkyl containing 1 to 12 C atoms, alkylaryl containing 1 to 12 C atoms, aryl containing 5 to 20 C atoms, ether containing 2 to 12 C atoms or glycol containing 2 to 12 C atoms, or wherein (b) the residue R3 is an organic residue W2, wherein the one organic residue W2 has the general formula (4), (5), (6), (7), (8), (9), or (10), preferably (4):

—(C(D)(E))$_h$-X, (4) 

-A-(C(D)(E))$_h$-X, (5) 

—(C(D)(E))$_k$-aryl-(C(D)(E))$_l$-X, (6) 

-A-(C(D)(E))$_k$-aryl-(C(D)(E))$_l$-X, (7) 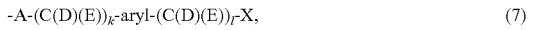

—[(C(D)(E))$_m$-A]$_p$—(C(D)(E))$_n$-X, (8) 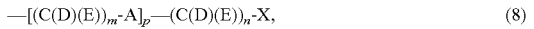

-A-[(C(D)(E))$_m$-A]$_p$—(C(D)(E))$_n$-X, (9)

—(—C(D)=C(E)-)$_r$-X, (10), and wherein, optionally, at least one of the residues $Q^3$, $Q^{3a}$, $Q^4$ and $Q^{4a}$, preferably each of the residues $Q^3$ and $Q^4$, preferably each of the residues $Q^3$ and $Q^{3a}$, preferably each of the residues $Q^3$, $Q^{3a}$ and $Q^4$, preferably each of the residues $Q^3$, $Q^{3a}$, $Q^4$ and $Q^{4a}$, respectively independently of each other, is substituted with at least one, preferably 1 to 9, more preferably 1 to 7, more preferably 1 to 5, more preferably 1 to 4, more preferably 2 to 3, organic residue(s) W1 with general formula (4), (5), (6), (7), (8), or (9), preferably (5), (7), or (9), wherein h represents a whole number from 1 to 20, preferably from 2 to 8, wherein k represents a whole number from 0 to 10, preferably from 1 to 8, preferably from 2 to 6, and wherein l represents a whole number from 0 to 10, preferably from 1 to 8, preferably from 2 to 6, and wherein m, n, p, and r, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, G-R$^{(I)}$, or G-C(=G)-R$^{(II)}$, wherein G, respectively independently of each other, represents oxygen or sulphur, preferably oxygen, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X, respectively independently of each other, is an organic residue which (i) contains at least one neutral nitrogen atom which can be protonated, (ii) contains at least one positively charged, preferably quaternary, nitrogen atom, or (iii) contains at least one positively charged, preferably quaternary, phosphorus atom, and wherein the residues R1, R2, R4 and R5, respectively independently of each other, represent hydrogen, halogen, alkyl containing 1 to 12 C atoms, alkylaryl containing 1 to 12 C atoms, aryl containing 5 to 20 C atoms, ether containing 2 to 12 C atoms or glycol containing 2 to 12 C atoms.

Preferably, the microorganisms and the at least one photosensitizer are irradiated with electromagnetic radiation of a suitable wavelength and energy density.

In a preferred embodiment of the invention, in the compound with formula (100), K is a cation $M^{z+}$ of a metal M, wherein z is the formal oxidation number of the metal M and wherein z represents a whole number from 1 to 7, preferably from 2 to 3, and wherein the compound has the formula (102):

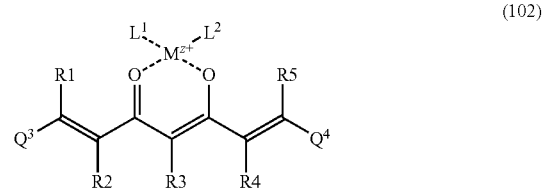

(102)

wherein $L^1$ and $L^2$, respectively independently of each other, represent water, fluoride, chloride, bromide, iodide, phosphate, hydrogen phosphate, dihydrogen phosphate, sulphate, hydrogen sulphate, tosylate, mesylate or at least one carboxylation of a carboxylic acid containing 1 to 15 carbon atoms and/or mixtures thereof. Preferably, a carboxylation of a carboxylic acid containing 1 to 15 carbon atoms is formate, acetate, n-propionate, lactate, oxalate, fumarate, maleinate, tartrate, succinylate, benzoate, salicylate, citrate and/or mixtures thereof.

Suitable 1,7-diaryl-1,6-heptadiene-3,5-dione derivatives with formula (100) and their production have been described, for example, in CA 2 888 140 A1, the content of which is hereby incorporated by reference.

Preferably, a suitable 1,7-diaryl-1,6-heptadiene-3,5-dione derivative with formula (100) is at least one compound with formula (111), (112), (114), (115), (122) to (125) or (137) to (138), preferably at least one compound with formula (114) or (115):

(111)
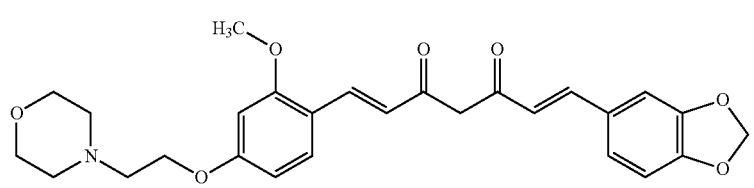
(112)
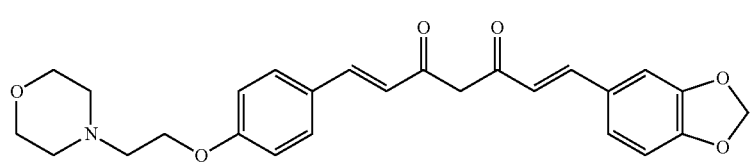
(114)
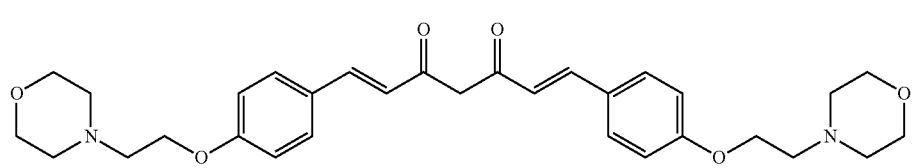
(115)
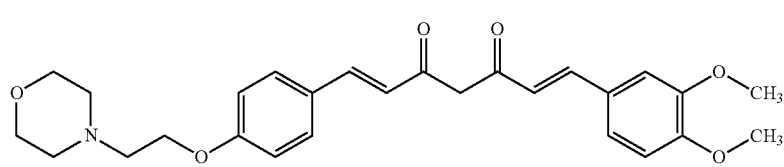
(122)
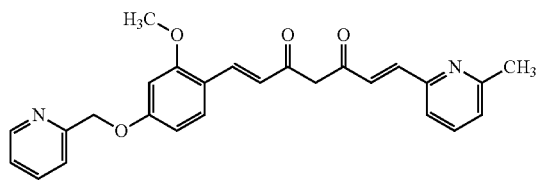
(123)
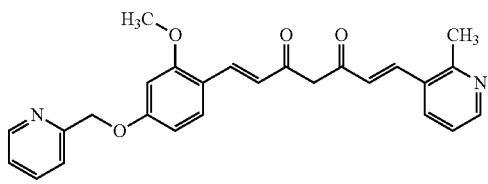
(124)
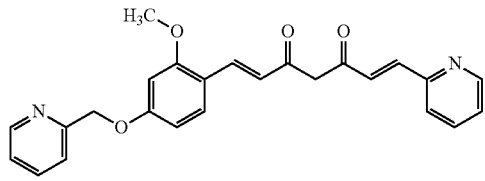
(125)
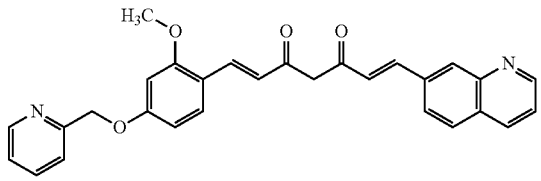
(137)
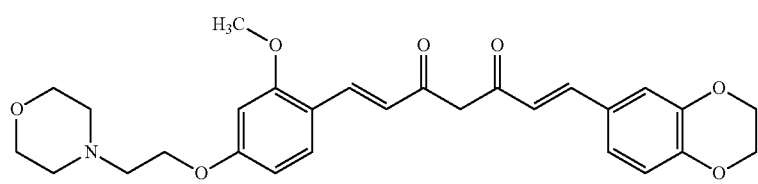
(138)
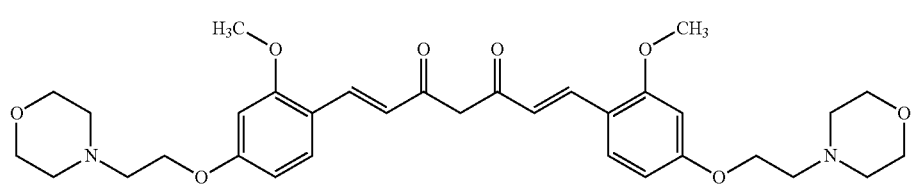

Suitable 1,7-diaryl-1,6-heptadiene-3,5-dione derivatives with formula (100) and their manufacture have also been described in EP 2 698 368 A1, the content of which is hereby incorporated by reference.
Preferably, a suitable 1,7-diaryl-1,6-heptadiene-3,5-dione derivative with formula (100) is at least one compound with formula (150), (177), (178), (202), (205), or (209), preferably at least one compound with formula (150) or (177):
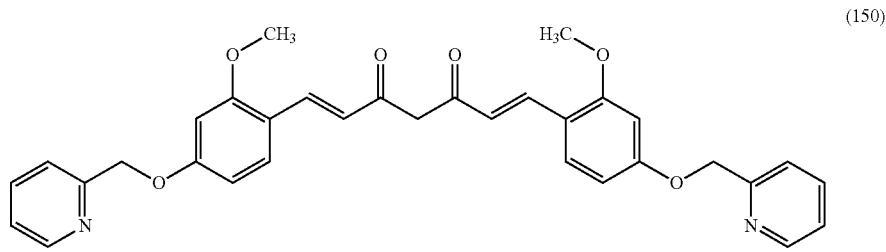
(150)
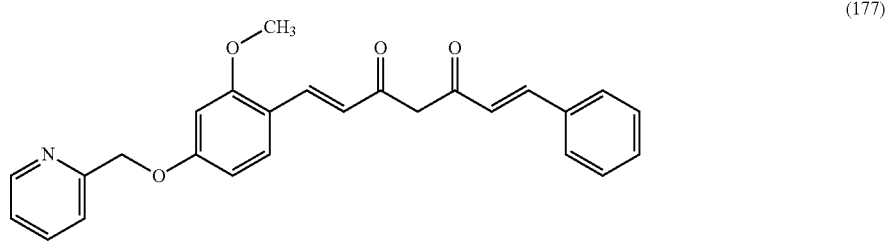
(177)
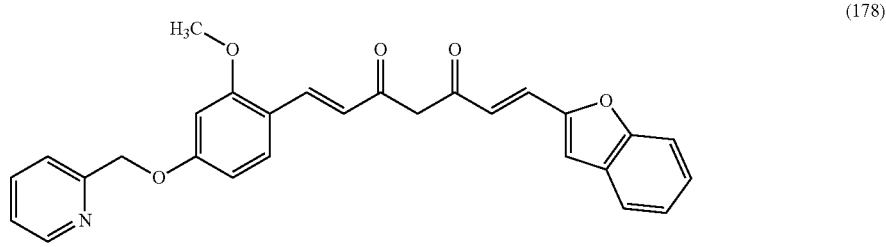
(178)
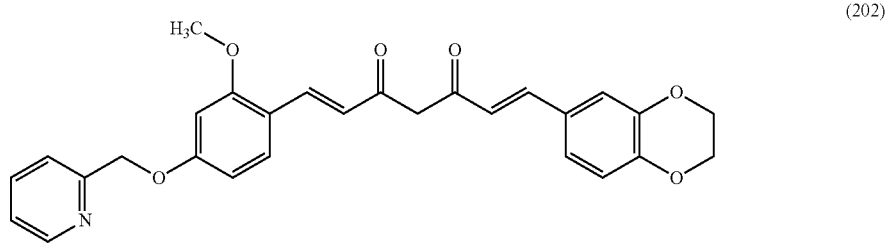
(202)
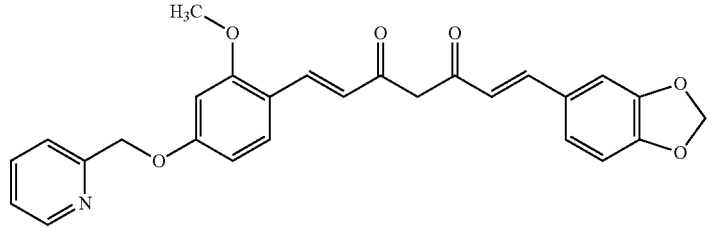
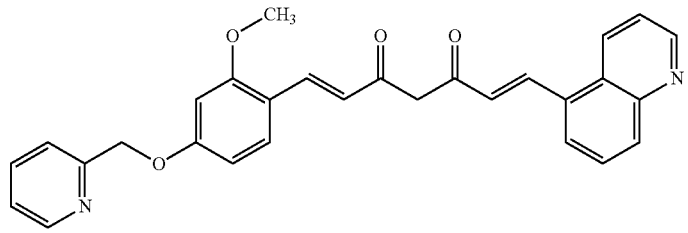

A suitable 1,7-diaryl-1,6-heptadiene-3,5-dione derivative with formula (100) and its production has also been described in Taka et al. (Bioorg. Med. Chem. Lett. 24, 2014, pages 5242 to 5246) the content of which is hereby incorporated by reference. Preferably, a suitable 1,7-diaryl-1,6-heptadiene-3,5-dione derivative with formula (100) is a compound with formula (228):

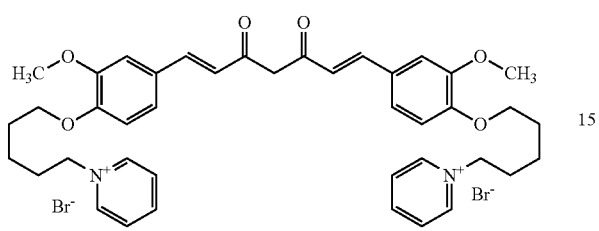
(228)

A suitable 1,7-diaryl-1,6-heptadiene-3,5-dione derivative with formula (100) and its manufacture has also been described in CN103952008 A1, the content of which is hereby incorporated by reference.

Preferably, a suitable 1,7-diaryl-1,6-heptadiene-3,5-dione derivative with formula (100) is a compound with formula (229):

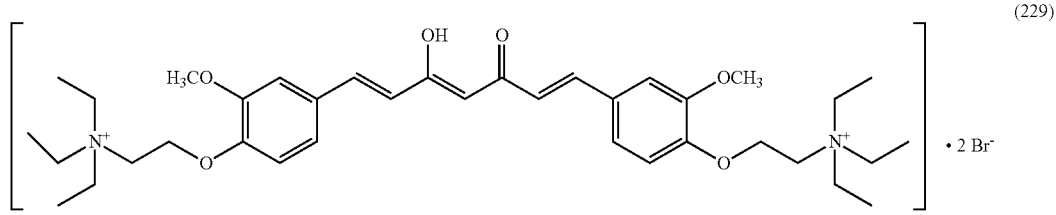
(229)

The aim of the present invention is also accomplished by the provision of a 1,7-diaryl-1,6-heptadiene-3,5-dione derivative with formula (1):

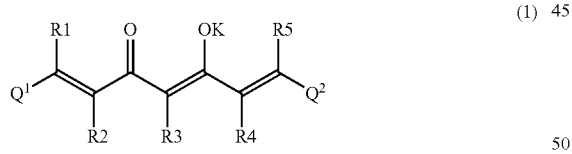
(1)

wherein the residues $Q^1$ and $Q^2$, respectively independently of each other, represent one (number=1) substituted or unsubstituted, monocyclic or polycyclic aromatic residue,
wherein K represents hydrogen or a cation, and
wherein the 1,7-diaryl-1,6-heptadiene-3,5-dione derivative with formula (1) does not contain an OH group which is bonded directly to the organic residue $Q^1$ or $Q^2$, and wherein
(a) at least one of the residues $Q^1$ and $Q^2$, preferably each of the residues $Q^1$ and $Q^2$, respectively independently of each other, is substituted with at least one, preferably 1 to 9, more preferably 1 to 7, more preferably 1 to 5, more preferably 1 to 4, more preferably 2 to 3, organic residue(s) W1a with general formula (5a), (6a), (7a), (8a), or (9a), preferably (5a), (7a), or (9a):

-A-(C(D)(E))$_h$-X$^a$, (5a)

—(C(D)(E))$_k$-aryl-(C(D)(E))$_l$-X$^a$, (6a)

-A-(C(D)(E))$_k$-aryl-(C(D)(E))$_l$-X$^a$, (7a)

—((C(D)(E))$_m$A)$_p$-(C(D)(E))$_n$-X$^a$, (8a)

-A-((C(D)(E))$_m$-A)$_p$-(C(D)(E))$_n$-X$^a$, (9a)

wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n and p, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, G-R$^{(I)}$, or G-C(=G)-R$^{(II)}$, wherein G, respectively independently of each other, represents oxygen or sulphur, preferably oxygen, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X$^a$, respectively independently of each other, represents a residue with formula (20c), (20d), (21), or (24), preferably a residue with formula (20c), (20d), or (21), more preferably a residue with formula (24):

(20c)

(20d)

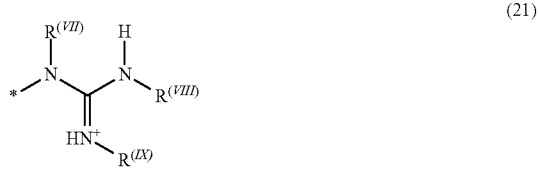
(21)

-continued

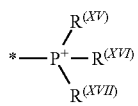
(24)

wherein each of the residues $R^{(VII)}$, $R^{(VIII)}$, and $R^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably hydrogen, and wherein each of the residues $R^{(XV)}$, $R^{(XVI)}$, and $R^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably an aryl residue containing 5 to 12 C atoms, an alkylaryl residue containing 5 to 12 C atoms, or an alkyl residue, which may be linear or branched, containing 1 to 8 C atoms, and wherein the residues R1, R2, R3, R4 and R5, respectively independently of each other, represent hydrogen, halogen, alkyl containing 1 to 12 C atoms, cycloalkyl containing 1 to 12 C atoms, alkylaryl containing 1 to 12 C atoms, aryl containing 5 to 20 C atoms, ether containing 2 to 12 C atoms or glycol containing 2 to 12 C atoms, or wherein (b) the residue R3 is an organic residue W2a, wherein the one organic residue W2a has the general formula (4b), (5b), (6b), (7b), (8b), or (9b), preferably (4b):

 (4b)

 (5b)

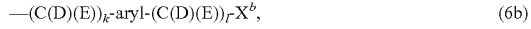 (6b)

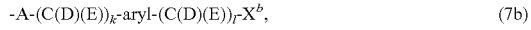 (7b)

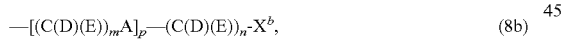 (8b)

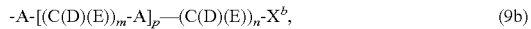 (9b)

and wherein, optionally, at least one of the residues $Q^1$ and $Q^2$, preferably each of the residues $Q^1$ and $Q^2$, respectively independently of each other, is substituted with at least one, preferably 1 to 9, more preferably 1 to 7, more preferably 1 to 5, more preferably 1 to 4, more preferably 2 to 3, organic residue(s) W1b with general formula (4b), (5b), (6b), (7b), (8b), or (9b), preferably (5b), (7b), or (9b), wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n, and p, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, G-$R^{(I)}$, or G-C(=G)-$R^{(II)}$, wherein G, respectively independently of each other, represents oxygen or sulphur, preferably oxygen, and wherein the residues $R^{(I)}$ and $R^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein $X^b$, respectively independently of each other, is an organic residue which (i) contains at least one neutral nitrogen atom which can be protonated, or (ii) contains at least one positively charged, preferably quaternary, nitrogen atom, or (iii) contains at least one positively charged, preferably quaternary, phosphorus atom, preferably (i) contains at least one neutral nitrogen atom which can be protonated, wherein preferably $X^b$, respectively independently of each other, represents a residue with formula (20c), (20d), (21), or (24), more preferably a residue with formula (20c), (20d), or (21), more preferably a residue with formula (24):

 (20c)

 (20d)

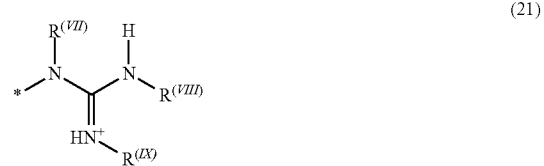 (21)

 (24)

wherein each of the residues $R^{(VII)}$, $R^{(VIII)}$, and $R^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably hydrogen, and wherein each of the residues $R^{(XV)}$, $R^{(XVI)}$, and $R^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably an aryl residue containing 5 to 12 C atoms, an alkylaryl residue containing 5 to 12 C atoms, or an alkyl residue, which may be linear or branched, containing 1 to 8 C atoms, and wherein the residues R1, R2, R4 and R5, respectively independently of each other, represent hydrogen, halogen, alkyl containing 1 to 12 C atoms, alkylaryl containing 1 to 12 C atoms, aryl containing 5 to 20 C atoms, ether containing 2 to 12 C atoms or glycol containing 2 to 12 C atoms.

In a preferred embodiment of the invention, in the compound with formula (1), K is a cation $M^{z+}$ of a metal M, wherein z is the formal oxidation number of the metal M and wherein z represents a whole number from 1 to 7, preferably from 2 to 3, and wherein the compound has the formula (2):

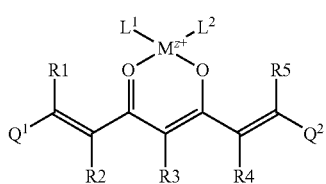

(2)

wherein $L^1$ and $L^2$, respectively independently of each other, represent water, fluoride, chloride, bromide, iodide, phosphate, hydrogen phosphate, dihydrogen phosphate, sulphate, hydrogen sulphate, tosylate, mesylate or at least one carboxylation of a carboxylic acid containing 1 to 15 carbon atoms and/or mixtures thereof. Preferably, a carboxylation of a carboxylic acid containing 1 to 15 carbon atoms is formate, acetate, n-propionate, lactate, oxalate, fumarate, maleinate, tartrate, succinylate, benzoate, salicylate, citrate and/or mixtures thereof.

The aim of the present invention is also accomplished by means of the provision of a compound with formula (3):

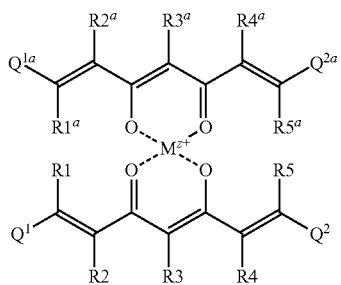

(3)

wherein $M^{z+}$ represents a cation of a metal, wherein z is the formal oxidation number of the metal M and wherein z represents a whole number from 1 to 7, preferably from 2 to 5, and wherein the residues $Q^1$ and $Q^2$, respectively independently of each other, represent one substituted or unsubstituted, monocyclic or polycyclic aromatic residue, and wherein the residues $Q^{1a}$ and $Q^{2a}$, respectively independently of each other, represent one substituted or unsubstituted, monocyclic or polycyclic aromatic residue or one substituted or unsubstituted, monocyclic or polycyclic heteroaromatic residue, preferably one substituted or unsubstituted, monocyclic or polycyclic aromatic residue, and wherein
(a) at least one of the residues $Q^1$ and $Q^2$, preferably each of the residues $Q^1$ and $Q^2$, respectively independently of each other, is substituted with at least one, preferably 1 to 9, more preferably 1 to 7, more preferably 1 to 5, more preferably 1 to 4, more preferably 2 to 3, organic residue(s) W1a with general formula (5a), (6a), (7a), (8a), or (9a), preferably (5a), (7a), or (9a):

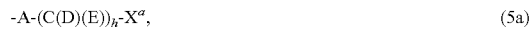 (5a)

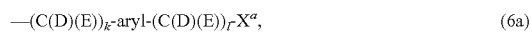 (6a)

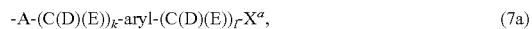 (7a)

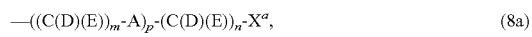 (8a)

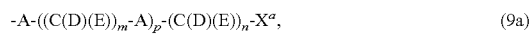 (9a)

wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n and p, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, G-$R^{(I)}$, or G-C(=G)-$R^{(II)}$, wherein G, respectively independently of each other, represents oxygen or sulphur, preferably oxygen, and wherein the residues $R^{(I)}$ and $R^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein $X^a$, respectively independently of each other, represents a residue with formula (20c), (20d), (21), or (24), more preferably a residue with formula (20c), (20d), or (21), more preferably a residue with formula (24):

 (20c)

 (20d)

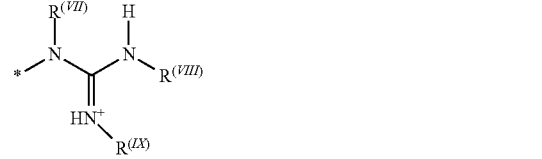 (21)

 (24)

wherein each of the residues R$^{(VII)}$, R$^{(VIII)}$, and R$^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably hydrogen, and wherein each of the residues R$^{(XV)}$, R$^{(XVI)}$, and R$^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably an aryl residue containing 5 to 12 C atoms, an alkylaryl residue containing 5 to 12 C atoms, or an alkyl residue, which may be linear or branched, containing 1 to 8 C atoms, and wherein at least one of the residues Q$^{1a}$ and Q$^{2a}$, preferably each of the residues Q$^{1a}$ and Q$^{2a}$, respectively independently of each other, is substituted with at least one, preferably 1 to 9, more preferably 1 to 7, more preferably 1 to 5, more preferably 1 to 4, more preferably 2 to 3, organic residue(s) W1c with general formula (4c), (5c), (6c), (7c), (8c), or (9c), preferably (5c), (7c), or (9c):

—(C(D)(E))$_h$-X$^b$, (4c)

-A-(C(D)(E))$_h$-X$^c$, (5c)

—(C(D)(E))$_k$-aryl-(C(D)(E))$_l$-X$^c$, (6c)

-A-(C(D)(E))$_k$-aryl-(C(D)(E))$_l$-X$^c$, (7c)

—((C(D)(E))$_m$-A)$_p$-(C(D)(E))$_n$-X$^c$, (8c)

-A-((C(D)(E))$_m$-A)$_p$-(C(D)(E))$_n$-X$^c$, (9c)

wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n and p, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, G-R$^{(I)}$, or G-C(=G)-R$^{(II)}$, wherein G, respectively independently of each other, represents oxygen or sulphur, preferably oxygen, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X$^c$, respectively independently of each other, is an organic residue which (i) contains at least one neutral nitrogen atom which can be protonated, or (ii) contains at least one positively charged, preferably quaternary, nitrogen atom, or (iii) contains at least one positively charged, preferably quaternary, phosphorus atom, wherein preferably, X$^c$, respectively independently of each other, represents a residue with formula (20c), (20d), (21), or (24), more preferably a residue with formula (20c), (20d), or (21), more preferably a residue with formula (24):

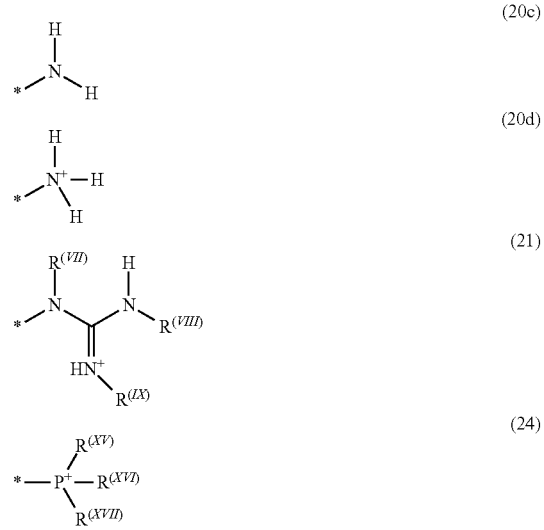

wherein each of the residues R$^{(VII)}$, R$^{(VIII)}$, and R$^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably hydrogen, and wherein each of the residues R$^{(XV)}$, R$^{(XVI)}$, and R$^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably an aryl residue containing 5 to 12 C atoms, an alkylaryl residue containing 5 to 12 C atoms, or an alkyl residue, which may be linear or branched, containing 1 to 8 C atoms, wherein the residues R1, R1$^a$, R2, R2$^a$, R3, R3$^a$, R4, R4$^a$, R5 and R5$^a$, respectively independently of each other, represent hydrogen, halogen, alkyl containing 1 to 12 C atoms, cycloalkyl containing 1 to 12 C atoms, alkylaryl containing 1 to 12 C atoms, aryl containing 5 to 20 C atoms, ether containing 2 to 12 C atoms or glycol containing 2 to 12 C atoms, or wherein (b) the residue R3 or R3$^a$, respectively independently of each other, is an organic residue W2a, wherein the one organic residue W2a has the general formula (4b), (5b), (6b), (7b), (8b), or (9b), preferably (4b):

—(C(D)(E))$_h$-X$^b$, (4b)

-A-(C(D)(E))$_h$-X$^b$, (5b)

—(C(D)(E))$_k$-aryl-(C(D)(E))$_l$-X$^b$, (6b)

-A-(C(D)(E))$_k$-aryl-(C(D)(E))$_l$-X$^b$, (7b)

—[(C(D)(E))$_m$A]$_p$—(C(D)(E))$_n$-X$^b$, (8b)

-A-[(C(D)(E))$_m$-A]$_p$—(C(D)(E))$_n$-X$^b$, (9b)

and wherein, optionally, at least one of the residues $Q^1$, $Q^{1a}$, $Q^2$ and $Q^{2a}$, preferably each of the residues $Q^1$ and $Q^2$, preferably each of the residues $Q^1$ and $Q^{1a}$, preferably each of the residues $Q^1$, $Q^{1a}$ and $Q^2$, preferably each of the residues $Q^1$, $Q^{1a}$, $Q^2$ and $Q^{2a}$, respectively independently of each other, is substituted with at least one, preferably 1 to 9, more preferably 1 to 7, more preferably 1 to 5, more preferably 1 to 4, more preferably 2 to 3, organic residue(s) W1b with general formula (4b), (5b), (6b), (7b), (8b), or (9b), preferably (5b), (7b), or (9b), wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n, and p, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, G-$R^{(I)}$, or G-C(=G)-$R^{(II)}$, wherein G, respectively independently of each other, represents oxygen or sulphur, preferably oxygen, and wherein the residues $R^{(I)}$ and $R^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein $X^b$, respectively independently of each other, is an organic residue which (i) contains at least one neutral nitrogen atom which can be protonated, or (ii) contains at least one positively charged, preferably quaternary, nitrogen atom, or (iii) contains at least one positively charged, preferably quaternary, phosphorus atom, wherein preferably, $X^b$, respectively independently of each other, represents a residue with formula (20c), (20d), (21), or (24), more preferably a residue with formula (20c), (20d), or (21), more preferably a residue with formula (24):

  (20c)

  (20d)

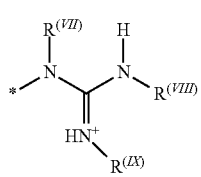  (21)

-continued

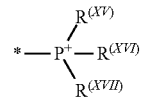  (24)

wherein each of the residues $R^{(VII)}$, $R^{(VIII)}$, and $R^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably hydrogen, and wherein each of the residues $R^{(XV)}$, $R^{(XVI)}$, and $R^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably an aryl residue containing 5 to 12 C atoms, an alkylaryl residue containing 5 to 12 C atoms, or an alkyl residue, which may be linear or branched, containing 1 to 8 C atoms, and wherein the residues R1, $R1^a$, R2, $R2^a$, R4, $R4^a$, R5 and $R5^a$, respectively independently of each other, represent hydrogen, halogen, alkyl containing 1 to 12 C atoms, alkylaryl containing 1 to 12 C atoms, aryl containing 5 to 20 C atoms, ether containing 2 to 12 C atoms or glycol containing 2 to 12 C atoms.

Preferably, in the compound with formula (3) the residues $Q^1$, $Q^{1a}$, $Q^2$ and $Q^{2a}$, respectively independently of each other, represent one substituted or unsubstituted, monocyclic or polycyclic aromatic residue, and (a) at least one of the residues $Q^1$, $Q^{1a}$, $Q^2$ and $Q^{2a}$, preferably each of the residues $Q^1$ and $Q^2$, preferably each of the residues $Q^1$ and $Q^{1a}$, preferably each of the residues $Q^1$, $Q^{1a}$ and $Q^2$, preferably each of the residues $Q^1$, $Q^{1a}$, $Q^2$ and $Q^{2a}$, respectively independently of each other, is substituted with at least one, preferably 1 to 9, more preferably 1 to 7, more preferably 1 to 5, more preferably 1 to 4, more preferably 2 to 3, organic residue(s) W1a with general formula (5a), (6a), (7a), (8a), or (9a), preferably (5a), (7a), or (9a):

-A-(C(D)(E))$_h$-$X^a$, (5a)

—(C(D)(E))$_k$-aryl-(C(D)(E))$_l$-$X^a$, (6a)

-A-(C(D)(E))$_k$-aryl-(C(D)(E))$_l$-$X^a$, (7a)

—((C(D)(E))$_m$A)$_p$-(C(D)(E))$_n$-$X^a$, (8a)

-A-((C(D)(E))$_m$-A)$_p$-(C(D)(E))$_n$-$X^a$, (9a)

wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n and p, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, G-$R^{(I)}$, or G-C(=G)-$R^{(II)}$, wherein G, respectively independently of each other, represents oxygen or sulphur, preferably oxygen, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X$^a$, respectively independently of each other, represents a residue with formula (20c), (20d), (21), or (24), more preferably a residue with formula (20c), (20d), or (21), more preferably a residue with formula (24):

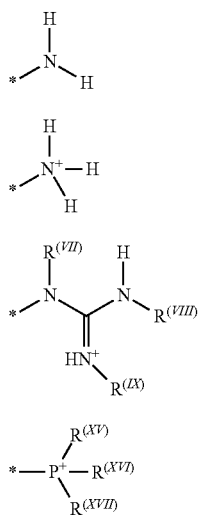

wherein each of the residues R$^{(VII)}$, R$^{(VIII)}$, and R$^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably hydrogen, and wherein each of the residues R$^{(XV)}$, R$^{(XVI)}$, and R$^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably an aryl residue containing 5 to 12 C atoms, an alkylaryl residue containing 5 to 12 C atoms, or an alkyl residue, which may be linear or branched, containing 1 to 8 C atoms, and wherein the residues R1, R1$^a$, R2, R2$^a$, R3, R3$^a$, R4, R4$^a$, R5 and R5$^a$, respectively independently of each other, represent hydrogen, halogen, alkyl containing 1 to 12 C atoms, cycloalkyl containing 1 to 12 C atoms, alkylaryl containing 1 to 12 C atoms, aryl containing 5 to 20 C atoms, ether containing 2 to 12 C atoms or glycol containing 2 to 12 C atoms, or wherein (b) the residue R3 or R3$^a$, respectively independently of each other, is an organic residue W2a, wherein the one organic residue W2a has the general formula (4b), (5b), (6b), (7b), (8b), or (9b), preferably (4b):

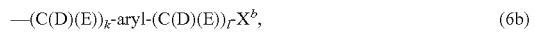

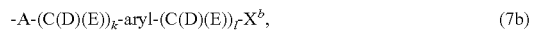

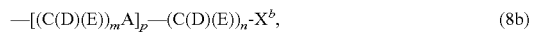

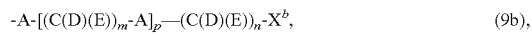

and wherein, optionally, at least one of the residues Q$^1$, Q$^{1a}$, Q$^2$ and Q$^{2a}$, preferably each of the residues Q$^1$ and Q$^2$, preferably each of the residues Q$^1$ and Q$^{1a}$, preferably each of the residues Q$^1$, Q$^{1a}$ and Q$^3$, preferably each of the residues Q$^1$, Q$^{1a}$, Q$^2$ and Q$^{2a}$, respectively independently of each other, is substituted with at least one, preferably 1 to 9, more preferably 1 to 7, more preferably 1 to 5, more preferably 1 to 4, more preferably 2 to 3, organic residue(s) W1 b with general formula (4b), (5b), (6b), (7b), (8b), or (9b), preferably (5b), (7b), or (9b), wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n, and p, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, G-R$^{(I)}$, or G-C(=G)-R$^{(II)}$, wherein G, respectively independently of each other, represents oxygen or sulphur, preferably oxygen, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X$^b$, respectively independently of each other, is an organic residue which (i) contains at least one neutral nitrogen atom which can be protonated, or (ii) contains at least one positively charged, preferably quaternary, nitrogen atom, or (iii) contains at least one positively charged, preferably quaternary, phosphorus atom, wherein preferably, X$^b$, respectively independently of each other, represents a residue with formula (20c), (20d), (21), or (24), more preferably a residue with formula (20c), (20d), or (21), more preferably a residue with formula (24):

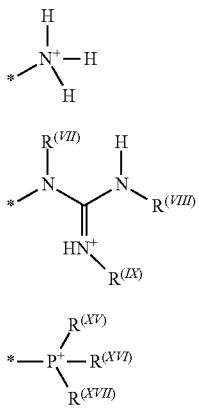

wherein each of the residues $R^{(VII)}$, $R^{(VIII)}$, and $R^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably hydrogen, and wherein each of the residues $R^{(XV)}$, $R^{(XVI)}$, and $R^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably an aryl residue containing 5 to 12 C atoms, an alkylaryl residue containing 5 to 12 C atoms, or an alkyl residue, which may be linear or branched, containing 1 to 8 C atoms, and wherein the residues R1, R1$^a$, R2, R2$^a$, R4, R4$^a$, R5 and R5$^a$, respectively independently of each other, represent hydrogen, halogen, alkyl containing 1 to 12 C atoms, alkylaryl containing 1 to 12 C atoms, aryl containing 5 to 20 C atoms, ether containing 2 to 12 C atoms or glycol containing 2 to 12 C atoms.

The compounds in accordance with the invention with formula (1), with formula (2) and with formula (3) are respectively a 1,7-diaryl-1,6-heptadiene-3,5-dione derivative, which is described as follows.

Any suitable anion may be used as the counter-ion to the positively charged nitrogen atom, for example protonated nitrogen atom or quaternary nitrogen atom, or positively charged phosphorus atom, for example quaternary phosphorus atom. Preferably, anions used as counter-ions to the positively charged nitrogen atom or phosphorus atom are those which enable a pharmacologically acceptable salt to be provided.

In a preferred embodiment of the present invention, X, $X^a$, $X^b$ and/or $X^c$ in the inventive 1,7-diaryl-1,6-heptadiene-3,5-dione derivative with formula (1), with formula (2) and/or with formula (3) as well as the 1,7-diaryl-1,6-heptadiene-3,5-dione derivative with formula (100), with formula (101) and/or with formula (102) to be used in accordance with the invention is an organic residue containing at least one protonated nitrogen atom, or at least one quaternary phosphorus atom, preferably an organic residue with general formula (20b), (20d), (21) or (24), which has a fluoride, chloride, bromide, iodide, sulphate, hydrogen sulphate, phosphate, hydrogen phosphate, dihydrogen phosphate, tosylate, mesylate, or at least one carboxylation of a carboxylic acid containing 1 to 15 carbon atoms and/or mixtures thereof as the counter-ion. Preferably, a carboxylation of a carboxylic acid containing 1 to 15 carbon atoms is formate, acetate, n-propionate, lactate, oxalate, fumarate, maleinate, tartrate, succinylate, benzoate, salicylate, citrate and/or mixtures thereof.

Further preferred embodiments of the present invention are described in the dependent claims.

In a further preferred embodiment, the inventive 1,7-diaryl-1,6-heptadiene-3,5-dione derivative with formula (1), with formula (2) and/or with formula (3), as well as the 1,7-diaryl-1,6-heptadiene-3,5-dione derivative with formula (100), with formula (101) and/or with formula (102) to be used in accordance with the invention does not contain a neutral nitrogen atom which can be protonated, for example as an amino residue, methylamino residue or dimethylamino residue, and does not contain a positively charged, preferably quaternary, nitrogen atom, for example as a pyridin-1-ium-1-yl residue or trimethylammonio residue, and also does not contain a positively charged, preferably quaternary, phosphorus atom which is bonded directly to the organic residue $Q^1$, $Q^{1a}$, $Q^2$, $Q^{2a}$, $Q^3$, $Q^{3a}$, $Q^4$, or $Q^{4a}$.

The term "direct" should be understood to mean that the nitrogen atom and/or the phosphorus atom is bonded directly to the aromatic residue $Q^1$, $Q^{1a}$, $Q^2$, $Q^{2a}$, $Q^3$, $Q^{3a}$, $Q^4$, or $Q^{4a}$.

The inventors have surprisingly discovered that by disposing the nitrogen atom and/or phosphorus atom directly on an aromatic ring system of the residues $Q^1$, $Q^{1a}$, $Q^2$, $Q^{2a}$, $Q^3$, $Q^{3a}$, $Q^4$, or $Q^4$, a significant reduction in the yield of reactive oxygen species occurs, for example.

A yield of reactive oxygen species which is as high as possible is required for antimicrobial effectiveness in photodynamic therapy or in the photodynamic cleaning of surfaces or fluids. When the nitrogen atom and/or phosphorus atom is disposed directly on the aromatic ring system of the residue $Q^1$, $Q^{1a}$, $Q^2$, $Q^{2a}$, $Q^3$, $Q^{3a}$, $Q^4$, or $Q^{4a}$, the energy which is absorbed is dissipated primarily by fluorescence effects. This results in a significant reduction in the photodynamic efficiency, i.e. to a reduction in the reactive oxygen species (ROS) formed by photodynamic processes and/or in the excited molecular oxygen formed by photodynamic processes.

Furthermore, the inventors have surprisingly discovered that by disposing the at least one neutral nitrogen atom which can be protonated and/or at least one positively charged, preferably quaternary nitrogen atom and/or at least one positively charged, preferably quaternary phosphorus atom over at least one carbon atom, for example in the form of a methylene group which is thus separated from the aromatic residue $Q^1$, $Q^{1a}$, $Q^2$, $Q^{2a}$, $Q^3$, $Q^{3a}$, $Q^4$, or $Q^{4a}$, the photophysical properties of the compound with formula (1) and/or of the compound with formula (2) and/or of the compound with formula (3) and/or of the compound with formula (100) and/or of the compound with formula (101) and/or of the compound with formula (102) are not influenced in a negative manner.

A positive charge on the nitrogen atom and/or phosphorus atom also results in an effective addition of the compound in accordance with the invention with formula (1), with formula (2) and/or with formula (3) and/or of the compound to be used in accordance with the invention with formula (100), with formula (101) and/or with formula (102) to negatively charged components in the cell wall of microorganisms. In this respect, the at least one carbon atom, for example in the form of a methylene group, also acts as a spacer, so that the bulky structure of the compound with formula (1) and/or of the compound with formula (2) and/or of the compound with formula (3) and/or of the compound with formula (100) and/or of the compound with formula (101) and/or of the compound with formula (102) can be arranged efficiently on the cell wall of the microorganisms.

Furthermore, the inventors have surprisingly discovered that because of the disposition of the at least one neutral nitrogen atom which can be protonated and/or at least one positively charged, preferably quaternary nitrogen atom and/or at least one positively charged, preferably quaternary phosphorus atom, the solubility of the compound in accordance with the invention with formula (1), with formula (2) and/or with formula (3) and/or of the compound to be used in accordance with the invention with formula (100), with formula (101) and/or with formula (102) in polar solvents, for example water, can be improved.

In a further preferred embodiment, the inventive 1,7-diaryl-1,6-heptadiene-3,5-dione derivative with formula (1), with formula (2) and/or with formula (3) as well as the 1,7-diaryl-1,6-heptadiene-3,5-dione derivative to be used in accordance with the invention with formula (100), with formula (101) and/or with formula (102) does not contain an OH group which is bonded directly to the organic residue $Q^1$, $Q^{1a}$, $Q^2$, $Q^{2a}$, $Q^3$, $Q^{3a}$, $Q^4$, or $Q^4$.

The term "direct" should be understood to mean that the OH group is bonded directly to the aromatic residue $Q^1$, $Q^{1a}$, $Q^2$, $Q^{2a}$, $Q^3$, $Q^{3a}$, $Q^4$, or $Q^4$.

The inventors have surprisingly discovered that a direct disposition of the OH group on an aromatic ring system of the residues $Q^1$, $Q^{1a}$, $Q^2$, $Q^{2a}$, $Q^3$, $Q^{3a}$, $Q^4$, or $Q^{4a}$ results in a significant deterioration of the photostability of the photosensitizer. A deterioration in the photostability results in faster bleaching and thus in faster inactivation of the photosensitizer when irradiated with electromagnetic radiation of an appropriate wavelength.

Preferably, the at least one neutral nitrogen atom which can be protonated and the at least one positively charged, preferably quaternary nitrogen atom is not a carboxylic acid amide.

In a further preferred embodiment, the inventive 1,7-diaryl-1,6-heptadiene-3,5-dione derivative with formula (1), with formula (2) and/or with formula (3) as well as the 1,7-diaryl-1,6-heptadiene-3,5-dione derivative to be used in accordance with the invention with formula (100), with formula (101) and/or with formula (102) is not a carbamate residue, which is preferably bonded directly to the organic residue $Q^1$, $Q^{1a}$, $Q^2$, $Q^{2a}$, $Q^3$, $Q^{3a}$, $Q^4$, or $Q^{4a}$.

The inventors have discovered that disposing a carbamate residue directly on an aromatic ring system of the residues $Q^1$, $Q^{1a}$, $Q^2$, $Q^{2a}$, $Q^3$, $Q^{3a}$, $Q^4$, or $Q^{4a}$ results in a significant deterioration of the photostability of the photosensitizer. A deterioration in the photostability results in faster bleaching and thus in faster inactivation of the photosensitizer when irradiated with electromagnetic radiation of an appropriate wavelength.

The term "photosensitizer" as used in the context of the invention should be understood to mean compounds which absorb electromagnetic radiation, preferably visible light, UV light and/or infrared light, and thus produce reactive oxygen species (ROS), preferably free radicals and/or singlet oxygen from triplet oxygen.

The term "photodynamic therapy" as used in the context of the invention should be understood to mean the light-induced inactivation of cells or microorganisms, preferably including viruses, archaea, bacteria, bacterial spores, fungi, fungal spores, protozoa, algae, blood-borne parasites or combinations thereof, on and/or in patients.

The term "photodynamic decontamination" as used in the context of the invention should be understood to mean the light-induced inactivation of microorganisms, preferably including viruses, archaea, bacteria, bacterial spores, fungi, fungal spores, protozoa, algae, blood-borne parasites or combinations thereof, on surfaces of articles and/or foodstuffs and/or in fluids.

The term "inactivation" as used in the context of the invention should be understood to mean a reduction in the viability or destruction of a microorganism, preferably its destruction A light-induced inactivation may, for example be ascertained by a reduction in the number of microorganisms after irradiation of a predefined starting quantity of said microorganisms in the presence of at least one compound in accordance with the invention with formula (1), with formula (2) and/or with formula (3) and/or of the compound to be used in accordance with the invention with formula (100), with formula (101) and/or with formula (102).

In accordance with the invention, the term "reduction in the viability" should be understood to mean that the number of microorganisms is reduced by at least 80.0%, preferably at least 99.0%, preferably at least 99.9%, more preferably by at least 99.99%, more preferably by at least 99.999%, yet more preferably by at least 99.9999%. Most preferably, the number of microorganisms is reduced by more than 99.9% to 100%, preferably by more than 99.99% to 100%.

Preferably, the reduction in the number of microorganisms is given in accordance with Boyce, J. M. and Pittet, D. ("Guidelines for hand hygiene in healthcare settings. Recommendations of the Healthcare Infection Control Practices Advisory Committee and the HIPAC/SHEA/APIC/IDSA Hand Hygiene Task Force", Am. J. Infect. Control 30 (8), 2002, page 1-46) as a $\log_{10}$ reduction factor.

In accordance with the invention, the term "$\log_{10}$ reduction factor" should be understood to mean the difference between the logarithm to base 10 of the number of microorganisms before and the log to base 10 of the number of microorganisms after irradiation of said microorganisms with electromagnetic radiation in the presence of at least one compound in accordance with the invention with formula (1), with formula (2) and/or with formula (3) and/or of the compound to be used in accordance with the invention with formula (100), with formula (101) and/or with formula (102).

Examples of suitable methods for determining the $\log_{10}$ reduction factors are described in DIN EN 14885:2007-01 "Chemical disinfectants and antiseptics. Application of European standards for chemical disinfectants and antiseptics" or in Rabenau, H. F. and Schwebke, I. ("Guidelines from the German Association for the Control of Viral Diseases (DVV) and the Robert Koch Institute (RKI) for testing chemical disinfectants for effectiveness against viruses in human medicine" Bundesgesundheitsblatt, Gesundheitsforschung, Gesundheitsschutz 51(8), (2008), pages 937-945).

Preferably, the $\log_{10}$ reduction factor after irradiation of microorganisms with electromagnetic radiation in the presence of at least one compound in accordance with the invention with formula (1), with formula (2) and/or with formula (3) and/or of the compound to be used in accordance with the invention with formula (100), with formula (101) and/or with formula (102) is at least 2 $\log_{10}$, preferably at least 3 $\log_{10}$, more preferably at least 4 $\log_{10}$, more preferably at least 4.5 $\log_{10}$, more preferably at least 5 $\log_{10}$, more preferably at least 6 $\log_{10}$, yet more preferably at least 7 $\log_{10}$, yet more preferably at least 7.5 $\log_{10}$.

As an example, a "reduction in the number of microorganisms after irradiation of microorganisms with electromagnetic radiation in the presence of at least one compound in accordance with the invention with formula (1), with formula (2) and/or with formula (3), and/or of the compound to be used in accordance with the invention with formula (100), with formula (101) and/or with formula (102) by 2 percentage points with respect to the starting quantity of said microorganisms" means a $\log_{10}$ reduction factor of 2 $\log_{10}$.

More preferably, the number of microorganisms after irradiation of microorganisms with electromagnetic radiation in the presence of at least one compound in accordance with the invention with formula (1), with formula (2) and/or with formula (3), and/or of the compound to be used in accordance with the invention with formula (100), with formula (101) and/or with formula (102) is reduced by at least 1 percentage point, more preferably by at least 2 percentage points, preferably by at least 4 percentage points, more preferably by at least 5 percentage points, more preferably by at least 6 percentage points, yet more preferably by at least 7 percentage points, respectively with respect to the starting quantity of said microorganisms.

The term "microorganisms" as used in the context of the invention in particular should be understood to refer to viruses, archaea, prokaryotic microorganisms, such as fungi, protozoa, fungal spores, single-celled algae. The microorganisms may be single-celled or multi-celled, for example fungal mycelium.

A 1,7-diaryl-1,6-heptadiene-3,5-dione derivative in accordance with the invention has the formula (1):

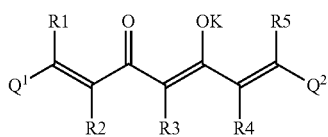

(1)

wherein the residues $Q^1$ and $Q^2$, respectively independently of each other, represent one substituted or unsubstituted, monocyclic or polycyclic aromatic residue, wherein the 1,7-diaryl-1,6-heptadiene-3,5-dione derivative with formula (1) does not contain an OH group which is bonded directly to the organic residue $Q^1$ or $Q^2$, and wherein K represents hydrogen or a cation.

In variation (a) of the inventive 1,7-diaryl-1,6-heptadiene-3,5-dione derivative with formula (1), the residues $Q^1$ and $Q^2$, respectively independently of each other, represent a substituted or unsubstituted, monocyclic or polycyclic aromatic residue, K represents hydrogen or a cation, and at least one of the residues $Q^1$ and $Q^2$, preferably each of the residues $Q^1$ and $Q^2$, respectively independently of each other, is substituted with at least one, preferably 1 to 9, more preferably 1 to 7, more preferably 1 to 5, more preferably 1 to 4, more preferably 2 to 3, organic residue(s) W1a with general formula (5a), (6a), (7a), (8a) or (9a), preferably (5a), (7a), or (9a):

(5a)

(6a)

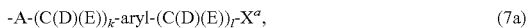

(7a)

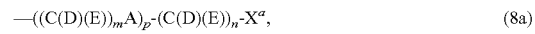

(8a)

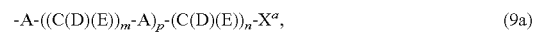

(9a)

wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n and p, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, G-R$^{(I)}$, or G-C(=G)-R$^{(II)}$, wherein G, respectively independently of each other, represents oxygen or sulphur, preferably oxygen, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X$^a$, respectively independently of each other, represents a residue with formula (20c), (20d), (21), or (24), more preferably a residue with formula (20c), (20d), or (21), more preferably a residue with formula (24):

(20c)

(20d)

(21)

(24)

wherein each of the residues R$^{(VII)}$, R$^{(VIII)}$, and R$^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably hydrogen, and wherein each of the residues R$^{(XV)}$, R$^{(XVI)}$, and R$^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably an aryl residue containing 5 to 12 C atoms, an alkylaryl residue containing 5 to 12 C atoms, or an alkyl residue, which may be linear or branched, containing 1 to 8 C atoms, and wherein the residues R1, R2, R3, R4 and R5, respectively independently of each other, represent hydrogen, halogen, alkyl containing 1 to 12 C atoms, cycloalkyl containing 1 to 12 C atoms, alkylaryl containing 1 to 12 C atoms, aryl containing 5 to 20 C atoms, ether containing 2 to 12 C atoms or glycol containing 2 to 12 C atoms.

In variation (b) of the inventive 1,7-diaryl-1,6-heptadiene-3,5-dione derivative with formula (1), the residues $Q^1$ and $Q^2$, respectively independently of each other, represent a substituted or unsubstituted, monocyclic or polycyclic aromatic residue, K represents hydrogen or a cation, and the residue R3 is an organic residue W2a which has the general formula (4b), (5b), (6b), (7b), (8b), or (9b), preferably (4b):

  (4b)

  (5b)

  (6b)

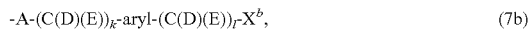  (7b)

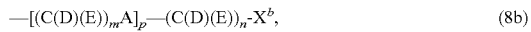  (8b)

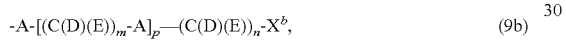  (9b)

and
wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n, and p, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, $G-R^{(I)}$, or $G-C(=G)-R^{(II)}$, wherein G, respectively independently of each other, represents oxygen or sulphur, preferably oxygen, and wherein the residues $R^{(I)}$ and $R^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein $X^b$, respectively independently of each other, is an organic residue which (i) contains at least one neutral nitrogen atom which can be protonated, or (ii) contains at least one positively charged, preferably quaternary, nitrogen atom, or (iii) contains at least one positively charged, preferably quaternary, phosphorus atom, preferably (i) contains at least one neutral nitrogen atom which can be protonated, or (ii) contains at least one positively charged, preferably quaternary, nitrogen atom, wherein more preferably, $X^b$, respectively independently of each other, represents a residue with formula (20c), (20d), (21), or (24), more preferably a residue with formula (20c), (20d), or (21), more preferably a residue with formula (24):

  (20c)

  (20d)

  (21)

  (24)

wherein each of the residues $R^{(VII)}$, $R^{(VIII)}$, and $R^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably hydrogen, and wherein each of the residues $R^{(XV)}$, $R^{(XVI)}$, and $R^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably an aryl residue containing 5 to 12 C atoms, an alkylaryl residue containing 5 to 12 C atoms, or an alkyl residue, which may be linear or branched, containing 1 to 8 C atoms, and wherein the residues R1, R2, R4 and R5, respectively independently of each other, represent hydrogen, halogen, alkyl containing 1 to 12 C atoms, alkylaryl containing 1 to 12 C atoms, aryl containing 5 to 20 C atoms, ether containing 2 to 12 C atoms or glycol containing 2 to 12 C atoms.

Optionally, in variation (b) of the inventive 1,7-diaryl-1,6-heptadiene-3,5-dione derivative with formula (1), at least one of the residues $Q^1$ and $Q^2$, preferably each of the residues $Q^1$ and $Q^2$, respectively independently of each other, is substituted with at least one, preferably 1 to 9, more preferably 1 to 7, more preferably 1 to 5, more preferably 1 to 4, more preferably 2 to 3, organic residue(s) W1 b with general formula (4b), (5b), (6b), (7b), (8b), or (9b), preferably (5b), (7b), or (9b):

  (4b)

  (5b)

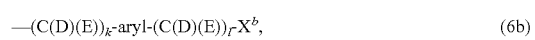  (6b)

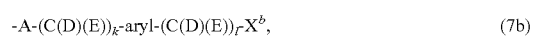  (7b)

—[(C(D)(E))$_m$A]$_p$—(C(D)(E))$_n$-X$^b$, (8b)

-A-[(C(D)(E))$_m$-A]$_p$—(C(D)(E))$_n$-X$^b$, (9b)

wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n and p, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, G-R$^{(I)}$, or G-C(=G)-R$^{(II)}$, wherein G, respectively independently of each other, represents oxygen or sulphur, preferably oxygen, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X$^b$, respectively independently of each other, is an organic residue which (i) contains at least one neutral nitrogen atom which can be protonated, or (ii) contains at least one positively charged, preferably quaternary, nitrogen atom, or (iii) contains at least one positively charged, preferably quaternary, phosphorus atom, preferably (i) contains at least one neutral nitrogen atom which can be protonated, or (ii) contains at least one positively charged, preferably quaternary, nitrogen atom, wherein more preferably, X$^b$, respectively independently of each other, represents a residue with formula (20c), (20d), (21), or (24), more preferably a residue with formula (20c), (20d), or (21), more preferably a residue with formula (24):

 (20c)

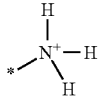 (20d)

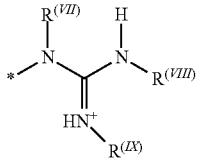 (21)

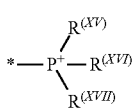 (24)

wherein each of the residues R$^{(VII)}$, R$^{(VIII)}$, and R$^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably hydrogen, and wherein each of the residues R$^{(XV)}$, R$^{(XVI)}$, and R$^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably an aryl residue containing 5 to 12 C atoms, an alkylaryl residue containing 5 to 12 C atoms, or an alkyl residue, which may be linear or branched, containing 1 to 8 C atoms.

In a preferred embodiment of the compound with formula (1), K is a cation M$^{z+}$ of a metal M, wherein z is the formal oxidation number of the metal M and wherein z represents a whole number from 1 to 7, preferably from 2 to 5, more preferably from 2 to 3, and wherein the compound has the formula (2):

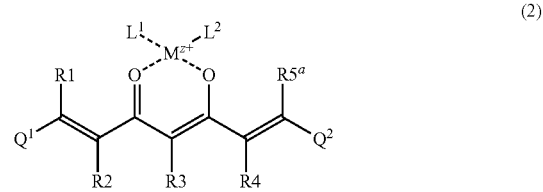 (2)

wherein L$^1$ and L$^2$, respectively independently of each other, represent water, fluoride, chloride, bromide, iodide, cyanide, carbonyl, thiocyanate, phosphate, hydrogen phosphate, dihydrogen phosphate, sulphate, hydrogen sulphate, acetylacetonate, acetic acid ester, acetonitrile, tosylate, mesylate or at least one carboxylation of a carboxylic acid containing 1 to 15 carbon atoms and/or combinations thereof. Preferably, a carboxylation of a carboxylic acid containing 1 to 15 carbon atoms is formate, acetate, n-propionate, lactate, oxalate, fumarate, maleinate, tartrate, succinylate, benzoate, salicylate, citrate and/or combinations thereof. More preferably, L1 and L2 are identical, for example a polydentate ligand. Suitable polydentate ligands have two or more coordination sites which can bind to the cation M$^{2+}$. Examples of suitable polydentate ligands are ethylenediamine, nitrilotriacetic acid (NTA), ethylenediaminetetraacetate salts (EDTA), acetylacetonate, acetic acid esters, citrate, bis(2-methoxyethyl)ether (diglyme), 8-hydroxyquinoline, 2,2'-bipyridine, 1,10-phenanthroline (phen), dimercaptosuccinic acid, tartrate or oxalate.

A 1,7-diaryl-1,6-heptadiene-3,5-dione derivative in accordance with the invention also has the formula (3):

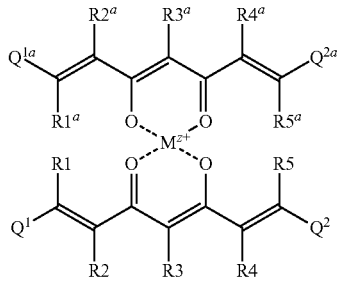

(3)

In variation (a) of the inventive 1,7-diaryl-1,6-heptadiene-3,5-dione derivative with formula (3), $M^{z+}$ represents a cation of a metal M, wherein z is the formal oxidation number of the metal M and wherein z represents a whole number from 1 to 7, preferably from 2 to 3, and wherein the residues $Q^1$ and $Q^2$, respectively independently of each other, represent one substituted or unsubstituted, monocyclic or polycyclic aromatic residue, wherein the residues $Q^{1a}$ and $Q^{2a}$, respectively independently of each other, represent one substituted or unsubstituted, monocyclic or polycyclic aromatic residue or one substituted or unsubstituted, monocyclic or polycyclic heteroaromatic residue, preferably one substituted or unsubstituted, monocyclic or polycyclic aromatic residue, and wherein at least one of the residues $Q^1$ and $Q^2$, preferably each of the residues $Q^1$ and $Q^2$, respectively independently of each other, is substituted with at least one, preferably 1 to 9, more preferably 1 to 7, more preferably 1 to 5, more preferably 1 to 4, more preferably 2 to 3, organic residue(s) W1a with general formula (5a), (6a), (7a), (8a), or (9a), preferably (5b), (7b), or (9b):

(5a)

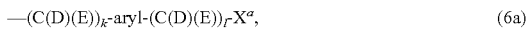

(6a)

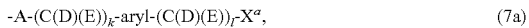

(7a)

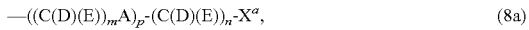

(8a)

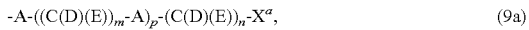

(9a)

wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n and p, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, G-$R^{(I)}$, or G-C(=G)-$R^{(II)}$, wherein G, respectively independently of each other, represents oxygen or sulphur, preferably oxygen, and wherein the residues $R^{(I)}$ and $R^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein $X^a$, respectively independently of each other, represents a residue with formula (20c), (20d), (21), or (24), more preferably a residue with formula (20c), (20d), or (21), more preferably a residue with formula (24):

(20c)

(20d)

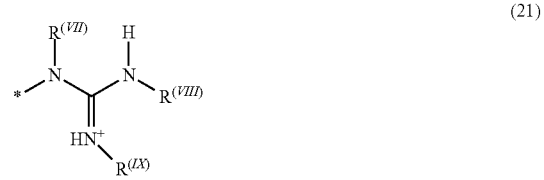

(21)

(24)

wherein each of the residues $R^{(VII)}$, $R^{(VIII)}$, and $R^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably hydrogen, and wherein each of the residues $R^{(XV)}$, $R^{(XVI)}$, and $R^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably an aryl residue containing 5 to 12 C atoms, an alkylaryl residue containing 5 to 12 C atoms, or an alkyl residue, which may be linear or branched, containing 1 to 8 C atoms, and wherein at least one of the residues $Q^{1a}$ and $Q^{2a}$, preferably each of the residues $Q^{1a}$ and $Q^{2a}$, respectively independently of each other, is substituted with at least one, preferably 1 to 9, more preferably 1 to 7, more preferably 1 to 5, more preferably 1 to 4, more preferably 2 to 3, organic residue(s) W1c with general formula (4c), (5c), (6c), (7c), (8c), or (9c), preferably (5c), (7c), or (9c):

(4c)

(5c)

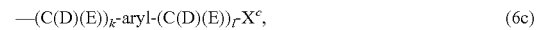

(6c)

-A-(C(D)(E))$_k$-aryl-(C(D)(E))$_l$-X$^c$, (7c)

—((C(D)(E))$_m$-A)$_p$-(C(D)(E))$_n$-X$^c$, (8c)

-A-((C(D)(E))$_m$-A)$_p$-(C(D)(E))$_n$-X$^c$, (9c)

wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n and p, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, G-R$^{(I)}$, or G-C(=G)-R$^{(II)}$, wherein G, respectively independently of each other, represents oxygen or sulphur, preferably oxygen, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X$^c$, respectively independently of each other, is an organic residue which (i) contains at least one neutral nitrogen atom which can be protonated, or (ii) contains at least one positively charged, preferably quaternary, nitrogen atom, or (iii) contains at least one positively charged, preferably quaternary, phosphorus atom, wherein preferably, X$^c$, respectively independently of each other, represents a residue with formula (20c), (20d), (21), or (24), more preferably a residue with formula (20c), (20d), or (21), more preferably a residue with formula (24):

(20c)

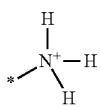
(20d)

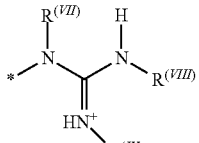
(21)

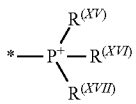
(24)

wherein each of the residues R$^{(VII)}$, R$^{(VIII)}$, and R$^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably hydrogen, and wherein each of the residues R$^{(XV)}$, R$^{(XVI)}$, and R$^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably an aryl residue containing 5 to 12 C atoms, an alkylaryl residue containing 5 to 12 C atoms, or an alkyl residue, which may be linear or branched, containing 1 to 8 C atoms, wherein the residues R1, R1$^a$, R2, R2$^a$, R3, R3$^a$, R4, R4$^a$, R5 and R5$^a$, respectively independently of each other, represent hydrogen, halogen, alkyl containing 1 to 12 C atoms, cycloalkyl containing 1 to 12 C atoms, alkylaryl containing 1 to 12 C atoms, aryl containing 5 to 20 C atoms, ether containing 2 to 12 C atoms or glycol containing 2 to 12 C atoms.

In variation (b) of the 1,7-diaryl-1,6-heptadiene-3,5-dione derivative with formula (3), M$^{z+}$ represents a cation of a metal M, wherein z is the formal oxidation number of the metal M and wherein z represents a whole number from 1 to 7, preferably from 2 to 5, and wherein the residues Q$^1$ and Q$^2$, respectively independently of each other, represent a substituted or unsubstituted, monocyclic or polycyclic aromatic residue, wherein the residues Q$^{1a}$ and Q$^{2a}$, respectively independently of each other, represent one substituted or unsubstituted, monocyclic or polycyclic aromatic residue or one substituted or unsubstituted, monocyclic or polycyclic heteroaromatic residue, preferably one substituted or unsubstituted, monocyclic or polycyclic aromatic residue, and wherein the residue R3 or R3$^a$, preferably the residues R3 and R3$^a$, respectively independently of each other, represents an organic residue W2a with general formula (4b), (5b), (6b), (7b), (8b), or (9b), preferably (4b):

—(C(D)(E))$_h$-X$^b$, (4b)

-A-(C(D)(E))$_h$-X$^b$, (5b)

—(C(D)(E))$_k$-aryl-(C(D)(E))$_l$-X$^b$, (6b)

-A-(C(D)(E))$_k$-aryl-(C(D)(E))$_l$-X$^b$, (7b)

—[(C(D)(E))$_m$A]$_p$—(C(D)(E))$_n$-X$^b$, (8b)

-A-[(C(D)(E))$_m$-A]$_p$—(C(D)(E))$_n$-X$^b$, (9b)

and wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n, and p, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, G-R$^{(I)}$, or G-C (=G)-R$^{(II)}$, wherein G, respectively independently of each other, represents oxygen or sulphur, preferably oxygen, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X$^b$, respectively independently of each other, is an organic residue which (i) contains at least one neutral nitrogen atom which can be protonated, (ii) contains at least one positively charged, preferably quaternary, nitrogen atom, or (iii) contains at least one positively charged, preferably quaternary, phosphorus atom, preferably (i) contains at least one neutral nitrogen atom which can be protonated, or (ii) contains at least one positively charged, preferably quaternary, nitrogen atom, wherein more preferably, X$^b$, respectively independently of each other, represents a residue with formula (20c), (20d), (21), or (24), more preferably a residue with formula (20c), (20d), or (21), more preferably a residue with formula (24):

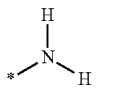

(20c)

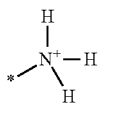

(20d)

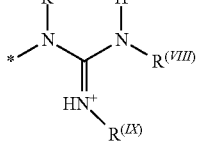

(21)

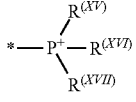

(24)

wherein each of the residues R$^{(VII)}$, R$^{(VIII)}$, and R$^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably hydrogen, and wherein each of the residues R$^{(XV)}$, R$^{(XVI)}$, and R$^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably an aryl residue containing 5 to 12 C atoms, an alkylaryl residue containing 5 to 12 C atoms, or an alkyl residue, which may be linear or branched, containing 1 to 8 C atoms, and wherein the residues R1, R1$^a$, R2, R2$^a$, R4, R4$^a$, R5 and R5$^a$, respectively independently of each other, represent hydrogen, halogen, alkyl containing 1 to 12 C atoms, alkylaryl containing 1 to 12 C atoms, aryl containing 5 to 20 C atoms, ether containing 2 to 12 C atoms or glycol containing 2 to 12 C atoms.

Optionally, in variation (b) of the 1,7-diaryl-1,6-heptadiene-3,5-dione derivative with formula (3), at least one of the residues Q$^1$, Q$^{1a}$, Q$^2$ and Q$^{2a}$, preferably each of the residues Q$^1$ and Q$^2$, preferably each of the residues Q$^1$ and Q$^{1a}$, preferably each of the residues Q$^1$, Q$^{1a}$ and Q$^2$, preferably each of the residues Q$^1$, Q$^{1a}$, Q$^2$ and Q$^{2a}$, respectively independently of each other, is substituted with at least one, preferably 1 to 9, more preferably 1 to 7, more preferably 1 to 5, more preferably 1 to 4, more preferably 2 to 3, organic residue(s) W1 b with general formula (4b), (5b), (6b), (7b), (8b), or (9b), preferably (5b), (7b), or (9b):

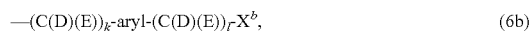

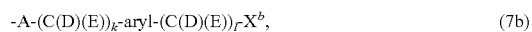

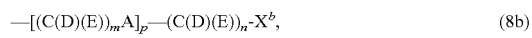

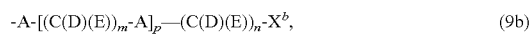

and wherein h represents a whole number from 1 to 20, preferably from 1 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n, and p, respectively independently of each other, represent a whole number from 1 to 6, preferably from 1 to 4, and wherein A, respectively independently of each other, represents oxygen or sulphur, preferably oxygen, wherein D and E, respectively independently of each other, represent hydrogen, halogen, G-R$^{(I)}$, or G-C(=G)-R$^{(II)}$, wherein G, respectively independently of each other, represents oxygen or sulphur, preferably oxygen, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X$^b$, respectively independently of each other, is an organic residue which (i) contains at least one neutral nitrogen atom which can be protonated, (ii) contains at least one positively charged, preferably quaternary, nitrogen atom, or (iii) contains at least one positively charged, preferably quaternary, phosphorus atom, preferably (i) contains at least one neutral nitrogen atom which can be protonated, or (ii) contains at least one positively charged, preferably quaternary, nitrogen atom, wherein more preferably, X$^b$, respectively independently of each other, represents a residue with formula (20c), (20d), (21), or (24), more preferably a residue with formula (20c), (20d), or (21), more preferably a residue with formula (24):

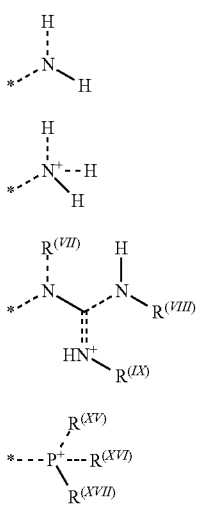

(20c)

(20d)

(21)

(24)

wherein each of the residues $R^{(VII)}$, $R^{(VIII)}$, and $R^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably hydrogen, and wherein each of the residues $R^{(XV)}$, $R^{(XVI)}$, and $R^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably an aryl residue containing 5 to 12 C atoms, an alkylaryl residue containing 5 to 12 C atoms, or an alkyl residue, which may be linear or branched, containing 1 to 8 C atoms.

In a preferred embodiment of the compound with formula (3), the compound has the formula (3a):

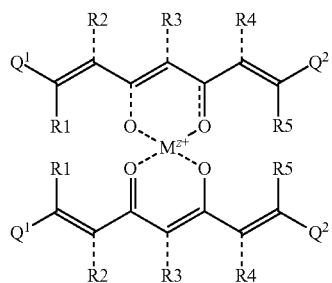

(3a)

In variation (a) of the inventive 1,7-diaryl-1,6-heptadiene-3,5-dione derivative with formula (3a), $M^{z+}$ represents a cation of a metal M, wherein z is the formal oxidation number of the metal M and wherein z represents a whole number from 1 to 7, preferably from 2 to 3, and wherein the residues $Q^1$ and $Q^2$, respectively independently of each other, represent one substituted or unsubstituted, monocyclic or polycyclic aromatic residue, and wherein at least one of the residues $Q^1$ and $Q^2$, preferably each of the residues $Q^1$ and $Q^2$, respectively independently of each other, is substituted with at least one, preferably 1 to 9, more preferably 1 to 7, more preferably 1 to 5, more preferably 1 to 4, more preferably 2 to 3, organic residue(s) W1a with general formula (5a), (6a), (7a), (8a), or (9a), preferably (5a), (7a), or (9a):

$$-A-(C(D)(E))_h-X^a, \quad (5a)$$

$$-(C(D)(E))_k\text{-aryl-}(C(D)(E))_l-X^a, \quad (6a)$$

$$-A-(C(D)(E))_k\text{-aryl-}(C(D)(E))_l-X^a, \quad (7a)$$

$$-((C(D)(E))_m-A)_p-(C(D)(E))_n-X^a, \quad (8a)$$

$$-A-((C(D)(E))_m-A)_p-(C(D)(E))_n-X^a, \quad (9a)$$

wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n and p, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, G-$R^{(I)}$, or G-C(=G)-$R^{(II)}$, wherein G, respectively independently of each other, represents oxygen or sulphur, preferably oxygen, and wherein the residues $R^{(I)}$ and $R^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein $X^a$, respectively independently of each other, represents a residue with formula (20c), (20d), (21), or (24), more preferably a residue with formula (20c), (20d), or (21), more preferably a residue with formula (24):

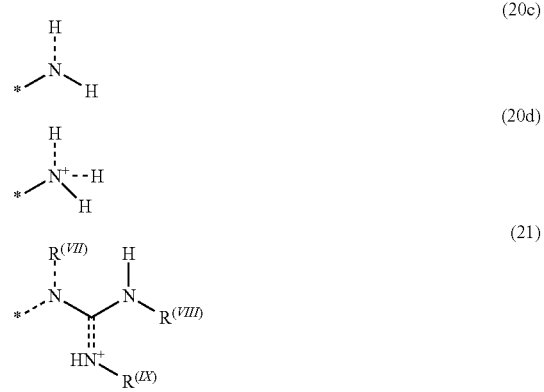

(20c)

(20d)

(21)

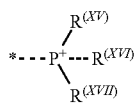
(24)

wherein each of the residues $R^{(VII)}$, $R^{(VIII)}$, and $R^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably hydrogen, and wherein each of the residues $R^{(XV)}$, $R^{(XVI)}$, and $R^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably an aryl residue containing 5 to 12 C atoms, an alkylaryl residue containing 5 to 12 C atoms, or an alkyl residue, which may be linear or branched, containing 1 to 8 C atoms, and wherein the residues R1, R2, R3, R4, and R5, respectively independently of each other, represent hydrogen, halogen, alkyl containing 1 to 12 C atoms, cycloalkyl containing 1 to 12 C atoms, alkylaryl containing 1 to 12 C atoms, aryl containing 5 to 20 C atoms, ether containing 2 to 12 C atoms or glycol containing 2 to 12 C atoms.

In variation (b) of the 1,7-diaryl-1,6-heptadiene-3,5-dione derivative with formula (3a), $M^{z+}$ represents a cation of a metal M, wherein z is the formal oxidation number of the metal M and wherein z represents a whole number from 1 to 7, preferably from 2 to 5, and wherein the residues $Q^1$ and $Q^2$, respectively independently of each other, represent a substituted or unsubstituted, monocyclic or polycyclic aromatic residue, and wherein the residue R3 respectively is an organic residue W2a, wherein the organic residue W2a has the general formula (4b), (5b), (6b), (7b), (8b), or (9b), preferably (4b):

 (4b)

 (5b)

 (6b)

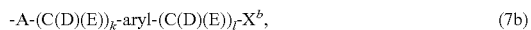 (7b)

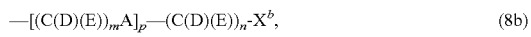 (8b)

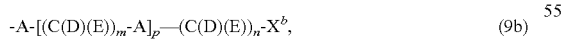 (9b)

and wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n, and p, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, G-$R^{(I)}$, or G-C(=G)-$R^{(II)}$, wherein G, respectively independently of each other, represents oxygen or sulphur, preferably oxygen, and wherein the residues $R^{(I)}$ and $R^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein $X^b$, respectively independently of each other, is an organic residue which (i) contains at least one neutral nitrogen atom which can be protonated, (ii) contains at least one positively charged, preferably quaternary, nitrogen atom, or (iii) contains at least one positively charged, preferably quaternary, phosphorus atom, preferably (i) contains at least one neutral nitrogen atom which can be protonated, or (ii) contains at least one positively charged, preferably quaternary, nitrogen atom, wherein more preferably, $X^b$, respectively independently of each other, represents a residue with formula (20c), (20d), (21), or (24), more preferably a residue with formula (20c), (20d), or (21), more preferably a residue with formula (24):

 (20c)

 (20d)

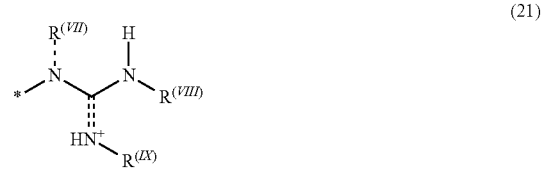 (21)

 (24)

wherein each of the residues $R^{(VII)}$, $R^{(VIII)}$, and $R^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably hydrogen, and wherein each of the residues $R^{(XV)}$, $R^{(XVI)}$, and $R^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably an aryl residue containing 5 to 12 C atoms, an alkylaryl residue containing 5 to 12 C atoms, or an alkyl residue, which may be linear or branched, containing 1 to 8 C atoms, and wherein the residues R1, R2, R4, and R5, respectively independently of each other, represent hydrogen, halogen, alkyl containing 1 to 12 C atoms, alkylaryl containing 1 to 12 C atoms, aryl containing 5 to 20 C atoms, ether containing 2 to 12 C atoms or glycol containing 2 to 12 C atoms.

Optionally, in variation (b) of the 1,7-diaryl-1,6-heptadiene-3,5-dione derivative with formula (3a), at least one of the residues $Q^1$ and $Q^2$, preferably each of the residues $Q^1$ and $Q^2$, respectively independently of each other, is substituted with at least one, preferably 1 to 9, more preferably 1 to 7, more preferably 1 to 5, more preferably 1 to 4, more preferably 2 to 3, organic residue(s) W1 b with general formula (4b), (5b), (6b), (7b), (8b), or (9b), preferably (5b), (7b), or (9b):

—(C(D)(E))$_h$-X$^b$,  (4b)

-A-(C(D)(E))$_h$-X$^b$,  (5b)

—(C(D)(E))$_k$-aryl-(C(D)(E))$_l$-X$^b$,  (6b)

-A-(C(D)(E))$_k$-aryl-(C(D)(E))$_l$-X$^b$,  (7b)

—[(C(D)(E))$_m$-A]$_p$—(C(D)(E))$_n$-X$^b$,  (8b)

-A-[(C(D)(E))$_m$-A]$_p$—(C(D)(E))$_n$-X$^b$,  (9b)

and wherein h represents a whole number from 1 to 20, preferably from 1 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n, and p, respectively independently of each other, represent a whole number from 1 to 6, preferably from 1 to 4, and wherein A, respectively independently of each other, represents oxygen or sulphur, preferably oxygen, wherein D and E, respectively independently of each other, represent hydrogen, halogen, G-R$^{(I)}$, or G-C(=G)-R$^{(II)}$, wherein G, respectively independently of each other, represents oxygen or sulphur, preferably oxygen, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X$^b$, respectively independently of each other, is an organic residue which (i) contains at least one neutral nitrogen atom which can be protonated, (ii) contains at least one positively charged, preferably quaternary, nitrogen atom, or (iii) contains at least one positively charged, preferably quaternary, phosphorus atom, preferably (i) contains at least one neutral nitrogen atom which can be protonated, or (ii) contains at least one positively charged, preferably quaternary, nitrogen atom, wherein more preferably, X$^b$, respectively independently of each other, represents a residue with formula (20c), (20d), (21), or (24), more preferably a residue with formula (20c), (20d), or (21), more preferably a residue with formula (24):

(20c)

(20d)

(21)

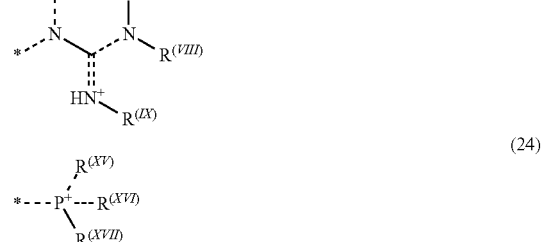

(24)

wherein each of the residues R$^{(VII)}$, R$^{(VIII)}$, and R$^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably hydrogen, and wherein each of the residues R$^{(XV)}$, R$^{(XVI)}$, and R$^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably an aryl residue containing 5 to 12 C atoms, an alkylaryl residue containing 5 to 12 C atoms, or an alkyl residue, which may be linear or branched, containing 1 to 8 C atoms.

In a preferred embodiment of the compound with formula (2), and/or of the compound with formula (3), and/or of the compound with formula (3a), and/or of the compound with formula (101), and/or of the compound with formula (102), the metal M is selected from the group which consists of alkali metals, alkaline-earth metals, transition metals, metals and metalloids from the third, fourth, fifth and sixth main group of the periodic table of the elements and combinations thereof; preferably, the metal M is selected from the group which consists of Be, Mg, Ca, Sr, Ba, Ti, Zr, Hf, V, Nb, Ta, Cr, Mo, W, Mn, Tc, Rh, Fe, Ru, Os, Co, Rh, Ir, Ni, Pd, Pt, Cu, Ag, Au, Zn, B, Al, Ga. In, Si, Ge, Sn, Bi, Se, Te and combinations thereof.

More preferably, the metal M is selected from the group which consists of B, Al, Zn, Cu, Mg, Ca, Fe, Si, Ga, Sn, Rh, Co, Ti, Zr, V, Cr, Mo, Mn, Ru, Pd, Ir, Ni, and combinations thereof. More preferably, M$^{z+}$ represents Mg$^{2+}$, Ca$^{2+}$, Fe$^{2+}$, Fe$^{3+}$, Zn$^{2+}$, Cu$^{2+}$, B$^{3+}$ or Si$^{4+}$.

In accordance with the invention, in the compound with formula (1) or the compound with formula (2) or the compound with formula (3a), the residues $Q^1$ and $Q^2$, or in the compound with formula (3) the residues $Q^1$, $Q^{1a}$, $Q^2$ and $Q^{2a}$, respectively independently of each other, represent a substituted or unsubstituted, monocyclic or polycyclic aromatic residue, which preferably, respectively independently of each other, is a phenyl residue, a naphthyl residue, an azulene residue, a phenalene residue, an acenaphthyl residue, a fluorene residue, a phenanthrene residue, an anthracene residue, a fluoranthene residue, a pyrene residue, a benzo[a]anthracene residue, a chrysene residue, a benzo[b]fluoranthene residue, a benzo[h]fluoranthene residue, a benzo[a]pyrene residue, a dibenzo[a,h]anthracene residue, a tetracene residue, a triphenylene residue, a pentacene residue, or a hexacene residue, more preferably a phenyl residue, a naphthyl residue, a phenalene residue, or an anthracene residue.

In accordance with the invention, in the compound with formula (100) or the compound with formula (102), the residues $Q^3$ and $Q^4$, or in the compound with formula (101), the residues $Q^3$, $Q^{3a}$, $Q^4$ and $Q^{4a}$, respectively independently of each other, represent a substituted or unsubstituted, monocyclic or polycyclic aromatic residue, which preferably, respectively independently of each other, represents a phenyl residue, a naphthyl residue, an azulene residue, a phenalene residue, an acenaphthyl residue, a fluorene residue, a phenanthrene residue, an anthracene residue, a fluoranthene residue, a pyrene residue, a benzo[a]anthracene residue, a chrysene residue, a benzo[b]fluoranthene residue, a benzo[h]fluoranthene residue, a benzo[a]pyrene residue, a dibenzo[a,h]anthracene residue, a tetracene residue, a triphenylene residue, a pentacene residue, or a hexacene residue, more preferably a phenyl residue, a naphthyl residue, a phenalene residue, or an anthracene residue, or a substituted or unsubstituted, monocyclic or polycyclic heteroaromatic residue, which preferably has at least 5 ring atoms, wherein the ring atoms contain at least one carbon atom and at least one nitrogen atom which preferably can be protonated, wherein more preferably, the one substituted or unsubstituted monocyclic or polycyclic, heteroatomic residue, respectively independently of each other, is a pyrrole residue, a pyridine residue, a quinoline residue, an isoquinoline residue, an indole residue, an isoindole residue, a pyrimidine residue, a pyrazine residue, an imidazole residue, or an acridine residue, more preferably a pyridine residue, a quinoline residue, an isoquinoline residue or an indole residue.

Preferably, the one substituted or unsubstituted, monocyclic or polycyclic, heteroatomic residue has 5 to 14, more preferably 6 to 10 ring atoms, wherein the ring atoms contain at least 1 carbon atom and at least 1 nitrogen atom which preferably can be protonated. More preferably, the ring atoms have 1 to 3 nitrogen atoms which preferably can be protonated, which yet more preferably are not disposed next to each other.

In variation (a1) of the compound with formula (100), the compound with formula (101) and/or the compound with formula (102), at least one of the residues $Q^3$, $Q^{3a}$, $Q^4$ and $Q^{4a}$, respectively independently of each other, is an unsaturated monocyclic or polycyclic, heteroaromatic residue, which has at least 5, preferably 5 to 14, more preferably 6 to 10 ring atoms, wherein the ring atoms contain at least one carbon atom and at least one nitrogen atom which preferably can be protonated. More preferably, the ring atoms contain 1 to 3, preferably 1 or 2, nitrogen atoms, which preferably can be protonated. Yet more preferably, the nitrogen atoms are not disposed adjacent to each other.

Preferably, said substituted monocyclic or polycyclic aromatic residues or substituted monocyclic or polycyclic, heteroatomic residues, with at least one organic residue W1 or one organic residue W1a or one organic residue W1b or one organic residue W1c and/or with halogen, nitro, carboxylate, aldehyde containing 1 to 8 C atoms, ketone containing 2 to 8 C atoms, O-alkyl containing 1 to 12 C atoms, O-alkenyl containing 2 to 12 C atoms, O-aryl containing 5 to 20 C atoms, ether containing 2 to 12 C atoms, carboxylic acid ester containing 1 to 12 C atoms, carboxylic acid amide containing 1 to 12 C atoms, wherein preferably, the C atom of the carboxamide group is bonded to said substituted monocyclic or polycyclic aromatic residues or substituted monocyclic or polycyclic, heteroatomic residues, alkyl containing 1 to 12 C atoms, alkenyl containing 2 to 12 C atoms, cycloalkyl containing 3 to 12 C atoms, cycloalkenyl containing 3 to 12 C atoms, alkylaryl containing 1 to 12 C atoms, aryl containing 5 to 20 C atoms or heteroaryl which does not contain a nitrogen atom, are substituted with 4 to 20 C atoms.

More preferably, said substituted monocyclic or polycyclic aromatic residues or substituted monocyclic or polycyclic, heteroatomic residues, with at least one organic residue W1 or one organic residue W1a or one organic residue W1b or one organic residue W1c and/or with halogen, nitro, aldehyde containing 1 to 8 C atoms, ketone containing 2 to 8 C atoms, O-alkyl containing 1 to 12 C atoms, O-alkenyl containing 2 to 12 C atoms, O-aryl containing 5 to 20 C atoms, ether containing 2 to 12 C atoms, carboxylic acid ester containing 1 to 12 C atoms, alkyl containing 1 to 12 C atoms, alkenyl containing 2 to 12 C atoms, cycloalkyl containing 3 to 12 C atoms, cycloalkenyl containing 3 to 12 C atoms, alkylaryl containing 1 to 12 C atoms, aryl containing 5 to 20 C atoms or heteroaryl which does not contain a nitrogen atom, are substituted with 4 to 20 C atoms.

Preferably, the one substituted or unsubstituted monocyclic or polycyclic aromatic residue has at least 5 ring atoms, preferably 5 to 16, more preferably 6 to 14, more preferably 6 to 10, which respectively contain at least 1 carbon atom and optionally at least one, preferably 1 to 2, oxygen atom(s), which more preferably are not adjacent to each other.

Preferably, in the compound with formula (1) and/or the compound with formula (2) and/or the compound with formula (3a), the residue $Q^1$, or in the compound with formula (100) and/or the compound with formula (102), the residue $Q^3$ is an aromatic residue with general formula (11a), (12a), (13a), (14a), (15a), (16a), (17a), (18a), or (19a):

(11a)

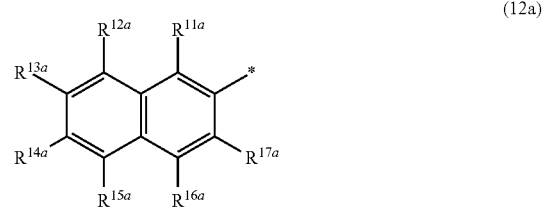

(12a)

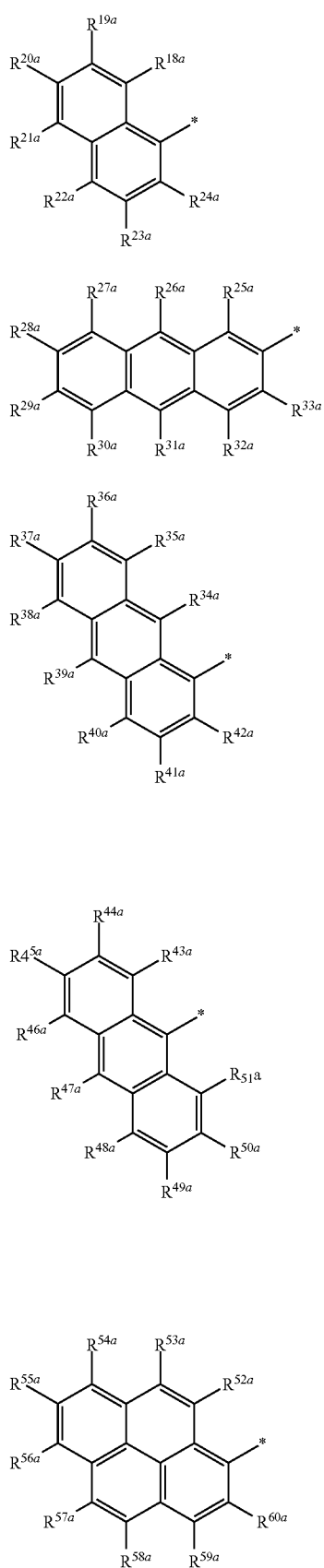
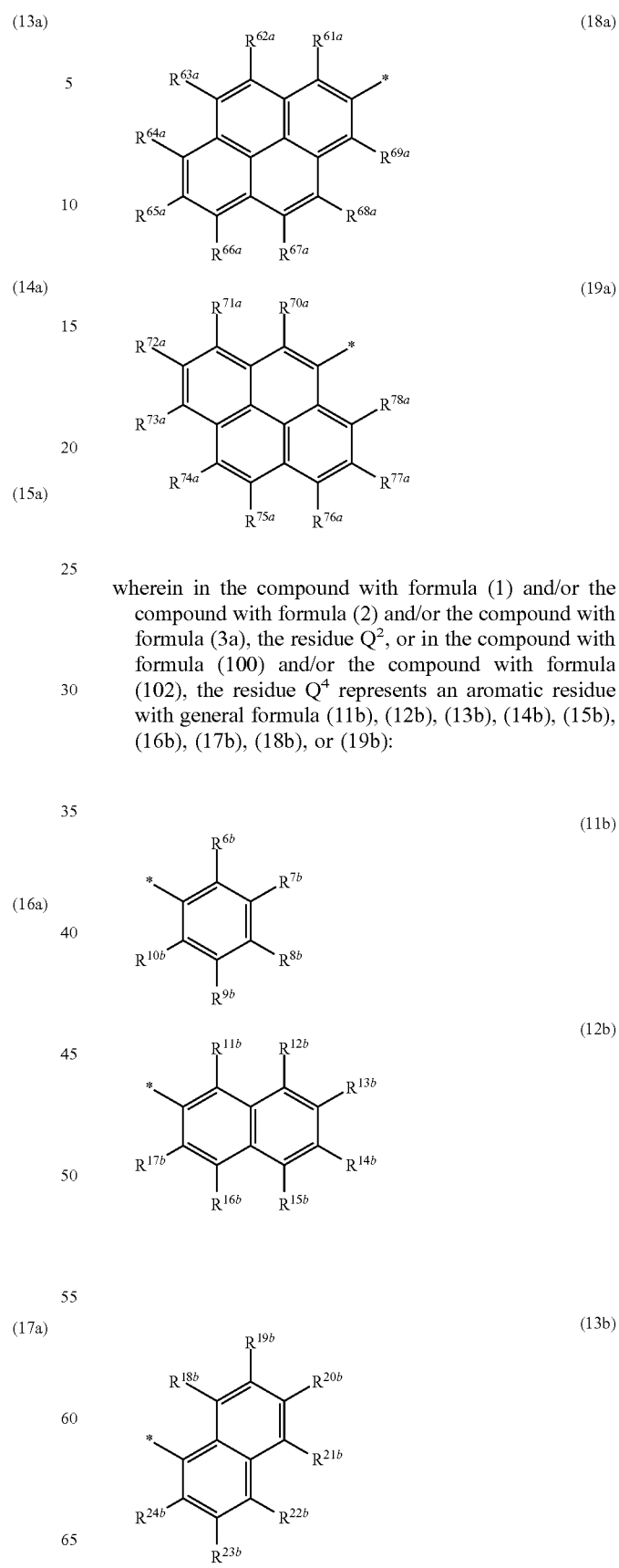
wherein in the compound with formula (1) and/or the compound with formula (2) and/or the compound with formula (3a), the residue $Q^2$, or in the compound with formula (100) and/or the compound with formula (102), the residue $Q^4$ represents an aromatic residue with general formula (11b), (12b), (13b), (14b), (15b), (16b), (17b), (18b), or (19b):

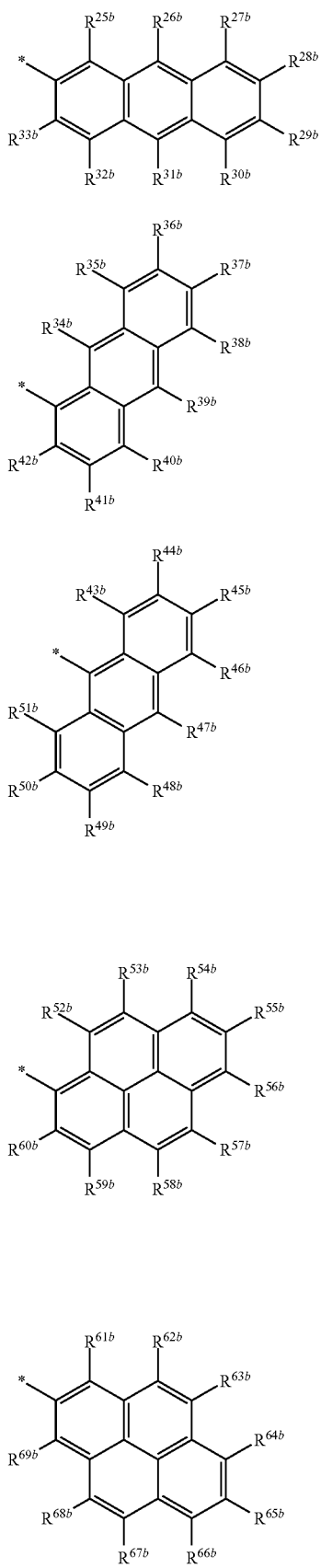

(14b)

(15b)

(16b)

(17b)

(18b)

(19b)

wherein respectively at least 1, preferably 1 to 9, more preferably 1 to 7, more preferably 1 to 5 more preferably 1 to 4, more preferably 2 to 3, residue(s) $R^{6a}$ to $R^{10a}$, $R^{11a}$ to $R^{17a}$, $R^{18a}$ to $R^{24a}$, $R^{25a}$ to $R^{33a}$, $R^{34a}$ to $R^{42a}$, $R^{43a}$ to $R^{51a}$, $R^{52a}$ to $R^{60a}$, $R^{61a}$ to $R^{69a}$, $R^{70a}$ to $R^{78a}$, $R^{6b}$ to $R^{10b}$, $R^{11b}$ to $R^{17b}$, $R^{18b}$ to $R^{24b}$, $R^{25b}$ to $R^{33b}$, $R^{34b}$ to $R^{42b}$, $R^{43b}$ to $R^{51b}$, $R^{52b}$ to $R^{60b}$, $R^{61b}$ to $R^{69b}$, or $R^{70b}$ to $R^{78b}$, respectively independently of each other, is an organic residue W1 or an organic residue W1a or an organic residue W1b or an organic residue W1c, and wherein the residues $R^{6a}$ to $R^{10a}$, $R^{11a}$ to $R^{17a}$, $R^{18a}$ to $R^{24a}$, $R^{25a}$ to $R^{33a}$, $R^{34a}$ to $R^{42a}$, $R^{43a}$ to $R^{51a}$, $R^{52a}$ to $R^{60a}$, $R^{61a}$ to $R^{69a}$, $R^{70a}$ to $R^{78a}$, $R^{6b}$ to $R^{10b}$, $R^{11b}$ to $R^{17b}$, $R^{18b}$ to $R^{24b}$, $R^{25b}$ to $R^{33b}$, $R^{34b}$ to $R^{42b}$, $R^{43b}$ to $R^{51b}$, $R^{52b}$ to $R^{60b}$, $R^{61b}$ to $R^{69b}$, or $R^{70b}$ to $R^{78b}$, which are not an organic residue W1 or an organic residue W1a or an organic residue W1b or an organic residue W1c, respectively independently of each other, are identical or different and represent hydrogen, halogen, nitro, carboxylate, aldehyde containing 1 to 8 C atoms, ketone containing 2 to 8 C atoms, O-alkyl containing 1 to 12 C atoms, O-alkenyl containing 2 to 12 C atoms, O-aryl containing 5 to 20 C atoms, ether containing 2 to 12 C atoms, carboxylic acid ester containing 1 to 12 C atoms, carboxylic acid amide containing 1 to 12 C atoms, wherein preferably, respectively the C atom of the carboxamide group is bonded to one of the residues $Q^1$ to $Q^4$, alkyl containing 1 to 12 C atoms, alkenyl containing 2 to 12 C atoms, cycloalkyl containing 3 to 12 C atoms, cycloalkenyl containing 3 to 12 C atoms, alkylaryl containing 1 to 12 C atoms, aryl containing 5 to 20 C atoms or heteroaryl, which does not contain a nitrogen atom, containing 4 to 20 C atoms, preferably hydrogen, halogen, nitro, carboxylate, aldehyde containing 1 to 8 C atoms, ketone containing 2 to 8 C atoms, O-alkyl containing 1 to 12 C atoms, O-alkenyl containing 2 to 12 C atoms, O-aryl containing 5 to 20 C atoms, ether containing 2 to 12 C atoms, carboxylic acid ester containing 1 to 12 C atoms, alkyl containing 1 to 12 C atoms, alkenyl containing 2 to 12 C atoms, cycloalkyl containing 3 to 12 C atoms, cycloalkenyl containing 3 to 12 C atoms, alkylaryl containing 1 to 12 C atoms, aryl containing 5 to 20 C atoms or heteroaryl, which does not contain a nitrogen atom, containing 4 to 20 C atoms.

More preferably, the residue $Q^1$ or the residue $Q^3$ is an aromatic residue with general formula (11a), (12a) or (13a)

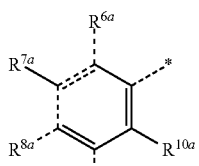
(11a)

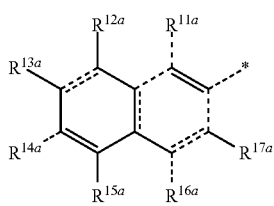
(12a)

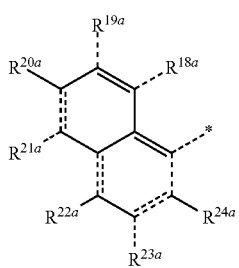
(13a)

and the residue $Q^2$ or the residue $Q^4$ is an aromatic residue with general formula (11 b), (12b) or (13b),

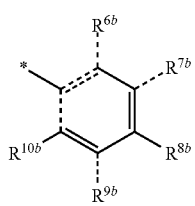
(11b)

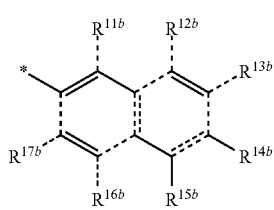
(12b)

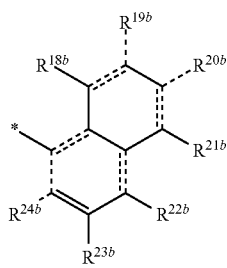
(13b)

wherein respectively at least 1, preferably 1 to 9, more preferably 1 to 7, more preferably 1 to 5, more preferably 1 to 4, more preferably 2 to 3, residue(s) $R^{6a}$ to $R^{10a}$, $R^{11a}$ to $R^{17a}$, $R^{18a}$ to $R^{24a}$, $R^{6b}$ to $R^{10b}$, $R^{11b}$ to $R^{17b}$ or $R^{18b}$ to $R^{24b}$, respectively independently of each other, is an organic residue W1 or an organic residue W1a or an organic residue W1b or an organic residue W1c, and wherein the residues $R^{10a}$, $R^{11a}$ to $R^{17a}$, $R^{18a}$ to $R^{24a}$, $R^{6b}$ to $R^{10b}$, $R^{11b}$ to $R^{17b}$ and $R^{18b}$ to $R^{24b}$ which are not an organic residue W1 or an organic residue W1a or an organic residue W1b or an organic residue W1c, respectively independently of each other, are identical or different and represent hydrogen, halogen, nitro, carboxylate, aldehyde containing 1 to 8 C atoms, ketone containing 2 to 8 C atoms, O-alkyl containing 1 to 12 C atoms, O-alkenyl containing 2 to 12 C atoms, O-aryl containing 5 to 20 C atoms, ether containing 2 to 12 C atoms, carboxylic acid ester containing 1 to 12 C atoms, carboxylic acid amide containing 1 to 12 C atoms, wherein preferably, respectively the C atom of the carboxamide group is bonded to one of the residues $Q^1$ to $Q^4$, alkyl containing 1 to 12 C atoms, alkenyl containing 2 to 12 C atoms, cycloalkyl containing 3 to 12 C atoms, cycloalkenyl containing 3 to 12 C atoms, alkylaryl containing 1 to 12 C atoms, aryl containing 5 to 20 C atoms or heteroaryl, which does not contain a nitrogen atom, containing 4 to 20 C atoms, preferably hydrogen, halogen, nitro, carboxylate, aldehyde containing 1 to 8 C atoms, ketone containing 2 to 8 C atoms, O-alkyl containing 1 to 12 C atoms, O-alkenyl containing 2 to 12 C atoms, O-aryl containing 5 to 20 C atoms, ether containing 2 to 12 C atoms, carboxylic acid ester containing 1 to 12 C atoms, alkyl containing 1 to 12 C atoms, alkenyl containing 2 to 12 C atoms, cycloalkyl containing 3 to 12 C atoms, cycloalkenyl containing 3 to 12 C atoms, alkylaryl containing 1 to 12 C atoms, aryl containing 5 to 20 C atoms or heteroaryl, which does not contain a nitrogen atom, containing 4 to 20 C atoms.

Preferably, in the compound with formula (3), the residues $Q^1$ and $Q^{1a}$, or in the compound with formula (101), the residues $Q^3$ and $Q^{3a}$, respectively independently of each other, are an aromatic residue with general formula (11a), (12a), (13a), (14a), (15a), (16a), (17a), (18a), or (19a):

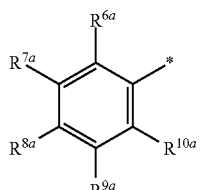
(11a)

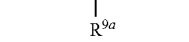

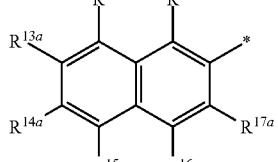
(12a)

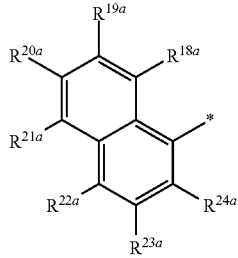
(13a)

(14a)
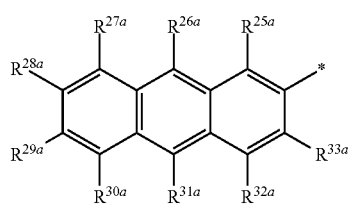
(15a)
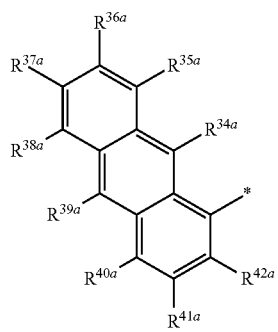
(16a)
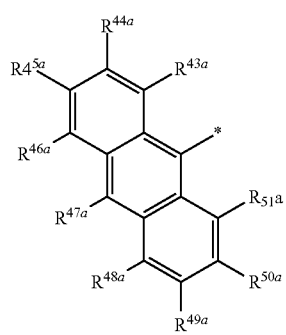
(17a)
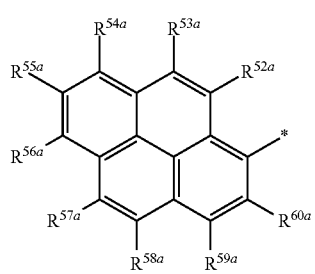
(18a)
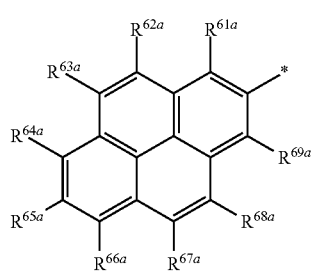
(19a)
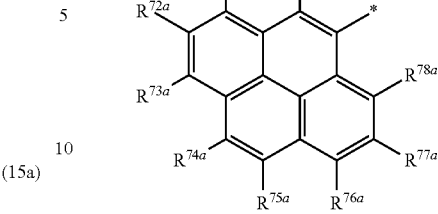
and wherein in the compound with formula (3) the residues $Q^2$ and $Q^{2a}$, or in the compound with formula (101) the residues $Q^4$ and $Q^{4a}$, respectively independently of each other, represent an aromatic residue with general formula (11 b), (12b), (13b), (14b), (15b), (16b), (17b), (18b), or (19b):
(11b)
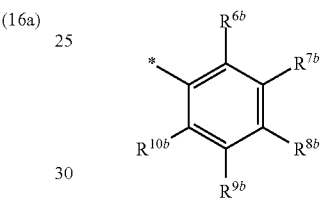
(12b)
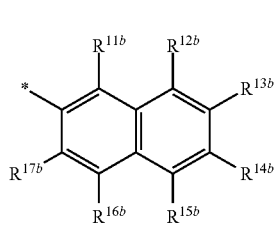
(13b)
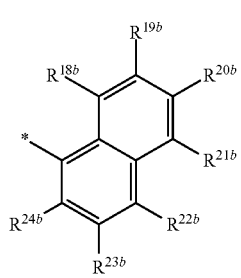
(14b)
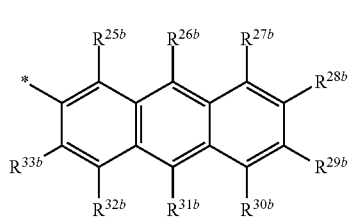

-continued

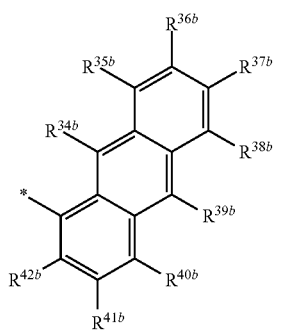
(15b)

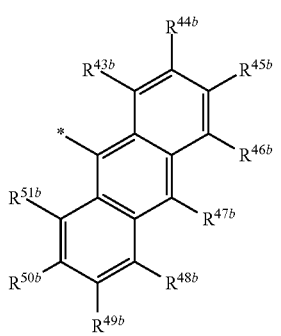
(16b)

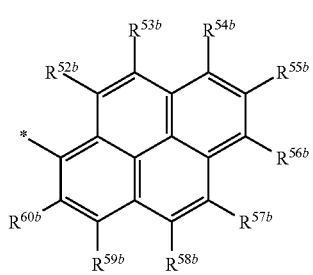
(17b)

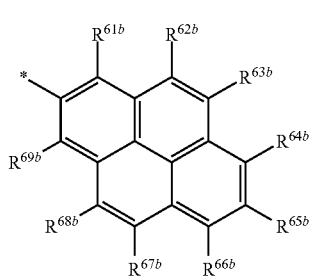
(18b)

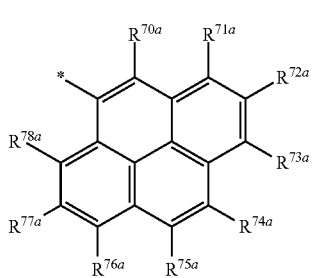
(19b)

wherein respectively at least 1, preferably 1 to 9, more preferably 1 to 7, more preferably 1 to 5, more preferably 1 to 4, more preferably 2 to 3, residue(s) $R^{6a}$ to $R^{10a}$, $R^{11a}$ to $R^{17a}$, $R^{18a}$ to $R^{24a}$, $R^{25a}$ to $R^{33a}$, $R^{34a}$ to $R^{42a}$, $R^{43a}$ to $R^{51a}$, $R^{52a}$ to $R^{60a}$, $R^{61a}$ to $R^{69a}$, $R^{70a}$ to $R^{78a}$, $R^{6b}$ to $R^{10b}$, $R^{11b}$ to $R^{17b}$, $R^{18b}$ to $R^{24b}$, $R^{25b}$ to $R^{33b}$, $R^{34b}$ to $R^{42b}$, $R^{43b}$ to $R^{51b}$, $R^{52b}$ to $R^{60b}$, $R^{61b}$ to $R^{69b}$, or $R^{70b}$ to $R^{78b}$, respectively independently of each other, is an organic residue W1 or an organic residue W1a or an organic residue W1b or an organic residue W1c, and wherein the residues $R^{6a}$, to $R^{10a}$, $R^{11a}$ to $R^{17a}$, $R^{18a}$ to $R^{24a}$, $R^{25a}$ to $R^{33a}$, $R^{34a}$ to $R^{42a}$, $R^{43a}$, to $R^{51a}$, $R^{52a}$ to $R^{60a}$, $R^{61a}$ to $R^{69a}$, $R^{70a}$ to $R^{78a}$, $R^{6b}$ to $R^{10b}$, $R^{11b}$ to $R^{17b}$, $R^{18b}$ to $R^{24b}$, $R^{25b}$ to $R^{33b}$, $R^{34b}$ to $R^{42b}$, $R^{43b}$ to $R^{51b}$, $R^{52b}$ to $R^{60b}$, $R^{61b}$ to $R^{69b}$, or $R^{70b}$ to $R^{78b}$, which are not an organic residue W1 or an organic residue W1a or an organic residue W1b or an organic residue W1c, respectively independently of each other, are identical or different and represent hydrogen, halogen, nitro, carboxylate, aldehyde containing 1 to 8 C atoms, ketone containing 2 to 8 C atoms, O-alkyl containing 1 to 12 C atoms, O-alkenyl containing 2 to 12 C atoms, O-aryl containing 5 to 20 C atoms, ether containing 2 to 12 C atoms, carboxylic acid ester containing 1 to 12 C atoms, carboxylic acid amide containing 1 to 12 C atoms, wherein preferably, respectively the C atom of the carboxamide group is bonded to one of the residues $Q^1$ to $Q^{4a}$, alkyl containing 1 to 12 C atoms, alkenyl containing 2 to 12 C atoms, cycloalkyl containing 3 to 12 C atoms, cycloalkenyl containing 3 to 12 C atoms, alkylaryl containing 1 to 12 C atoms, aryl containing 5 to 20 C atoms or heteroaryl, which does not contain a nitrogen atom, containing 4 to 20 C atoms, preferably hydrogen, halogen, nitro, carboxylate, aldehyde containing 1 to 8 C atoms, ketone containing 2 to 8 C atoms, O-alkyl containing 1 to 12 C atoms, O-alkenyl containing 2 to 12 C atoms, O-aryl containing 5 to 20 C atoms, ether containing 2 to 12 C atoms, carboxylic acid ester containing 1 to 12 C atoms, alkyl containing 1 to 12 C atoms, alkenyl containing 2 to 12 C atoms, cycloalkyl containing 3 to 12 C atoms, cycloalkenyl containing 3 to 12 C atoms, alkylaryl containing 1 to 12 C atoms, aryl containing 5 to 20 C atoms or heteroaryl, which does not contain a nitrogen atom, containing 4 to 20 C atoms.

More preferably, in the compound with formula (3), the residues $Q^1$ and $Q^{1a}$, or in the compound with formula (101), the residues $Q^3$ and $Q^{3a}$, respectively independently of each other, are an aromatic residue with general formula (11a), (12a) or (13a):

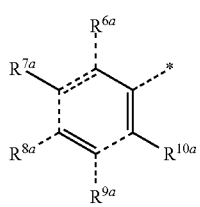
(11a)

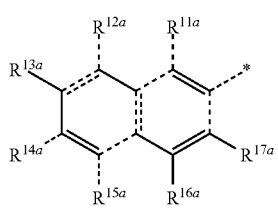
(12a)

-continued

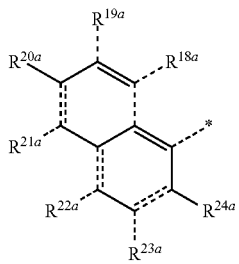

(13a)

and wherein in the compound with formula (3), the residues $Q^2$ and $Q^{2a}$, or in the compound with formula (101), the residues $Q^4$ and $Q^{4a}$, respectively independently of each other, are an aromatic residue with general formula (11 b), (12b) or (13b):

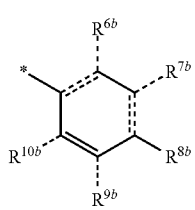

(11b)

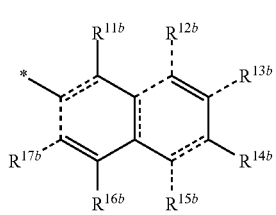

(12b)

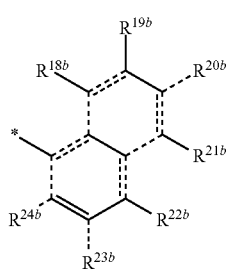

(13b)

wherein respectively at least 1, preferably 1 to 9, more preferably 1 to 7, more preferably 1 to 5, more preferably 1 to 4, more preferably 2 to 3, residue(s) $R^{6a}$ to $R^{10a}$, $R^{11a}$ to $R^{17a}$, $R^{18a}$ to $R^{24a}$, $R^{6b}$ to $R^{10b}$, $R^{11b}$ to $R^{17b}$ or $R^{18b}$ to $R^{24b}$, respectively independently of each other, is an organic residue W1 or an organic residue W1a or an organic residue W1b or an organic residue W1c, wherein the residues $R^{10a}$, $R^{11a}$ to $R^{17a}$, $R^{18a}$ to $R^{24a}$, $R^{6b}$ to $R^{10b}$, $R^{11b}$ to $R^{17b}$ and $R^{18b}$ to $R^{24b}$ which are not an organic residue W1 or an organic residue W1a or an organic residue W1b or an organic residue W1c, respectively independently of each other, are identical or different and represent hydrogen, halogen, nitro, carboxylate, aldehyde containing 1 to 8 C atoms, ketone containing 2 to 8 C atoms, O-alkyl containing 1 to 12 C atoms, O-alkenyl containing 2 to 12 C atoms, O-aryl containing 5 to 20 C atoms, ether containing 2 to 12 C atoms, carboxylic acid ester containing 1 to 12 C atoms, carboxylic acid amide containing 1 to 12 C atoms, wherein preferably, respectively the C atom of the carboxamide group is bonded to one of the residues $Q^1$ to $Q^{4a}$, alkyl containing 1 to 12 C atoms, alkenyl containing 2 to 12 C atoms, cycloalkyl containing 3 to 12 C atoms, cycloalkenyl containing 3 to 12 C atoms, alkylaryl containing 1 to 12 C atoms, aryl containing 5 to 20 C atoms or heteroaryl, which does not contain a nitrogen atom, containing 4 to 20 C atoms, preferably hydrogen, halogen, nitro, carboxylate, aldehyde containing 1 to 8 C atoms, ketone containing 2 to 8 C atoms, O-alkyl containing 1 to 12 C atoms, O-alkenyl containing 2 to 12 C atoms, O-aryl containing 5 to 20 C atoms, ether containing 2 to 12 C atoms, carboxylic acid ester containing 1 to 12 C atoms, alkyl containing 1 to 12 C atoms, alkenyl containing 2 to 12 C atoms, cycloalkyl containing 3 to 12 C atoms, cycloalkenyl containing 3 to 12 C atoms, alkylaryl containing 1 to 12 C atoms, aryl containing 5 to 20 C atoms or heteroaryl, which does not contain a nitrogen atom, containing 4 to 20 C atoms.

In an alternative embodiment of the variation (b) of the compound with formula (1) and/or the compound with formula (2) and/or the compound with formula (3) and/or the compound with formula (3a), the at least one organic residue W2a has the general formula (4b), (5b), (6b), (7b), (8b), or (9b), preferably the general formula (5b), (7b), or (9b):

$$—(C(D)(E))_h-X^b, \tag{4b}$$

$$-A-(C(D)(E))_h-X^b, \tag{5b}$$

$$—(C(D)(E))_k\text{-aryl-}(C(D)(E))_l-X^b, \tag{6b}$$

$$-A-(C(D)(E))_k\text{-aryl-}(C(D)(E))_l-X^b, \tag{7b}$$

$$—[(C(D)(E))_m A]_p—(C(D)(E))_n-X^b, \tag{8b}$$

$$-A-[(C(D)(E))_m-A]_p—(C(D)(E))_n-X^b, \tag{9b}$$

wherein, optionally, at least one of the residues $Q^1$ and $Q^2$, preferably each of the residues $Q^1$ and $Q^2$, respectively independently of each other, is substituted with at least one, preferably 1 to 9, more preferably 1 to 7, more preferably 1 to 5, more preferably 1 to 4, more preferably 2 to 3, organic residue W1b with general formula (4b), (5b), (6b), (7b), (8b), or (9b), preferably with general formula (5b), (7b), or (9b), wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n and p, respectively independently of each other, represent a whole number from 1 to 6, preferably from 2 to 4, and wherein A, respectively independently of each other, represents oxygen or sulphur, preferably oxygen, wherein D and E, respectively independently of each other, represent hydrogen, halogen, G-$R^{(I)}$, or G-C(=G)-$R^{(II)}$, wherein G, respectively independently of each other, represents oxygen or sulphur, preferably oxygen, and wherein the residues $R^{(I)}$ and $R^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein $X^b$, respectively independently of each other, is an organic residue which (i) contains at least one neutral nitrogen atom which can be protonated, or (ii) contains at least one positively charged, preferably quaternary, nitrogen atom, or (iii) contains at least one positively charged, preferably quaternary, phosphorus atom, preferably (i) contains at least one neutral nitrogen atom which can be protonated, or (ii) contains at least one positively charged, preferably quaternary, nitrogen atom, wherein the at least one neutral nitrogen atom which can be protonated is not an amino residue ($—NH_2$) and wherein the at least one positively charged nitrogen atom is not a protonated amino residue ($—NH_3^+$) and is not a guanidylate residue.

Preferably, in an alternative embodiment of variation (b) of the compound with formula (1) and/or the compound with formula (2) and/or the compound with formula (3) and/or the compound with formula (3a), the organic residue $X^b$, respectively independently of each other, is a residue with formula (20a), (20b), (21), (22a), (22b), (23a), (23b), or (24), preferably a residue with formula (20a), (20b), (21), or (24), preferably a residue with formula (20a), (20b) or (21):

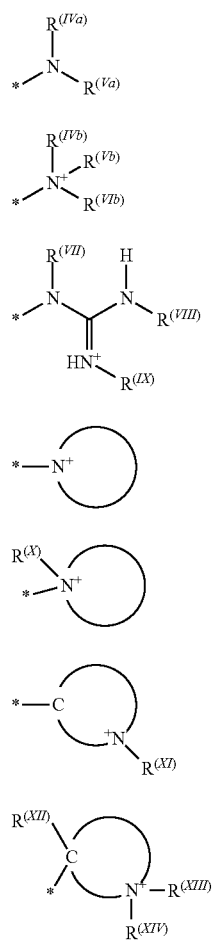

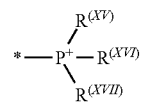

(24)

wherein each of the residues $R^{(IVa)}$, $R^{(IVb)}$, $R^{(X)}$, $R^{(XI)}$, $R^{(XII)}$, $R^{(XIII)}$ and $R^{(XIV)}$, preferably each of the residues $R^{(IVa)}$ and $R^{(IVb)}$, respectively independently of each other, represents hydrogen, an aryl residue containing 5 to 12 C atoms, an alkyl residue, which may be linear or branched, containing 1 to 8 C atoms, or an ether residue, which may be linear or branched, containing 1 to 8 C atoms, and wherein each of the residues $R^{(Va)}$, $R^{(Vb)}$, $R^{(VIb)}$, $R^{(VII)}$, $R^{(VIII)}$, $R^{(IX)}$, $R^{(XV)}$, $R^{(XVI)}$, and $R^{(XVII)}$ preferably each of $R^{(Va)}$, $R^{(Vb)}$, $R^{(VIb)}$, $R^{(XV)}$, $R^{(XVI)}$, and $R^{(XVII)}$, respectively independently of each other, represent an aryl residue containing 5 to 12 C atoms, an alkyl residue, which may be linear or branched, containing 1 to 8 C atoms, or an ether residue, which may be linear or branched, containing 1 to 8 C atoms, and wherein the residue with formula (22a) and the residue with formula (23a):

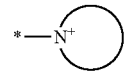

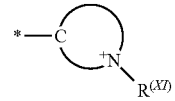

represents a substituted or unsubstituted heterocyclic residue with 5 to 7 ring atoms, which comprise at least 1 carbon atom and at least 1 nitrogen atom as well as, optionally, 1 or 2 oxygen atoms, wherein 1 nitrogen atom forms a double bond, and wherein the residue with formula (22b) and the residue with formula (23b):

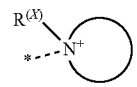

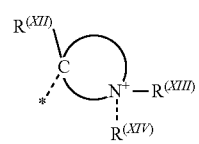

represent a substituted or unsubstituted heterocyclic residue with 5 to 7 ring atoms, which comprise at least 1 carbon atom and at least 1 nitrogen atom as well as, optionally, 1 or 2 oxygen atoms, wherein 1 nitrogen atom forms a single bond.

In a preferred embodiment of the compound with formula (100), the compound with formula (101) and/or the compound with formula (103), the organic residue X, respectively independently of each other, is a residue with formula (20a), (20b), (21), (22a), (22b), (23a), (23b), or (24), preferably a residue with formula (20a), (20b) or (21):

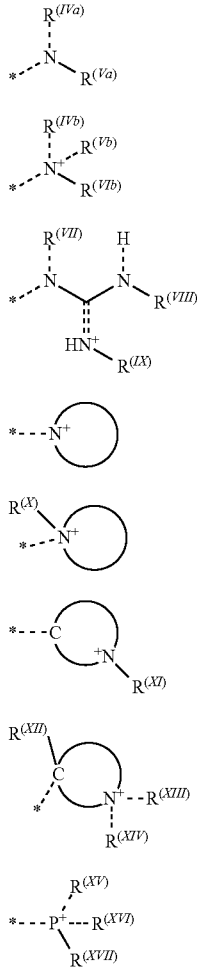

wherein each of the residues $R^{(IVa)}$, $R^{(Va)}$, $R^{(IVb)}$, $R^{(Vb)}$, $R^{(VIb)}$, $R^{(VII)}$, $R^{(VIII)}$, $R^{(IX)}$, $R^{(X)}$, $R^{(XI)}$, $R^{(XII)}$, $R^{(XIII)}$, and $R^{(XIV)}$, respectively independently of each other, represents hydrogen, an aryl residue containing 5 to 12 C atoms, an alkyl residue, which may be linear or branched, containing 1 to 8 C atoms, or an ether residue, which may be linear or branched, containing 1 to 8 C atoms, and wherein each of the residues $R^{(XV)}$, $R^{(XVI)}$, and $R^{(XVII)}$, respectively independently of each other, represent an aryl residue containing 5 to 12 C atoms, an alkyl residue, which may be linear or branched, containing 1 to 8 C atoms, or an ether residue, which may be linear or branched, containing 1 to 8 C atoms, and wherein the residue with formula (22a) and the residue with formula (23a):

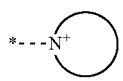   (22a)

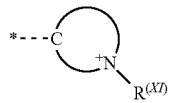   (23a)

represents a substituted or unsubstituted heterocyclic residue with 5 to 7 ring atoms, which comprise at least 1 carbon atom and at least 1 nitrogen atom as well as, optionally, 1 or 2 oxygen atoms, wherein 1 nitrogen atom forms a double bond, and wherein the residue with formula (22b) and the residue with formula (23b):

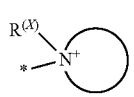   (22b)

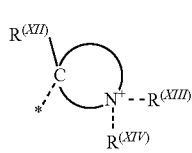   (23b)

represents a substituted or unsubstituted heterocyclic residue with 5 to 7 ring atoms, which comprise at least 1 carbon atom and at least 1 nitrogen atom as well as, optionally, 1 or 2 oxygen atoms, wherein 1 nitrogen atom forms a single bond.

In a preferred embodiment of the compound with formula (1), the compound with formula (2) and/or the compound with formula (3), the organic residue $X^b$ and/or $X^c$, respectively independently of each other, is a residue with formula (20a), (20b), (21), (22a), (22b), (23a), (23b), or (24):

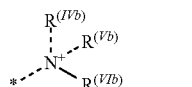   (22a)

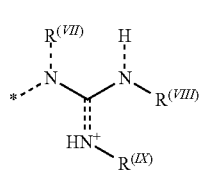   (22b)

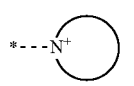   (23a)

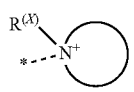

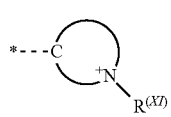

-continued

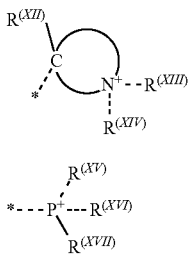
(23b)

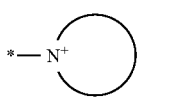
(24)

wherein each of the residues $R^{(IVa)}$, $R^{(Va)}$, $R^{(IVb)}$, $R^{(Vb)}$, $R^{(VIb)}$, $R^{(VII)}$, $R^{(VIII)}$, $R^{(IX)}$, $R^{(X)}$, $R^{(XI)}$, $R^{(XII)}$, $R^{(XIII)}$ and $R^{(XIV)}$, respectively independently of each other, represents hydrogen, an aryl residue containing 5 to 12 C atoms, an alkyl residue, which may be linear or branched, containing 1 to 8 C atoms, or an ether residue, which may be linear or branched, containing 1 to 8 C atoms, and wherein each of the residues $R^{(XV)}$, $R^{(XVI)}$, and $R^{(XVII)}$, respectively independently of each other, represents an aryl residue containing 5 to 12 C atoms, an alkyl residue, which may be linear or branched, containing 1 to 8 C atoms, or an ether residue, which may be linear or branched, containing 1 to 8 C atoms, and wherein the residue with formula (22a) and the residue with formula (23a):

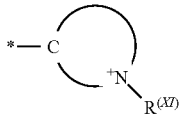
(22a)

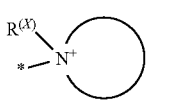
(23a)

represents a substituted or unsubstituted heterocyclic residue with 5 to 7 ring atoms, which comprise at least 1 carbon atom and at least 1 nitrogen atom as well as, optionally, 1 or 2 oxygen atoms, wherein 1 nitrogen atom forms a double bond, and wherein the residue with formula (22b) and the residue with formula (23b):

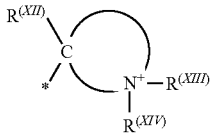
(22b)

(23b)

represents a substituted or unsubstituted heterocyclic residue with 5 to 7 ring atoms, which comprise at least 1 carbon atom and at least 1 nitrogen atom as well as, optionally, 1 or 2 oxygen atoms, wherein 1 nitrogen atom forms a single bond.

More preferably, each residue with formula (23a) is selected from the group consisting of residues with formulae (25a), (25b) and (25c):

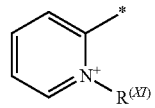
(25a)

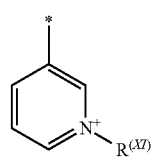
(25b)

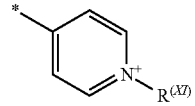
(25c)

wherein $R^{(XI)}$ may respectively be an aryl residue containing 5 to 20 C atoms, for example phenyl or benzyl, an alkyl residue, which may be linear or branched, containing 1 to 20 C atoms, for example methyl, ethyl, n-propyl, i-propyl, n-butyl or t-butyl, an alkenyl residue, which may be linear or branched, containing 2 to 20 C atoms, a hydroxyalkyl residue, which may be linear or branched, containing 1 to 20 C atoms, for example hydroxymethyl, 2-hydroxyethyl, 3-hydroxypropyl or 1-hydroxy-1-methyl-ethyl, or an ether residue, which may be linear or branched, containing 2 to 20 C atoms, for example methoxymethyl, methoxyethyl, methoxypropyl, ethoxymethyl, ethoxyethyl, ethoxypropyl, propoxymethyl, propoxyethyl or propoxypropyl.

In a further preferred embodiment, each residue with formula (22a) is selected from the group consisting of residues with formula (26):

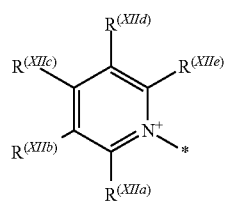
(26)

wherein the residues $R^{(XIIa)}$ to $R^{(XIIe)}$ respectively independently of each other, may be hydrogen, an aryl residue containing 5 to 20 C atoms, for example phenyl or benzyl, an alkyl residue, which may be linear or branched, containing 1 to 20 C atoms, for example methyl, ethyl, n-propyl, i-propyl, n-butyl or t-butyl, an alkenyl residue, which may be linear or branched, containing 2 to 20 C atoms, a hydroxyalkyl residue, which may be linear or branched, containing 1 to 20 C atoms, for example hydroxymethyl, 2-hydroxyethyl, 3-hydroxypropyl or 1-hydroxy-1-methyl-ethyl, or an ether residue, which may be linear or branched, containing 2 to 20 C atoms, for example methoxymethyl, methoxyethyl, methoxypropyl, ethoxymethyl, ethoxyethyl, ethoxypropyl, propoxymethyl, propoxyethyl or propoxypropyl. Preferably, the residues $R^{(XIIa)}$ to $R^{(XIIe)}$ respectively, independently of each other, are hydrogen, methyl, ethyl, prop-1-yl, but-1-yl, pent-1-yl, hex-1-yl, hept-1- or oct-1-yl.

In a further preferred embodiment, the residue with formula (21b) is 1-methylpyrrolidin-1-ium-1-yl, 1-methylpiperazin-1-ium-1-yl or 4-methylmorpholin-4-ium-4-yl.

In a further preferred embodiment of the compound with formula (100), the compound with formula (101) and/or the compound with formula (103), the organic residue X, respectively independently of each other, is a residue with formula (20c), (20d), (21), or (24), preferably a residue with formula (20c), (20d), or (21), more preferably a residue with formula (24):

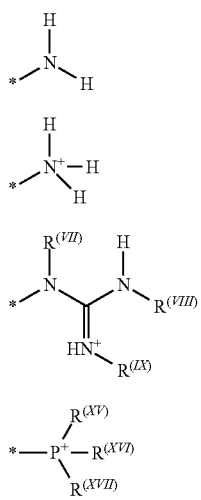

wherein each of the residues $R^{(VII)}$, $R^{(VIII)}$, and $R^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably hydrogen, and wherein each of the residues $R^{(XV)}$, $R^{(XVI)}$, and $R^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, preferably an aryl residue containing 5 to 12 C atoms, an alkylaryl residue containing 5 to 12 C atoms, or an alkyl residue, which may be linear or branched, containing 1 to 8 C atoms.

In a further preferred embodiment, in the compound with formula (100), the compound with formula (101) and/or the compound with formula (103), the residues $R^{(IVa)}$, $R^{(Va)}$, $R^{(IVb)}$, $R^{(Vb)}$, $R^{(VIb)}$, $R^{(VII)}$, $R^{(VIII)}$, $R^{(IX)}$, $R^{(X)}$, $R^{(XI)}$, $R^{(XII)}$, $R^{(XIII)}$, $R^{(XIV)}$, $R^{(XV)}$, $R^{(XVI)}$, and $R^{(XVII)}$ independently of each other, are selected from hydrogen and alkyl groups with general formula —(CH$_2$)$_n$—CH$_3$, wherein n is a whole number from 0 to 19, preferably from 1 to 17.

In a further preferred embodiment, in the compound with formula (1) and/or the compound with formula (2) and/or the compound with formula (3) and/or the compound with formula (3a) and/or the compound with formula (100) and/or the compound with formula (101) and/or the compound with formula (102), the residues $R^{(IVa)}$, $R^{(Va)}$, $R^{(IVb)}$, $R^{(Vb)}$, $R^{(VIb)}$, $R^{(VII)}$, $R^{(VIII)}$, $R^{(IX)}$, $R^{(X)}$, $R^{(XI)}$, $R^{(XII)}$, $R^{(XIII)}$, and $R^{(XIV)}$ independently of each other, are selected from the group which consists of hydrogen, methyl, ethyl, prop-1-yl, prop-2-yl, but-1-yl, but-2-yl, 2-methylprop-1-yl, 2-methylprop-2-yl, pent-1-yl, pent-2-yl, pent-3-yl, 2-methylbut-1-yl, 2-methylbut-2-yl, 2-methylbut-3-yl, 2-methylbut-4-yl, 2,2-dimethylprop-1-yl, hex-1-yl, hex-2-yl, hex-3-yl, hept-1-yl, oct-1-yl, 2-methylpent-1-yl, 2-methylpent-2-yl, 2-methylpent-3-yl, 2-methylpent-4-yl, 2-methylpent-5-yl, 3-methylpent-1-yl, 3-methylpent-2-yl, 3-methylpent-3-yl, 2,2-dimethylbut-1-yl, 2,2-dimethylbut-3-yl, 2,2-dimethylbut-4-yl, 2,3-dimethylbut-1-yl, 2,3-dimethylbut-2-yl, phenyl and benzyl.

In a particularly preferred embodiment of the inventive 1,7-diaryl-1,6-heptadiene-3,5-dione derivative with formula (1), with formula (2), with formula (3) and/or with formula (3a) as well as the 1,7-diaryl-1,6-heptadiene-3,5-dione derivative with formula (100), with formula (101) and/or with formula (102) for use in accordance with the invention, the residues $R^{(XV)}$, $R^{(XVI)}$, and $R^{(XVII)}$ of the residue with formula (24),

independently of each other, are selected from methyl, ethyl, prop-1-yl, prop-2-yl, but-1-yl, but-2-yl, 2-methylprop-1-yl, 2-methyl-prop-2-yl, pent-1-yl, pent-2-yl, pent-3-yl, 2-methylbut-1-yl, 2-methylbut-2-yl, 2-methylbut-3-yl, 2-methylbut-4-yl, 2,2-dimethylprop-1-yl, hex-1-yl, hex-2-yl, hex-3-yl, hept-1-yl, oct-1-yl, 2-methylpent-1-yl, 2-methylpent-2-yl, 2-methylpent-3-yl, 2-methylpent-4-yl, 2-methylpent-5-yl, 3-methylpent-1-yl, 3-methylpent-2-yl, 3-methylpent-3-yl, 2,2-dimethylbut-1-yl, 2,2-dimethylbut-3-yl, 2,2-dimethylbut-4-yl, 2,3-dimethylbut-1-yl and 2,3-dimethylbut-2-yl, phenyl and benzyl.

In a further preferred embodiment of the compound with formula (100), the compound with formula (101) and/or the compound with formula (103), the residues $R^{(IVa)}$, $R^{(Va)}$, $R^{(IVb)}$, $R^{(Vb)}$, $R^{(VIb)}$, $R^{(VII)}$, $R^{(VIII)}$, $R^{(IX)}$, $R^{(X)}$, $R^{(XI)}$, $R^{(XII)}$, $R^{(XIII)}$, $R^{(XIV)}$, $R^{(XV)}$, $R^{(XVI)}$, and $R^{(XVII)}$, independently of each other, are selected from hydrogen or the residue with formula (10):

wherein respectively, r represents a whole number from 1 to 20, preferably from 1 to 8, more preferably from 1 to 4.

In a further preferred embodiment of the 1,7-diaryl-1,6-hepta-diene-3,5-dione derivative with formula (100) and/or with formula (101) and/or with formula (102), the organic residue W2 and/or W1, respectively independently of each other, represents an organic residue with general formula (30a), (30b), (30c), (30d), (30e), (30f), (30g), (30h), (30i), (30k), (30m), (30n), (30p), (31a), (31b), (32), (33), (34), (35), (36), (37a) or (37b), preferably an organic residue with general formula (30a), (30b), (30c), (30d), (30e), (30f), (30g), (30h), (30i), (30k), (30m), (30n), (30p), (31a), (31b), (32), (33), (34), (35) or (36), preferably an organic residue with general formula (37a):

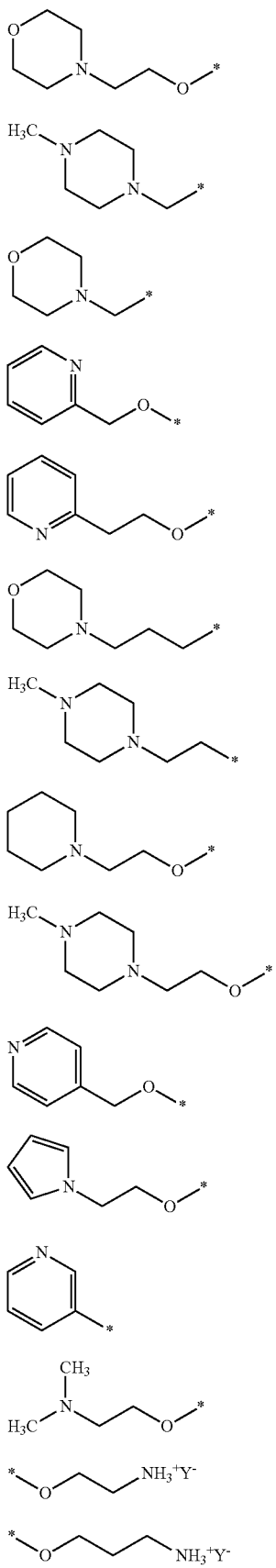

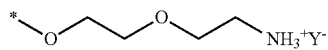
(32)

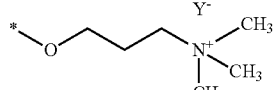
(33)

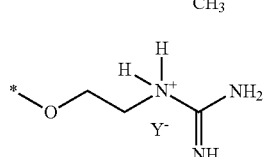
(34)

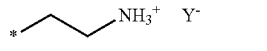
(35)

(36)

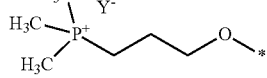
(37a)

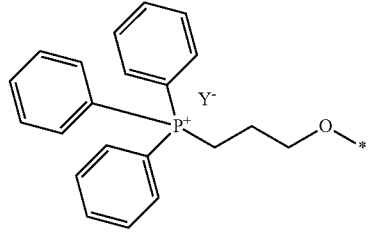
(37b)

wherein $Y^-$ is an anion which, respectively independently of each other, represents fluoride, chloride, bromide, iodide, sulphate, hydrogen sulphate, phosphate, hydrogen phosphate, dihydrogen phosphate, tosylate, mesylate, or at least one carboxylation of a carboxylic acid containing 1 to 15 carbon atoms. Preferably, a carboxylation of a carboxylic acid containing 1 to 15 carbon atoms is, independently of each other, formate, acetate, n-propionate, lactate, oxalate, fumarate, maleinate, tartrate, succinylate, benzoate, salicylate, or citrate.

In a further preferred embodiment of the inventive 1,7-diaryl-1,6-hepta-diene-3,5-dione derivative with formula (1) and/or with formula (2) and/or with formula (3) and/or with formula (3a), the organic residue W1a, respectively independently of each other, represents an organic residue with general formula (31a), (31b), (32), (34), (37a) or (37b), preferably an organic residue with general formula (31a), (31b), (32) or (34), preferably an organic residue with general formula (37a):

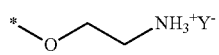
(31a)

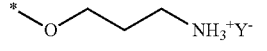
(31b)

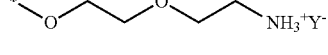
(32)

(34)
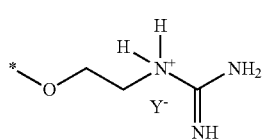

(37a)
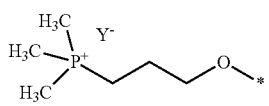

(37b)
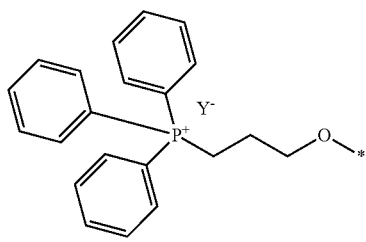

wherein Y⁻ is an anion which, respectively independently of each other, represents fluoride, chloride, bromide, iodide, sulphate, hydrogen sulphate, phosphate, hydrogen phosphate, dihydrogen phosphate, tosylate, mesylate, or at least one carboxylation of a carboxylic acid containing 1 to 15 carbon atoms. Preferably, a carboxylation of a carboxylic acid containing 1 to 15 carbon atoms is, independently of each other, formate, acetate, n-propionate, lactate, oxalate, fumarate, maleinate, tartrate, succinylate, benzoate, salicylate, or citrate.

In a further preferred embodiment of the inventive 1,7-diaryl-1,6-hepta-diene-3,5-dione derivative with formula (1) and/or with formula (2) and/or with formula (3) and/or with formula (3a), the organic residue W2a and/or W1b and/or W1c, respectively independently of each other, represents an organic residue with general formula (31a), (31b), (32), (34), (35), (37a) or (37b), preferably an organic residue with general formula (31a), (31b), (32), (34) or (35), preferably an organic residue with general formula (37a):

(31a)
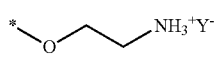

(31b)
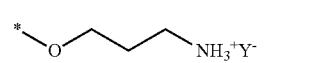

(32)
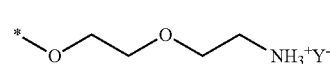

(34)
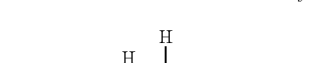

(35)
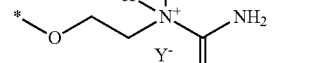

(37a)
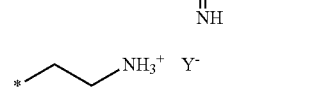

(37b)
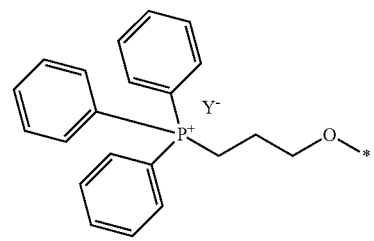

wherein Y⁻ is an anion which, respectively independently of each other, represents fluoride, chloride, bromide, iodide, sulphate, hydrogen sulphate, phosphate, hydrogen phosphate, dihydrogen phosphate, tosylate, mesylate, or at least one carboxylation of a carboxylic acid containing 1 to 15 carbon atoms. Preferably, a carboxylation of a carboxylic acid containing 1 to 15 carbon atoms is, independently of each other, formate, acetate, n-propionate, lactate, oxalate, fumarate, maleinate, tartrate, succinylate, benzoate, salicylate, or citrate.

In a further preferred embodiment of the 1,7-diaryl-1,6-heptadiene-3,5-dione derivative with formula (100) to be used in accordance with the invention, the compound is at least one compound with formula (40) to (67), preferably at least one compound with formula (40) to (63), (66) or (67), preferably a compound with formula (64):

(40)
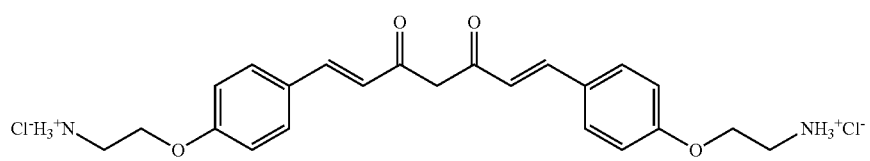

(41)
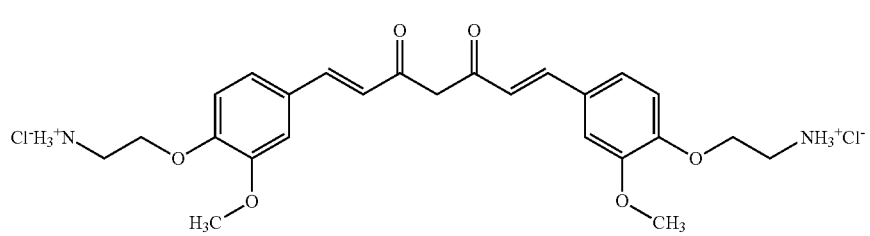

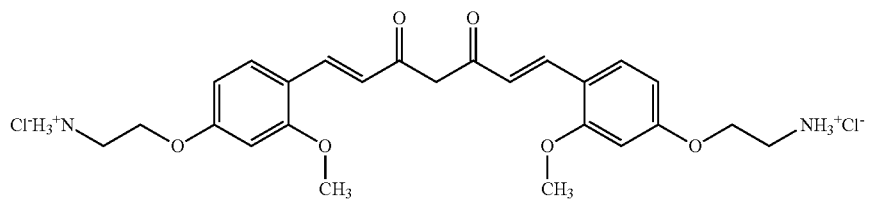
(42)
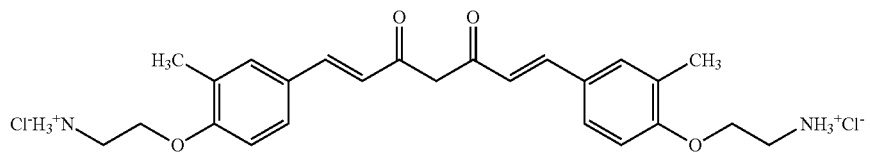
(43)
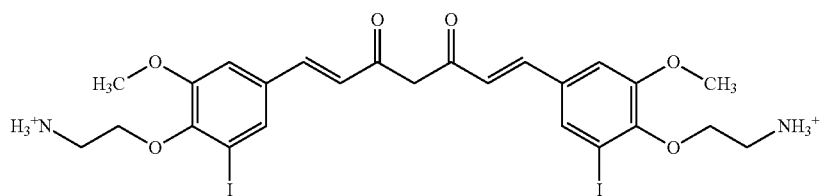
(44)
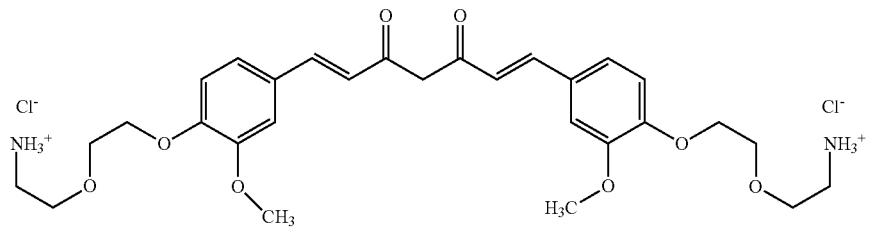
(45)
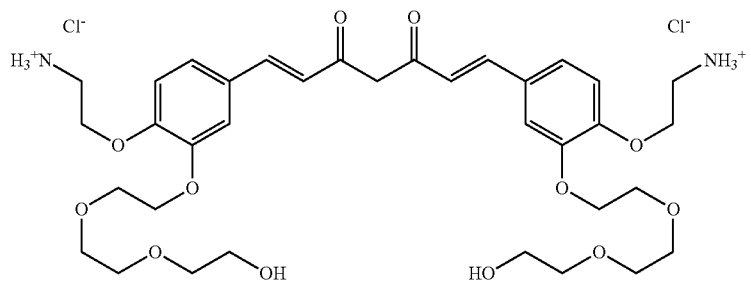
(46)
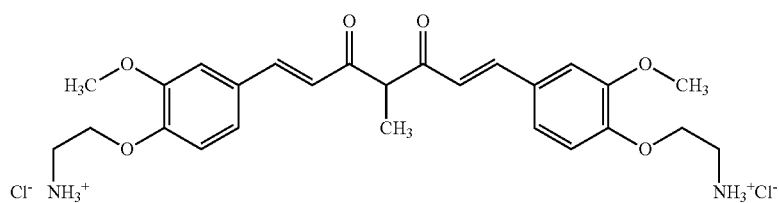
(47)
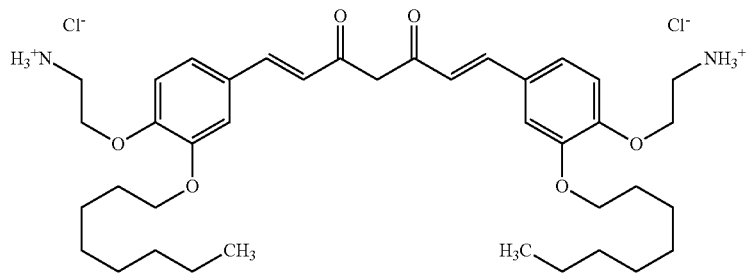
(48)

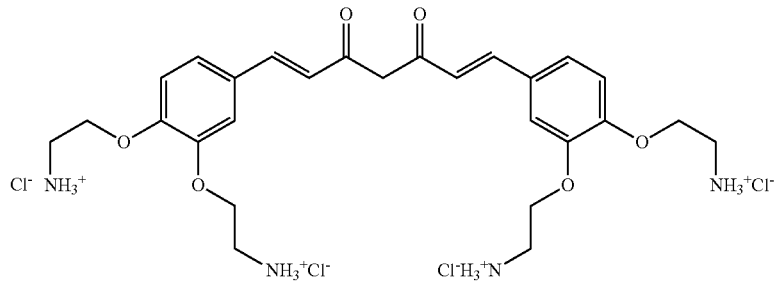
(49)
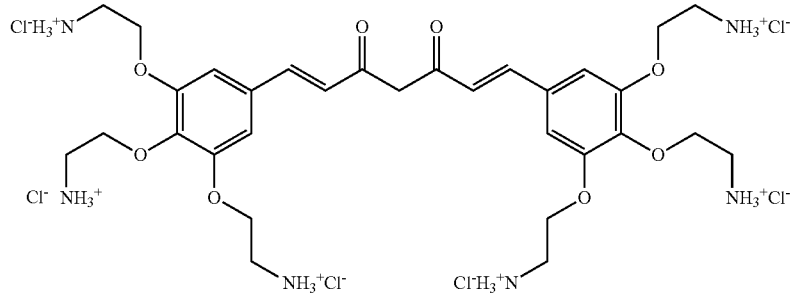
(50)
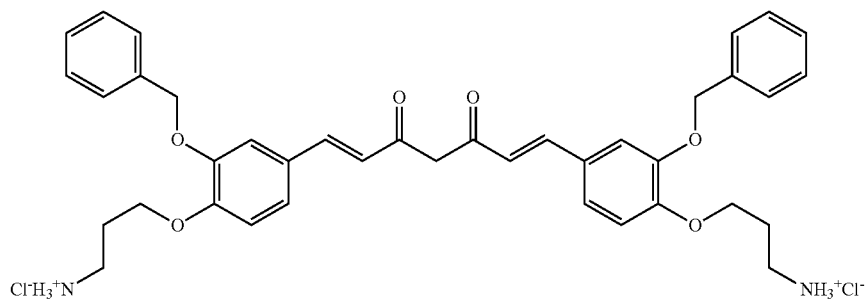
(51)
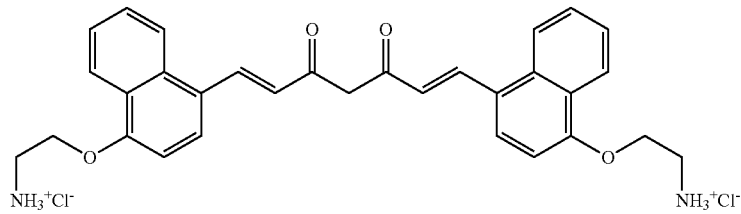
(52)
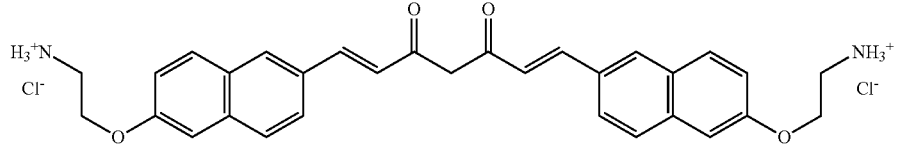
(53)
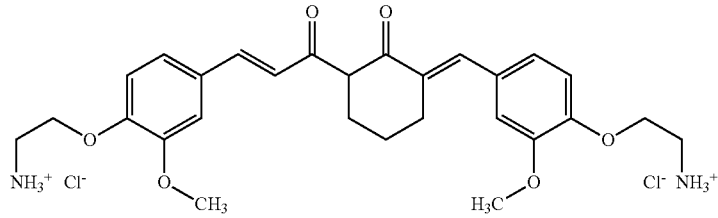
(54)

(55)
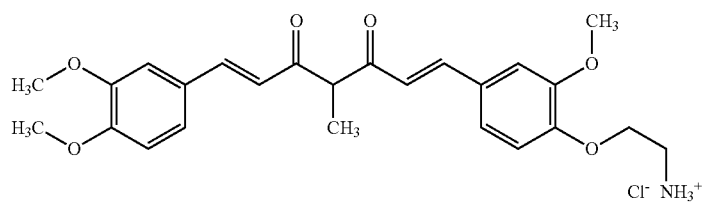
(56)
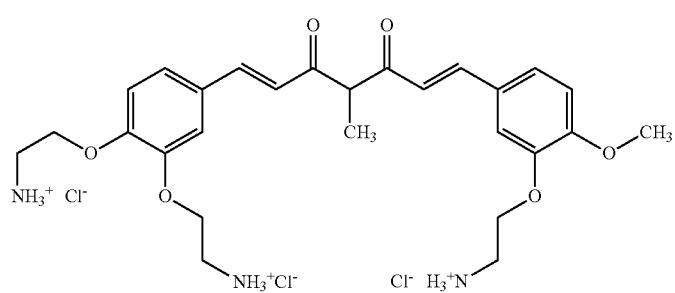
(57)
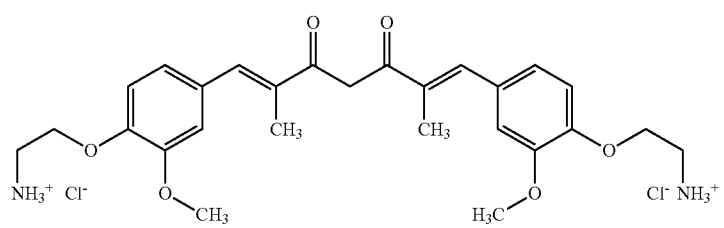
(58)
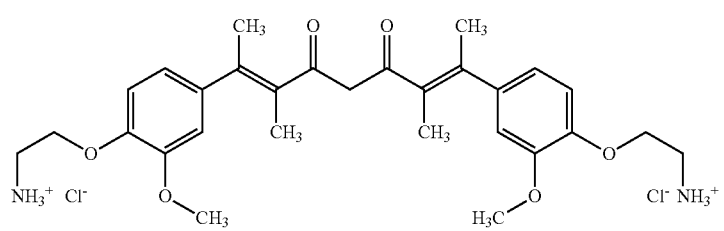
(59)
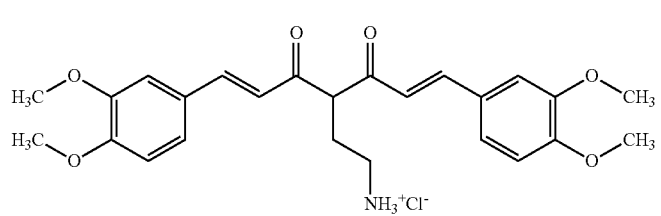
(60)
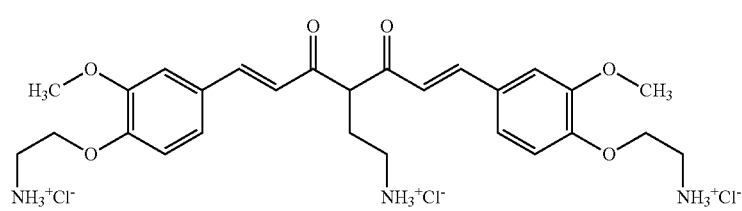
(61)
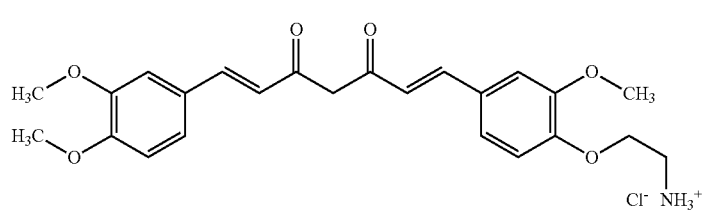

(62)
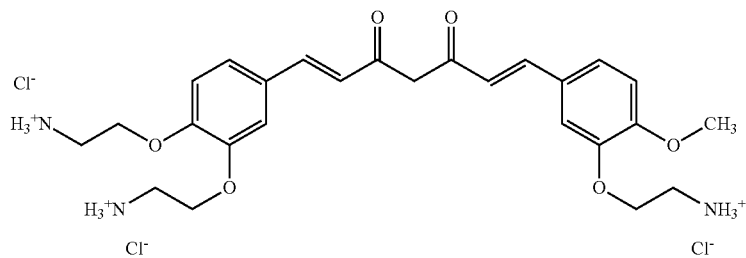
(63)
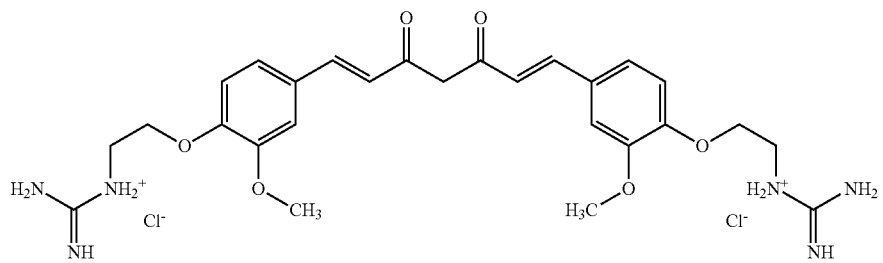
(64)
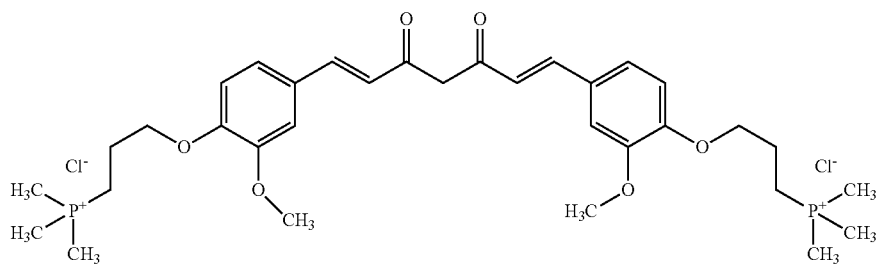
(65)
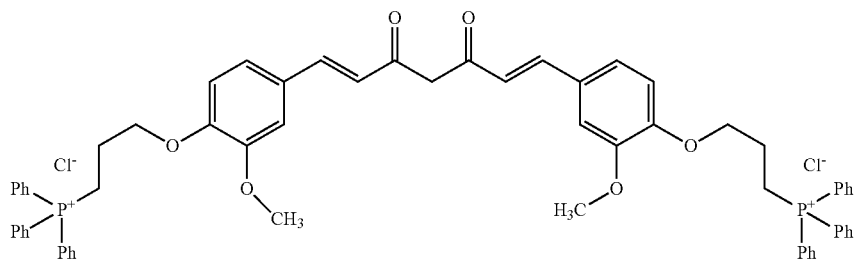
(66)
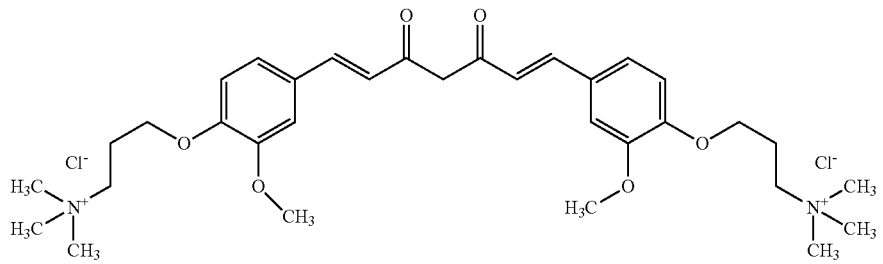

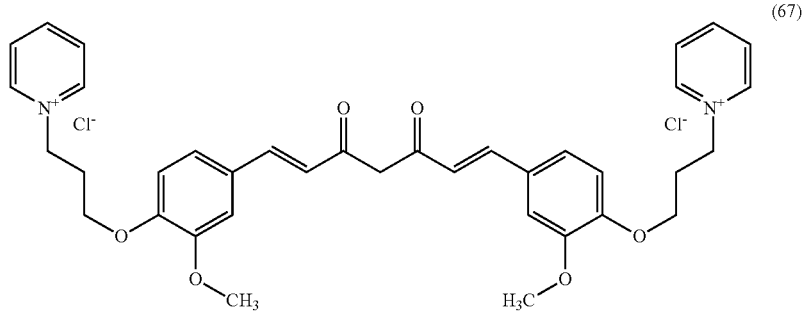 [SMILES: COc1cc(/C=C/C(=O)CC(=O)/C=C/c2ccc(OCCC[n+]3ccccc3)c(OC)c2)ccc1OCCC[n+]1ccccc1 ; [Cl-] ; [Cl-]]
(67)

In a further preferred embodiment of the 1,7-diaryl-1,6-heptadiene-3,5-dione derivative with formula (100) to be used in accordance with the invention, the compound is at least one compound with formula (40) to (67) and (110) to (229).

In a further preferred embodiment of the inventive 1,7-diaryl-1,6-heptadiene-3,5-dione derivative with formula (1), the compound is at least one compound with formula (40) to (65), preferably at least one compound with formula (40) to (62), preferably at least one compound with formula (40) to (58), (60), (61), (62) or (63), preferably at least one compound with formula (64):

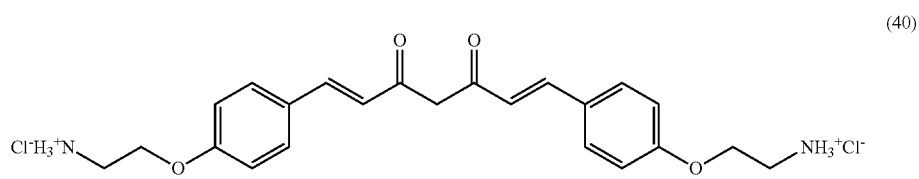
(40)

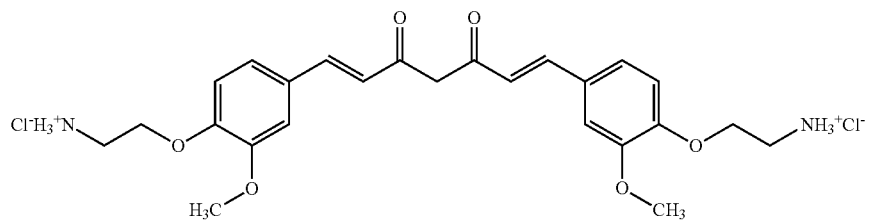
(41)

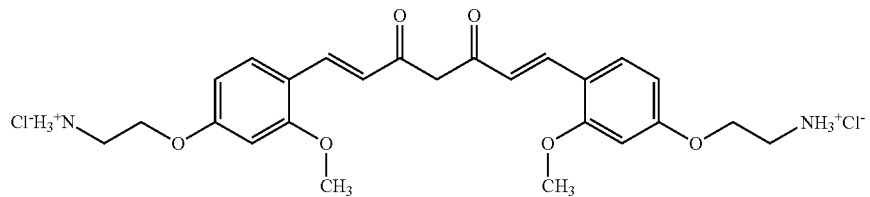
(42)

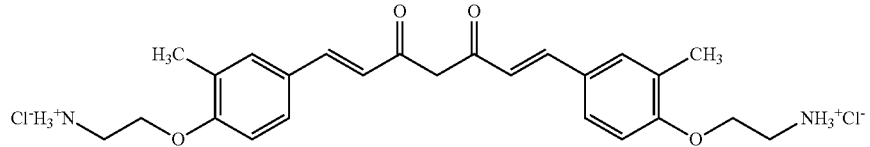
(43)

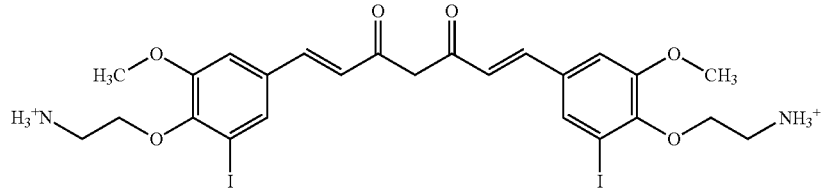
(44)

(45)
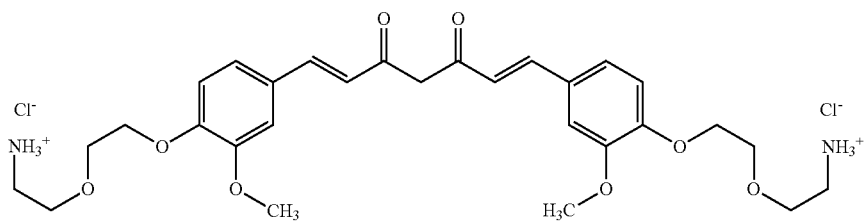
(46)
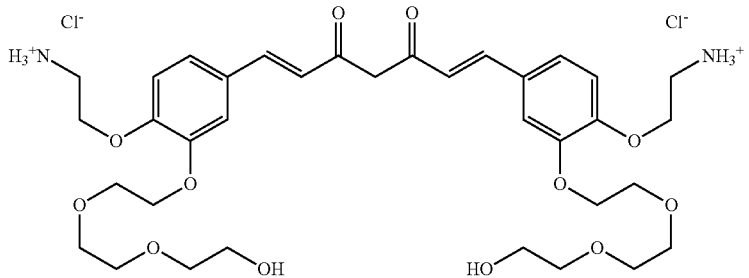
(47)
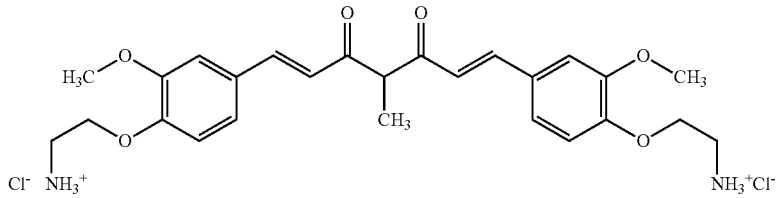
(48)
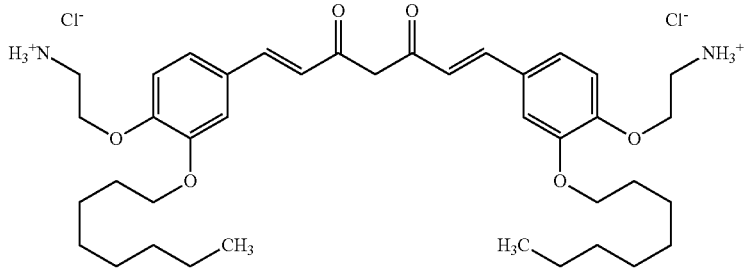
(49)
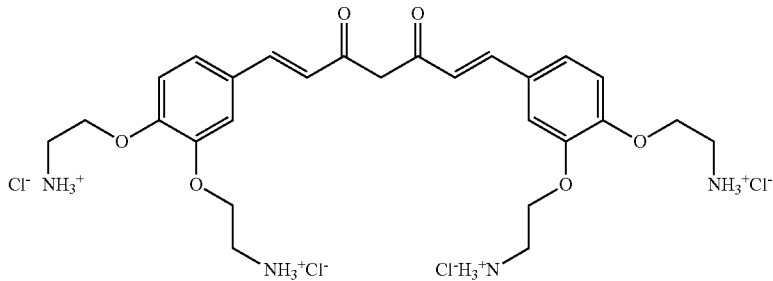
(50)
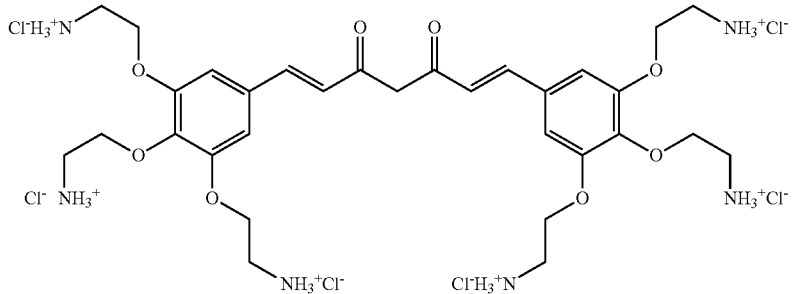

(51)
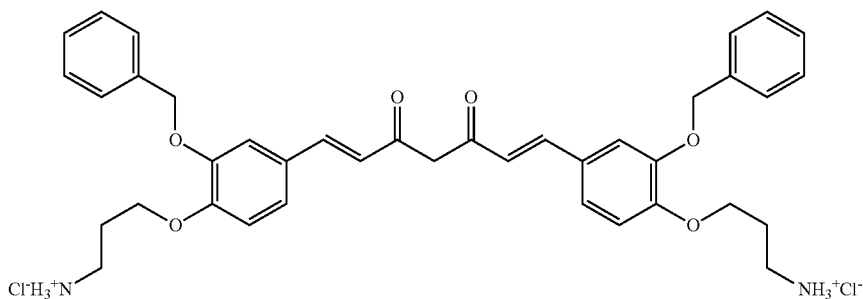
(52)
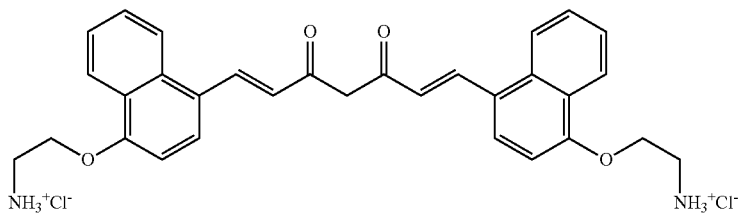
(53)
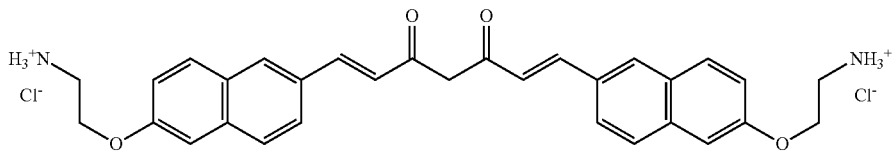
(54)
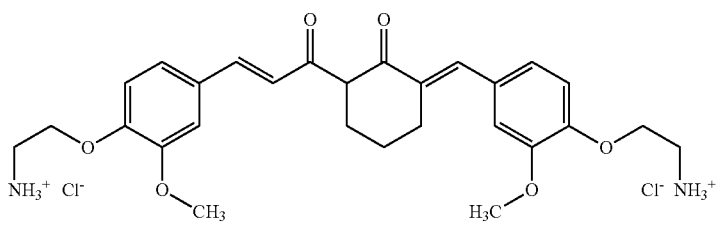
(55)
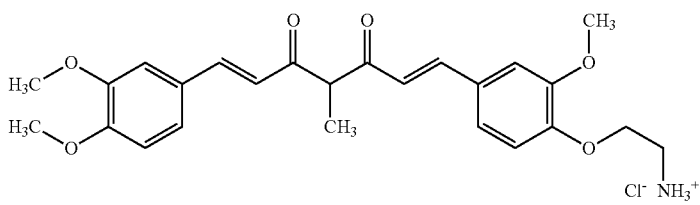
(56)
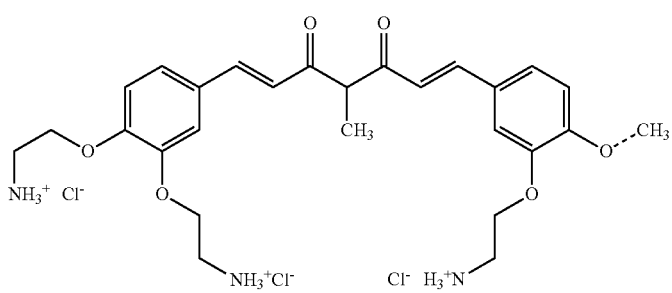
(57)
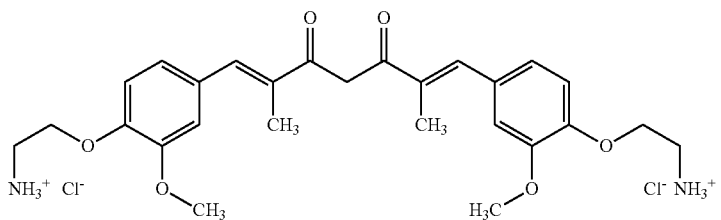

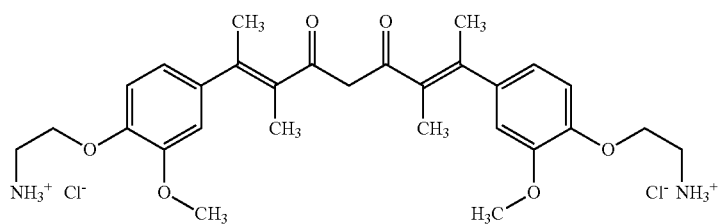
(58)
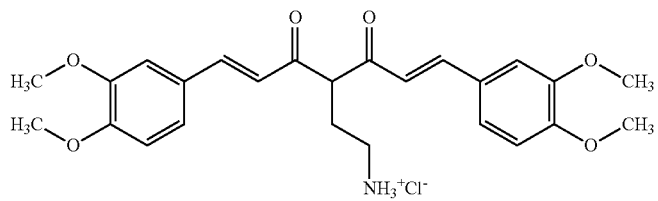
(59)
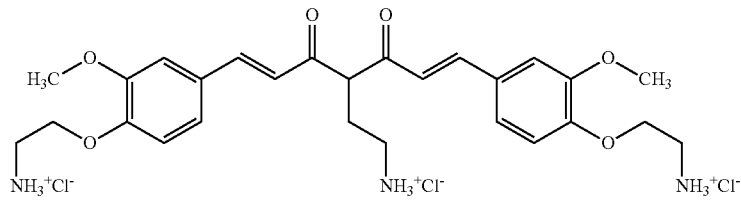
(60)
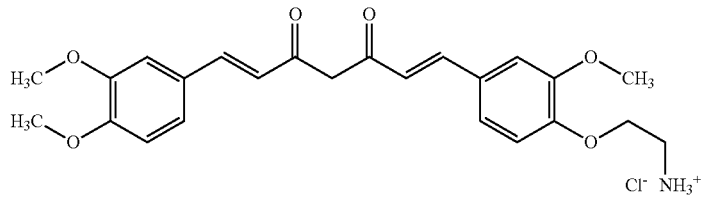
(61)
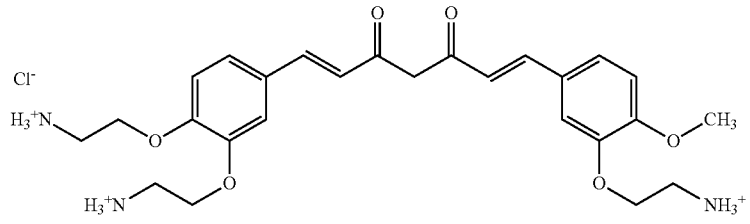
(62)
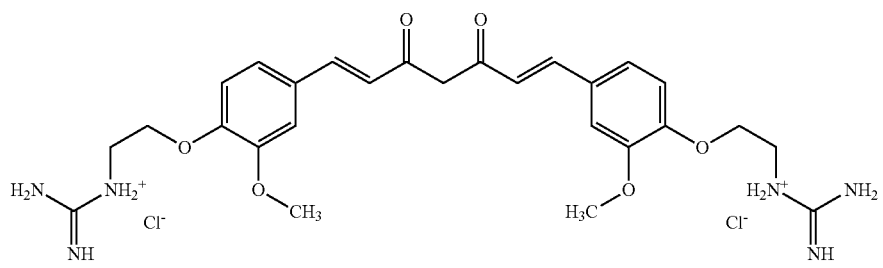
(63)
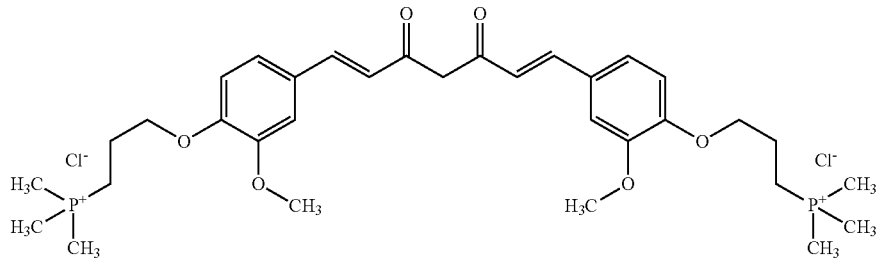
(64)

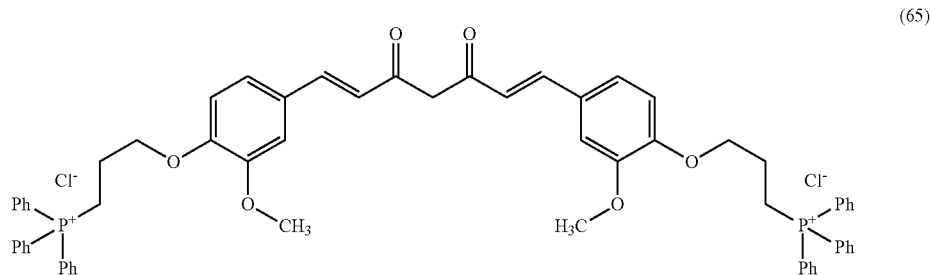

(65)

In a further preferred embodiment of the inventive 1,7-diaryl-1,6-heptadiene-3,5-dione derivative with formula (2) or of the 1,7-diaryl-1,6-heptadiene-3,5-dione derivative with formula (102) to be used in accordance with the invention, the compound is at least one compound with formula (68), (69a) or (69b):

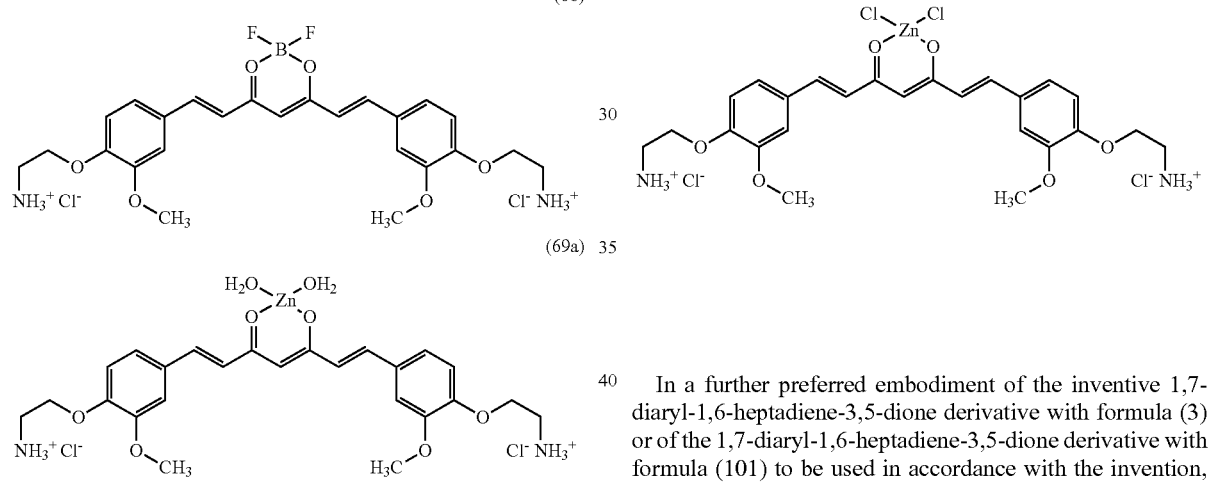

In a further preferred embodiment of the inventive 1,7-diaryl-1,6-heptadiene-3,5-dione derivative with formula (3) or of the 1,7-diaryl-1,6-heptadiene-3,5-dione derivative with formula (101) to be used in accordance with the invention, the compound is at least one compound with formula (70):

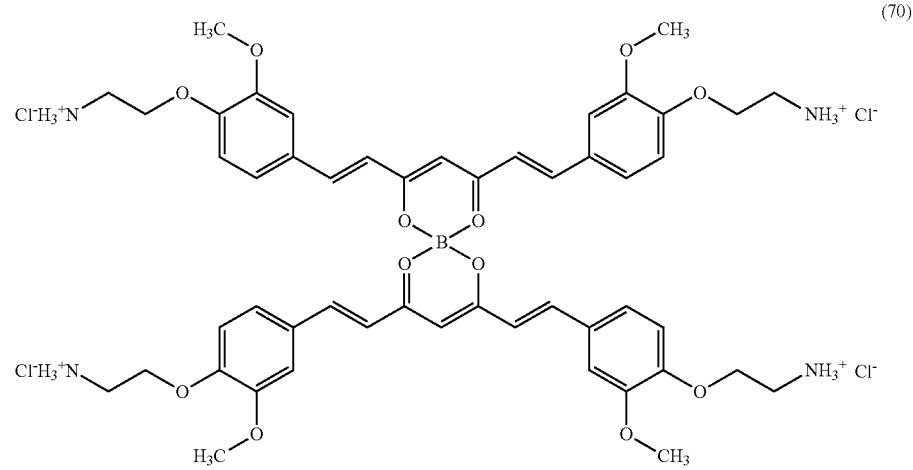

In the 1,7-diaryl-1,6-heptadiene-3,5-dione derivative with formula (1) and/or with formula (2) and/or with formula (3) and/or with formula (3a) in accordance with the invention as well as in the 1,7-diaryl-1,6-heptadiene-3,5-dione derivative with formula (100) and/or with formula (101) and/or with formula (102) and/or with formula (3a) to be used in accordance with the invention, said aldehyde residues, ketone residues, carboxylic acid residues, carboxylic acid amide residues, cycloalkyl residues, cycloalkenyl residues, alkyl residues and alkenyl residues may be linear or branched, preferably linear, and also may be unsubstituted or be substituted with at least one residue, which is a halogen, preferably chlorine, bromine, iodine or fluorine, nitro, hydroxy, alkyloxy, preferably methoxy, ethoxy, n-propyloxy, i-propyloxy, n-butyloxy or n-pentyloxy, or alkanoyloxy, preferably formyloxy, acetoxy or n-propanoyloxy.

In a further preferred embodiment, said alkyl residues, respectively independently of each other, are selected from the group consisting of methyl, ethyl, n-propyl, iso-propyl, n-butyl, iso-butyl, tert-butyl, n-pentyl, 3-methylbutyl, 2,2-dimethylpropyl, n-hexyl, n-heptyl and n-octyl.

In a further preferred embodiment, said alkyl residues may be selected from non-cyclic polyol residues with general formula —$CH_2(CH(OH))_gCH_2OH$, wherein g is a whole number from 1 to 10, preferably 1 to 4. More preferably, the non-cyclic polyol residues are selected from the group consisting of arabityl, ribityl, xylityl, erythrityl, threityl, lactityl, mannityl and sorbityl, more preferably D-ribityl and D-arabityl.

In a further preferred embodiment, said cycloalkyl residues and cycloalkenyl residues may contain oxygen atoms as ring atoms and may be both unsubstituted or be substituted with at least one residue selected from hydroxyl, alkyloxy, preferably methoxy, ethoxy, n-propyloxy, i-propyloxy, n-butyloxy or n-pentyloxy, or alkanoyloxy, preferably formyloxy, acetoxy or n-propanoyloxy.

In a further preferred embodiment, said cycloalkyl residues and cycloalkenyl residues which contain oxygen atoms as ring atoms, respectively independently of each other, are selected from the group which consists of tetrahydrofuranyl, tetrahydropyranyl, dioxolanyl and dioxanyl.

In a further preferred embodiment, said aryl residues respectively contain at most 4, more preferably at most 3, more preferably at most 2, condensed rings. Yet more preferably, the aryl residues each have 1 ring.

Preferably, said aryl residues, respectively independently of each other, are selected from the group which consists of phenyl, benzyl, naphthyl, anthracenyl, phenanthrenyl and pyrenyl.

In a preferred embodiment, said alkenyl residues, respectively independently of each other, contain 2 to 17 C atoms, more preferably 2 to 13 C atoms, more preferably 2 to 9 C atoms, more preferably 2 to 5 C atoms. In a further preferred embodiment, said alkenyl residues, respectively independently of each other, are selected from the group which consists of ethenyl, n-propenyl and n-butenyl.

In a further preferred embodiment, said aldehydes, respectively independently of each other, contain 1 to 17 C atoms, more preferably 1 to 13 C atoms, more preferably 1 to 9 C atoms, more preferably 1 to 5 C atoms. In a further preferred embodiment, said aldehydes, respectively independently of each other, are selected from the group which consists of methanal-1-yl (formyl), ethanal-1-yl (2-oxoethyl), n-propanal-1-yl (3-oxopropyl) and n-butanal-1-yl (4-oxobutyl).

In a further preferred embodiment, said ketones, respectively independently of each other, contain 2 to 17 C atoms, more preferably 3 to 14 C atoms, more preferably 3 to 9 C atoms. In a further preferred embodiment, said ketones, respectively independently of each other, are selected from the group which consists of dimethylketyl, methyl-ethyl-ketyl, ethyl-methyl-ketyl, diethylketyl, methyl-propyl-ketyl, ethyl-propyl-ketyl, propyl-methyl-ketyl, propyl-ethyl-ketyl and dipropyl-ketyl, which may be linear or branched.

In a further preferred embodiment, said aldehyde residues and/or ketone residues may be monosaccharide residues, preferably pentose or ketose residues.

Preferably, suitable monosaccharide residues, respectively independently of each other, contain 3 to 7 carbon atoms, preferably 5 to 6 carbon atoms, and have a carbonyl group, preferably an aldehyde group or keto group, as well as at least a hydroxyl group, and may be open-chained or cyclic, preferably as a furanose or pyranose.

Preferably, suitable monosaccharide residues are derived from monosaccharide residues which, respectively independently of each other, are selected from the group which consists of D-glycerine aldehyde, L-glycerine aldehyde, D-erythrose, L-erythrose, D-threose, L-threose, D-ribose, L-ribose, D-arabinose, L-arabinose, D-xylose, L-xylose, D-Lyxose, L-Lyxose, D-allose, L-allose, D-altrose, L-altrose, D-glucose, L-glucose, D-mannose, L-mannose, D-gulose, L-gulose, D-idose, L-idose, D-galactose, L-galactose, D-talose, L-talose, dihydroxyacetone, D-erythrulose, L-erythrulose, D-ribulose, L-ribulose, D-xylulose, L-xylulose, D-psicose, L-psicose, D-fructose, L-fructose, D-sorbose, L-sorbose, D-tagatose and L-tagatose. More preferably, suitable monosaccharides are selected from the group which consists of D-ribose, L-ribose, D-arabinose, L-arabinose, D-xylose, L-xylose, D-Lyxose, L-Lyxose, D-allose, L-allose, D-altrose, L-altrose, D-glucose, L-glucose, D-mannose, L-mannose, D-gulose, L-gulose, D-idose, L-idose, D-galactose, L-galactose, D-talose, L-talose, D-ribulose, L-ribulose, D-xylulose, L-xylulose, D-psicose, L-psicose, D-fructose, L-fructose, D-sorbose, L-sorbose, D-tagatose and L-tagatose.

In a further preferred embodiment, said carboxylic acid esters, respectively independently of each other, contain 1 to 17 C atoms, more preferably 1 to 15 C atoms, more preferably 1 to 12 C atoms, wherein preferably, the C atom of the carboxylate group is bonded to one of the residues $Q^1$ to $Q^{4a}$. In a further preferred embodiment, said carboxylic acid esters, respectively independently of each other, are selected from the group which consists of ethyl ester, n-propyl ester, i-propyl ester, n-butyl ester, sec-butyl ester, tert-butyl ester and benzyl ester. More preferably, said carboxylic acid esters are selected from the group which consists of methoxycarboyl, 2-methoxy-2-oxo-eth-1-yl, 3-methoxy-3-oxo-prop-1-yl, 4-methoxy-4-oxo-but-1-yl, ethoxycarboyl, 2-ethoxy-2-oxo-eth-1-yl, 3-ethoxy-3-oxo-prop-1-yl, 4-ethoxy-4-oxo-but-1-yl, propoxycarboyl, 2-oxy-2-propoxy-eth-1-yl, 3-oxo-3-propoxy-prop-1-yl, 4-oxo-4-propoxy-but-1-yl, isopropoxycarbonyl, 2-isopropoxy-2-oxo-eth-1-yl, 3-isopropoxy-3-oxo-prop-1-yl, 4-isopropoxy-4-oxo-but-1-yl, butoxycarbonyl, 2-butoxy-2-oxo-eth-1-yl, 3-butoxy-3-oxo-prop-1-yl, 4-butoxy-4-oxo-but-1-yl, isobutoxycarbonyl, 2-isobutoxy-2-oxo-eth-1-yl, 3-isobutoxy-3-oxo-prop-1-yl, 4-isobutoxy-4-oxo-but-1-yl, tert-butoxycarbonyl, 2-tert-butoxy-2-oxo-eth-1-yl, 3-tert-butoxy-3-oxo-prop-1-yl, 4-tert-butoxy-4-oxo-but-1-yl, phenoxycarbonyl, 2-oxy-2-phenoxy-eth-1-yl, 3-oxo-3-phenoxy-prop-1-yl, 4-oxo-4-phenoxy-but-1-yl, benzyloxycarbonyl, 2-benzyloxy-2-oxo-eth-1-yl, 3-benzyloxy-3-oxo-prop-1-yl, and 4-benzyloxy-4-oxo-but-1-yl.

In a further preferred embodiment, said carboxylic acid amides, respectively independently of each other, contain 1 to 17 C atoms, more preferably 1 to 15 C atoms, more preferably 1 to 12 C atoms, wherein preferably, the C atom of the carboxamide group is respectively bonded to one of the residues $Q^1$ to $Q^4$.

Said carboxylic acid amides are preferably not carbamides.

In a further preferred embodiment, said carboxylic acid amides, respectively independently of each other, are selected from the group which consists of carbamoyl, 2-amino-2-oxo-eth-1-yl, 3-amino-3-oxo-prop-1-yl, 4-amino-4-oxo-but-1-yl, methylcarbamoyl, 2-(methylamino)-2-oxo-eth-1-yl, 3-(methylamino)-3-oxo-prop-1-yl, 4-(methylamino)-4-oxo-but-1-yl, dimethylcarbamoyl, 2-(dimethylamino)-2-oxo-eth-1-yl, 3-(dimethylamino)-3-oxo-prop-1-yl, 4-(dimethylamino)-4-oxo-but-1-yl, ethylcarbamoyl, 2-(ethylamino)-2-oxo-eth-1-yl, 3-(ethylamino)-3-oxo-prop-1-yl, 4-(ethylamino)-4-oxo-but-1-yl, ethyl(methyl)carbamoyl, 2-[ethyl(methyl)amino]-2-oxo-eth-1-yl, 3-[ethyl(methyl)amino]-3-oxo-prop-1-yl, 4-[ethyl(methyl)amino]-4-oxo-but-1-yl, dimethylcarbamoyl, 2-(dimethylamino)-2-oxo-eth-1-yl, 3-(dimethylamino)-3-oxo-prop-1-yl, 4-(dimethylamino)-4-oxo-but-1-yl, dipropylcarbamoyl, 2-(dipropylamino)-2-oxo-eth-1-yl, 3-(dipropylamino)-3-oxo-prop-1-yl, 4-(dipropylamino)-4-oxo-but-1-yl, diisopropylcarbamoyl, 2-(diisopropylamino)-2-oxo-eth-1-yl, 3-(diisopropylamino)-3-oxo-prop-1-yl, 4-(diisopropylamino)-4-oxo-but-1-yl, dibutylcarbamoyl, 2-(dibutylamino)-2-oxo-eth-1-yl, 3-(dibutylamino)-3-oxo-propyl, 4-(dibutylamino)-4-oxo-but-1-yl, di-tert-butylcarbamoyl, 2-(di-tert-butylamino)-2-oxo-eth-1-yl, 3-(di-tert-butylamino)-3-oxo-propyl, and 4-(di-tert-butylamino)-4-oxo-but-1-yl.

In a further preferred embodiment, said heteroaryl residue which does not contain a nitrogen atom and containing 4 to 20 C atoms is selected from the group consisting of furanyl and benzofuranyl.

In a further preferred embodiment, said ether residues, respectively independently of each other, contain 2 to 17 C atoms, more preferably 2 to 13 C atoms, more preferably 2 to 9 C atoms. In a further preferred embodiment, said ether residues are, for example, selected from the group which consists of methoxymethyl, methoxyethyl, methoxy-n-propyl, ethoxymethyl, n-propoxymethyl, 2-ethoxyethoxymethyl, 2-(2-ethoxyethoxy)ethyl, i-propoxymethyl, tert-butyloxymethyl, dioxa-3,6-heptyl and benzyloxymethyl. In a further preferred embodiment, said ether residues may be single ether residues, oligoether residues, polyether residues or mixtures thereof.

In accordance with the invention, the term "halogen", respectively independently of each other, should be understood to mean fluorine, chlorine, bromine or iodine. In accordance with the invention, the term "halide", respectively independently of each other, should be understood to mean fluoride, chloride, bromide or iodide.

Unless otherwise stated, chiral centres may be in the R or in the S configuration. The invention encompasses both optically pure volumes as well as stereoisomeric mixtures such as enantiomeric mixtures and diastereoisomeric mixtures, in any ratio.

The invention preferably also concerns mesomers and/or tautomers of the compound with formula (1) and/or the compound with formula (2) and/or the compound with formula (3) and/or the compound with formula (100) and/or the compound with formula (101) and/or the compound with formula (102), as well as the pure compounds and also mixtures of isomers, in any ratio.

As an example, the compound with formula (1) may be in the keto form (1a) or the enol form (1b):

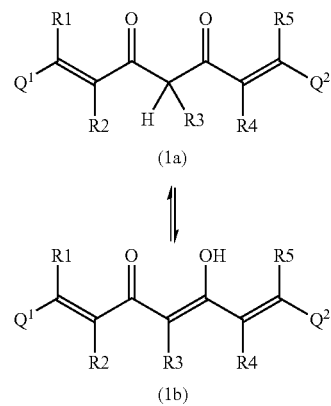

(1a)

(1b)

A variation of the method for the manufacture of a 1,7-diaryl-1,6-heptadione-3,6-dione derivative with formula (1) comprises the following steps:

(A) reacting a substituted aryl ketone with formula (80) with a substituted acetyl acetone with formula (81) in the presence of a solvent, preferably ethyl acetate, dimethyl sulphoxide (DMSO), dimethyl formate (DMF) or mixtures thereof, in the presence of a dehydrating agent, preferably tributylborate, $B_2O_3$ or mixtures thereof, and of a primary and/or secondary amine, preferably n-butylamine, morpholine, piperidine or mixtures thereof, to obtain a compound with formula (82):

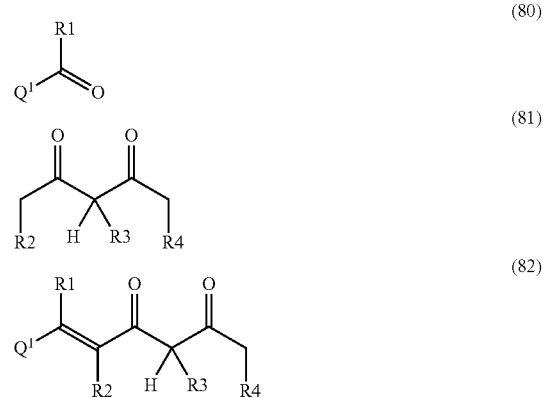

wherein $Q^1$ represents a substituted or unsubstituted, monocyclic or polycyclic aromatic residue, and wherein the residue $Q^1$ is substituted with at least one organic residue W1a which has the general formula (5a), (6a), (7a), (8a), or (9a):

  (5a)

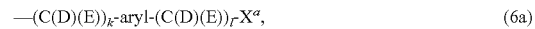  (6a)

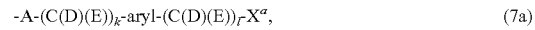  (7a)

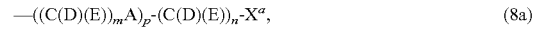  (8a)

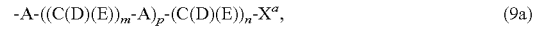  (9a)

wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n and p, respectively independently of each other, represent a whole number from 1 to 6, preferably from 2 to 4, and wherein A, respectively independently of each other, represents oxygen or sulphur, wherein D and E, respectively independently of each other, represent hydrogen, halogen, G-$R^{(I)}$, or G-C(=G)-$R^{(II)}$, wherein G, respectively independently of each other, represents oxygen or sulphur, and wherein the residues $R^{(I)}$ and $R^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein $X^a$, respectively independently of each other, represents a residue with formula (20e), (21), or (24), preferably a residue with formula (20c), (20d), or (21), more preferably a residue with formula (24):

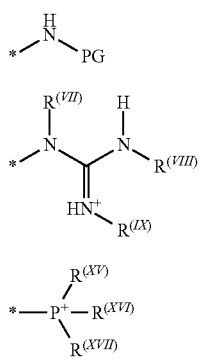

wherein each of the residues $R^{(VII)}$, $R^{(VIII)}$, and $R^{(IX)}$, respectively independently of each other, represents a protective group PG, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, and wherein each of the residues $R^{(XV)}$, $R^{(XVI)}$, and $R^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, and wherein the residues R1, R2, R3, and R4, respectively independently of each other, represent hydrogen, halogen, alkyl containing 1 to 12 C atoms, cycloalkyl containing 1 to 12 C atoms, alkylaryl containing 1 to 12 C atoms, aryl containing 5 to 20 C atoms, ether containing 2 to 12 C atoms or glycol containing 2 to 12 C atoms, (B) reacting the compound with formula (82) with a substituted aryl ketone with formula (83) in the presence of a solvent, preferably ethyl acetate, dimethyl sulphoxide (DMSO), dimethyl formate (DMF) or mixtures thereof, in the presence of a dehydrating agent, preferably tributylborate, $B_2O_3$ or mixtures thereof, and of a primary and/or secondary amine, preferably n-butylamine, morpholine, piperidine or mixtures thereof, to obtain a 1,7-diaryl-1,6-heptadione-3,6-dione derivative with formula (1a):

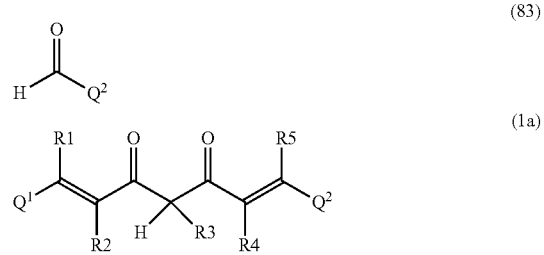

wherein $Q^2$ represents a substituted or unsubstituted, monocyclic or polycyclic aromatic residue, and wherein the residue $Q^2$ optionally has at least one organic residue W1a which has the general formula (5a), (6a), (7a), (8a), or (8a), and wherein the residue R5 represents hydrogen, halogen, alkyl containing 1 to 12 C atoms, cycloalkyl containing 1 to 12 C atoms, alkylaryl containing 1 to 12 C atoms, aryl containing 5 to 20 C atoms, ether containing 2 to 12 C atoms or glycol containing 2 to 12 C atoms, (C) optionally, removing any protective groups PG which are present.

Alternatively, a 1,7-diaryl-1,6-heptadione-3,6-dione derivative with formula (1) in accordance with the invention may be produced by:

(A1) reacting curcumin with a compound with general formula $X^a$—(C(D)(E))$_h$-OH in the presence of diethylazodicarboxylate (DEAD) and triphenylphosphine (PPh$_3$) as well as a solvent, preferably ethyl acetate, dimethyl sulphoxide (DMSO), dimethyl formate (DMF) or mixtures thereof, or (A2) reacting curcumin with a compound with general formula $X^a$—(C(D)(E))$_h$-Z in the presence of $K_2CO_3$ and KI as well as a solvent, preferably ethyl acetate, dimethyl sulphoxide (DMSO), dimethyl formate (DMF) or mixtures thereof, wherein h represents a whole number from 1 to 20, preferably from 2 to 8, wherein the residue Z, independently of each other, represents Cl, Br, I, tosylate (OTs) or mesylate (OMs), and wherein $X^a$, respectively independently of each other, represents a residue with formula (20e), (21) or (24), preferably a residue with formula (20c), (20d), or (21), more preferably a residue with formula (24):

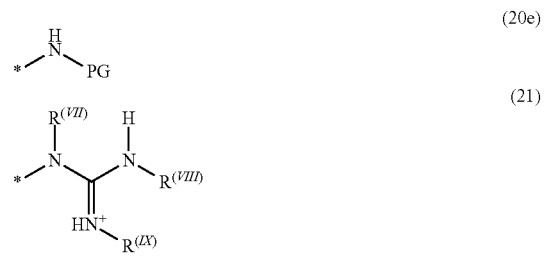

-continued

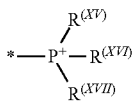
(24)

wherein each of the residues $R^{(VII)}$, $R^{(VIII)}$, and $R^{(IX)}$, respectively independently of each other, represents a protective group PG, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, and wherein each of the residues $R^{(XV)}$, $R^{(XVI)}$, and $R^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, and (B) removing the protective groups PG which are present.

A further variation of the method for the manufacture of a 1,7-diaryl-1,6-heptadione-3,6-dione derivative with formula (1) comprises the following steps:

(A) reacting a substituted or unsubstituted aryl ketone with formula (80a) with a substituted acetyl acetone with formula (81a) in the presence of a solvent, preferably ethyl acetate, dimethyl sulphoxide (DMSO), dimethyl formate (DMF) or mixtures thereof, in the presence of a dehydrating agent, preferably tributylborate, $B_2O_3$ or mixtures thereof, and of a primary and/or secondary amine, preferably n-butylamine, morpholine, piperidine or mixtures thereof, to obtain a compound with formula (82a),

(80a)

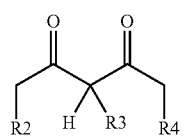
(81a)

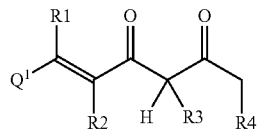
(82a)

wherein the residue R3 is an organic residue W2a which has the general formula (4b), (5b), (6b), (7b), (8b), or (9b):

—(C(D)(E))$_h$-X$^b$,  (4b)

-A-(C(D)(E))$_h$-X$^b$,  (5b)

—(C(D)(E))$_k$-aryl-(C(D)(E))$_l$-X$^b$,  (6b)

-A-(C(D)(E))$_k$-aryl-(C(D)(E))$_l$-X$^b$,  (7b)

—[(C(D)(E))$_m$-A]$_p$—(C(D)(E))$_n$-X$^b$,  (8b)

-A-[(C(D)(E))$_m$-A]$_p$—(C(D)(E))$_n$-X$^b$,  (9b)

wherein $Q^1$ represents a substituted or unsubstituted, monocyclic or polycyclic aromatic residue, and wherein the residue $Q^1$ is optionally substituted with at least one organic residue W1b which has the general formula (4b), (5b), (6b), (7b), (8b), or (9b), and wherein h represents a whole number from 1 to 20, preferably from 2 to 8, wherein k represents a whole number from 0 to 10, preferably from 1 to 8, preferably from 2 to 6, wherein l represents a whole number from 0 to 10, preferably from 1 to 8, preferably from 2 to 6, and wherein m, n and p, respectively independently of each other, represent a whole number from 1 to 6, preferably from 2 to 4, and wherein A, respectively independently of each other, represents oxygen or sulphur, wherein D and E, respectively independently of each other, represent hydrogen, halogen, G-R$^{(I)}$, or G-C(=G)-R$^{(II)}$, wherein G, respectively independently of each other, represents oxygen or sulphur, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein $X^b$, respectively independently of each other, is an organic residue which (i) contains at least one neutral nitrogen atom which can be protonated, or (ii) contains at least one positively charged, preferably quaternary, nitrogen atom, or (iii) contains at least one positively charged, preferably quaternary, phosphorus atom, wherein preferably, $X^b$, respectively independently of each other, represents a residue with formula (20e), (21), or (24), preferably a residue with formula (20c), (20d), or (21), more preferably a residue with formula (24):

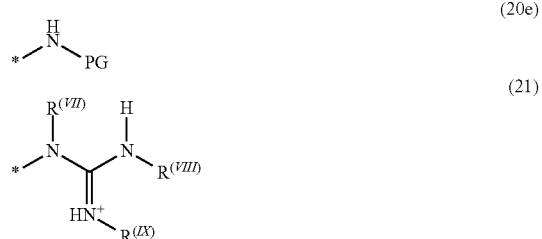

(20e)

(21)

(24)

wherein each of the residues $R^{(VII)}$, $R^{(VIII)}$, and $R^{(IX)}$, respectively independently of each other, represents a protective group PG, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, and wherein each of the residues $R^{(XV)}$, $R^{(XVI)}$, and $R^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, and wherein the residues R1, R2, and R4, respectively independently of each other, represent hydrogen, halogen, alkyl containing 1 to 12 C atoms, cycloalkyl containing 1 to 12 C atoms, alkylaryl containing 1 to 12 C atoms, aryl containing 5 to 20 C atoms, ether containing 2 to 12 C atoms or glycol containing 2 to 12 C atoms, (B) reacting the compound with formula (82a) with a substituted aryl ketone with formula (83a) in the presence of a solvent, preferably ethyl acetate, dimethyl sulphoxide (DMSO), dimethyl formate (DMF) or mixtures thereof, in the presence of a dehydrating agent, preferably tributylborate, $B_2O_3$ or mixtures thereof, and of a primary and/or secondary amine, preferably n-butylamine, morpholine, piperidine or mixtures thereof, to obtain a 1,7-diaryl-1,6-heptadione-3,6-dione derivative with formula (1a):

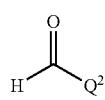
(83)

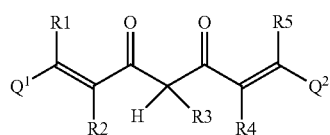
(1a)

wherein $Q^2$ represents a substituted or unsubstituted, monocyclic or polycyclic aromatic residue, and wherein the residue $Q^2$ is optionally substituted with at least one organic residue W1a which has the general formula (4b), (5b), (6b), (7b), (8b), or (9b), and wherein the residue R5 represents hydrogen, halogen, alkyl containing 1 to 12 C atoms, cycloalkyl containing 1 to 12 C atoms, alkylaryl containing 1 to 12 C atoms, aryl containing 5 to 20 C atoms, ether containing 2 to 12 C atoms or glycol containing 2 to 12 C atoms, (C) optionally, removing any protective groups PG which are present.

A method for the manufacture of a 1,7-diaryl-1,6-heptadione-3,6-dione derivative with formula (2) comprises the following steps:

(A) reacting a compound with formula (1) with a metal salt $M(L^1)(L^2)$

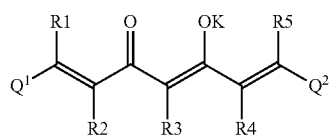
(1)

to obtain a 1,7-diaryl-1,6-heptadione-3,6-dione derivative with formula (2):

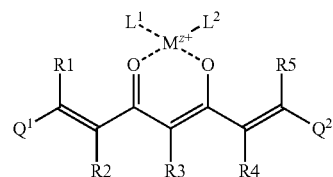
(2)

wherein $L^1$ and $L^2$, respectively independently of each other, represent water, halide, cyanide, thiocyanate, phosphate, hydrogen phosphate, or a carboxylation of a carboxylic acid containing 1 to 10 carbon atoms, preferably formate, acetate, n-propionate, lactate, oxalate, fumarate, maleinate, tartrate, succinylate, benzoate, salicylate, or citrate, and wherein the residues $Q^1$ and $Q^2$, respectively independently of each other, represent one substituted or unsubstituted, monocyclic or polycyclic aromatic residue, and wherein (a) at least one of the residues $Q^1$ and $Q^2$, respectively independently of each other, is substituted with at least one organic residue W1a which has the general formula (5a), (6a), (7a), (8a), or (9a):

-A-(C(D)(E))$_h$-X$^a$, (5a)

—(C(D)(E))$_k$-aryl-(C(D)(E))$_l$-X$^a$, (6a)

-A-(C(D)(E))$_k$-aryl-(C(D)(E))$_l$-X$^a$, (7a)

—((C(D)(E))$_m$A)$_p$-(C(D)(E))$_n$-X$^a$, (8a)

-A-((C(D)(E))$_m$-A)$_p$-(C(D)(E))$_n$-X$^a$, (9a)

wherein h represents a whole number from 1 to 20, wherein k represents a whole number from 0 to 10, wherein l represents a whole number from 0 to 10, and wherein m, n and p, respectively independently of each other, represent a whole number from 1 to 6, and wherein A, respectively independently of each other, represents oxygen or sulphur, wherein D and E, respectively independently of each other, represent hydrogen, halogen, G-R$^{(I)}$, or G-C(=G)-R$^{(II)}$, wherein G, respectively independently of each other, represents oxygen or sulphur, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X$^a$, respectively independently of each other, represents a residue with formula (20e), (21), or (24), preferably a residue with formula (20c), (20d), or (21), more preferably a residue with formula (24):

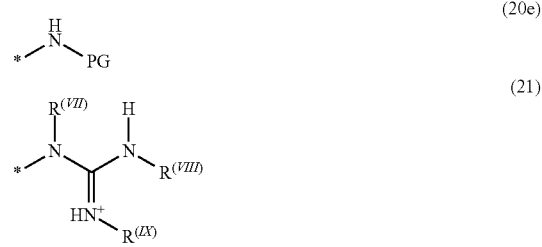

-continued

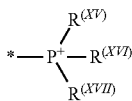
(24)

wherein each of the residues $R^{(VII)}$, $R^{(VIII)}$, and $R^{(IX)}$, respectively independently of each other, represents a protective group PG, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, and wherein each of the residues $R^{(XV)}$, $R^{(XVI)}$, and $R^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, and wherein the residues R1, R2, R3, R4 and R5, respectively independently of each other, represent hydrogen, halogen, alkyl containing 1 to 12 C atoms, cycloalkyl containing 1 to 12 C atoms, alkylaryl containing 1 to 12 C atoms, aryl containing 5 to 20 C atoms, ether containing 2 to 12 C atoms or glycol containing 2 to 12 C atoms, or wherein (b) the residue $R^3$ is an organic residue W2a which has the general formula (4b), (5b), (6b), (7b), (8b), or (9b):

 (4b)

 (5b)

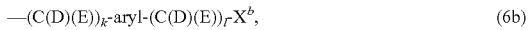 (6b)

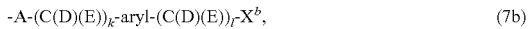 (7b)

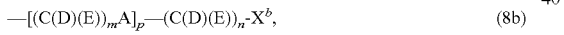 (8b)

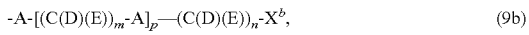 (9b)

and wherein, optionally, at least one of the residues $Q^1$ and $Q^2$, respectively independently of each other, is substituted with at least one organic residue W1b which has the general formula (4b), (5b), (6b), (7b), (8b), or (9b), wherein h represents a whole number from 1 to 20,
wherein k represents a whole number from 0 to 10,
wherein l represents a whole number from 0 to 10, and
wherein m, n and p, respectively independently of each other, represent a whole number from 1 to 6, and wherein A, respectively independently of each other, represents oxygen or sulphur, wherein D and E, respectively independently of each other, represent hydrogen, halogen, G-$R^{(I)}$, or G-C(=G)-$R^{(II)}$, wherein G, respectively independently of each other, represents oxygen or sulphur, and wherein the residues $R^{(I)}$ and $R^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein $X^b$, respectively independently of each other, is an organic residue which (i) contains at least one neutral nitrogen atom which can be protonated, or (ii) contains at least one positively charged, preferably quaternary, nitrogen atom, or (iii) contains at least one positively charged, preferably quaternary, phosphorus atom, wherein preferably, $X^b$, respectively independently of each other, represents a residue with formula (20e), (21), or (24), preferably a residue with formula (20c), (20d), or (21), more preferably a residue with formula (24):

 (20e)

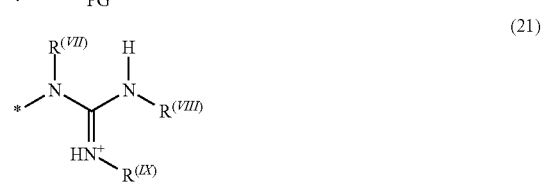 (21)

 (24)

wherein each of the residues $R^{(VII)}$, $R^{(VIII)}$, and $R^{(IX)}$, respectively independently of each other, represents a protective group PG, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, and wherein each of the residues $R^{(XV)}$, $R^{(XVI)}$, and $R^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, and wherein the residues R1, R2, R4 and R5, respectively independently of each other, represent hydrogen, halogen, alkyl containing 1 to 12 C atoms, alkylaryl containing 1 to 12 C atoms, aryl containing 5 to 20 C atoms, ether containing 2 to 12 C atoms or glycol containing 2 to 12 C atoms.

A method for the manufacture of a 1,7-diaryl-1,6-heptadione-3,6-dione derivative with formula (3) comprises the following steps:

(A) reacting a compound with formula (2):

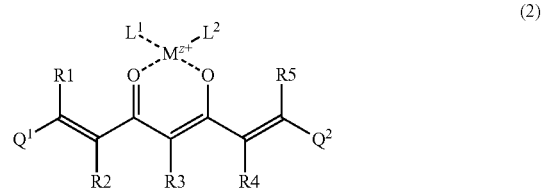 (2)

with a compound with formula (1e):

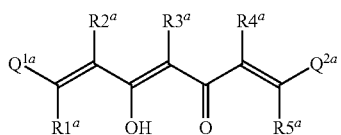

(1e)

to obtain a 1,7-diaryl-1,6-heptadione-3,6-dione derivative with formula (3):

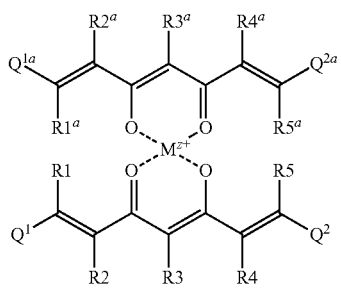

(3)

wherein $L^1$ and $L^2$, respectively independently of each other, represent water, fluoride, chloride, bromide, iodide, phosphate, hydrogen phosphate, dihydrogen phosphate, sulphate, hydrogen sulphate, tosylate, mesylate or at least one carboxylation of a carboxylic acid containing 1 to 15 carbon atoms and/or mixtures thereof, wherein $M^{z+}$ represents a cation of a metal, wherein z is the formal oxidation number of the metal M and wherein z represents a whole number from 1 to 7, preferably from 2 to 5, and wherein the residues $Q^1$ and $Q^2$, respectively independently of each other, represent 1 substituted or unsubstituted, monocyclic or polycyclic aromatic residue, and wherein the residues $Q^{1a}$ and $Q^{2a}$, respectively independently of each other, represent 1 substituted or unsubstituted, monocyclic or polycyclic aromatic residue or one substituted or unsubstituted, monocyclic or polycyclic heteroaromatic residue, and wherein (a) at least one of the residues $Q^1$ and $Q^2$, respectively independently of each other, is substituted with at least one organic residue W1a, wherein the at least one organic residue W1a has the general formula (5a), (6a), (7a), (8a), or (9a):

  (5a)

  (6a)

  (7a)

  (8a)

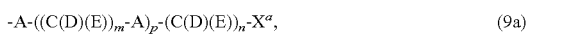  (9a)

wherein h represents a whole number from 1 to 20, wherein k represents a whole number from 0 to 10, wherein l represents a whole number from 0 to 10, and wherein m, n and p, respectively independently of each other, represent a whole number from 1 to 6, and wherein A, respectively independently of each other, represents oxygen or sulphur, wherein D and E, respectively independently of each other, represent hydrogen, halogen, $G\text{-}R^{(I)}$, or $G\text{-}C(=G)\text{-}R^{(II)}$, wherein G, respectively independently of each other, represents oxygen or sulphur, and wherein the residues $R^{(I)}$ and $R^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein $X^a$, respectively independently of each other, represents a residue with formula (20c), (20d), (21), or (24), more preferably a residue with formula (20c), (20d), or (21), more preferably a residue with formula (24):

  (20c)

  (20d)

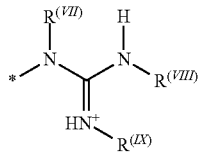  (21)

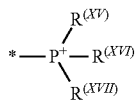  (24)

wherein each of the residues $R^{(VII)}$, $R^{(VIII)}$, and $R^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, and wherein each of the residues $R^{(XV)}$, $R^{(XVI)}$, and $R^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, and wherein at least one of the residues $Q^{1a}$ and $Q^{2a}$, respectively independently of each other, is substituted with at least one organic residue W1c, wherein the at least one organic residue W1c has the general formula (5c), (6c), (7c), (8c), or (9c):

  (5c)

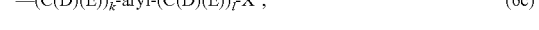  (6c)

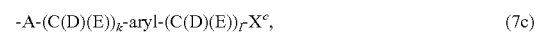  (7c)

—((C(D)(E))$_m$-A)$_p$-(C(D)(E))$_n$-X$^c$, (8c)

-A-((C(D)(E))$_m$-A)$_p$-(C(D)(E))$_n$-X$^c$, (9c)

wherein h represents a whole number from 1 to 20,
wherein k represents a whole number from 0 to 10,
wherein l represents a whole number from 0 to 10, and
wherein m, n and p, respectively independently of each other, represent a whole number from 1 to 6, and wherein A, respectively independently of each other, represents oxygen or sulphur, wherein D and E, respectively independently of each other, represent hydrogen, halogen, G-R$^{(I)}$, or G-C(=G)-R$^{(II)}$, wherein G, respectively independently of each other, represents oxygen or sulphur, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X$^c$, respectively independently of each other, is an organic residue which (i) contains at least one neutral nitrogen atom which can be protonated, or (ii) contains at least one positively charged, preferably quaternary, nitrogen atom, or (iii) contains at least one positively charged, preferably quaternary, phosphorus atom, wherein preferably, X$^c$, respectively independently of each other, represents a residue with formula (20c), (20d), (21), or (24), more preferably a residue with formula (20c), (20d), or (21), more preferably a residue with formula (24):

(20c)

(20d)

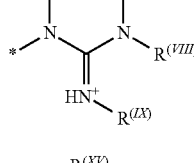

(21)

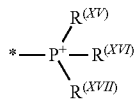

(24)

wherein each of the residues R$^{(VII)}$, R$^{(VIII)}$, and R$^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, and wherein each of the residues R$^{(XV)}$, R$^{(XVI)}$, and R$^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, wherein the residues R$^1$, R1$^a$, R$^2$, R2$^a$, R$^3$, R3$^a$, R$^4$, R4$^a$, R$^5$ and R5$^a$, respectively independently of each other, represent hydrogen, halogen, alkyl containing 1 to 12 C atoms, cycloalkyl containing 1 to 12 C atoms, alkylaryl containing 1 to 12 C atoms, aryl containing 5 to 20 C atoms, ether containing 2 to 12 C atoms or glycol containing 2 to 12 C atoms, or wherein (b) the residue R$^3$ or R$^{3a}$, respectively independently of each other, is an organic residue W2a, wherein the one organic residue W2a has the general formula (4b), (5b), (6b), (7b), (8b), or (9b):

—(C(D)(E))$_h$-X$^b$, (4b)

-A-(C(D)(E))$_h$-X$^b$, (5b)

—(C(D)(E))$_k$-aryl-(C(D)(E))$_l$-X$^b$, (6b)

-A-(C(D)(E))$_k$-aryl-(C(D)(E))$_l$-X$^b$, (7b)

—[(C(D)(E))$_m$A]$_p$—(C(D)(E))$_n$-X$^b$, (8b)

-A-[(C(D)(E))$_m$-A]$_p$—(C(D)(E))$_n$-X$^b$, (9b)

and wherein, optionally, at least one of the residues Q$^1$, Q$^{1a}$, Q$^2$ and Q$^{2a}$, respectively independently of each other, is substituted with at least one organic residue W1 b which has the general formula (4b), (5b), (6b), (7b), (8b), or (9b), wherein h represents a whole number from 1 to 20,
wherein k represents a whole number from 0 to 10,
wherein l represents a whole number from 0 to 10, and
wherein m, n, and p, respectively independently of each other, represent a whole number from 1 to 6, and wherein A, respectively independently of each other, represents oxygen or sulphur, preferably oxygen, wherein D and E, respectively independently of each other, represent hydrogen, halogen, G-R$^{(I)}$, or G-C(=G)-R$^{(II)}$, wherein G, respectively independently of each other, represents oxygen or sulphur, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X$^b$, respectively independently of each other, is an organic residue which (i) contains at least one neutral nitrogen atom which can be protonated, or (ii) contains at least one positively charged, preferably quaternary, nitrogen atom, or (iii) contains at least one positively charged, preferably quaternary, phosphorus atom, wherein preferably, X$^b$, respectively independently of each other, represents a residue with formula (20c), (20d), (21), or (24), more preferably a residue with formula (20c), (20d), or (21), more preferably a residue with formula (24):

(20c)

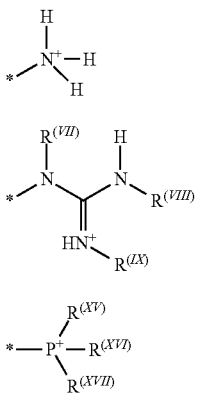

wherein each of the residues $R^{(VII)}$, $R^{(VIII)}$, and $R^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, and wherein each of the residues $R^{(XV)}$, $R^{(XVI)}$, and $R^{(XVII)}$, respectively independently of each other, represents an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, and wherein the residues R1, $R1^a$, R2, $R2^a$, R4, $R4^a$, R5 and $R5^a$, respectively independently of each other, represent hydrogen, halogen, alkyl containing 1 to 12 C atoms, alkylaryl containing 1 to 12 C atoms, aryl containing 5 to 20 C atoms, ether containing 2 to 12 C atoms or glycol containing 2 to 12 C atoms.

When using different amino protective groups PG in a synthesis, it is possible to use an orthogonal protective group strategy, wherein different amino functions of a molecule can be intentionally released one after the other and caused to react.

Suitable methods for removing the amino protective groups PG are known in the prior art. As an example, benzyloxycarbonyl (Cbz) can be removed again by treatment with Lewis acids, for example $ZnBr_2$, in acetic acid. Di-tert-butyloxycarbonyl (boc) can be removed by acid hydrolysis, for example. Allyloxycarbonyl (alloc) can, for example, be split off by the action of tetrakis(triphenylphosphine)palladium(0) and a nucleophile.

The active or passive introduction, adhesion and proliferation of pathogens in a host is termed an infection. Sources of infectious particles are ubiquitous. Thus, for example, the human body is colonized by a large number of microorganisms which are usually kept under control by the normal metabolism and an intact immune system. However, when the immune system is weakened, for example, a strong proliferation of the pathogens may occur and, depending on the type of the pathogen, various symptoms of disease may manifest themselves. The medical profession has specific remedies prepared for many diseases caused by pathogens, for example antibiotics against bacteria or antimycotics against fungi or antivirals against viruses. However, when these remedies are employed, an increase in the occurrence of resistant pathogens is observed which sometimes also have resistance to more than one remedy. Because of the occurrence of these resistant or multi-resistant pathogens, the therapy of infectious diseases is becoming more and more difficult. The clinical consequence of resistance is indicated by a failure of treatment, especially in immuno-suppressed patients.

Single-celled or multi-celled microorganisms can trigger infectious diseases. By application of at least one pathogen-specific remedy, for example antibiotic, antimycotic or antiviral, the number of pathogens can be reduced and/or the pathogen can be inactivated. The application of a pathogen-specific remedy may be systemic and/or topical.

In systemic application, the pathogen-specific remedy is transferred into the blood and/or lymph system of the body to be treated and thus distributed through the entire body. In the systemic administration of the pathogen-specific remedy, degradation of the remedy and/or side effects, for example by a biochemical transformation (metabolization) of the remedy may occur.

In the topical application of the pathogen-specific remedy, the remedy is applied where it is to act therapeutically, for example onto an infected part of the skin, while healthy skin is not affected. In this manner, systemic side effects can be largely avoided.

Superficial skin or soft tissue infections do not necessarily have to be treated with a systemic application of an pathogen-specific remedy because the remedy can be applied directly to the infected parts of the skin.

Known pathogen-specific remedies exhibit side effects and interactions, some of which may be severe, both with systemic and with topical application. Furthermore, with topical application, an inadmissible intake of medication (compliance) of the patient, in particular when using antibiotics, may give rise to resistance.

An alternative here is the photodynamic inactivation of microorganisms, because resistance to photodynamic inactivation is unknown. Independently of the type of the microorganisms to be combatted and the associated infectious diseases, the number of pathogens is reduced and/or the pathogens are eradicated. As an example, mixtures of various microorganisms, for example fungi and bacteria or different bacterial strains can be controlled.

The aim of the present invention is accomplished by the provision of a method for inactivating microorganisms, which preferably include viruses, archaea, bacteria, bacterial spores, fungi, fungal spores, protozoa, algae, blood-borne parasites or combinations thereof, wherein the method comprises the following steps:

(A) bringing the microorganisms into contact with at least one photosensitizer, wherein the photosensitizer is at least one 1,7-diaryl-1,6-heptadiene-3,5-dione derivative with formula (100) and/or at least one 1,7-diaryl-1,6-heptadiene-3,5-dione derivative with formula (101) and/or at least one 1,7-diaryl-1,6-heptadiene-3,5-dione derivative with formula (1) and/or at least one 1,7-diaryl-1,6-heptadiene-3,5-dione derivative with formula (2) and/or at least one 1,7-diaryl-1,6-heptadiene-3,5-dione derivative with formula (3) or respectively a pharmacologically acceptable salt and/or ester and/or complex thereof, and (B) irradiating the microorganisms and the at least one photosensitizer with electromagnetic radiation of a suitable wavelength and energy density.

Preferably, the method in accordance with the invention is carried out in order to inactivate microorganisms for the photodynamic therapy of a patient and/or photodynamic decontamination of at least one surface of an article and/or at least one surface of an area.

In a preferred embodiment of the method in accordance with the invention, irradiation of the microorganisms and of the at least one photosensitizer with electromagnetic radiation of a suitable wavelength and energy density is carried out in the presence of at least one oxygen-donating compound, preferably peroxide, and/or at least one oxygen-containing gas, preferably oxygen.

The at least one oxygen-donating compound and/or the at least one oxygen-containing gas may preferably be applied before or during step (B) of the method in accordance with the invention.

By adding extra oxygen in the form of at least one oxygen-containing compound and/or at least one oxygen-containing gas before or during irradiation of the microorganisms and of the at least one photosensitizer with electromagnetic radiation of a suitable wavelength and energy density, the yield of reactive oxygen species (ROS) formed, preferably oxygen radicals and/or singlet oxygen, is increased.

Preferably, the photosensitizer is at least one compound with formula (100), at least one compound with formula (101), at least one compound with formula (102), at least one compound with formula (1), at least one compound with formula (2), at least one compound with formula (3) or a combination thereof, or respectively a pharmacologically acceptable salt and/or ester and/or complex thereof.

More preferably, the photosensitizer is a 1,7-diaryl-1,6-heptadiene-3,5-dione derivative in accordance with the invention with formula (1) and/or a 1,7-diaryl-1,6-heptadiene-3,5-dione derivative in accordance with the invention with formula (2) and/or a 1,7-diaryl-1,6-heptadiene-3,5-dione derivative in accordance with the invention with formula (3) and/or a 1,7-diaryl-1,6-heptadiene-3,5-dione derivative in accordance with the invention with formula (3a), or respectively a pharmacologically acceptable salt and/or ester and/or complex thereof.

The aim of the present invention is also accomplished by the use of at least one 1,7-diaryl-1,6-heptadiene-3,5-dione derivative with formula (100) and/or at least one 1,7-diaryl-1,6-heptadiene-3,5-dione derivative with formula (101) and/or at least one 1,7-diaryl-1,6-heptadiene-3,5-dione derivative with formula (102) or respectively a pharmacologically acceptable salt and/or ester and/or complex thereof, as a photosensitizer for the inactivation of microorganisms, which preferably include viruses, archaea, bacteria, bacterial spores, fungi, fungal spores, protozoa, algae, blood-borne parasites or combinations thereof.

More preferably, a 1,7-diaryl-1,6-heptadiene-3,5-dione derivative in accordance with the invention with formula (1) and/or a 1,7-diaryl-1,6-heptadiene-3,5-dione derivative in accordance with the invention with formula (2) and/or a 1,7-diaryl-1,6-heptadiene-3,5-dione derivative in accordance with the invention with formula (3) and/or a 1,7-diaryl-1,6-heptadiene-3,5-dione derivative in accordance with the invention with formula (3a) or respectively a pharmacologically acceptable salt and/or ester and/or complex thereof is used as a photosensitizer for the inactivation of microorganisms, which preferably include viruses, archaea, bacteria, bacterial spores, fungi, fungal spores, protozoa, algae, blood-borne parasites or combinations thereof.

A 1,7-diaryl-1,6-heptadiene-3,5-dione derivative for use in accordance with the invention with formula (100) and/or with formula (101) and/or with formula (102) and/or a 1,7-diaryl-1,6-heptadiene-3,5-dione derivative in accordance with the invention with formula (1) and/or a 1,7-diaryl-1,6-heptadiene-3,5-dione derivative in accordance with the invention with formula (2) and/or a 1,7-diaryl-1,6-heptadiene-3,5-dione derivative in accordance with the invention with formula (3) and/or a 1,7-diaryl-1,6-heptadiene-3,5-dione derivative in accordance with the invention with formula (3a), has a high yield of singlet oxygen after irradiation with electromagnetic radiation of a suitable wavelength and energy density.

In the method in accordance with the invention and/or the use in accordance with the invention, the electromagnetic irradiation is preferably in the visible, ultraviolet and/or infrared spectral range. More preferably, the electromagnetic irradiation has a wavelength in the range from 280 to 1000 nm, more preferably from 380 to 1000 nm.

More preferably, the electromagnetic irradiation has an energy density in the range from 1 $\mu W/cm^2$ to 1 $kW/cm^2$, more preferably from 1 $mW/cm^2$ to 100 $W/cm^2$, more preferably from 2 $mW/cm^2$ to 50 $W/cm^2$, more preferably from 6 $mW/cm^2$ to 30 $W/cm^2$, more preferably from 7 $mW/cm^2$ to 25 $W/cm^2$.

The irradiation period may be varied as a function of the type of microorganisms and/or the severity of the infection. Preferably, the irradiation period is in the range from 1 $\mu s$ to 1 h, more preferably from 1 ms to 1000 s.

As an example, the irradiation procedure carried out for the irradiation may be that described in one of WO 96/29943 A1, EP 0 437 183 B1 or WO 2013/172977 A1.

Preferably, the irradiation device also comprises a device for dispensing at least one oxygen-containing compound, preferably peroxide, and/or the at least one oxygen-containing gas, preferably oxygen.

Preferably, the electromagnetic radiation is produced by a source of radiation which is selected from the group consisting of artificial sources of irradiation, for example UV lamps, IR lamps, fluorescent lamps, light-emitting diodes, lasers or chemical light.

Furthermore, the inventors have surprisingly discovered that a 1,7-diaryl-1,6-heptadiene-3,5-dione derivative for use in accordance with the invention with formula (100) and/or with formula (101) and/or with formula (102) and/or a 1,7-diaryl-1,6-heptadiene-3,5-dione derivative in accordance with the invention with formula (1) and/or a 1,7-diaryl-1,6-heptadiene-3,5-dione derivative in accordance with the invention with formula (2) and/or a 1,7-diaryl-1,6-heptadiene-3,5-dione derivative in accordance with the invention with formula (3) and/or a 1,7-diaryl-1,6-heptadiene-3,5-dione derivative in accordance with the invention with formula (3a) and/or respective pharmacologically acceptable salts and/or esters and/or complexes thereof, preferably exhibits a high affinity for microorganisms.

Because of affinity, the at least one 1,7-diaryl-1,6-heptadiene-3,5-dione derivative for use in accordance with the invention with formula (100) and/or with formula (101) and/or with formula (102), and/or the at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof bind effectively to microorganisms and produce sufficient local singlet oxygen to inactivate the microorganisms, preferably to kill them.

In a preferred use as a photosensitizer, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a)

and/or respective pharmacologically acceptable salts and/or esters and/or complexes thereof, are bound by microorganisms. After irradiation with electromagnetic radiation of a suitable wavelength and energy density, the microorganisms are inactivated, preferably killed, by the reactive oxygen species (ROS), preferably oxygen radicals and/or singlet oxygen, which are produced.

Preferably, binding of at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof to microorganisms brings about a staining or localization of the microorganisms. In this manner, the progress of the inactivation of microorganisms or their decolonization can be monitored.

In the context of the invention, the term "decolonization" should be understood to mean the removal, preferably complete removal of microorganisms.

In a further preferred embodiment, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof is used in the inactivation of single-celled or multi-celled microorganisms, which are preferably selected from the group formed by viruses, archaea, bacteria, bacterial spores, fungi, for example mycelial fungi and yeasts, fungal spores, protozoa, algae and blood-borne parasites.

Preferably, body surfaces, for example skin or mucous membranes, of humans and animals, preferably mammals, can be treated. In this preferred embodiment, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof, preferably in a pharmaceutical preparation, is used for the decontamination and/or decolonization of skin or soft tissue surfaces, wherein preferably, the integrity of the skin is maintained.

In a further preferred embodiment, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof, is used in a pharmaceutical preparation for local and/or topical, preferably nasal, oral, anal, vaginal or dermal application.

The term "topical application" should also be understood to mean application on or in the ear, preferably the outer ear. The outer ear comprises the ear cartilage, the auricle, the earlobe, the outer auditory or ear canal and the outside of the eardrum.

The term "topical application" should also be understood to mean application on or in the nose and/or the paranasal sinuses such as, for example, the maxillary sinus, the frontal sinus and/or the sphenoid sinus.

The term "topical application" should also be understood to mean application to the surface of the eye, preferably the outer, apical side of the epithelial layer of the cornea and/or the outer surface of the associated organs of the eye, preferably the tear ducts, the conjunctiva and/or the eyelids.

The term "topical application" should also be understood to mean application to the outer, apical side of the epithelia of hollow organs, for example the oesophagus, the gastrointestinal tract, the gall bladder, the bile ducts, the larynx, the airways, the bronchia, the ovaries, the uterus, the vagina, the ureta, the bladder or the urethra.

The term "topical application" should also be understood to mean application to or into teeth, for example in a root canal and/or a root cavity and/or tooth fissure, or gingival pockets and/or bone fenestrations.

In a further preferred embodiment, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof is used for the production of a pharmaceutical preparation for the prophylaxis and/or treatment of an infectious, preferably viral, bacterial and/or mycotic skin disease which is preferably selected from the group which consists of staphylococcal scalded skin syndrome, impetigo, skin abscesses, boils, carbuncles, phlegmon, cellulitis, acute lymphadenitis, pilonidial disease, pyoderma, dermatitis purulenta, dermatitis septica, dermatitis suppurativa, erythrasma, erysipelas, acne vulgaris or fungal infections.

In a further preferred embodiment, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof is used for the production of a pharmaceutical preparation for healing wounds, for example in the event of healing disorders following surgical intervention.

Preferably, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof or a pharmaceutical preparation containing at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof is used for decontamination and/or reduction of the bacterial count in infected wounds.

In a further preferred embodiment, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof is used for the production of a pharmaceutical preparation for the prophylaxis and/or treatment of infectious, preferably viral, bacterial and/or mycotic, diseases of the ear, the upper airways, the oral cavity, the throat, the larynx, the lower airways and/or the oesophagus.

The predominance of pathogenic microorganisms is, for example, the main cause of infection in the oral cavity. In this regard, the problem arises that the microorganisms are organized synergistically into extremely complex biofilms. These biofilms, for example plaque or tartar, consist of a plurality of complex layers and the proteins, carbohydrates, phosphates and microorganisms contained therein. Tartar occurs in particular when the surface of the tooth cannot be kept free of deposits by natural or artificial cleaning. This situation makes it difficult to obtain access to the microorganisms which are bound into the biofilm.

Conventional therapies such as antibiotics and mouthwashes or mechanical tooth cleaning can only be used to a limited extent, because either they cannot affect the bacteria directly, for example during tooth cleaning, are difficult to dose and apply, for example with antibiotics and mouthwashes, or a general application is not justified because of negative side effects.

As an example, in the United States, 20 million root canal treatments are carried out annually, within which more than 2 million endodontic re-treatments are carried out which could be avoided by improved decontamination of the root canals.

Preferably, the method in accordance with the invention and the use in accordance with the invention is suitable for effective elimination of microorganisms in root canal systems of a human tooth, encompassing the root canal and dental canaliculi.

In a preferred embodiment, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof is used as a photosensitizer in the photodynamic inactivation of microorganisms in the oral cavity.

In a further preferred embodiment, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof is used for the production of a pharmaceutical preparation for the treatment and/or prophylaxis of an infectious, preferably viral, bacterial and/or mycotic, disorder of the tooth tissue, preferably plaque, caries or pulpitis, and/or infectious, preferably viral, bacterial and/or mycotic, disorder of the periodontal apparatus, preferably gingivitis, paradontitis, endodontitis or periimplantitis.

In a further preferred embodiment, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof, or a pharmaceutical preparation containing at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof is used in cleaning teeth, dental prostheses and/or braces.

In a further preferred embodiment, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof, or a pharmaceutical preparation containing at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof is used in the nasal decolonization of microorganisms.

As an example, methicillin-resistant *Staphylococcus aureus* (MRSA) strains persist for a month in nasal colonization and also have a high resistance to the environment. Thus, a nasal decolonization, i.e. removal of microorganisms, also reduces the colonization in other sites on the body.

Furthermore, the present invention concerns a pharmaceutical composition containing at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof and one or more physiologically acceptable excipient(s).

Preferably, the pharmaceutical composition comprises at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof, and one or more physiologically acceptable excipient(s).

Preferably, the pharmaceutical composition is produced by mixing at least one compound with formula (100) and/or with formula (101) and/or with formula (102) and/or with formula (1) and/or with formula (2) and/or with formula (3) and/or with formula (3a) or respective pharmacologically acceptable salts and/or esters and/or complexes thereof, with one or more physiologically acceptable excipient(s) and placing it in a suitable form for administration.

A suitable form of administration for the pharmaceutical composition in accordance with the invention is preferably selected from the group which consists of ointments, creams, gels, lotions, shaking mixtures, solutions, for example in drop or spray form, powders, microcapsules and pastes.

The pharmaceutical composition in accordance with the invention may be administered locally or topically, preferably nasally, orally, anally, vaginally or dermally.

Examples of physiologically acceptable excipients are the pharmaceutically routine fluid or solid fillers and extenders, solvents, emulsifiers, lubricants, flavour correctors, colorants and/or buffer substances.

Preferably, the physiologically acceptable excipient is polyvinylpyrrolidone (PVP), cyclodextrin, polyethyleneglycol (PEG) or mixtures thereof.

More preferably, the pharmaceutically acceptable composition comprises liposomes.

In a further preferred embodiment, the pharmaceutical composition contains an effective quantity of at least one 1,7-diaryl-1,6-heptadiene-3,5-dione derivative to be used in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof, wherein the effective quantity is respectively from 0.01 µg to 1000 µg per gram of composition, preferably respectively 0.1 µg to 500 µg per gram of composition.

In a preferred embodiment of the invention, the pharmaceutical composition comprises at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof, and at least one further pharmaceutically active component.

Preferably, the at least one further pharmaceutically active component is selected from the group which consists of antibiotics, antimycotics, antivirals, antihistamines, sympathomimetics, antihaemorrhagics, emollients and skin-protecting agents, analgesics, disinfection agents, immunosera and immunglobulins, antiparasitic substances, insecticides, repellents and corticosteroids.

In a further preferred embodiment, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof, or a pharmaceutical preparation containing at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof is self-applied by the consumer and, optionally, subsequently irradiated with a suitable source of radiation which produces electromagnetic radiation of a suitable wavelength and energy density.

In a further preferred embodiment, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof, or a preparation containing at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof, is used in the inactivation of microorganisms in biological fluids, preferably medical blood products.

Suitable equipment for irradiating a biological fluid is known to the person skilled in the art and has been described, for example, in WO 99/43790 A1, US 2009/0010806 A1 or WO 2010/141564 A2.

Examples of suitable biological fluids are blood and blood products, including frozen fresh plasma, erythrocyte concentrate, thrombocyte concentrate, granulocyte concentrate, thrombocyte-rich plasma, stem cell preparations, concentrates of individual coagulation factors, human albumin, immunoglobulins, fibrin adhesive, antithrombin, protein C, protein S, fibrinolytics or combinations thereof.

In a preferred embodiment, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof is used for the photodynamic decontamination of surfaces of all types. A photodynamic decontamination of surfaces causes a photodynamic inactivation of microorganisms on the treated surface.

Examples of suitable surfaces are surfaces formed from plastic, metal, glass, textiles, wood, stone or combinations thereof.

More preferably, the 1,7-diaryl-1,6-heptadiene-3,5-dione derivative in accordance with the invention with formula (1) and/or with formula (3) and/or with formula (3a) or respectively a pharmacologically acceptable salt and/or ester and/or complex thereof is used in the photodynamic decontamination, surface cleaning and/or coating, preferably of medical products, electronic devices, hygiene articles, food packaging, foodstuffs, furniture, building materials or areas.

More preferably, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof, is applied and/or introduced to surfaces and, optionally, subsequently irradiated with a suitable source of radiation which produces electromagnetic radiation of a suitable wavelength and energy density. Preferably, the at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof brings about "self-disinfection" of the surface during the irradiation.

The irradiation may be carried out in this regard directly after treatment of the surface with at least one 1,7-diaryl-1,6-heptadiene-3,5-dione derivative for use in accordance with the invention with formula (100) and/or with formula (101) and/or with formula (102) and/or at least one inventive 1,7-diaryl-1,6-heptadiene-3,5-dione derivative with formula (1) and/or with formula (2) and/or with formula (3) and/or with formula (3a) and/or respective pharmacologically acceptable salts and/or esters and/or complexes thereof, preferably after applying the at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof onto the surface and/or introducing the at least one 1,7-diaryl-1,6-heptadiene-3,5-dione derivative for use in accordance with the invention with formula (100) and/or with formula (101) and/or with formula (102) and/or at least one inventive 1,7-diaryl-1,6-heptadiene-3,5-dione derivative with formula (1) and/or with formula (2) and/or with formula (3) and/or with formula (3a) and/or respective pharmacologically acceptable salts and/or esters and/or complexes thereof into the surface, and/or at a later point in time.

More preferably, articles are treated which have a thermally limited shelf life, for example articles formed from thermoplastic plastics or which are attacked by disinfectants.

Articles which have a thermally limited shelf life cannot be sufficiently sterilized, for example, because they lose their shape or become brittle at higher temperatures.

Furthermore, the improper and/or excessive use of disinfectants can lead to the build-up of resistance by selection of more robust microorganisms if, for example, the concentration of the substance and exposure time and thus the pathogen-reducing action is too small.

In a further preferred embodiment, the method in accordance with the invention is used to prevent a bacterial infection, for example prior to implantation or after successful decolonization, for example to prevent a fresh colonization with disease-inducing microorganisms such as, for example, pathogenic paradontal microorganisms.

In order to avoid infections by microorganisms, the method in accordance with the invention may also be used for the decolonization of surfaces.

As an example, contact by immunosuppressed patients with contaminated articles often leads to the build-up of an infection, because immunosuppressed patients are usually susceptible to infections, for example even from low bacterial counts. In particular, the surfaces of medical products, preferably medical accessories or dental accessories, more preferably invasive medical accessories such as catheters, hollow probes, tubes or needles, have to be disinfected before they are introduced into the human body.

Thus, in a further preferred embodiment, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof is used for the inactivation of microorganisms on surfaces of medical products, preferably invasive medical accessories such as, for example, contact lenses, surgical instruments, dental drills, dental mirrors, curettes, dental files, catheters, hollow probes, tubes or needles.

Preferably, the medical products are selected from wound dressings, bandages, surgical instruments, catheters, hollow probes, tubes or needles.

More preferably, the term "medical products" should also be understood to include dental bridges, impression trays, occlusal splints or dentures, for example prostheses, crowns or implants.

Preferably, by means of a treatment of the surface of articles of all types with at least one 1,7-diaryl-1,6-heptadiene-3,5-dione derivative for use in accordance with the invention with formula (100) and/or with formula (101) and/or with formula (102) and/or at least one inventive 1,7-diaryl-1,6-heptadiene-3,5-dione derivative with formula (1) and/or with formula (2) and/or with formula (3) and/or with formula (3a) and/or respective pharmacologically acceptable salts and/or esters and/or complexes thereof, and/or coating and/or immobilizing at least one 1,7-diaryl-1,6-heptadiene-3,5-dione derivative used in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof on the surface of medical products and subsequent irradiation with electromagnetic radiation of a suitable wavelength and energy density, colonization of microorganisms on the treated surfaces is reduced, preferably prevented.

Preferably, the treatment of the surface is carried out by atomization, painting, injection, spraying, immersion or combinations thereof.

The irradiation may be carried out directly after the treatment of the surface with at least one 1,7-diaryl-1,6-heptadiene-3,5-dione derivative for use in accordance with the invention with formula (100) and/or with formula (101) and/or with formula (102) and/or at least one inventive 1,7-diaryl-1,6-heptadiene-3,5-dione derivative with formula (1) and/or with formula (2) and/or with formula (3) and/or with formula (3a) and/or respective pharmacologically acceptable salts and/or esters and/or complexes thereof, preferably after applying the at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salt and/or ester and/or complex thereof onto the surface and/or introducing the at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salt and/or ester and/or complex thereof into the surface, and/or at a later point in time, before or during the use of the treated article, for example a medical product.

In a further preferred use of the at least one 1,7-diaryl-1,6-heptadiene-3,5-dione derivative for use in accordance with the invention with formula (100) and/or with formula (101) and/or with formula (102), and/or of the at least one inventive 1,7-diaryl-1,6-heptadiene-3,5-dione derivative with formula (1) and/or with formula (2) and/or with formula (3) and/or with formula (3a) and/or respective pharmacologically acceptable salt and/or ester and/or complex thereof in wound dressings and/or bandages, for example cotton gauze, during or after applying a wound dressing and/or bandage, which contains the at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof, an irradiation with electromagnetic radiation of a suitable wavelength and energy density can be carried out, whereupon subsequently, microorganisms in the region of the wound or treated skin parts are reduced, preferably inactivated.

In a further preferred embodiment, in addition to the at least one 1,7-diaryl-1,6-heptadiene-3,5-dione derivative for use in accordance with the invention with formula (100) and/or with formula (101) and/or with formula (102) and/or at least one inventive 1,7-diaryl-1,6-heptadiene-3,5-dione derivative with formula (1) and/or with formula (2) and/or with formula (3) and/or with formula (3a) and/or respective pharmacologically acceptable salts and/or esters and/or complexes thereof, the wound dressing and/or bandage comprises further components, preferably adsorbents, for example calcium alginate or polyurethane foam, or further pharmaceutically acceptable substances.

In a further preferred embodiment, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof is used for the inactivation of microorganisms on surfaces of food packaging.

Examples of suitable food packaging includes containers formed from glass, metal, plastic, paper, card or combinations thereof.

Before filling with a foodstuff or beverage, suitable containers may, for example, be treated with at least one 1,7-diaryl-1,6-heptadiene-3,5-dione derivative to be used in accordance with the invention with formula (100) and/or with formula (101) and/or with formula (102) and/or at least one inventive 1,7-diaryl-1,6-heptadiene-3,5-dione derivative with formula (1) and/or with formula (2) and/or with formula (3) and/or with formula (3a) and/or respective pharmacologically acceptable salts and/or complexes thereof and subsequently irradiated with a suitable source of radiation which produces electromagnetic radiation of a suitable wavelength and energy density. Subsequently, the appropriate foodstuff or beverage can be placed into the decontaminated container and the container can be sealed.

In a further preferred embodiment, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof is used for the inactivation of microorganisms on surfaces of foodstuffs.

Curcumin is an approved food additive which has the E number E100. Thus, modified curcumins, for example a 1,7-diaryl-1,6-heptadiene-3,5-dione derivative for use in accordance with the invention with formula (100) and/or with formula (101) and/or with formula (102) and/or a 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof, are advantageously also suitable food additives.

Examples of suitable foodstuffs are foodstuffs such as meat, fish, eggs, seeds, grain, nuts, berries, spices, fruit or vegetables which may come into contact with pathogenic bacterial species such as *Salmonella, Clostridium, Escherichia coli*— or *Camphylobacter* species. Advantageously, hatching eggs may also be photodynamically decontaminated.

The term "gastro-intestinal infection" is used to describe a group of diseases which are primarily distinguished by symptoms in the upper gastro-intestinal tract such as vomiting, diarrhoea and stomach pain. Gastro-intestinal infections are caused by viruses, bacteria or parasites. The pathogens are usually picked up via contaminated water and/or contaminated food.

The best known sources of gastro-intestinal infections include, for example, *Salmonella, Campylobacter* species or *Escherichia coli* species such as, for example, enterohaemorrhagic *Escherichia coli* (EHEC). Diarrhoea and vomiting due to food poisoning is primarily caused by staphylococci.

Most usually, pathogens of gastro-intestinal infections such as Salmonella, for example, get into the digestive tract of human beings via foodstuffs. The inventors have discovered that using the method in accordance with the invention can efficiently remove microorganisms from the surface of foodstuffs.

Salmonella, for example, are bacteria which occur worldwide. A Salmonella disease is a typical infection of foodstuff which causes diarrhoea. The pathogens multiply in the gastro-intestinal tract of humans and animals. Salmonella can multiply rapidly on non-chilled foodstuffs. Under certain circumstances, the bacteria get into food due to poor kitchen hygiene, for example via dirty cutting boards and/or knives.

Examples of foodstuffs which are often loaded with Salmonella are raw, i.e. incompletely cooked eggs and egg products such as mayonnaise, creams or salads based on eggs or raw dough. Further examples of foodstuffs which are often loaded with Salmonella are ice cream, raw meat, for example raw mince or tartare, raw sausages, for example smoked sausage or salami. Vegetable foodstuffs may also be colonized with Salmonella.

*Campylobacter* are globally occurring bacteria which trigger infectious diarrohea. *Campylobacter* species live mainly in the digestive tract of animals which usually do not become ill themselves. *Campylobacter* are the most common bacterial cause of diarrohea in Germany.

The main source of infection for *Campylobacter* is the consumption of foodstuffs which are contaminated with the bacteria. It is often transmitted via poultry meat. *Campylobacter* cannot multiply in foodstuffs, but *Campylobacter* can survive for some time in the environment. Again, poor kitchen hygiene can lead to an infection, for example via cutting boards and/or knives which are not adequately cleaned after preparing raw meat.

Examples of foodstuffs which are often contaminated with *Campylobacter* are insufficiently cooked poultry meat and poultry products, unpasteurized milk or unpasteurized milk products, mince which has not been thoroughly cooked or fresh raw sausages such as smoked sausage, and contaminated drinking water, for example from a well system.

Enterohaemorrhagic *Escherichia coli* (EHEC) is in the gut of ruminants such as cattle, sheep, goats or deer. The bacteria are expelled with the faeces of infected animals. Because EHEC are relatively insensitive, they can survive in the environment for weeks. They are still highly infectious and even a small amount of pathogens is sufficient for transmission. The coats of cattle and other ruminants can be contaminated with traces of faeces. By touching and stroking the animals, the bacteria can reach the hands and from there get into the mouth. Even playing in meadows where ruminants have been kept runs the risk of infection for children.

By using the method in accordance with the invention, surfaces of shoes, for example soles, can easily be decontaminated photodynamically.

Furthermore, the inventors have discovered that the method in accordance with the invention is also suitable for the photodynamic decontamination of the surfaces of animal products such as coats, leather, hair, fibres or wool.

As an example, because of poor hand hygiene, the EHEC bacteria may remain on articles which are touched and be spread further from there.

Transfer to human beings can also occur by means of foodstuffs which are eaten raw or have been heated insufficiently. Examples of foodstuffs which are often contaminated with EHEC are unpasteurized milk and unpasteurized milk products, raw or insufficiently cooked meat products such as, for example, ground beef (for example hamburgers) and spreadable raw sausages, for example teewurst. Vegetable foodstuffs are also often contaminated with EHEC, for example vegetables which are contaminated with the pathogens by fertilization or contaminated water, unpasteurized fruit juices which are produced from contaminated fruit, seeds which are used to cultivate shoots, and all foods onto which the pathogens from contaminated foodstuffs can be transferred directly or indirectly by dirty hands or cooking utensils.

*Clostridium difficile* is for example, a bacterium which occurs globally. In healthy people, *Clostridium difficile* is a harmless gut bacterium. If competing types of normal gut flora are suppressed by antibiotics, *Clostridium difficile* can multiply and produce toxins which under some circumstances can lead to life-threatening diarrhoea, for example antibiotic-associated colitis, in particular if an antibiotic-associated diarrohea has already occurred.

*Clostridium difficile* is one of the most common hospital pathogens (nosocomial pathogen). Furthermore, *Clostridium difficile* can form resistant permanent forms, what are known as spores, by means of which, under certain circumstances, the bacteria can survive for years outside the gastro-intestinal tract. Thus, it is also possible to transmit it via articles and surfaces such as, for example, toilets, door handles, handles and/or hand rails to which the pathogens adhere.

The problems described above can be avoided by using the method in accordance with the invention, because disease-causing pathogens on contaminated surfaces are effectively removed after using the method in accordance with the invention.

In a further preferred embodiment, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a), and/or respective pharmacologically acceptable salts and/or esters and/or complexes thereof is used for the inactivation of microorganisms in an area, for example a clean room or an operating theatre. After introduction into the area, for example by misting, spraying, injection or evaporation, the area can be irradiated with a suitable source of radiation which produces electromagnetic radiation of a suitable wavelength and energy density, whereupon the microorganisms present are inactivated.

In a further preferred embodiment, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a), and/or respective pharmacologically acceptable salts and/or esters and/or complexes thereof, is used for the inactivation of microorganisms in a fluid or fluid preparation. Examples of suitable fluids or fluid preparations are emulsion paints, coolants, cooling lubricants, lubricants, brake fluids, paints, adhesives or oils. Preferably, the fluid preparation is an aqueous preparation.

Preferably, the fluid is water.

In this regard, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof can be used for the preparation of water for the beverage and foodstuff industry, the pharmaceuticals, chemicals and cosmetics industry, and the electrical industry. Furthermore, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof can be used for drinking water and rain water preparation, for the treatment of waste water or for the preparation of water for use in air conditioning technology.

In this preferred use of the at least one 1,7-diaryl-1,6-heptadiene-3,5-dione derivative for use in accordance with the invention with formula (100) and/or with formula (101)

and/or with formula (102), and/or of the at least one inventive 1,7-diaryl-1,6-heptadiene-3,5-dione derivative with formula (1) and/or with formula (2) and/or with formula (3) and/or with formula (3a) and/or respective pharmacologically acceptable salts and/or esters and/or complexes thereof, the fluid or fluid preparation can subsequently be irradiated with a suitable source of radiation which produces electromagnetic radiation of a suitable wavelength and energy density. Preferably, the at least one 1,7-diaryl-1,6-heptadiene-3,5-dione derivative for use in accordance with the invention with formula (100) and/or with formula (101) and/or with formula (102), and/or the at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof carries out a "self-disinfection" of the fluid or of the fluid preparation during the irradiation.

In a further preferred use of at least one 1,7-diaryl-1,6-heptadiene-3,5-dione derivative for use in accordance with the invention with formula (100) and/or with formula (101) and/or with formula (102), and/or of the at least one inventive 1,7-diaryl-1,6-heptadiene-3,5-dione derivative with formula (1) and/or with formula (2) and/or with formula (3) and/or with formula (3a) and/or respective pharmacologically acceptable salts and/or esters and/or complexes thereof, the 1,7-diaryl-1,6-heptadiene-3,5-dione derivative for use in accordance with the invention with formula (100) and/or with formula (101) and/or with formula (102), and/or the 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof may be affixed to a solid support and thus be used as a part of a solid matrix.

Particularly preferably, at least one 1,7-diaryl-1,6-heptadiene-3,5-dione derivative for use in accordance with the invention with formula (100) and/or with formula (101) and/or with formula (102) which is fixed on a solid support, and/or at least one inventive 1,7-diaryl-1,6-heptadiene-3,5-dione derivative with formula (1) and/or with formula (2) and/or with formula (3) and/or with formula (3a) which is fixed on a solid support and/or respective pharmacologically acceptable salts and/or esters and/or complexes thereof is introduced into the fluid to be treated, preferably water or blood.

Particularly preferably, the support is a polymer which carries the at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof in a covalently bound manner. This composition comprising the support and at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof, develops an antimicrobial activity as soon as it is exposed to the electromagnetic radiation of a suitable wavelength and energy density.

Furthermore, the present invention concerns a coated article which contains or is coated with at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof. Preferably, the article contains at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof and/or is coated therewith.

Preferably, the surface of the coated article is provided with at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof.

More preferably, the surface of the coated article is provided with at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof.

The coated article may subsequently be irradiated with a suitable source of radiation which produces electromagnetic radiation of a suitable wavelength and energy density. Preferably, the 1,7-diaryl-1,6-heptadiene-3,5-dione derivative for use in accordance with the invention with formula (100) and/or with formula (101) and/or with formula (102), and/or the 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof carries out a "self-disinfection" of the surface of the coated article during the irradiation.

In this regard, the irradiation may be carried out directly after treating the coated article with at least one 1,7-diaryl-1,6-heptadiene-3,5-dione derivative to be used in accordance with the invention with formula (100) and/or with formula (101) and/or with formula (102) and/or with at least one inventive 1,7-diaryl-1,6-heptadiene-3,5-dione derivative with formula (1) and/or with formula (2) and/or with formula (3) and/or with formula (3a) and/or respective pharmacologically acceptable salts and/or esters and/or complexes thereof, preferably after applying the at least one 1,7-diaryl-1,6-heptadiene-3,5-dione derivative for use in accordance with the invention with formula (100) and/or with formula (101) and/or with formula (102), and/or the at least one inventive 1,7-diaryl-1,6-heptadiene-3,5-dione derivative with formula (1) and/or with formula (2) and/or with formula (3) and/or with formula (3a) and/or respective pharmacologically acceptable salts and/or esters and/or complexes thereof onto the surface of the coated article and/or introducing the at least one 1,7-diaryl-1,6-heptadiene-3,5-dione derivative for use in accordance with the invention with formula (100) and/or with formula (101) and/or with formula (102), and/or the at least one inventive 1,7-diaryl-1,6-heptadiene-3,5-dione derivative with formula (1) and/or with formula (2) and/or with formula (3) and/or with formula (3a) and/or respective pharmacologically acceptable salts and/or esters and/or complexes thereof onto the surface of the coated article, and/or at a later point in time, preferably before or during use of the coated article.

Examples of suitable articles are medical products, foodstuff packaging, hygiene articles, textiles, handles, hand rails, contact lenses, building materials, banknotes, coins, gaming chips, cards, sports equipment, textiles, crockery, cutlery or electronic devices.

Further suitable articles are devices or units with water-carrying lines and/or water-carrying containers in which, for example during operation of the device or the unit, condensed water is formed.

Examples of suitable articles are seals, membranes, screens, filters, containers and/or pipes for hot water producing units, hot water distribution units, heat exchangers, air conditioning units, air humidifiers, chillers, refrigerators, drinks dispensers, washing machines or dryers.

As an example, small quantities of microorganisms, despite filtration of the air fed in from outside, can gain ingress into an air conditioning unit and exist there at least for a short period. The metabolic products from these microorganisms could give rise to stale and musty odours.

Furthermore, in order to operate an air conditioning unit, moisture has to be removed from the air and trapped. A large proportion of the condensed water is removed and, for example, runs through a condensed water line. However, residual dampness remains on the surface of the evaporator of the air conditioning unit, in particular when the air conditioning unit is only switched off in a passenger vehicle when the engine is switched off and the temperature can no longer be equilibrated.

The microorganisms which reach the evaporator from the air, for example fungal spores and/or bacteria, now find themselves in an ideal warm, moist climate and can proliferate unchecked.

Since moulds, for example, constitute a risk to health, the air conditioning unit should be decontaminated regularly and any microorganisms present should be eradicated by carrying out the method in accordance with the invention.

When changing the filter of the air conditioning unit, for example the dust and/or pollen filter, again, the filter housing and the surrounding air ducts of the air conditioning unit can be cleaned by using the method in accordance with the invention. By cleaning the evaporator of the air conditioning unit using the method in accordance with the invention, odours which arise in the air conditioning unit can also be removed.

*Legionella* bacteria are, for example, bacteria which cause different symptoms in human beings, for example flu-like symptoms or severe lung infections. *Legionella* bacteria preferably multiply at temperatures between 25° C. and 45° C. Particularly in artificial water systems such as water pipes in buildings, the pathogens find good conditions for growth because of the prevailing temperatures. *Legionella* bacteria can also multiply well in sediments and/or linings of a piping system. Thus, the method in accordance with the invention, for example in combination with a method for removing sediments and/or linings, could be used.

*Legionella* bacteria are transmitted by atomized, cloudy water. The droplets containing the pathogens can be distributed in the air and breathed in. Examples of possible sources of infection are hot water supplies, in particular showers, air humidifiers or water taps, as well as cooling towers or air conditioning units or other units which atomize water into water droplets, for example misters, mist fountains, water features or the like. Transfer is also possible in swimming baths via waterfalls, slides, whirlpools and/or fountains. Infection with *Legionella* bacteria is prevented by using the method in accordance with the invention on surfaces of contaminated articles.

The method in accordance with the invention may, for example, be used in equipment or units with water-supplying lines and/or water-supplying containers, for example equipment or units which are used in fish farming.

Epidemic-like diseases of fish are an example of a huge economic threat for all intensively operated fish farms where farmed fish are kept in confined spaces. In order to combat the fish diseases, antibiotics and/or chemical additives are added, for example. Examples of chemical additives which are used are calcium hydroxide, hydrogen peroxide, peracetic acid preparations, copper sulphate, chloramines, sodium carbonate, sodium chloride or formaldehyde.

In order to reduce the use of antibiotics and/or the chemical additives mentioned above, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof may be used for the photodynamic decontamination of equipment or units in fish farming, for example fish ponds, pools, pumps, filters, pipes, nets, hooks or mats. Similarly, fish and/or fish eggs could be photodynamically decontaminated.

Similarly, terraria, aquarium containers, sand, gravel and/or green plants could be photodynamically decontaminated before and/or during their use.

Examples of suitable electronic equipment include hot plates, remote controls, headphones, hands-free modules, headsets, mobile telephones, or control elements such as buttons, switches, touch screens or keys.

Examples of suitable building materials include concrete, glass, sand, gravel, wall claddings, plaster, screed or the like.

Examples of suitable wall claddings include wood panelling, tiles, solid wood panels, medium density fibreboard, plywood panels, multiplex board, fibre-reinforced concrete panels, plasterboard, gypsum fibreboard, and plastic, foam or cellulose wallpapers.

As an example, at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respectively a pharmacologically acceptable salt and/or ester and/or complex thereof may be used to remove mould.

Preferably, a surface coated with mould is treated with at least one 1,7-diaryl-1,6-heptadiene-3,5-dione derivative to be used in accordance with the invention with formula (100) and/or with formula (101) and/or with formula (102) and/or at least one inventive 1,7-diaryl-1,6-heptadiene-3,5-dione derivative with formula (1) and/or with formula (2) and/or with formula (3) and/or with formula (3a) and/or respective pharmacologically acceptable salts and/or esters and/or complexes thereof and subsequently irradiated with a suitable source of radiation which produces electromagnetic radiation of a suitable wavelength and energy density, whereupon a reduction, preferably inactivation, in the mould occurs on the treated surface.

In a further preferred embodiment, particles coated with at least one 1,7-diaryl-1,6-heptadiene-3,5-dione derivative to be used in accordance with the invention with formula (100) and/or with formula (101) and/or with formula (102) and/or at least one inventive 1,7-diaryl-1,6-heptadiene-3,5-dione derivative with formula (1) and/or with formula (2) and/or with formula (3) and/or with formula (3a) and/or respective pharmacologically acceptable salts and/or esters and/or complexes thereof, for example inorganic or organic particles, constitute the coated article.

More preferably, the particles comprise at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respectively a pharmacologically acceptable salt and/or ester and/or complex thereof, which is covalently bonded to the particles.

In the said preferred embodiment of the use in accordance with the invention or of the method in accordance with the invention, the irradiation of the microorganisms and of the at least one 1,7-diaryl-1,6-heptadiene-3,5-dione derivative for use in accordance with the invention with formula (100) and/or with formula (101) and/or with formula (102) and/or at least one 1,7-diaryl-1,6-heptadiene-3,5-dione derivative in accordance with the invention with formula (1) and/or with formula (2) and/or with formula (3) and/or with formula (3a) and/or respectively a pharmacologically acceptable salt and/or ester and/or complex thereof with electromagnetic radiation of a suitable wavelength and energy density is carried out in the presence of at least one oxygen-donating compound, preferably peroxide, and/or at least one oxygen-containing gas, preferably oxygen.

The at least one oxygen-donating compound and/or the at least one oxygen-containing gas may preferably be applied before or during the irradiation with electromagnetic radiation of a suitable wavelength and energy density.

By additionally providing oxygen in the form of at least one oxygen-containing compound and/or at least one oxygen-containing gas before or during the irradiation of the microorganisms and of the at least one photosensitizer with electromagnetic radiation of a suitable wavelength and energy density, the yield of reactive oxygen species (ROS), preferably oxygen radicals and/or singlet oxygen, is increased.

In accordance with the invention, at least one 1,7-diaryl-1,6-heptadiene-3,5-dione derivative in accordance with the invention with formula (1) and/or with formula (2) and/or with formula (3) and/or with formula (3a) and/or respective pharmacologically acceptable salts and/or esters and/or complexes thereof may be used as a medication.

The said pharmacologically acceptable complexes are preferably inclusion complexes of the at least one 1,7-diaryl-1,6-heptadiene-3,5-dione derivative for use in accordance with the invention with formula (100) and/or with formula (101) and/or with formula (102), and/or of the at least one inventive 1,7-diaryl-1,6-heptadiene-3,5-dione derivative with formula (1) and/or with formula (2) and/or with formula (3) and/or with formula (3a), preferably of the at least one inventive 1,7-diaryl-1,6-heptadiene-3,5-dione derivative with formula (1) and/or with formula (2) and/or with formula (3) and/or with formula (3a), with polyvinylpyrrolidone (PVP), cyclodextrins or mixtures thereof.

A suitable method for the production of inclusion complexes of the corresponding 1,7-diaryl-1,6-heptadiene-3,5-dione derivatives is described, for example, in: S. Winter, N. Tortik, A. Kubin, B. Krammer, K. Plaetzer, Back to the roots: photodynamic inactivation of bacteria based on water-soluble curcumin bound to polyvinylpyrrolidone as a photosensitizer, Photochem. Photobiol. Sci., 2013, 12, 1795-1802. DOI: 10.1039/C3PP50095K.

The invention will now be illustrated by the following non-limiting figures and examples.

BRIEF DESCRIPTION OF THE DRAWINGS

FIG. 21 shows the result of the phototoxicity test using SACUR-01a against *E. coli* ATCC 25922 (left) and against *S. aureus* ATCC 25923 (right).

FIG. 22 shows the result of the phototoxicity test using SACUR-03 against *E. coli* ATCC 25922 (left) and against *S. aureus* ATCC 25923 (right).

FIG. 23 shows the result of the phototoxicity test using SACUR-07 against *E. coli* ATCC 25922 (left) and against *S. aureus* ATCC 25923 (right).

FIG. 24 shows the result of the phototoxicity test using SACUR-01a BF2 against *S. aureus* ATCC 25923.

FIG. 25 shows the result of the phototoxicity test using SACUR-09a against *S. aureus* ATCC 25923.

FIG. 26 shows the result of the phototoxicity test using SACUR-11a against *S. aureus* ATCC 25923.

FIG. 27 shows the result of the phototoxicity test using SACUR-11c against *S. aureus* ATCC 25923.

FIG. 28 shows the result of the phototoxicity test using SACUR-12b against *S. aureus* ATCC 25923.

FIG. 29 shows the result of the phototoxicity test using SACUR-13a against *S. aureus* ATCC 25923.

FIG. 30 shows the result of the phototoxicity test using SACUR-13c against *S. aureus* ATCC 25923.

FIG. 31 shows the result of the phototoxicity test using SACUR-14a against *S. aureus* ATCC 25923.

FIG. 32 shows the result of the phototoxicity test using SACUR-15a against *S. aureus* ATCC 25923.

FIG. 33 shows the result of the phototoxicity test using SACUR-15b against *S. aureus* ATCC 25923.

EXAMPLES

Figure 1:
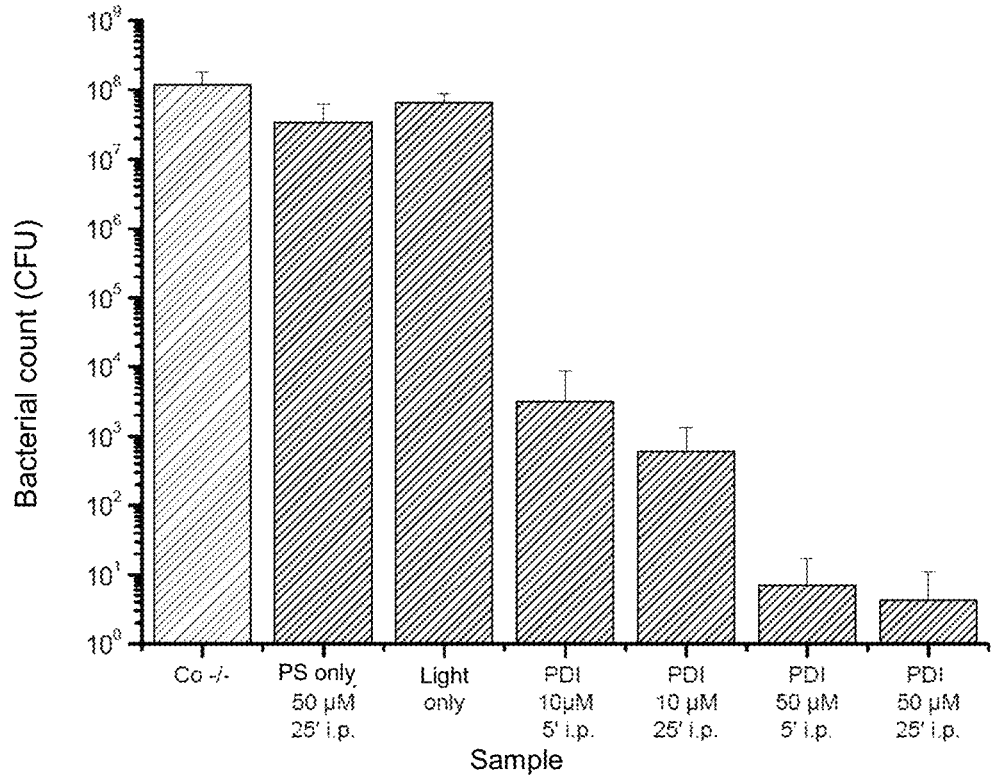
FIG. 1 shows the photodynamic inactivation (PDI) of *E. coli* by SACUR-0 hydrochloride compared with the controls (no light, no PS).

Example 1) Production of Various 1,7-diaryl-1,6-heptadiene-3,5-dione Derivatives Overview of the Syntheses All of the chemicals were purchased from conventional suppliers (TCI, ABCR, Acros, Merck and Fluka) and used without further purification. The solvents were distilled before use and if required, were dried in the normal manner. Dry DMF was purchased from Fluka (Taufkirchen, DE).

Thin film chromatography was carried out on thin film aluminium foils coated with silica gel 60 F254, from Merck (Darmstadt, DE). Preparative thin film chromatography was carried out on commercially available glass plates coated with silica gel 60 (20 cm×20 cm, Carl Roth GmbH & Co. KG, Karlsruhe, DE). The compounds were detected with UV light (λ=254 nm, 333 nm) and some detected with the naked eye or stained with ninhydrin. The chromatography was carried out with silica gel (0.060-0.200) from Acros (Waltham, US). NMR spectra were recorded on a Bruker Avance 300 spectrometer (300 MHz [$^1$H-NMR], 75 MHz [$^{13}$C-NMR]) (Bruker Corporation, Billerica, US).

All of the chemical displacements are given in δ [ppm] relative to an external standard (tetramethylsilane, TMS).

The coupling constants are respectively given in Hz; Characterization of the signals: s=singlet, d=doublet, t=triplet, m=multiplet, dd=doublet of doublets, br=broad. Integration determined the relative number of atoms. The definitive identification of the signals in the carbon spectra was carried out using the DEPT method (pulse angle: 135°). Error limits: 0.01 ppm for $^1$H-NMR, 0.1 ppm for $^{13}$C-NMR and 0.1 Hz for coupling constants. The solvent used is noted for each spectrum.

The IR spectra were recorded on a Biorad Excalibur FTS 3000 spectrometer (Bio-Rad Laboratories GmbH, Munich, DE).

ES-MS was measured using a ThermoQuest Finnigan TSQ 7000 spectrometer, all of the HR-MS were determined on a ThermoQuest Finnigan MAT 95 (respectively Thermo Fisher Scientific Inc, Waltham, US) spectrometer; argon was used as the ionization gas for FAB.

The melting points were determined with the aid of the Büchi SMP-20 melting point instrument (Büchi Labortechnik GmbH, Essen, DE) using a glass capillary.

All of the UV/VIS spectra were recorded using a Varian Cary 50 Bio UV/VIS spectrometer; the fluorescence spectra were recorded with a Varian Cary Eclipse spectrometer.

The solvents for absorption and emission measurements were purchased in special spectroscopic purity grade from Acros or Baker, or Uvasol from Merck. Millipore water (18 MO, Milli $Q_{plus}$) was used for all of the measurements.

1. Synthesis of Aldehyde Components

The educts and alkylation agents listed in Table 1 were obtained commercially.

The alkylation agents used were the corresponding alkyl bromides or alkyl tosylates.

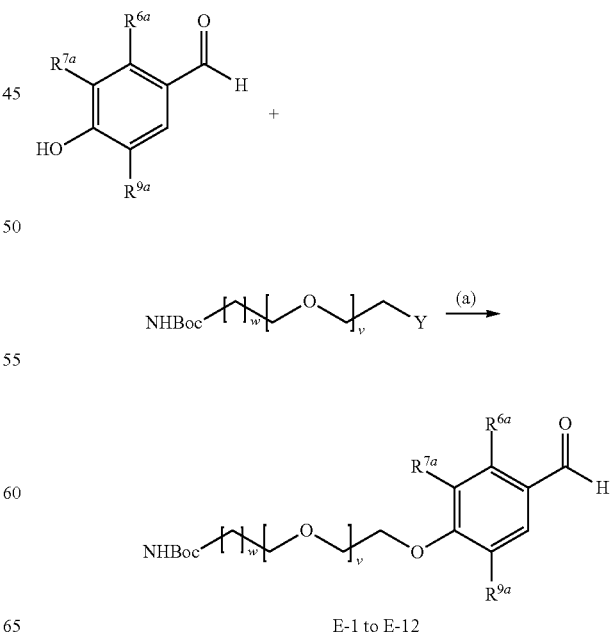

E-1 to E-12

TABLE 1

Synthesis of aldehyde components: Conditions: (a) $K_2CO_3$, KI, DMF or DMSO, T = 60-80° C.

| Example | Educt | | | Alkylation agent | | | Product | | | | | Yield |
|---|---|---|---|---|---|---|---|---|---|---|---|---|
| | $R^{6a}=$ | $R^{7a}=$ | $R^{9a}=$ | w | v | Y | $R^{6a}=$ | $R^{7a}=$ | $R^{9a}=$ | w | v | |
| E-1 | H | H | H | 1 | 0 | Br | H | H | H | 1 | 0 | 76% |
| E-2 | H | Me | H | 1 | 0 | Br | H | Me | H | 1 | 0 | 73% |
| E-3 | H | OMe | H | 1 | 0 | Br | H | OMe | H | 1 | 0 | 79% |
| E-4 | OMe | H | H | 1 | 0 | Br | OMe | H | H | 1 | 0 | 71% |
| E-5 | H | OMe | I | 1 | 0 | Br | H | OMe | I | 1 | 0 | 66% |
| E-6 | H | OMe | H | 1 | 1 | TsO | H | OMe | H | 1 | 1 | 72% |
| E-7 | H | OBz | H | 2 | 0 | Br | H | OBz | H | 2 | 0 | 82% |
| E-8 | H | OH | H | 1 | 0 | Br | H | OH | H | 1 | 0 | 17% |
| E-9 | H | OH | H | 1 | 0 | Br | H | $OC_8H_{17}$ | H | 1 | 0 | 39% (2 steps) |
| E-10 | H | OH | H | 1 | 0 | Br | H | $O(CH_2CH_2)_3OH$ | H | 1 | 0 | 33% (2 steps) |
| E-11 | H | OH | H | 1 | 0 | Br | H | $OCH_2CH_2NHBoc$ | H | 1 | 0 | 69% |
| E-12 | H | OH | OH | 1 | 0 | Br | H | $OCH_2CH_2NHBoc$ | $OCH_2CH_2NHBoc$ | 1 | 0 | 61% |

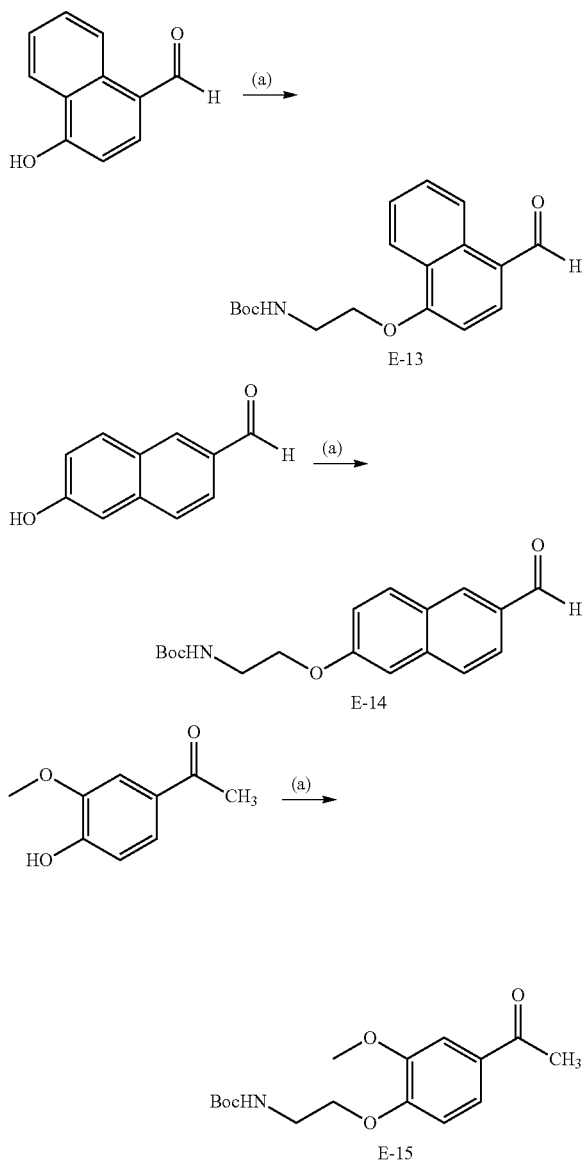

Overview 2: Synthesis of further aldehyde components: Conditions: (a) $K_2CO_3$, KI, DMF or DMSO, T=60-80° C.

1.1 Substituted Vanillins 1.1.1 General Procedure:

10 mmol of the appropriate educt was placed under nitrogen in 20 mL of DMF:

(I) 4-hydroxybenzaldehyde (1.22 g, 10 mmol)
(II) vanillin (1.52 g, 10 mmol)
(III) benzyloxyvanillin (2.28 g, 10 mmol)
(IV) 6-hydroxy-2-naphthaldehyde (1.72 g, 10 mmol)
(V) 4-hydroxy-3-methoxy-acetophenone (1.66 g, 10 mmol)

The corresponding alkylation reagent (12-15 mmol, 1.2-1.5 eq) in DMF (10 mL) and $K_2CO_3$ (2.76 g, 20 mmol) were added one after the other. The formulation was stirred under a nitrogen atmosphere for 24 h at 80° C. After cooling to room temperature, the reaction mixture was diluted with 60 mL ethyl acetate and the organic phase was shaken three times, each time with 40 mL of saturated aqueous sodium chloride solution, and once with 50 mL of water. The organic phase was separated, dried over $MgSO_4$ and rotary evaporated.

In order to purify the product, column chromatography was carried out on silica gel.

E-1: 4-(2-N-tert-butyloxycarbonyl-aminoethoxy) benzaldehyde

Educt: 4-hydroxybenzaldehyde.

The alkylation reagent used was 2-(tert-butoxycarbonylamino)ethyl bromide (3.34 g, 15 mmol).

Yield: 76% of theory, 2.5 g of pale yellow solid

Molecular mass=265.30 g/mol; Empirical formula=$C_{14}H_{19}NO_4$

¹H NMR (300 MHz, CDCl₃), δ=9.87 (s, 1H), 7.82 (d, J=8.8 Hz, 2H), 6.98 (d, J=8.7 Hz, 2H), 5.05 (s, 1H), 4.09 (t, J=5.2 Hz, 2H), 3.55 (dd, J=10.4, 5.1 Hz, 2H), 1.44 (s, 9H). MS (ESI, CH₂Cl₂/MeOH+10 mmol NH₄OAc): 288.1 (17%, MNa⁺), 265.1 (1%, MH⁺), 210.1 (100%, MH⁺—C₄H₉), 166.1 (19%, MH⁺-boc)

E-3: 3-methoxy-4-(2-N-tert-butyloxycarbonyl-aminoethoxy)benzaldehyde

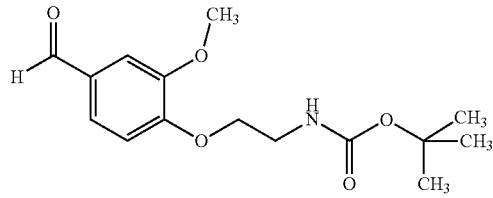 [SMILES: COc1cc(C=O)ccc1OCCNC(=O)OC(C)(C)C]

Educt: vanillin (4-hydroxy-3-methoxybenzaldehyde).

The alkylation reagent used was 2-(tert-butoxycarbonylamino)ethylbromide (3.34 g, 15 mmol).

Yield: 79% of theory, 2.54 g of pale yellow solid
Molecular mass=295.34 g/mol; Empirical formula=$C_{15}H_{21}NO_5$ ¹H NMR: (300 MHz, CDCl₃), δ=9.85 (s, 1H), 7.43 (d, J=1.8 Hz, 1H), 7.42 (m, 1H), 6.98 (d, J=8.0 Hz, 1H), 5.10 (s, 1H), 4.15 (t, J=5.1 Hz, 2H), 3.92 (s, 3H), 3.60 (dd, J=10.6, 5.3 Hz, 2H), 1.44 (s, 9H). MS: (ESI, CH₂Cl₂/MeOH+10 mmol NH₄OAc): 318.1 (13%, MNa⁺), 296.1 (100%, MH⁺), 240.1 (45%, MH⁺—C₄H₉), 196.1 (9%, MH⁺-boc).

E-15: 3-methoxy-4-(2-N-tert-butyloxycarbonyl-aminoethoxy)acetophenone

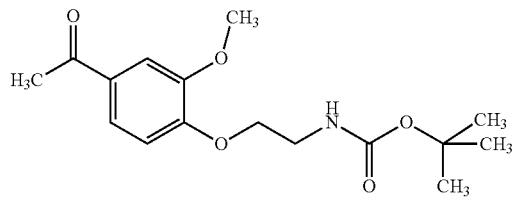 [SMILES: COc1cc(C(C)=O)ccc1OCCNC(=O)OC(C)(C)C]

Production as described in A.1).

Educt: 4-hydroxy-3-methoxyacetophenone (acetovanillone).

The alkylation reagent used was 2-(tert-butoxycarbonylamino)ethyl bromide (3.34 g, 15 mmol).

Yield: 77% of theory, 2.75 g of pale yellow solid
Molecular mass=309.36 g/mol; Empirical formula=$C_{16}H_{23}NO_5$ ¹H NMR: (300 MHz, CDCl₃), δ=7.51 (d, J=1.9 Hz, 1H), 7.49 (s, 1H), 6.94 (d, J=7.9 Hz, 1H), 5.19 (s, 1H), 4.12 (t, J=5.1 Hz, 2H), 3.89 (s, 3H), 3.58 (q, J=5.3 Hz, 2H), 2.52 (s, 3H), 1.43 (s, 9H). MS: (ESI, CH₂Cl₂/MeOH+10 mmol NH₄OAc): 332.1 (29%, MNa⁺), 309.1 (2%, MH⁺), 254.1 (33%, MH⁺—C₄H₉), 210.1 (100%, MH⁺-boc).

E-14: 6-(2-N-tert-butyloxycarbonyl-aminoethoxy)naphthalene-2-carbaldehyde

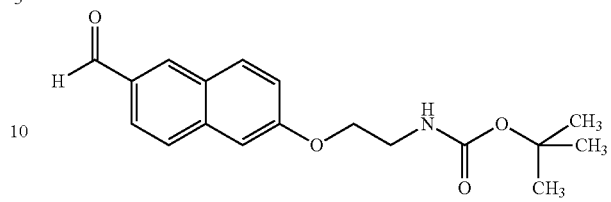

Educt: 6-hydroxy-2-naphthaldehyde.

The alkylation reagent used was 2-(tert-butoxycarbonylamino)ethylbromide (3.34 g, 15 mmol).

Yield: 71% of theory, 2.30 g of pale yellow solid
Molecular mass=315.37 g/mol; Empirical formula=$C_{18}H_{21}NO_4$ ¹H NMR: (300 MHz, CDCl₃), δ=10.09 (s, 1H), 8.25 (s, 1H), 7.94-7.85 (m, 2H), 7.79 (d, J=8.5 Hz, 1H), 7.23 (dd, J=8.9, 2.5 Hz, 1H), 7.17 (d, J=2.3 Hz, 1H), 5.05 (s, 1H), 4.18 (t, J=5.1 Hz, 2H), 3.62 (dd, J=10.5, 5.3 Hz, 2H), 1.46 (s, 9H). MS: (ESI, CH₂Cl₂/MeOH+10 mmol NH₄OAc): 338.2 (11%, MNa⁺), 316.2 (12%, MH⁺), 260.1 (100%, MH⁺—C₄H₉), 216.1 (14%, MH⁺-boc)

E-7: 3-benzyloxy-4-(2-N-tert-butyloxycarbonyl-aminopropyloxy)benzaldehyde

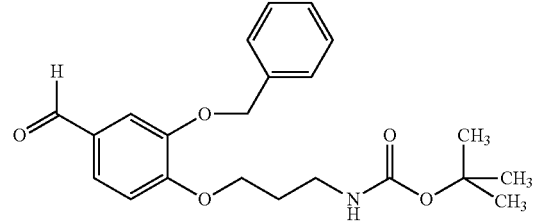 [SMILES: CC(C)(C)OC(=O)NCCCOc1ccc(C=O)cc1OCc1ccccc1]

Educt: benzyloxyvanillin (4-benzyloxy-3-methoxybenzaldehyde).

The alkylation reagent used was 2-(tert-butoxycarbonylamino)propyl bromide (3.34 g, 15 mmol).

Yield: 82% of theory, 2.64 g of pale yellow solid
Molecular mass=385.45 g/mol; Empirical formula=$C_{22}H_{27}NO_5$ ¹H NMR: (300 MHz, CDCl₃), δ=9.74 (s, 1H), 7.44-7.16 (m, 7H), 6.91 (dd, J=8.1, 1.4 Hz, 1H), 5.47 (s, 1H), 5.21 (m, 2H), 4.08 (td, J=5.6, 2.2 Hz, 2H), 3.33 (d, J=5.2 Hz, 2H), 2.03-1.92 (m, 2H), 1.36 (s, 9H). MS: (ESI, CH₂Cl₂/MeOH+10 mmol NH₄OAc): 408.2 (37%, MNa⁺), 386.1 (2%, MH⁺), 330.1 (63%, MH⁺—C₄H₉), 286.1 (100%, MH⁺-boc).

E-6: 3-methoxy-4-(2-N-tert-butyloxycarbonyl-aminoethoxy-ethoxy)benzaldehyde

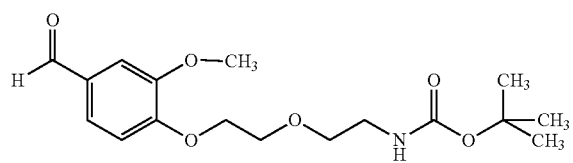 [SMILES: COc1cc(C=O)ccc1OCCOCCNC(=O)OC(C)(C)C]

Educt: vanillin (4-hydroxy-3-methoxybenzaldehyde).

The alkylation reagent used was 2-[2-(tert-butoxycarbonylamino)ethoxy]ethyl-4-methyl benzenesulphonate (4.26 g, 12 mmol).

Yield: 72% of theory; 2.78 g of pale yellow solid

Molecular mass=339.39 g/mol; Empirical formula=$C_{17}H_{25}NO_6$ $^1$H NMR: (300 MHz, CDCl$_3$), δ=9.76 (s, 1H), 7.42-7.26 (m, 2H), 6.92 (d, J=8.1 Hz, 1H), 5.08 (s, 1H), 4.21-4.12 (m, 2H), 3.86-3.78 (m, 2H), 3.84 (s, 3H), 3.54 (dd, J=7.4, 2.6 Hz, 2H), 3.26 (m, 2H), 1.35 (s, 9H). MS: (ESI, CH$_2$Cl$_2$/MeOH+ 10 mmol NH$_4$OAc): 356.9 (100%, MNH$_4^+$), 339.9 (41%, MH$^+$), 239.9 (6%, MH$^+$-boc).

1.1.2 General Procedure:

15 mmol of the appropriate educt was placed under nitrogen in 10 mL of DMF:

(VI) 4-hydroxy-3-methyl-benzaldehyde (2.04 g, 15 mmol)

(VII) 4-hydroxy-2-methoxy-benzaldehyde (2.28 g, 15 mmol)

The corresponding alkylation reagent (12-15 mmol, 1.2-1.5 eq) in DMF (20 mL) and K$_2$CO$_3$ (4.14 g, 30 mmol) were added one after the other. The formulation was stirred under a nitrogen atmosphere for 24 h at 80° C. After cooling to room temperature, the reaction mixture was diluted with 120 mL ethyl acetate and the organic phase was shaken three times, each time with 40 mL of saturated aqueous sodium chloride solution, and once with 40 mL of water. The organic phase was separated, dried over MgSO$_4$ and rotary evaporated. In order to purify the product, column chromatography was carried out on silica gel.

E-2: 3-methyl-4-(2-N-tert-butyloxycarbonyl-aminoethoxy)benzaldehyde

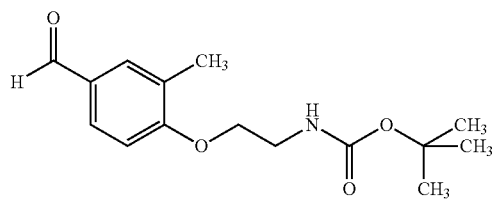

Educt: 4-hydroxy-3-methyl-benzaldehyde.

The alkylation reagent used was 2-(tert-butoxycarbonylamino)ethyl bromide (5.02 g, 22.5 mmol).

Yield: 73% of theory, 3.44 g yellowish solid

Molecular mass=279.34 g/mol; Empirical formula=$C_{15}H_{21}NO_4$ $^1$H NMR: (300 MHz, CDCl$_3$), δ=9.85 (s, 1H), 7.75-7.66 (m, 2H), 6.90 (d, J=8.9 Hz, 1H), 4.95 (s, 1H), 4.11 (t, J=5.2 Hz, 2H), 3.59 (m, 2H), 2.27 (s, 3H), 1.45 (s, 9H). MS: (ESI, CH$_2$Cl$_2$/MeOH+10 mmol NH$_4$OAc): 302.1 (11%, MNa$^+$), 280.1 (9%, MH$^+$), 224.1 (100%, MH$^+$—C$_4$H$_9$), 180.1 (4%, MH$^+$-boc).

E-4: 2-methoxy-4-(2-N-tert-butyloxycarbonyl-aminoethoxy)benzaldehyde

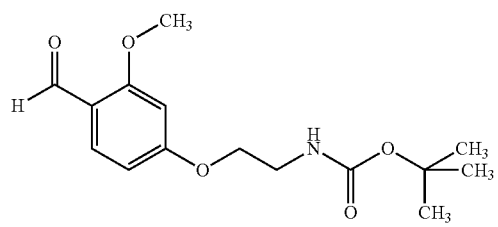 [SMILES: COc1cc(OCCNC(=O)OC(C)(C)C)ccc1C=O]

Educt: 4-hydroxy-2-methoxy-benzaldehyde.

The alkylation reagent used was 2-(tert-butoxycarbonylamino)ethyl bromide (5.02 g, 22.5 mmol).

Yield: 71% of theory, 3.94 g of pale yellow solid

Molecular mass=295.34 g/mol; Empirical formula=$C_{15}H_{21}NO_5$ $^1$H NMR: (300 MHz, CDCl$_3$), δ=10.25 (d, J=1.2 Hz, 1H), 7.76 (dd, J=8.6, 1.5 Hz, 1H), 6.58-6.46 (m, 1H), 6.44 (s, 1H), 5.06 (s, 1H), 4.07 (t, J=5.0 Hz, 2H), 3.87 (s, 3H), 3.53 (m, 2H), 1.43 (s, 9H). MS: (ESI, CH$_2$Cl$_2$/MeOH+10 mmol NH$_4$OAc): 318.1 (8%, MNa$^+$), 296.1 (100%, MH$^+$), 240.1 (87%, MH$^+$—C$_4$H$_9$), 196.1 (3%, MH$^+$-boc).

E-5: 3-methoxy-4-(2-N-tert-butyloxycarbonyl-aminoethoxy)-5-iodo-benzaldehyde

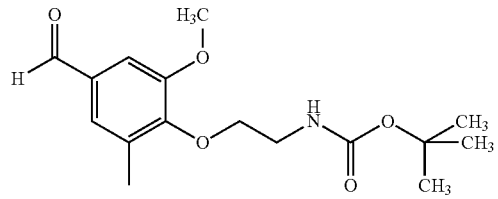 [SMILES: COc1cc(C=O)cc(C)c1OCCNC(=O)OC(C)(C)C]

5-Iodovanillin (4.17 g, 15 mmol) was placed under nitrogen in 10 mL of DMF.

The alkylation reagent used was 2-(tert-butoxycarbonylamino)ethyl bromide (5.02 g, 22.5 mmol) dissolved in 20 mL of DMF. The alkylation reagent and K$_2$CO$_3$ (4.14 g, 30 mmol) were added one after the other. The formulation was stirred under a nitrogen atmosphere for 24 h at 80° C. After cooling to room temperature, the reaction mixture was diluted with 120 mL ethyl acetate and the organic phase was shaken three times, each time with 40 mL of saturated aqueous sodium chloride solution, and once with 40 mL of water. The organic phase was separated, dried over MgSO$_4$ and rotary evaporated. In order to purify the product, column chromatography was carried out on silica gel.

Yield: 66% of theory, 3.07 g of yellow solid

Molecular mass=421.23 g/mol; Empirical formula=$C_{15}H_{20}INO_5$ $^1$H NMR: (300 MHz, CDCl$_3$), δ=9.82 (s, 1H), 7.84 (d, J=1.7 Hz, 1H), 7.39 (d, J=1.8 Hz, 1H), 5.40 (s, 1H), 4.17 (t, J=4.9 Hz, 2H), 3.91 (s, 3H), 3.52 (dd, J=10.3, 5.3 Hz, 2H), 1.45 (s, 9H). MS: (ESI, CH$_2$Cl$_2$/MeOH+10 mmol NH$_4$OAc): 444.1 (6%, MNa$^+$), 422.1 (3%, MH$^+$), 366.0 (63%, MH$^+$—C$_4$H$_9$), 322.0 (100%, MH$^+$-boc).

1.2 Multi-Substituted Aldehydes

The corresponding educt was placed under nitrogen in 10 mL of DMF:
(VIII) 3,4-dihydroxybenzaldehyde (3.45 g, 25 mmol)
(IX) 3,4,5-trihydroxybenzaldehyde (2.31 g, 15 mmol)

The alkylation reagent used was 2-(tert-butoxycarbonylamino)ethyl bromide (11.2 g, 50 mmol, 2 eq) dissolved in 30 mL of DMF. The alkylation reagent and $K_2CO_3$ (13.8 g, 100 mmol) were added one after the other. The formulation was stirred under a nitrogen atmosphere for 16 h at 80° C. A second portion of the alkylation reagent (50 mmol, 2 eq) in 20 mL of DMF was added and the formulation was stirred for a further 24 h at 80° C. After cooling to room temperature, the reaction mixture was diluted with 250 mL ethyl acetate and the organic phase was shaken three times, each time with 150 mL of saturated aqueous sodium chloride solution, and once with 100 mL of water. The organic phase was separated, dried over $MgSO_4$ and rotary evaporated. In order to purify the product, column chromatography was carried out on silica gel (Eluent: initially PE:EE=3:1, then PE:EE=3:2).

E-11: 3,4-bis-(2-N-tert-butyloxycarbonyl-aminoethoxy)benzaldehyde

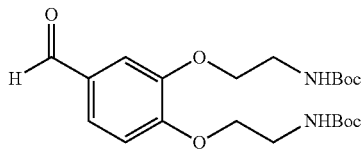 [SMILES: CC(C)(C)OC(=O)NCCOc1ccc(C=O)cc1OCCNC(=O)OC(C)(C)C]

Educt: 3,4-dihydroxybenzaldehyde
Yield: 8.1 g of pale yellow glass, 69% of theory
Molecular mass=424.50 g/mol; Empirical formula=$C_{21}H_{32}N_2O_7$
$^1$H NMR: (300 MHz, $CDCl_3$), δ=9.83 (s, 1H), 7.52-7.37 (m, 2H), 6.99 (d, J=8.2 Hz, 1H), 5.20 (s, 2H), 4.17-4.06 (m, 4H), 3.56 (m, 4H), 1.44 (s, 9H), 1.43 (s, 9H). MS: (ESI, $CH_2Cl_2$/MeOH+10 mmol $NH_4OAc$): 447.2 (100%, $MNa^+$), 425.2 (70%, $MH^+$), 369.2 (49%, $MH^+$—$C_4H_9$), 269.1 (78%, $MH^+$-boc).

E-12: 3,4,5-tris-(2-N-tert-butyloxycarbonyl-aminoethoxy)benzaldehyde

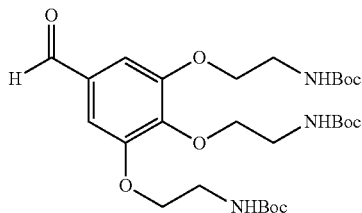 [SMILES: CC(C)(C)OC(=O)NCCOc1cc(C=O)cc(OCCNC(=O)OC(C)(C)C)c1OCCNC(=O)OC(C)(C)C]

Educt: 3,4,5-Trihydroxybenzaldehyde
Yield: 6.22 g pale yellow glass, 61% of theory
Molecular mass=583.68 g/mol; Empirical formula=$C_{28}H_{45}N_3O_{10}$
$^1$H NMR: (300 MHz, $CDCl_3$), δ=9.82 (s, 1H), 7.11 (s, 2H), 5.71 (s, 1H), 5.21 (s, 2H), 4.12 (t, J=4.6 Hz, 6H), 3.62-3.51 (m, 4H), 3.42 (d, J=4.9 Hz, 2H), 1.44 (d, J=8.7 Hz, 27H). MS: (ESI, $CH_2Cl_2$/MeOH+10 mmol $NH_4OAc$): 606.3 (47%, $MNa^+$), 584.3 (100%, $MH^+$), 528.3 (4%, $MH^+$—$C_4H_9$), 484.3 (23%, $MH^+$-boc).

1.3 Mixed Substituted Benzaldehydes

Step 1:

3,4-dihydroxybenzaldehyde (3.45 g, 25 mmol) was placed under nitrogen in 20 mL of DMF. 2-(tert-butoxycarbonylamino)ethyl bromide (6.72 g, 30 mmol) in 30 mL of DMF and $K_2CO_3$ (4.6 g, 33 mmol) were added one after the other. The formulation was stirred under a nitrogen atmosphere for 24 h at 80° C. After cooling to room temperature, the reaction mixture was diluted with 150 mL ethyl acetate and the organic phase was shaken three times, each time with 100 mL of saturated aqueous sodium chloride solution, and once with 100 mL of water. The organic phase was separated, dried over $MgSO_4$ and rotary evaporated. In order to purify the products, column chromatography was carried out on silica gel.

E-8: 3-hydroxy-4-(2-N-tert-butyloxycarbonyl-aminoethoxy)benzaldehyde

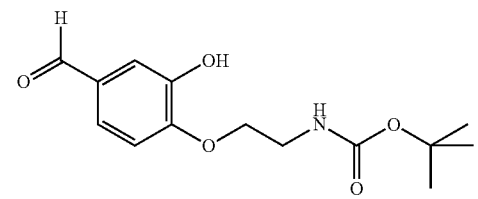 [SMILES: CC(C)(C)OC(=O)NCCOc1ccc(C=O)cc1O]

Yield: 1.48 g of pale yellow glass, 17% of theory
Molecular mass=281.31 g/mol; Empirical formula=$C_{14}H_{19}NO_5$
$^1$H NMR: (300 MHz, $CDCl_3$), δ=9.78 (s, 1H), 7.42 (d, J=1.9 Hz, 1H), 7.36 (dd, J=8.2, 1.9 Hz, 1H), 7.14 (s, 1H), 6.89 (d, J=8.2 Hz, 1H), 5.53 (s, 1H), 4.13 (t, J=4.9 Hz, 2H), 3.58 (dd, J=10.6, 5.2 Hz, 2H), 1.42 (s, 9H). MS: (ESI, $CH_2Cl_2$/MeOH+10 mmol $NH_4OAc$): 304.1 (19%, $MNa^+$), 282.1 (2%, $MH^+$), 226.1 (100%, $MH^+$—$C_4H_9$), 182.1 (42%, $MH^+$-boc).

E-8a: 4-hydroxy-3-(2-N-tert-butyloxycarbonyl-aminoethoxy)benzaldehyde

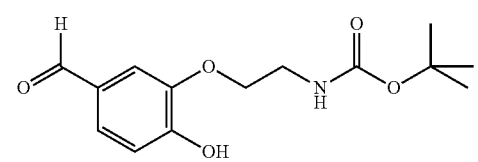 [SMILES: CC(C)(C)OC(=O)NCCOc1cc(C=O)ccc1O]

Yield: 2.60 g of pale yellow glass, 37% of theory
Molecular mass=281.31 g/mol; —Empirical formula=$C_{14}H_{19}NO_5$

E-11: 3,4-bis-(2-N-tert-butyloxycarbonyl-aminoethoxy)benzaldehyde

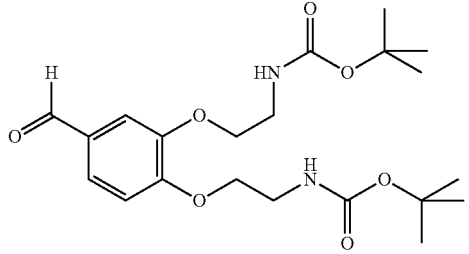 [SMILES: CC(C)(C)OC(=O)NCCOc1ccc(C=O)cc1OCCNC(=O)OC(C)(C)C]

Yield: 1.38 g of pale yellow glass, 13% of theory

Molecular mass=424.50 g/mol; Empirical formula=$C_{21}H_{32}N_2O_7$ $^1$H-NMR and MS as above.

Step 2:

1.41 g (5 mmol) of 3-hydroxy-4-(2-N-tert-butyloxycarbonyl-aminoethoxy)benzaldehyde (E-8) was placed under nitrogen in 10 mL of DMF. The alkylation reagent, each time dissolved in 10 mL of DMF, namely triethylene glycol monotosylate or 1-bromooctanol, as well as $K_2CO_3$ (2.07 g, 15 mmol) were added one after the other. The formulation was stirred under a nitrogen atmosphere for 24 h at 80° C. After cooling to room temperature, the reaction mixture was diluted with 80 mL ethyl acetate and the organic phase was shaken three times, each time with 50 mL of saturated aqueous sodium chloride solution, and once with 50 mL of water. The organic phase was separated, dried over $MgSO_4$ and rotary evaporated. In order to purify the product, column chromatography was carried out on silica gel.

E-10: 3-(2-(2-(2-hydroxy-ethoxy)ethoxy)ethoxy)-4-(2-N-tert-butyloxycarbonyl-aminoethoxy)benzaldehyde

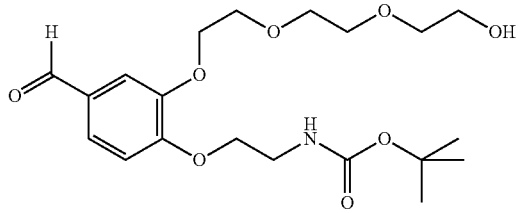 [SMILES: CC(C)(C)OC(=O)NCCOc1ccc(C=O)cc1OCCOCCOCCO]

The alkylation reagent used was triethylene glycol monotosylate (3.04 g, 10 mmol). Column chromatography with EE→EE/EtOH=3:1

Yield: 1.53 g of pale yellow glass, 74% of theory

Molecular mass=413.47 g/mol; Empirical formula=$C_{20}H_{31}NO_8$ $^1$H NMR: (300 MHz, CDCl$_3$), δ=9.83 (s, 1H), 7.48-7.38 (m, 2H), 6.96 (d, J=8.1 Hz, 1H), 4.24 (dd, J=5.3, 3.4 Hz, 2H), 4.12 (t, J=4.8 Hz, 2H), 3.92 (dd, J=5.3, 3.4 Hz, 2H), 3.74 (t, J=4.6 Hz, 6H), 3.66-3.61 (m, 2H), 3.58 (t, J=4.7 Hz, 2H), 1.43 (s, 9H). MS: (ESI, CH$_2$Cl$_2$/MeOH+10 mmol NH$_4$OAc): 436.2 (35%, MNa$^+$), 414.2 (33%, MH$^+$), 370.2 (5%, MH$^+$—C$_4$H$_9$), 314.2 (100%, MH$^+$-boc).

E-9: 3-octyloxy-4-(2-N-tert-butyloxycarbonyl-aminoethoxy)benzaldehyde

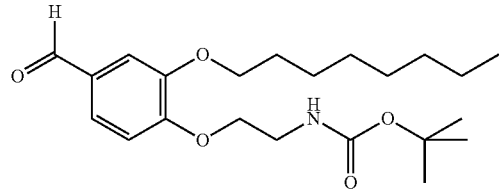 [SMILES: CCCCCCCCOc1cc(C=O)ccc1OCCNC(=O)OC(C)(C)C]

The alkylation reagent used was 1-bromooctanol (1.93 g, 10 mmol).

Column chromatography with PE:EE=3:1

Yield: 1.53 g of pale yellow glass, 78% of theory

Molecular mass=393.53 g/mol; Empirical formula=$C_{22}H_{35}NO_5$ $^1$H NMR: (300 MHz, CDCl$_3$), δ=9.81 (s, 1H), 7.43-7.32 (m, 2H), 6.96 (d, J=8.4 Hz, 1H), 4.11 (t, J=5.3 Hz, 2H), 4.02 (t, J=6.7 Hz, 2H), 3.55 (dd, J=10.2, 5.0 Hz, 2H), 1.91-1.76 (m, 2H), 1.47-1.39 (m, 2H), 1.42 (s, 9H), 1.36-1.16 (m, 8H), 0.90-0.80 (m, 3H). MS: (ESI, CH$_2$Cl$_2$/MeOH+10 mmol NH$_4$OAc): 416.2 (51%, MNa$^+$), 396.2 (4%, MH$^+$), 338.2 (7%, MH$^+$-C$_4$H$_9$), 294.2 (100%, MH$^+$-boc).

1.4 Substituted naphthaldehyde

E-13: 4-(2-N-tert-butyloxycarbonyl-aminoethoxy)naphthalene-1-carbaldehyde

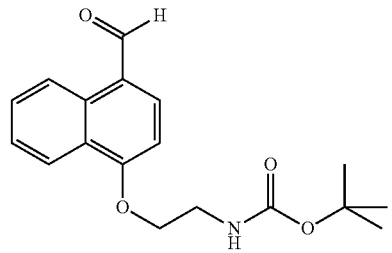 [SMILES: CC(C)(C)OC(=O)NCCOc1ccc(C=O)c2ccccc12]

4-hydroxynaphth-1-aldehyde (1.74 g, 10 mmol) was placed under nitrogen in 10 mL of DMF. 2-(tert-butoxycarbonylamino)ethyl bromide (4.4 g, 20 mmol) in 10 mL of DMF, potassium iodide (10 mmol, 1.66 g) and Cs$_2$CO$_3$ (6.5 g, 20 mmol) were added one after the other. The formulation was stirred under a nitrogen atmosphere for 24 h at 80° C. After cooling to room temperature, the reaction mixture was diluted with 80 mL ethyl acetate and the organic phase was shaken three times, each time with 50 mL of saturated aqueous sodium chloride solution, and once with 100 mL of water. The organic phase was separated, dried over MgSO$_4$ and rotary evaporated. The impure product was washed with EE/PE 1:19 in order to remove the excess reagent. Next, the orange solid was extracted with EE/PE 1:2 (3×, each 100 mL) and the precipitate was filtered out. The solution was rotary evaporated and the residue was dissolved in 250 mL of diethylether. The organic phase was shaken twice, each time with 50 mL of 3 M NaOH, and once with 100 mL of water. The organic phase was separated, dried over MgSO$_4$ and rotary evaporated. In order to further purify the product, column chromatography was carried out on silica gel. Yield: 2.08 g of pale yellow solid, 47% of theory Molecular mass=315.37 g/mol; Empirical formula=$C_{18}H_{21}NO_4$ ¹H NMR: (300 MHz, CDCl₃), δ=10.19 (s, 1H), 9.30 (d, J=8.5 Hz, 1H), 8.33 (d, J=8.4 Hz, 1H), 7.94-7.86 (m, 1H), 7.76-7.64 (m, 1H), 7.62-7.51 (m, 1H), 6.94-6.82 (m, 1H), 5.07 (s, 1H), 4.29 (dd, J=6.9, 3.2 Hz, 2H), 3.73 (m, 2H), 1.46 (s, 9H). MS: (ESI, CH$_2$Cl$_2$/MeOH+10 mmol NH$_4$OAc): 338.2 (16%, MNa⁺), 316.2 (19%, MH⁺), 260.1 (100%, MH⁺—C$_4$H$_9$), 216.1 (4%, MH⁺-boc).

2. Synthesis of Substituted Curcumins

The corresponding curcumins were synthesized from the preliminary steps described above as curcumins protected with tert-butyloxycarbonyl (boc). The boc protective group was then removed.

2.1 Synthesis of Symmetrically Substituted Curcumins

Overview 3: Synthesis of various symmetrically substituted curcumins: Conditions: (a) acetyl acetone, B$_2$O$_3$, B(OBu)$_3$, n-butylamine, ethyl acetate, 80° C., 6 h, then hydrolysis with HOAc 40% overnight, RT; (b) acetyl acetone, B$_2$O$_3$, B(OBu)$_3$, n-butylamine, DMF, 80° C., 6 h, then hydrolysis with HOAc 40% overnight, RT; (c) 3,5-heptanedione, B$_2$O$_3$, B(OBu)$_3$, n-butylamine, DMF, 80° C., 6 h, then hydrolysis with HOAc 40% overnight, RT; (d) DCM, TFA, RT, 5 h; then Amberlite IRA-958 ion exchange resin, water.

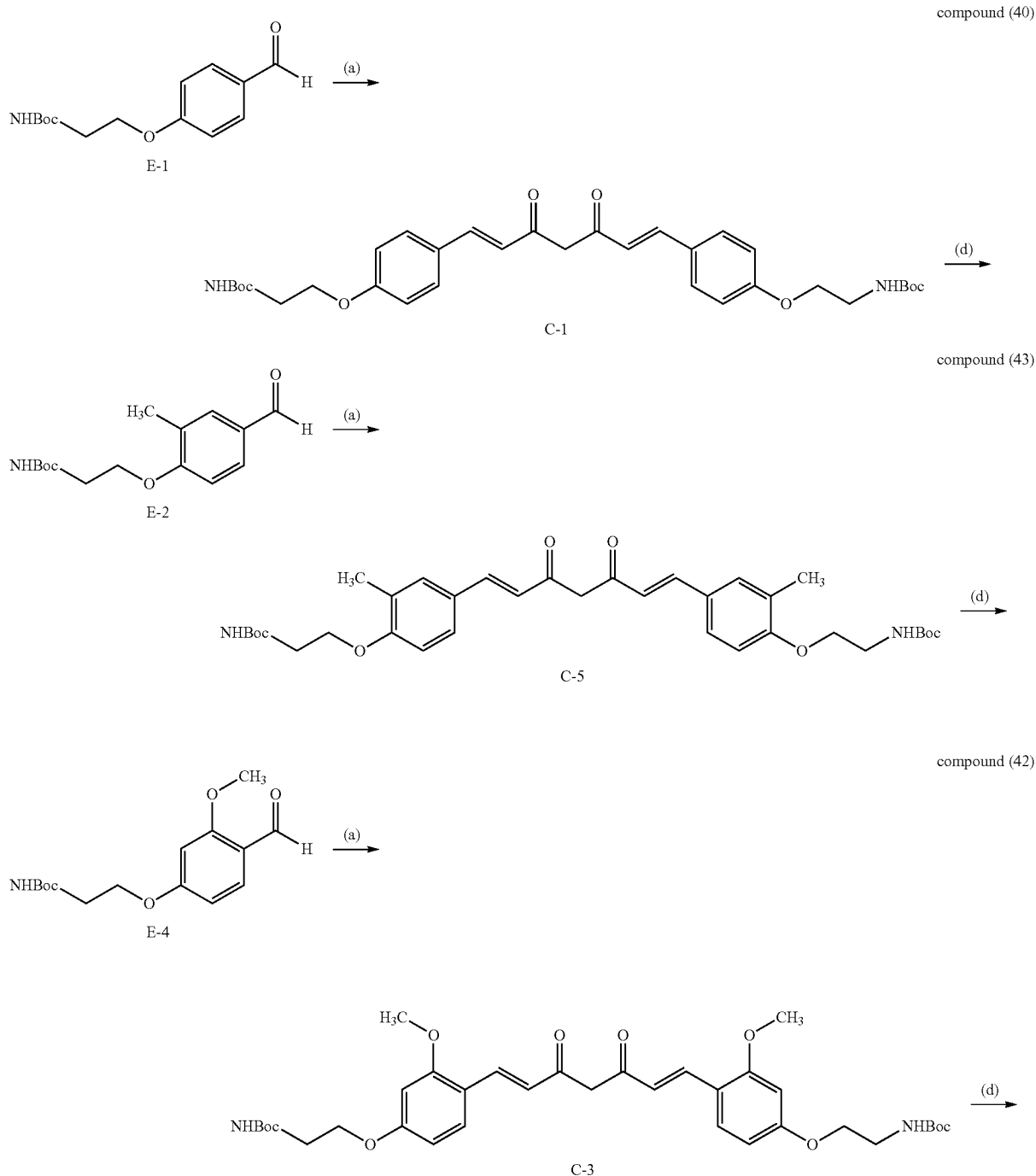

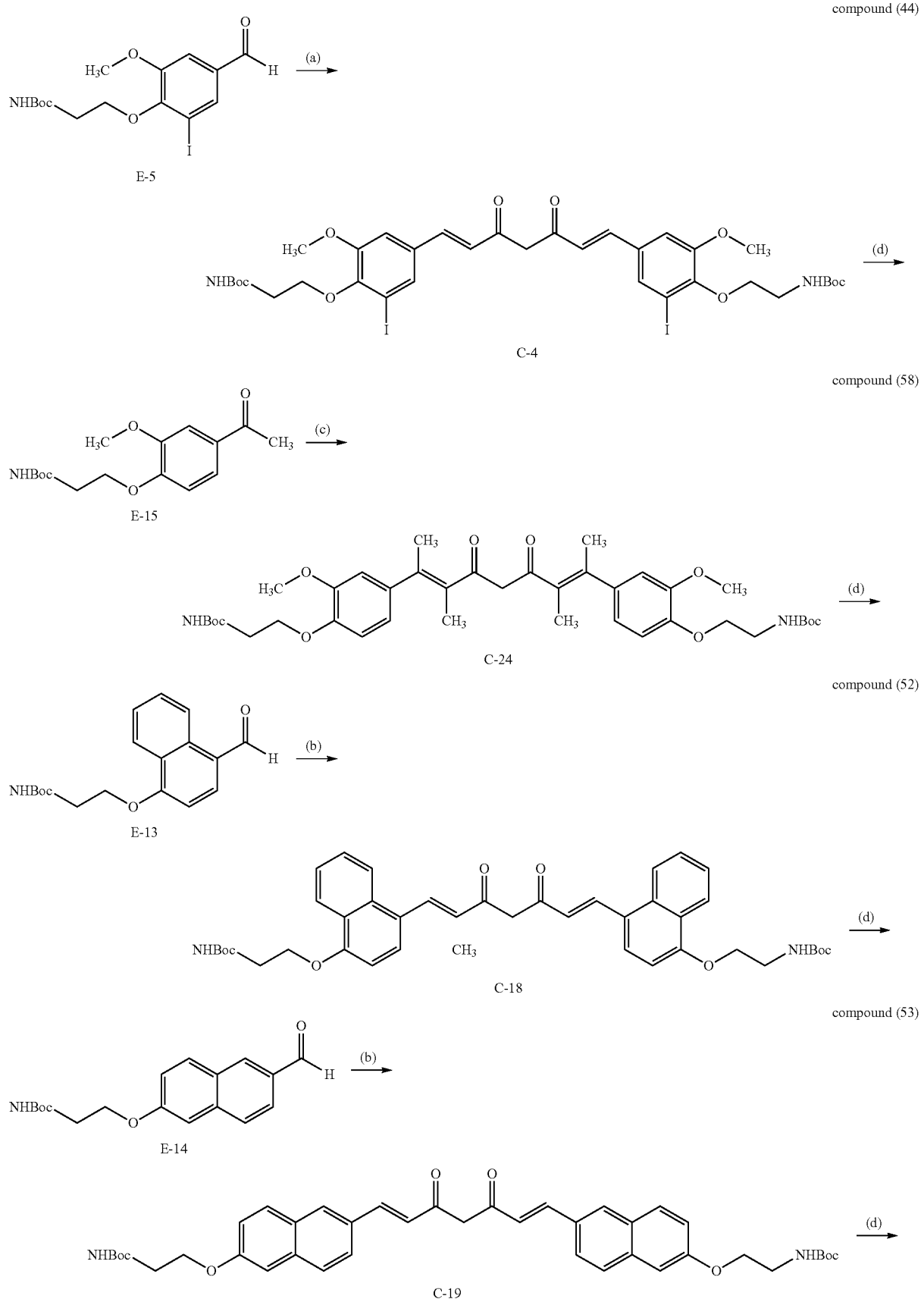

-continued
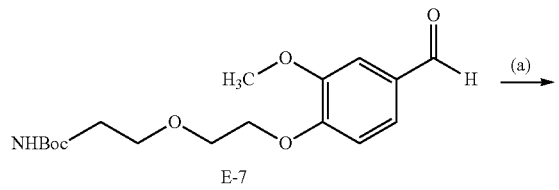
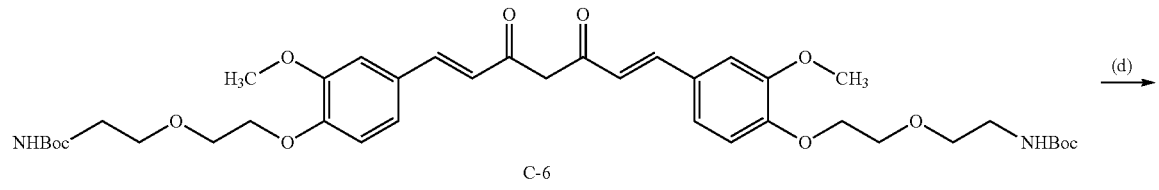
compound (45)
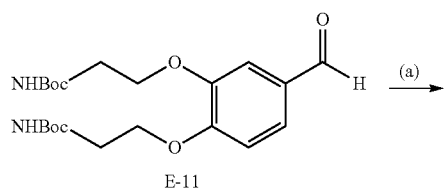
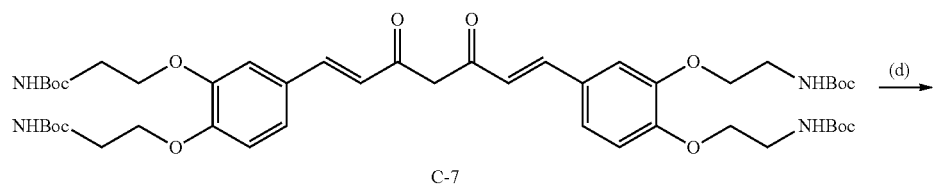
compound (49)
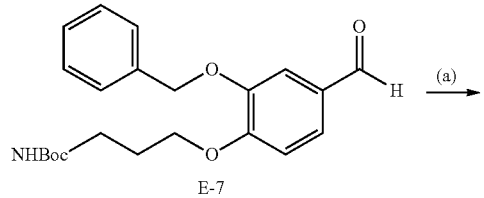
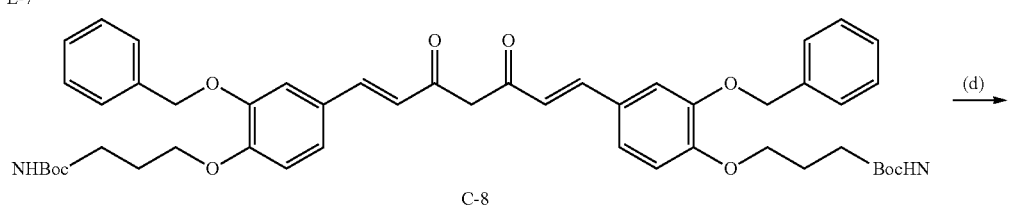
compound (51)
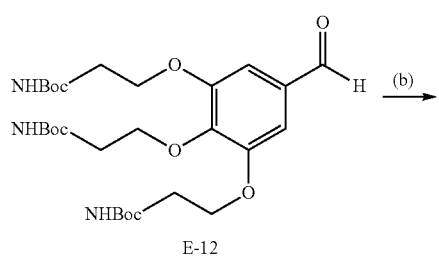
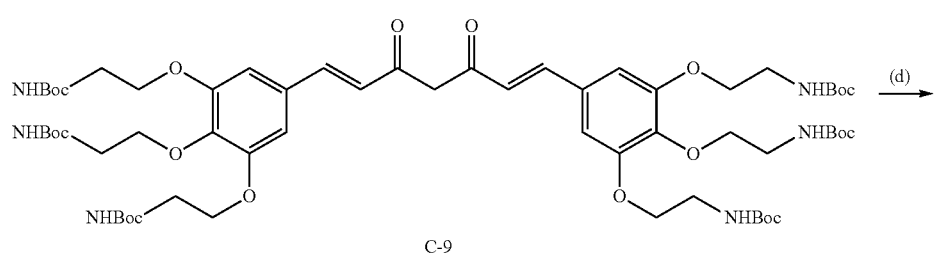
compound (50)

-continued
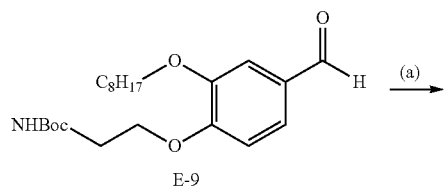
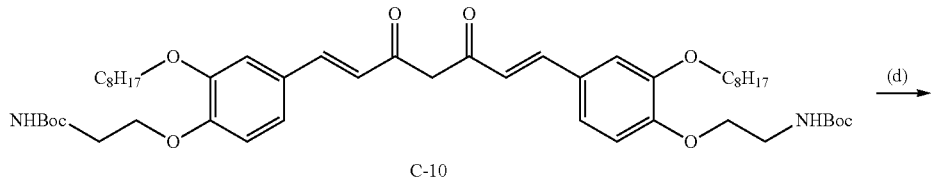
compound (48)
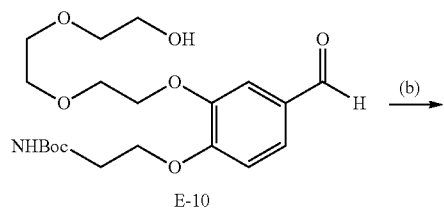
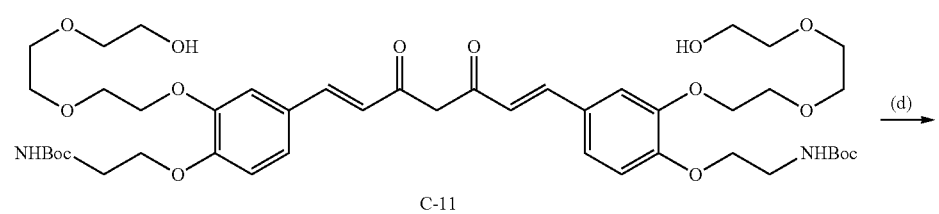
compound (46)
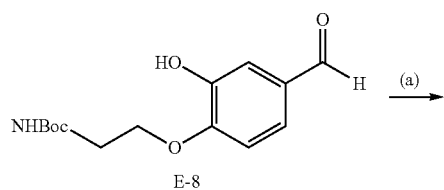
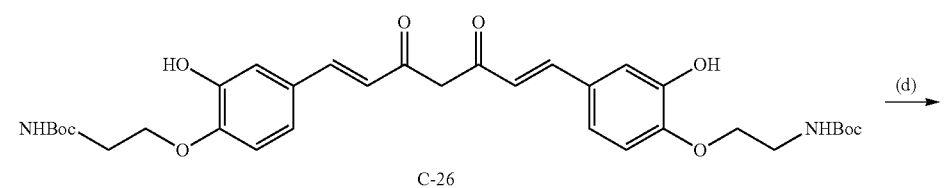
compound (71)
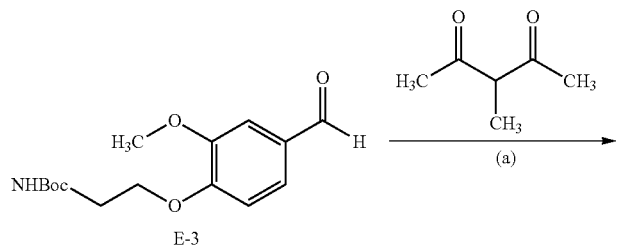
compound (47)
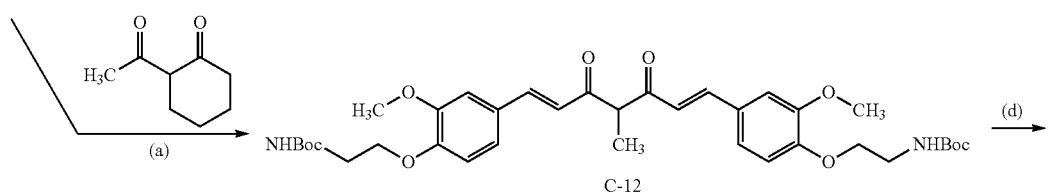
compound (54)

-continued compound (58)

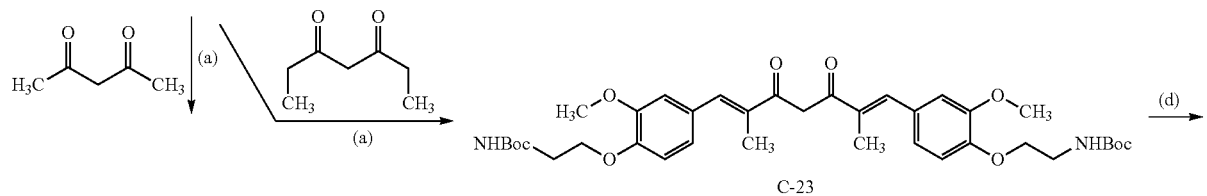

C-23 compound (63)

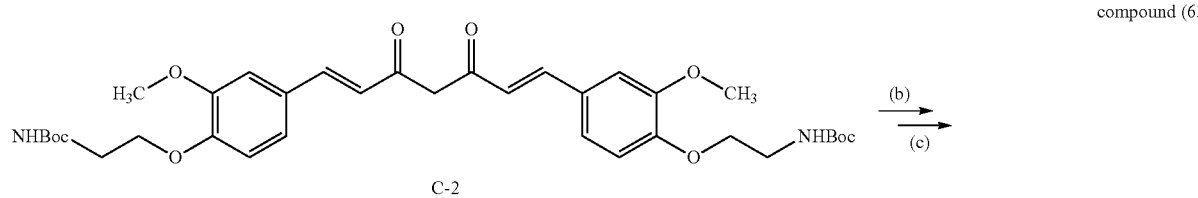

C-2

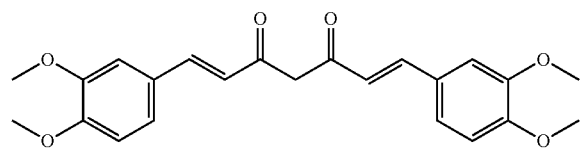

C-14

2.1.1 General Procedure:

Acetyl acetone (0.1 g, 1 mmol) and boron oxide $B_2O_3$ (0.07 g, 1 mmol) were dissolved in ethyl acetate (2 mL) and stirred for 30 minutes at 50° C. The substituted benzaldehyde (20 mmol) in ethyl acetate (3 mL) along with tributylborate (0.7 g, 3 mmol) were added one after the other and the formulation was stirred for a further half an hour. Next, n-butylamine (0.1 mL in 1 mL EE) was added dropwise over 5 minutes. After stirring for a further five hours at 50° C., the reaction was left to stand overnight. The solution was rotary evaporated and the residue was quickly dried under high vacuum. 10 mL of ethyl acetate was added per 1 g of impure product and the impure product was dissolved. For the subsequent hydrolysis of the boron complex, double the volume of 50% acetic acid was added (20 mL per 1 g of impure product). After stirring for 24 h at room temperature protected from light, the mixture of solvents was withdrawn under reduced pressure. The residue was extracted three times with EE (3×20 mL) and the insoluble salt was filtered off. The combined organic phases were washed with water (30 mL), dried over $MgSO_4$ and finally, the solvent was withdrawn under reduced pressure. Purification was carried out using column chromatography on silica gel with acetone/PE. The purified fraction of the curcumin which was obtained was then dissolved in as little ethyl acetate as possible. By dripping this solution into an excess of petroleum ether, the product was precipitated out as a fine yellow-orange powder.

1,7-bis(3,4-dimethoxyphenyl)hepta-1,6-diene-3,5-dione (tetramethoxycurcumin)

Quantity of corresponding aldehyde used: 334 mg=2 mmol

Column chromatography on silica gel with acetone/PE=2:5→1:2

Yield: 289 mg, 73% of theory, orange, viscous solid or orangey-yellow powder. Molecular mass=396.44 g/mol; Empirical formula=$C_{23}H_{24}O_6$ C-1: [2-(4-{7-[4-(2-tert-butoxycarbonylamino-ethoxy)-phenyl]-3,5-dioxo-hepta-1,6-dienyl}-phenoxy)-ethyl]-carbamic acid tert-butyl ester

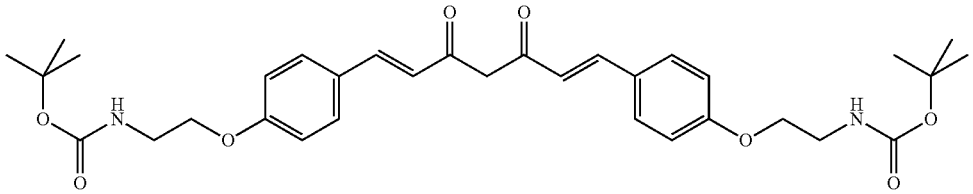 [SMILES: CC(C)(C)OC(=O)NCCOc1ccc(/C=C/C(=O)CC(=O)/C=C/c2ccc(OCCNC(=O)OC(C)(C)C)cc2)cc1]

Quantity of corresponding aldehyde E-1 used: 530 mg=2 mmol
Column chromatography on silica gel with acetone/PE=1: 3→2:3
Yield: 363 mg, 67% of theory, yellow solid or yellow powder
Molecular mass=594.71 g/mol; Empirical formula=$C_{33}H_{42}N_2O_8$
$^1$H NMR: (300 MHz, CDCl$_3$), δ=7.61 (d, J=15.8 Hz, 2H), 7.50 (d, J=8.8 Hz, 4H), 6.89 (d, J=8.7 Hz, 4H), 6.50 (d, J=15.8 Hz, 2H), 5.02 (s, 2H), 4.05 (t, J=5.1 Hz, 4H), 3.60-3.48 (m, 4H), 1.45 (s, 18H). MS: (ESI, CH$_2$Cl$_2$/MeOH+10 mmol NH$_4$OAc): 595.3 (100%, MH$^+$), 539.2 (18%, MH$^+$—C$_4$H$_9$).

C-5: [2-(4-{7-[4-(2-tert-butoxycarbonylamino-ethoxy)-3-methyl-phenyl]-3,5-dioxo-hepta-1,6-dienyl}-2-methyl-phenoxy)-ethyl]-carbamic acid tert-butylester

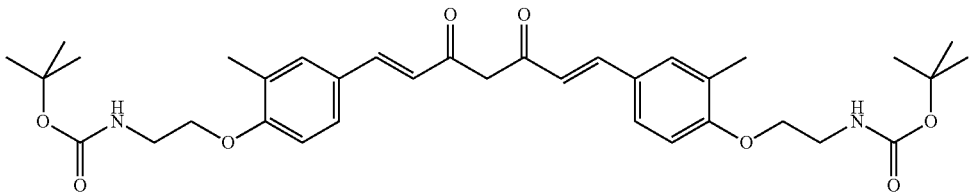 [SMILES: Cc1cc(/C=C/C(=O)CC(=O)/C=C/c2ccc(OCCNC(=O)OC(C)(C)C)c(C)c2)ccc1OCCNC(=O)OC(C)(C)C]

Quantity of corresponding aldehyde E-2 used: 559 mg=2 mmol
Column chromatography on silica gel with acetone/PE=1: 3→2:3
Yield: 442 mg, 59% of theory, orangey-yellow solid or orangey-yellow powder. Molecular
mass=622.77 g/mol; Empirical formula=$C_{35}H_{46}N_2O_8$
$^1$H NMR: (300 MHz, CDCl$_3$), δ=7.59 (d, J=15.8 Hz, 2H), 7.36 (d, J=10.8 Hz, 4H), 6.80 (d, J=8.3 Hz, 2H), 6.49 (d, J=15.8 Hz, 2H), 4.94 (s, 2H), 4.06 (t, J=5.0 Hz, 4H), 3.58 (m, 4H), 2.25 (s, 6H), 1.46 (s, 18H). MS: (ESI, CH$_2$Cl$_2$/MeOH+10 mmol NH$_4$OAc): 623.3 (100%, MH$^+$), 567.3 (21%, MH$^+$—C$_4$H$_9$).

C-3: [2-(4-{7-[4-(2-tert-butoxycarbonylamino-ethoxy)-2-octyloxy-phenyl]-3,5-dioxo-hepta-1,6-dienyl}-3-octyloxy-phenoxy)-ethyl]-carbamic acid tert-butylester

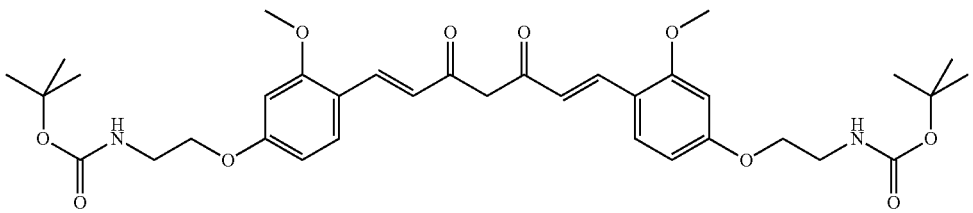 [SMILES: COc1cc(OCCNC(=O)OC(C)(C)C)ccc1/C=C/C(=O)CC(=O)/C=C/c1ccc(OCCNC(=O)OC(C)(C)C)cc1OC]

Quantity of corresponding aldehyde E-4 used: 591 mg=2 mmol

Column chromatography on silica gel with acetone/PE=1: 3→2:3

Yield: 393 mg, 58% of theory, orange, viscous solid or orangey-yellow powder. Molecular mass=654.76 g/mol; Empirical formula=C$_{35}$H$_{46}$N$_2$O$_{10}$ $^1$H NMR: (300 MHz, CDCl$_3$), δ=7.89 (d, J=16.0 Hz, 2H), 7.47 (d, J=8.5 Hz, 2H), 6.62 (d, J=16.0 Hz, 2H), 6.52-6.39 (m, 4H), 4.99 (s, 2H), 4.06 (t, J=5.1 Hz, 4H), 3.88 (s, 6H), 3.55 (m, 4H), 1.45 (s, 18H). MS: (ESI, CH$_2$Cl$_2$/MeOH+10 mmol NH$_4$OAc): 655.3 (100%, MH$^+$).

C-4: [2-(4-{7-[4-(2-tert-butoxycarbonylamino-ethoxy)-3-methoxy-5-iodo-phenyl]-3,5-dioxo-hepta-1,6-dienyl}-2-octyloxy-6-iodo-phenoxy)-ethyl]-carbamic acid tert-butylester

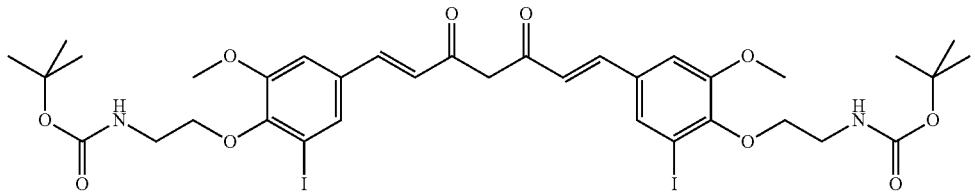 [SMILES: COc1cc(/C=C/C(=O)CC(=O)/C=C/c2cc(I)c(OCCNC(=O)OC(C)(C)C)c(OC)c2)cc(I)c1OCCNC(=O)OC(C)(C)C]

Quantity of corresponding aldehyde E-5 used: 842 mg=2 mmol

Column chromatography on silica gel with acetone/PE=1: 4→1:2

Yield: 580 mg, 64% of theory, orange, viscous solid or orangey-yellow powder. Molecular mass=906.56 g/mol; Empirical formula=C$_{35}$H$_{44}$I$_2$N$_2$O$_{10}$ $^1$H NMR: (300 MHz, CDCl$_3$), δ=7.57 (d, J=1.5 Hz, 2H), 7.50 (d, J=15.8 Hz, 2H), 7.02 (d, J=1.5 Hz, 2H), 6.51 (d, J=15.8 Hz, 2H), 5.47 (s, 2H), 4.11 (t, J=4.7 Hz, 4H), 3.90 (s, 6H), 3.52 (m, 4H), 1.46 (s, 18H). MS: (ESI, CH$_2$Cl$_2$/MeOH+10 mmol NH$_4$OAc): 929.1 (100%, MNa$^+$), 907.1 (100%, MH$^+$), 807.1 (42%, MH$^+$-boc).

C-2: [2-(4-{7-[4-(2-tert-butoxycarbonylamino-ethoxy)-3-methoxy-phenyl]-3,5-dioxo-hepta-1,6-dienyl}-2-methoxy-phenoxy)-ethyl]-carbamic acid tert-butylester

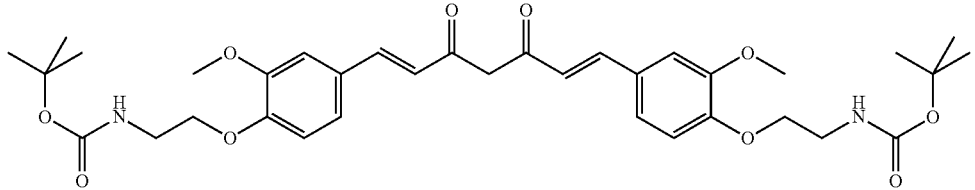 [SMILES: COc1cc(/C=C/C(=O)CC(=O)/C=C/c2ccc(OCCNC(=O)OC(C)(C)C)c(OC)c2)ccc1OCCNC(=O)OC(C)(C)C]

Quantity of corresponding aldehyde E-15 used: 590 mg=2 mmol

Column chromatography on silica gel with acetone/PE=1: 3→2:3

Yield: 354 mg, 54% of theory, orange, viscous solid or orangey-yellow powder. Molecular mass=654.76 g/mol, Empirical formula=C$_{35}$H$_{46}$N$_2$O$_{10}$ $^1$H NMR: (300 MHz, CDCl$_3$), δ=7.58 (d, J=15.7 Hz, 2H), 7.14-6.99 (m, 4H), 6.87 (d, J=8.3 Hz, 2H), 6.48 (d, J=15.8 Hz, 2H), 5.16 (s, 2H), 4.09 (t, J=4.9 Hz, 4H), 3.90 (s, 6H), 3.56 (m, 4H), 1.44 (s, 18H). MS: (ESI, CH$_2$Cl$_2$/MeOH+10 mmol NH$_4$OAc): 655.3 (100%, MH$^+$), 555.3 (26%, MH$^+$-boc).

C-6: (2-{2-[4-(7-{4-[2-(2-tert-butoxycarbo-nylamino-ethoxy)-ethoxy]-3-methoxy-phenyl}-3,5-dioxo-hepta-1,6-dienyl)-2-methoxy-phenoxy]-ethoxy}-ethyl)-carbamic acid tert-butyl ester

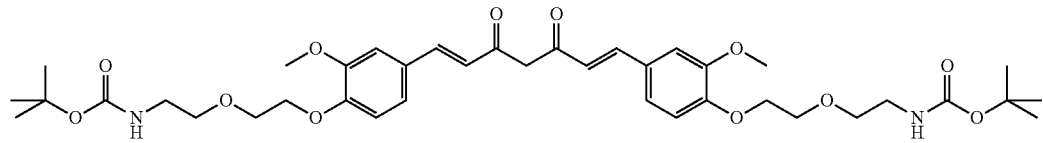 [SMILES: COc1cc(/C=C/C(=O)CC(=O)/C=C/c2ccc(OCCOCCNC(=O)OC(C)(C)C)c(OC)c2)ccc1OCCOCCNC(=O)OC(C)(C)C]

Quantity of corresponding aldehyde E-7 used: 679 mg=2 mmol
Yield: 349 mg, 47% of theory, orange, viscous solid or orange powder
Column chromatography on silica gel with acetone/PE=1:2→1:1
Molecular mass=742.87 g/mol; Empirical formula=$C_{39}H_{54}N_2O_{12}$
$^1$H NMR: (300 MHz, $CDCl_3$), δ=7.59 (d, J=15.8 Hz, 2H), 7.18-7.03 (m, 4H), 6.90 (d, J=8.3 Hz, 2H), 6.49 (d, J=15.8 Hz, 2H), 5.07 (s, 2H), 4.24-4.15 (m, 4H), 3.91 (s, 6H), 3.88-3.83 (m, 4H), 3.61 (t, J=5.1 Hz, 4H), 3.33 (m, 4H), 1.43 (s, 18H). MS: (ESI, $CH_2Cl_2$/MeOH+10 mmol $NH_4OAc$): 671.3 (51%, $MNa^+$), 655.3 (86%, $MH^+$), 555.3 (100%, $MH^+$-boc).

C-7: {2-[4-{7-[3,4-bis-(2-tert-butoxycarbonylamino-ethoxy)-phenyl]-3,5-dioxo-hepta-1,6-dienyl}-2-(2-tert-butoxycarbonylamino-ethoxy)-phenoxy]-ethyl}-carbamic acid tert-butyl ester

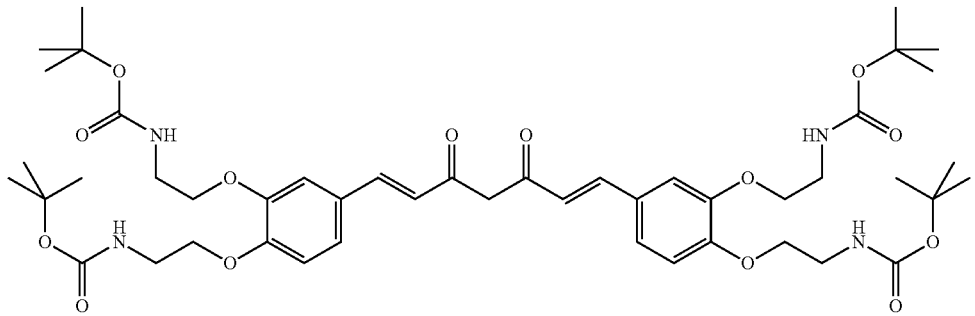 [SMILES: CC(C)(C)OC(=O)NCCOc1ccc(/C=C/C(=O)CC(=O)/C=C/c2ccc(OCCNC(=O)OC(C)(C)C)c(OCCNC(=O)OC(C)(C)C)c2)cc1OCCNC(=O)OC(C)(C)C]

Quantity of corresponding aldehyde E-11 used: 850 mg=2 mmol
Yield: 374 mg, 41% of theory, orange, very viscous solid or orangey-red powder
Column chromatography on silica gel with acetone/PE=1:3→1:2

Molecular mass=913.08 g/mol; Empirical formula=$C_{47}H_{68}N_4O_{14}$
$^1$H NMR (300 MHz, $CDCl_3$), δ=7.57 (d, J=15.8 Hz, 2H), 7.19-7.12 (m, 4H), 6.98-6.86 (m, 2H), 6.50 (d, J=15.8 Hz, 2H), 5.28 (s, 4H), 4.10 (t, J=4.4 Hz, 8H), 3.55 (m, 8H), 1.46 (s, 18H), 1.45 (s, 18H). MS (ESI, $CH_2Cl_2$/MeOH+10 mmol $NH_4OAc$): 913.5 (100%, $MH^+$), 457.3 (7%, $(M+2H^+)^{2+}$):

C-8: [2-(4-{7-[4-(2-tert-butoxycarbonylamino-ethoxy)-3-benzyloxy-phenyl]-3,5-dioxo-hepta-1,6-dienyl}-2-benzyloxy-phenoxy)-ethyl]-carbamic acid tert-butyl ester

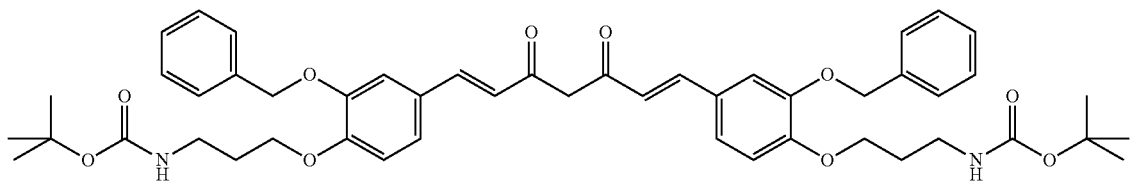 [SMILES: CC(C)(C)OC(=O)NCCCOc1ccc(/C=C/C(=O)CC(=O)/C=C/c2ccc(OCCCNC(=O)OC(C)(C)C)c(OCc3ccccc3)c2)cc1OCc1ccccc1]

Quantity of corresponding aldehyde E-7 used: 738 mg=2 mmol
Yield: 518 mg, 62% of theory, orange solid or orange powder
Column chromatography on silica gel with acetone/PE=1:3→2:3
Molecular mass=835.02 g/mol; Empirical formula=$C_{49}H_{58}N_2O_{10}$
$^1$H NMR (300 MHz, CDCl$_3$), δ=7.55 (d, J=15.8 Hz, 2H), 7.45-7.31 (m, 10H), 7.14-7.04 (m, 4H), 6.86 (d, J=8.3 Hz, 2H), 6.46 (d, J=15.8 Hz, 2H), 5.39 (s, 2H), 5.22 (s, 4H), 4.14 (t, J=5.9 Hz, 4H), 3.39 (m, 4H), 2.09-2.00 (m, 4H), 1.41 (s, 18H). MS (ESI, CH$_2$Cl$_2$/MeOH+10 mmol NH$_4$OAc): 857.4 (100%, MNa$^+$), 835.4 (76%, MH$^+$), 735.4 (53%, MH$^+$-boc).

C-9: {2-[4-{7-[3,4,5-tris-(2-tert-butoxycarbonylamino-ethoxy)-phenyl]-3,5-dioxo-hepta-1,6-dienyl}-2,6-bis-(2-tert-butoxycarbonylamino-ethoxy)-phenoxy]-ethyl}-carbamic acid tert-butyl ester

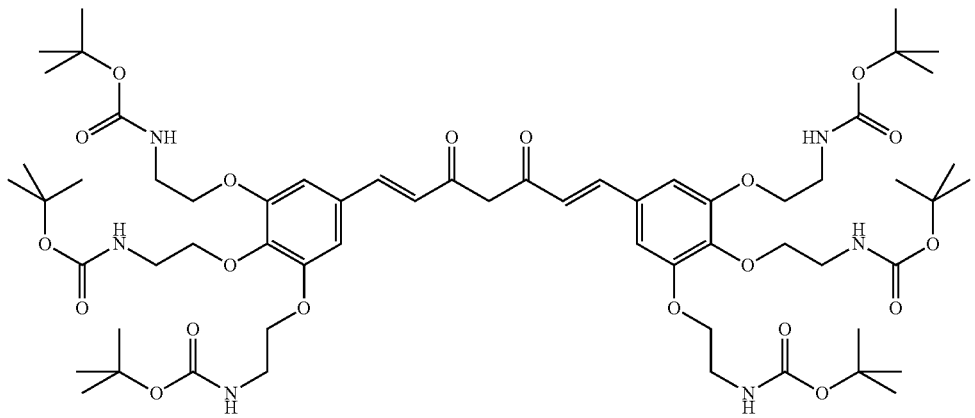 [SMILES: CC(C)(C)OC(=O)NCCOc1cc(/C=C/C(=O)CC(=O)/C=C/c2cc(OCCNC(=O)OC(C)(C)C)c(OCCNC(=O)OC(C)(C)C)c(OCCNC(=O)OC(C)(C)C)c2)cc(OCCNC(=O)OC(C)(C)C)c1OCCNC(=O)OC(C)(C)C]

Quantity of corresponding aldehyde E-11 used: 1166 mg=2 mmol
Yield: 554 mg, 45% of theory, orange, very viscous solid or orangey-red powder. Column chromatography on silica gel with acetone/PE=1:4→1:2. Molecular mass=1231.46 g/mol;
Empirical formula=$C_{61}H_{94}N_6O_{20}$ $^1$H NMR (300 MHz, CDCl$_3$), δ=7.52 (d, J=15.1 Hz, 2H), 6.79 (s, 4H), 6.51 (d, J=15.1 Hz, 2H), 5.75 (s, 2H), 5.25 (s, 3H), 4.10 (m, 12H), 3.57 (m, 8H), 3.41 (m, 4H), 1.47 (s, 18H), 1.47 (s, 36H). MS (ESI, CH$_2$Cl$_2$/MeOH+10 mmol NH$_4$OAc): 1253.6 (100%, MNa$^+$), 1231.6 (49%, MH$^+$), 1131.3 (51%, MH$^+$-boc).

C-10: [2-(4-{7-[4-(2-tert-butoxycarbonylamino-ethoxy)-3-octyloxy-phenyl]-3,5-dioxo-hepta-1,6-dienyl}-2-octyloxy-phenoxy)-ethyl]-carbamic acid tert-butyl ester

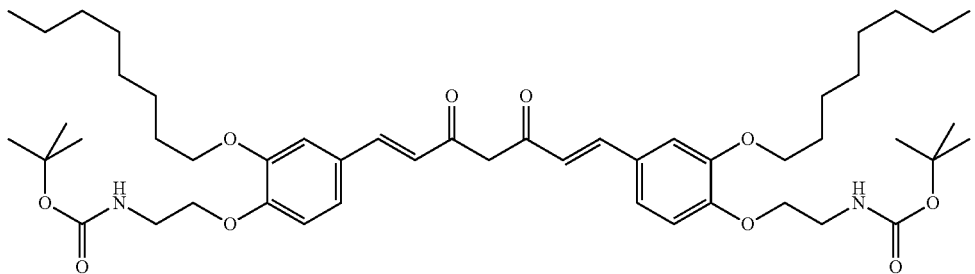 [SMILES: CCCCCCCCOc1cc(/C=C/C(=O)CC(=O)/C=C/c2ccc(OCCNC(=O)OC(C)(C)C)c(OCCCCCCCC)c2)ccc1OCCNC(=O)OC(C)(C)C]

Quantity of corresponding aldehyde E-10 used: 787 mg=2 mmol

Column chromatography on silica gel with acetone/PE=1: 4→1:2

Yield: 400 mg, 47% of theory, orange, viscous solid or orangey-yellow powder. Molecular mass=851.14 g/mol; Empirical formula=$C_{49}H_{74}N_2O_{10}$ $^1$H NMR (300 MHz, CDCl$_3$), δ=7.58 (d, J=15.7 Hz, 2H), 7.15-7.05 (m, 4H), 6.89 (d, J=8.2 Hz, 2H), 6.48 (d, J=15.8 Hz, 2H), 5.17 (s, 2H), 4.09 (t, J=5.0 Hz, 4H), 4.03 (t, J=6.7 Hz, 4H), 3.54 (m, 4H), 1.91-1.80 (m, 4H), 1.41 (s, 18H), 1.51-1.26 (m, 20H), 0.89 (t, 4.5 Hz, 6H). MS (ESI, CH$_2$Cl$_2$/MeOH+10 mmol NH$_4$OAc): 873.5 (100%, MNa$^+$), 851.4 (13%, MH$^+$), 751.5 (38%, MH$^+$-boc).

2.1.2 General Procedure:

The reaction was carried out under an atmosphere of nitrogen and protected from light. The beta-diketone used was:

(X) acetyl acetone (0.1 g, 1 mmol)
(XI) 3-methyl-2,4-pentanedione (0.12 g, 1 mmol)
(XII) 3,5-heptanedione (0.13 g, 0.137 mL, 1 mmol), or
(XIII) 2-acetylcyclohexanone (0.14 g, 1 mmol).

The respective beta-diketone and boron oxide B$_2$O$_3$ (0.05 g, 0.7 mmol) were dissolved in dry DMF (2 mL) and stirred for 30 minutes at 70° C. The corresponding substituted aldehyde (2 mmol) along with tributylborate (0.46 g, 2 mmol) were dissolved in dry DMF (5 mL). This solution was added to the formulation and it was stirred for a further half hour at 85° C. Next, n-butylamine (0.1 mL in 1 mL of DMF) was added dropwise and the formulation was stirred at 70° C. for 4 hours. After cooling to room temperature, all of the volatile components in the nitrogen stream were driven off overnight (outlet, pipe behind baffle wall). 10 mL of ethyl acetate was added per 1 g of impure product and the impure product was dissolved. For the subsequent hydrolysis of the boron complex, double the volume of 50% acetic acid was added (20 mL per 1 g of impure product). After stirring for 24 h at room temperature protected from light, the mixture of solvents was withdrawn under reduced pressure (max. water bath temperature 50° C.). The residue was extracted three times with EE (3×50 mL) and the insoluble salt was filtered off. The combined organic phases were washed with water (50 mL), dried over MgSO$_4$ and finally, the solvent was withdrawn under reduced pressure. Purification was carried out using column chromatography on silica gel with acetone/PE. The pure fraction of the curcumin was then dissolved in as little ethyl acetate as possible. By dripping this solution into an excess of petroleum ether, the product was precipitated out as a fine yellow-orange powder.

C-26: [2-(4-{7-[4-(2-tert-butoxycarbonylamino-ethoxy)-3-hydroxy-phenyl]-3,5-dioxo-hepta-1,6-dienyl}-2-hydroxy-phenoxy)-ethyl]-carbamic acid tert-butyl ester

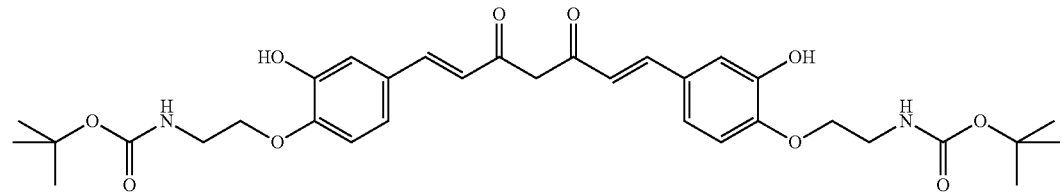 [SMILES: CC(C)(C)OC(=O)NCCOc1ccc(/C=C/C(=O)CC(=O)/C=C/c2ccc(OCCNC(=O)OC(C)(C)C)c(O)c2)cc1O]

Beta-diketone: acetyl acetone

Quantity of corresponding aldehyde E-10 used: 560 mg=2 mmol

Column chromatography on silica gel with acetone/PE=1: 2→2:3

Yield: 28% of theory, orange, viscous solid (180 mg).

Molecular mass=626.71 g/mol; Empirical formula=$C_{33}H_{42}N_2O_{10}$ $^1$H NMR (300 MHz, CDCl$_3$), δ=7.57 (d, J=15.8 Hz, 2H), 7.34 (m, H), 7.19-7.08 (m, 2H), 6.85 (d, J=8.4 Hz, 2H), 6.64 (d, J=15.8 Hz, 2H), 5.17 (s, 2H), 4.07 (t, J=5.0 Hz, 4H), 3.58-3.44 (m, 4H), 1.43 (s, 18H). MS (ESI, CH$_2$Cl$_2$/MeOH+10 mmol NH$_4$OAc): 627.2 (100%, MH$^+$), 527.2 (37%, MH$^+$-boc).

C-18: [2-(4-{7-[4-(2-tert-butoxycarbonylamino-ethoxy)-napthyl]-3,5-dioxo-hepta-1,6-dienyl}-naphthoxy)-ethyl]-carbamic acid tert-butyl ester

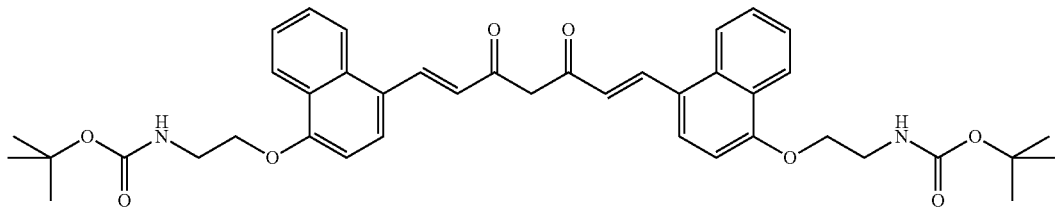 [SMILES: CC(C)(C)OC(=O)NCCOc1ccc(/C=C/C(=O)CC(=O)/C=C/c2ccc(OCCNC(=O)OC(C)(C)C)c3ccccc23)c2ccccc12]

Beta-diketone: acetyl acetone
Quantity of corresponding aldehyde E-13 used: 630 mg=2 mmol
Column chromatography on silica gel with acetone/PE=2:7→1:2
Yield: 62% of theory, orange, viscous solid (430 mg).
Molecular mass=694.83 g/mol; Empirical formula=$C_{41}H_{46}N_2O_8$
$^1$H NMR (300 MHz, CDCl$_3$), δ=8.48 (d, J=15.5 Hz, 2H), 8.33 (d, J=8.1 Hz, 2H), 8.25 (d, J=8.0 Hz, 2H), 7.80 (d, J=8.1 Hz, 2H), 7.63 (t, J=6.9 Hz, 2H), 7.55 (t, J=6.8 Hz, 2H), 6.86 (d, J=8.2 Hz, 2H), 6.68 (d, J=15.5 Hz, 2H), 5.04 (s, 2H), 4.26 (t, J=5.0 Hz, 4H), 3.72 (q, J=5.0 Hz, 5H), 1.47 (s, 18H). MS (ESI, CH$_2$Cl$_2$/MeOH+10 mmol NH$_4$OAc): 717.3 (100%, MNa$^+$), 695.3 (56%, MH$^+$), 639.3 (73%, MH$^+$—C$_4$H$_9$).

C-19: [2-(6-{7-[6-(2-tert-butoxycarbonylamino-ethoxy)-napthyl]-3,5-dioxo-hepta-1,6-dienyl}-naphthoxy)-ethyl]-carbamic acid tert-butyl ester

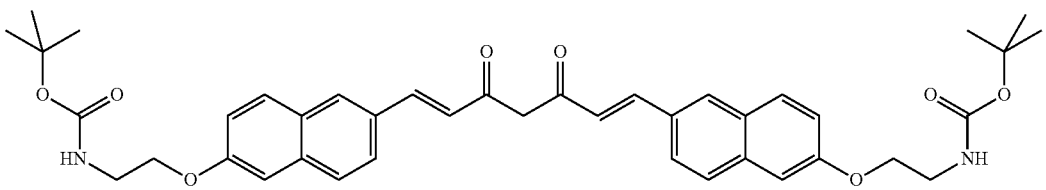 [SMILES: CC(C)(C)OC(=O)NCCOc1ccc2cc(/C=C/C(=O)CC(=O)/C=C/c3ccc4cc(OCCNC(=O)OC(C)(C)C)ccc4c3)ccc2c1]

Beta-diketone: acetyl acetone
Quantity of corresponding aldehyde E-19 used: 1.26 g=4 mmol
Yield: 820 mg, 59% of theory, reddish, viscous solid or orange powder.
Molecular mass=694.83 g/mol; Empirical formula=$C_{41}H_{46}N_2O_8$
$^1$H NMR (300 MHz, CDCl$_3$), δ=7.85 (d, J=15.8 Hz, 2H), 7.79-7.63 (m, 8H), 7.20-7.08 (m, 4H), 6.71 (d, J=15.8 Hz, 2H), 5.06 (s, 2H), 4.15 (t, J=5.0 Hz, 4H), 3.61 (m, 4H), 1.46 (s, 18H). MS (ESI, CH$_2$Cl$_2$/MeOH+10 mmol NH$_4$OAc): 717.3 (58%, MNa$^+$), 695.3 (100%, MH$^+$), 639.3 (97%, MH$^+$—C$_4$H$_9$).

C-13: tert-butyl-N-[2-[4-[(E)-3-[(3E)-3-[[4-(2-(tert-butoxycarbonylamino)ethoxy]-3-methoxy-phenylmethylene]-2-oxo-cyclohexyl]-3-oxo-prop-1-enyl]-2-methoxy-phenoxy]ethyl]carbamate

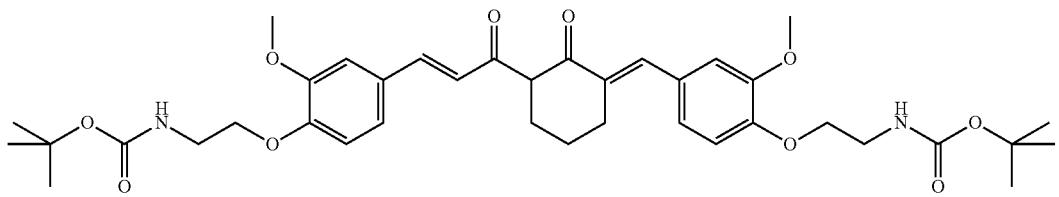 [SMILES: COc1cc(/C=C/C(=O)C2CCC/C(=C\c3ccc(OCCNC(=O)OC(C)(C)C)c(OC)c3)C2=O)ccc1OCCNC(=O)OC(C)(C)C]

Beta-diketone: 2-acetylcyclohexanone
Quantity of corresponding aldehyde used: 580 mg=2 mmol Flash chromatography on silica gel with acetone/PE=2: 5→1:2

The fractions containing product were rotary evaporated and the impure product was recrystallized from acetone/PE 1:3. After cooling slowly to RT, it was first cooled slowly overnight in a refrigerator, then cooled for 3 h in the freezer. The solid was extracted several times with a little ice-cold acetone/PE 1:3 and finally washed with PE. The product was dried in the air. A further, small crystalline fraction was obtained by concentrating the mother liquor.

Yield: 68% of theory, orange, matted crystal needles (472 mg).

Molecular mass=694.83 g/mol; Empirical formula=$C_{38}H_{50}N_2O_{10}$ $^1$H NMR (300 MHz, CDCl$_3$), δ=7.76-7.62 (m, 2H), 7.17 (dd, J=8.3, 1.5 Hz, 1H), 7.09 (d, J=1.7 Hz, 1H), 7.06-6.85 (m, 5H), 5.22-5.08 (m, 2H), 4.11 (t, J=4.5 Hz, 4H), 3.92 (s, 3H), 3.89 (s, 3H), 3.57 (m, 4H), 2.83-2.73 (m, 2H), 2.71-2.64 (m, 2H), 1.86-1.77 (m, 2H), 1.45 (s, 18H). MS (ESI, CH$_2$Cl$_2$/MeOH+10 mmol NH$_4$OAc): 717.4 (24%, MNa$^+$), 695.4 (100%, MH$^+$), 595.3 (30%, MH$^+$-boc).

C-9: {2-[4-{7-[3,4,5-tris-(2-tert-butoxycarbo-nylamino-ethoxy)-phenyl]-3,5-dioxo-hepta-1,6-di-enyl}-2,6-bis-(2-tert-butoxycarbonylamino-ethoxy)-phenoxy]-ethyl}-carbamic acid tert-butyl ester

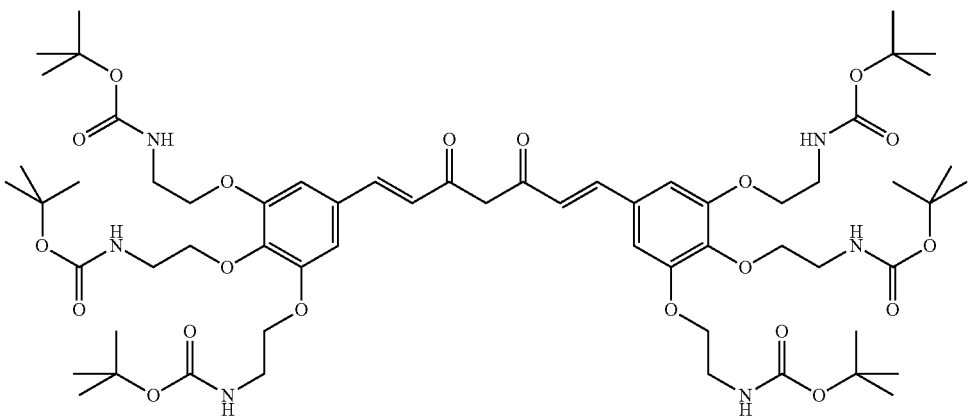 [SMILES: CC(C)(C)OC(=O)NCCOc1cc(/C=C/C(=O)CC(=O)/C=C/c2cc(OCCNC(=O)OC(C)(C)C)c(OCCNC(=O)OC(C)(C)C)c(OCCNC(=O)OC(C)(C)C)c2)cc(OCCNC(=O)OC(C)(C)C)c1OCCNC(=O)OC(C)(C)C]

Beta-diketone: acetyl acetone
Quantity of corresponding aldehyde E-12 used: 1160 mg=2 mmol
Yield: 66% of theory, orange, viscous solid or orangey-red powder (810 mg).
Column chromatography on silica gel with acetone/PE=1: 4→2:3.
Molecular mass=1231.46 g/mol; Empirical formula=$C_{61}H_{94}N_6O_{20}$
$^1$H-NMR and MS as above.

C-11: tert-butyl-N-[2-[4-[(1E,6E)-7-[4-[2-(tert-bu-toxycarbonylamino)ethoxy]-3-[2-[2-(2-hydroxy-ethoxy)ethoxy]ethoxy]phenyl]-3,5-dioxo-hepta-1,6-dienyl]-2-[2-[2-(2-hydroxyethoxy)ethoxy]ethoxy] phenoxy]ethyl]carbamate

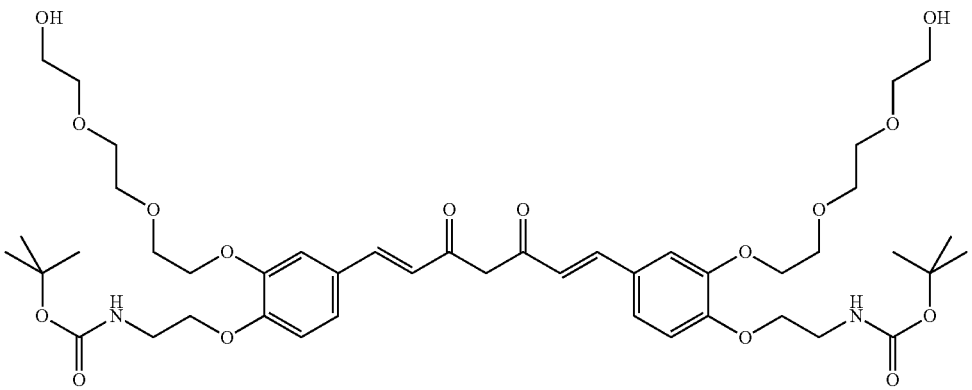 [SMILES: CC(C)(C)OC(=O)NCCOc1ccc(/C=C/C(=O)CC(=O)/C=C/c2ccc(OCCNC(=O)OC(C)(C)C)c(OCCOCCOCCO)c2)cc1OCCOCCOCCO]

Beta-diketone: acetyl acetone

Quantity of corresponding aldehyde E-10 used: 830 mg=2 mmol

Yield: 37% of theory, orange, very viscous solid (330 mg)

Column chromatography on silica gel, acetone/PE=1:2→1:1; prep. TLC, acetone/petroleum ether (PE)=1:1. Molecular mass=891.03 g/mol; Empirical formula=$C_{45}H_{66}N_2O_{16}$ $^1$H NMR (600 MHz, CDCl$_3$), δ=7.58 (d, J=15.7 Hz, 2H), 7.20-7.06 (m, 4H), 6.88 (d, J=8.1 Hz, 2H), 6.48 (d, J=15.8 Hz, 2H), 5.91 (s, 2H), 4.25-4.17 (m, 4H), 4.12-4.04 (m, 4H), 3.93-3.86 (m, 4H), 3.83-3.46 (m, 20H), 1.44 (s, 18H). MS (ESI, CH$_2$Cl$_2$/MeOH+10 mmol NH$_4$OAc): 891.7 (92%, MH$^+$), 446.3 (100%, (M+2H$^+$)$^{2+}$).

C-23: tert-butyl-N-[2-[4-[(1E,6E)-7-[4-[2-(tert-butoxycarbonylamino)ethoxy]-3-methoxy-phenyl]-2,6-dimethyl-3,5-dioxo-hepta-1,6-dienyl]-2-methoxy-phenoxy]ethyl]carbamate

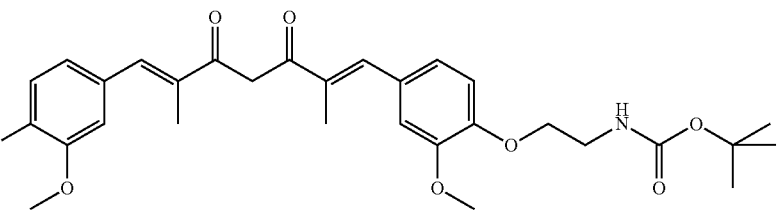

Beta-diketone: 3,5-heptanedione.

Quantity of corresponding acetophenone E-3 used: 608 mg=2 mmol

Yield: 72% of theory, orange solid (490 mg).

Column chromatography on silica gel, acetone/PE=2:5→1:2; prep. TLC, acetone/PE=1:2. Molecular mass=682.82 g/mol; Empirical formula=$C_{37}H_{50}N_2O_{10}$ $^1$H NMR (300 MHz, CDCl$_3$), δ=7.55 (s, 2H), 7.07-6.88 (m, 6H), 6.31 (s, 1H), 5.16 (s, 2H), 4.12 (t, J=5.0 Hz, 4H), 3.89 (s, 6H), 3.57 (q, J=5.1 Hz, 4H), 2.18 (s, 6H), 1.45 (s, 18H). MS (ESI, CH$_2$Cl$_2$/MeOH+10 mmol NH$_4$OAc): 705.2 (MNa$^+$, 67%), 683.4 (MH$^+$, 100%), 627.3 (MH$^+$-C$_4$H$_9$, 4%), 583.3 (MH$^+$-boc, 63%), 527.2 (MH$^+$-boc-C$_4$H$_9$, 27%).

C-24: tert-butyl-N-[2-[4-[(1E,6E)-7-[4-[2-(tert-butoxycarbonylamino)ethoxy]-3-methoxy-phenyl]-1,2,6-trimethyl-3,5-dioxo-octa-1,6-dienyl]-2-methoxy-phenoxy]ethyl]carbamate

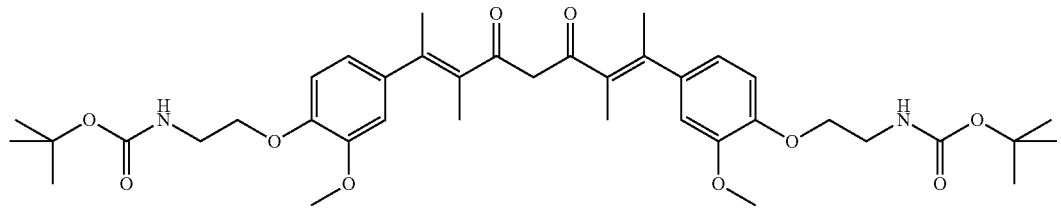 [SMILES: COc1cc(/C(C)=C(\C)C(=O)CC(=O)/C(C)=C(\C)c2ccc(OCCNC(=O)OC(C)(C)C)c(OC)c2)ccc1OCCNC(=O)OC(C)(C)C]

Beta-diketone: 3,5-heptanedione

Quantity of corresponding acetophenone E-15 used: 608 mg=2 mmol

Yield: 19% of theory, orange, very viscous solid (137 mg)

Column chromatography on silica gel, acetone/PE=2:5→1:2; prep. TLC, acetone/PE=1:2.

Molecular mass=710.87 g/mol; Empirical formula=$C_{39}H_{54}N_2O_{10}$ $^1$H NMR (300 MHz, CDCl$_3$), δ=7.12-6.91 (m, 6H), 6.26 (s, 1H), 5.14 (s, 2H), 4.13 (t, J=5.3 Hz, 4H), 3.91 (s, 6H), 3.56 (q, J=5.2 Hz, 4H), 2.17 (s, 6H), 2.12 (s, 6H), 1.44 (s, 18H). MS (ESI, CH$_2$Cl$_2$/MeOH+10 mmol NH$_4$OAc): 732.4 (MNa$^+$, 88%), 710.4 (MH$^+$, 100%), 654.4 (8%, MH$^+$—C$_4$H$_9$), 610.4 (53%, MH$^+$-boc).

C-12: [2-(4-{7-[4-(2-tert-butoxycarbonylamino-ethoxy)-3-methoxy-phenyl]-3,5-dioxo-hepta-4-methyl-1,6-dienyl}-2-methoxy-phenoxy)-ethyl]-carbamic acid tert-butyl ester

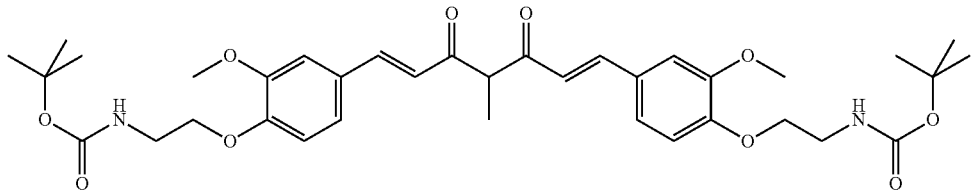 [SMILES: COc1cc(/C=C/C(=O)C(C)C(=O)/C=C/c2ccc(OCCNC(=O)OC(C)(C)C)c(OC)c2)ccc1OCCNC(=O)OC(C)(C)C]

Beta-diketone: 3-methyl-2,4-pentanedione
Quantity of corresponding aldehyde E-3 used: 2.94 g=0.01 mol
Column chromatography on silica gel with acetone/PE=1:3→2:3
Yield: 59% of theory, orange, viscous solid or orangey-yellow powder (403 mg).
Molecular mass=682.82 g/mol; Empirical formula=$C_{36}H_{48}N_2O_{10}$
$^1$H NMR (300 MHz, CDCl$_3$), δ=7.74-7.56 (m, 2H), 7.20-6.82 (m, 7H), 6.70 (d, J=15.9 Hz, 1H), 5.13 (s, 2H), 4.10 (dd, J=10.7, 5.3 Hz, 4H), 3.92 (s, 3H), 3.88 (s, 3H), 3.56 (m, 4H), 2.17 (m, 3H), 1.44 (s, 9H), 1.43 (s, 9H). MS (ESI, CH$_2$Cl$_2$/MeOH+10 mmol NH$_4$OAc): 691.3 (43%, MNa$^+$), 669.3 (100%, MH$^+$), 569.3 (17%, MH$^+$-boc).

2.2 Modification with Guanidine

C-14: tert-butyl-(2,2'-(4,4'-((1E,6E)-3,5-dioxohepta-1,6-diene-1,7-diyl)bis(2-methoxy-4,1-phenylene))bis(oxy)bis(ethane-2,1-diyl))bis(azanediyl)bis((tert-butoxycarbonylamino)methan-1-yl-1-ylidene dicarbamate N,N'-di-boc-N''-triflylguanidine was produced in a manner analogous to that described in Organic Syntheses, Coll. Vol. 10, p. 266 (2004); Vol. 78, p. 91 (2002.

Curcumin C-2 was precipitated in dichloromethane (DCM) at room temperature (RT) for 5 h with trifluoroacetic acid (TFA). The trifluoroacetate salt obtained was centrifuged off. Triethylamine (0.51 g, 0.66 mL, 5 mmol) was slowly added dropwise to N,N'-di-boc-N''-triflylguanidine (0.82 g, 2 mmol) in dichloromethane (10 mL) using a syringe at 2-5° C. Curcumin C-2 trifluoroacetate (550 mg, 0.8 mmol) was added. After stirring for 5 h at room temperature, it was diluted with dichloromethane (30 mL) and the organic phase was washed with aqueous potassium hydrogen sulphate (3%, 20 mL) and water (20 mL). After drying over MgSO$_4$, the solution was filtered and rotary evaporated. The impure material was purified using column chromatography on silica gel with acetone/petroleum ether (PE) (acetone/PE=1:3→1:2). Yield: 47% of theory, orange, viscous solid or orangey-yellow powder (437 mg).
Molecular mass=930.08 g/mol; Empirical formula=$C_{47}H_{66}N_6O_{14}$
$^1$H NMR (300 MHz, CDCl$_3$), δ=11.47 (s, 2H), 8.79 (s, 2H), 7.59 (d, J=15.8 Hz, 2H), 7.16-7.05 (m, 4H), 7.01 (d, J=8.3 Hz, 2H), 6.50 (d, J=15.8 Hz, 2H), 4.20 (t, J=5.3 Hz, 4H), 3.92 (s, 6H), 3.89-3.81 (m, 4H), 1.51 (s, 18H), 1.49 (s, 18H). MS (ESI, CH$_2$Cl$_2$/MeOH+10 mmol NH$_4$OAc): 939.6 (9%, MH$^+$), 470.4 (100%, (M+2H$^+$)$^{2+}$).

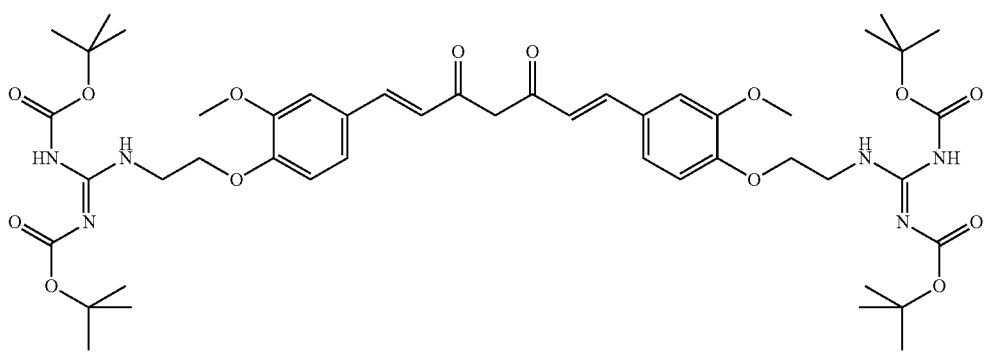 [SMILES: COc1cc(/C=C/C(=O)CC(=O)/C=C/c2ccc(OCCN/C(=N/C(=O)OC(C)(C)C)NC(=O)OC(C)(C)C)c(OC)c2)ccc1OCCN/C(=N/C(=O)OC(C)(C)C)NC(=O)OC(C)(C)C]

2.3 Synthesis of Substituted Curcumins Using the Mitsunobu Reaction

The synthesis was carried out in a manner analogous to the methods described in Lepore, S. D. and He, Y.: ("Use of Sonication for the Coupling of Sterically Hindered Substrates in the phenolic Mitsunobu Reaction"; J. Org. Chem. 68, 2003, pages 8261 to 8263).

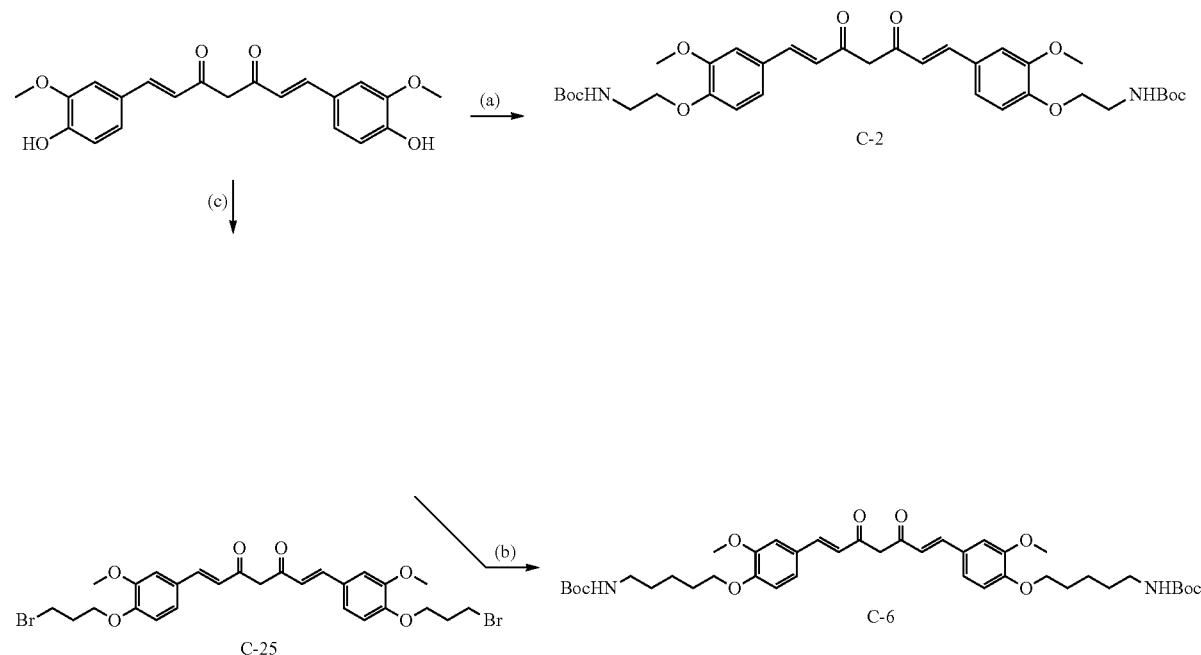

Overview 5: Synthesis of substituted curcumins by the Mitsunobu reaction starting from curcumin: Conditions: (a) 2-N-tert-butyloxycarbonyl-aminoethanol, DEAD, PPh₃, DMF or THE or DCM, 0° C.→RT; (b) 2-(2-N-tert-butoxycarbonyl-aminoethoxy)ethanol, DEAD, PPh₃, DMF or THE or DCM, 0° C.→RT; (c) 3-bromo-propan-1-ol, DEAD, PPh₃, THE or DCM, 0° C.→RT;

2.3.1 General Procedure:

Curcumin (0.36 g, 1 mmol) was provided together with triphenylphosphine (1.04 g, 4 mmol) and the corresponding boc-protected aminoalcohol (1 mmol or 3 mmol) in dry THE (4 mL). Diethylazodicarboxylate (DEAD) (0.7 g, 4 mmol, 40% in toluene) in dry THE (6 mL) was added dropwise over 20 minutes at approximately 2° C. to 5° C. and the formulation was then stirred for 4 h at RT in the dark. The formulation was diluted with 40 mL of acetic acid ethyl ester (EE) and the organic solution was shaken three times, each time with 20 mL of water. The organic phase was separated, dried over MgSO₄ and rotary evaporated. The residue was purified by CC on silica gel with acetone/PE (dryload). For further purification, the product was dissolved in as little EE as possible and precipitated by adding a 10-fold quantity of petroleum ether.

[2-(4-{7-[4-hydroxy-3-methoxy-phenyl]-3,5-dioxo-hepta-1,6-dienyl}-2-methoxy-phenoxy)-ethyl]-carbamic acid tert-butyl ester

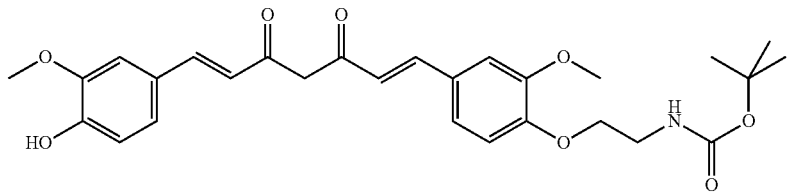 [SMILES: COc1cc(/C=C/C(=O)CC(=O)/C=C/c2ccc(OCCNC(=O)OC(C)(C)C)c(OC)c2)ccc1O]

Quantity of corresponding boc-protected aminoalcohol tert-butyl-N-(2-hydroxyethyl)carbamate used: 161 mg=1 mmol.
Column chromatography on silica gel with acetone/petroleum ether (PE)=1:2;
Preparative thin layer chromatography with acetone/petroleum ether (PE)=2:3.
Yield: 41% of theory, orange, viscous solid or orangey-yellow powder (210 mg).
Molecular mass=511.58 g/mol; Empirical formula=$C_{28}H_{33}NO_8$ C-2: [2-(4-{7-[4-(2-tert-butoxycarbonylamino-ethoxy)-3-methoxy-phenyl]-3,5-dioxo-hepta-1,6-dienyl}-2-methoxy-phenoxy)-ethyl]-carbamic acid tert-butyl ester

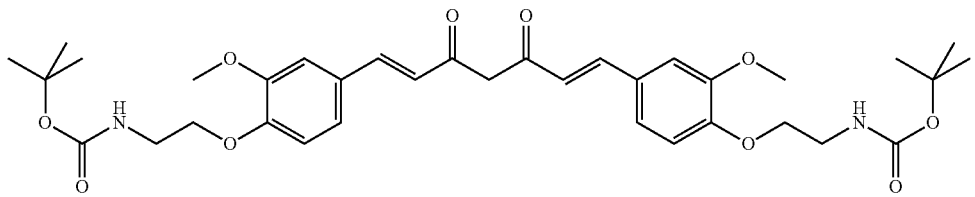 [SMILES: COc1cc(/C=C/C(=O)CC(=O)/C=C/c2ccc(OCCNC(=O)OC(C)(C)C)c(OC)c2)ccc1OCCNC(=O)OC(C)(C)C]

Quantity of corresponding boc-protected aminoalcohol tert-butyl-N-(2-hydroxyethyl)carbamate used: 483 mg=3 mmol.
Column chromatography on silica gel with acetone/petroleum ether (PE)=1:3→1:2. Yield: 71% of theory, orange, viscous solid (465 mg).
Molecular mass=654.76 g/mol; Empirical formula=$C_{35}H_{46}N_2O_{10}$
$^1$H-NMR and MS as above.

C-6: (2-{2-[4-(7-{4-[2-(2-tert-butoxycarbo-nylamino-ethoxy)-ethoxy]-3-methoxy-phenyl}-3,5-dioxo-hepta-1,6-dienyl)-2-methoxy-phenoxyl]-ethoxy}-ethyl)-carbamic acid tert-butyl ester

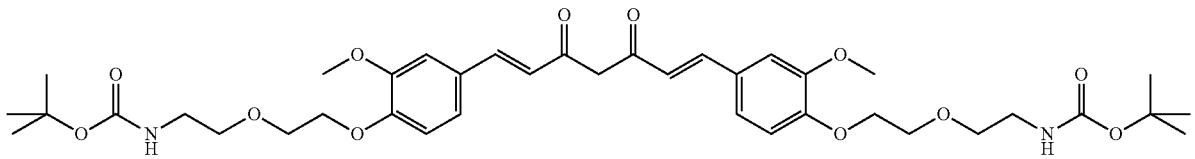 [SMILES: COc1cc(/C=C/C(=O)CC(=O)/C=C/c2ccc(OCCOCCNC(=O)OC(C)(C)C)c(OC)c2)ccc1OCCOCCNC(=O)OC(C)(C)C]

Quantity of corresponding boc-protected aminoalcohol 2-(2-N-tert-butoxycarbonyl-aminoethoxy)ethanol used: 715 mg=3 mmol.
Yield: 52% of theory, orange, viscous solid or orange powder (386 mg)
Column chromatography on silica gel with acetone/PE=1:2→2:3
Molecular mass=742.87 g/mol; Empirical formula=$C_{39}H_{54}N_2O_{12}$
$^1$H-NMR and MS as above.

C-25: (1E,6E)-1,7-bis[4-(3-bromopropoxy)-3-methoxy-phenyl]hepta-1,6-diene-3,5-dione

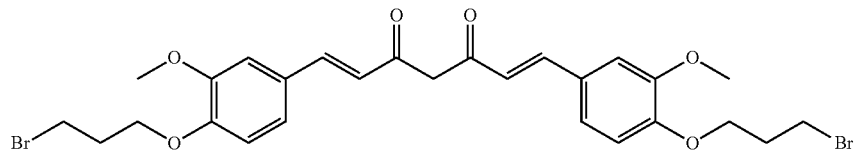 [SMILES: COc1cc(/C=C/C(=O)CC(=O)/C=C/c2ccc(OCCCBr)c(OC)c2)ccc1OCCCBr]

Curcumin (2.00 g, 5.4 mmol) was placed together with triphenylphosphine (5.26 g, 20 mmol) and 3-bromo-propan-1-ol (2.25 g, 1.51 mL, 16.2 mmol) in dry THF (40 mL) and degassed at 0° C. Diethylazodicarboxylate (DEAD) (7 mL, 40% in toluene, 20 mmol) was added dropwise over 20 minutes and the formulation was stirred overnight in a thawing ice bath in the dark and with the exclusion of moisture. The formulation was poured into a three-fold quantity of diethylether. After the precipitate had settled out, the supernatant solution was carefully decanted off.

The residue was extracted twice, each time with 50 mL of diethylether. The combined organic solutions were shaken with 100 mL of water. The organic phase was separated, dried over $MgSO_4$ and rotary evaporated. The residue was suspended in acetone/PE 1:2 and the yellow-orange solution was filtered off from the colourless crystals. The filter cake was washed several times with small portions of the cold solvent mixture and the filtrate was rotary evaporated. A preliminary purification of the residue was carried out by plug filtration over silica gel with acetone/PE 1:2. After withdrawing the solvent mixture, the remaining solid was suspended in ethanol in an ultrasound bath (30 mL), centrifuged and the supernatant solution was poured off. This washing step was repeated a total of three times, and afterwards, the product was air dried.

Yield: 2.08 g of orange powder, 63% of theory. Molecular mass=610.34 g/mol; Empirical formula=$C_{27}H_{30}Br_2O_6$ $^1$H NMR (300 MHz, $CDCl_3$), δ=7.61 (d, J=15.8 Hz, 2H), 7.16-7.04 (m, 4H), 6.92 (d, J=8.3 Hz, 2H), 6.50 (d, J=15.8 Hz, 2H), 4.20 (t, J=6.0 Hz, 4H), 3.91 (s, 6H), 3.64 (t, J=6.4 Hz, 4H), 2.39 (p, J=6.1 Hz, 4H). MS (ESI, $CH_2Cl_2$/MeOH+ 10 mmol $NH_4OAc$): 609.1 (57%, MH$^+$), 611.0 (100%, MH$^+$).

The curcumins C-27 to C-30 were produced from bis-(3-bromo-propoxy)curcumin C-25:

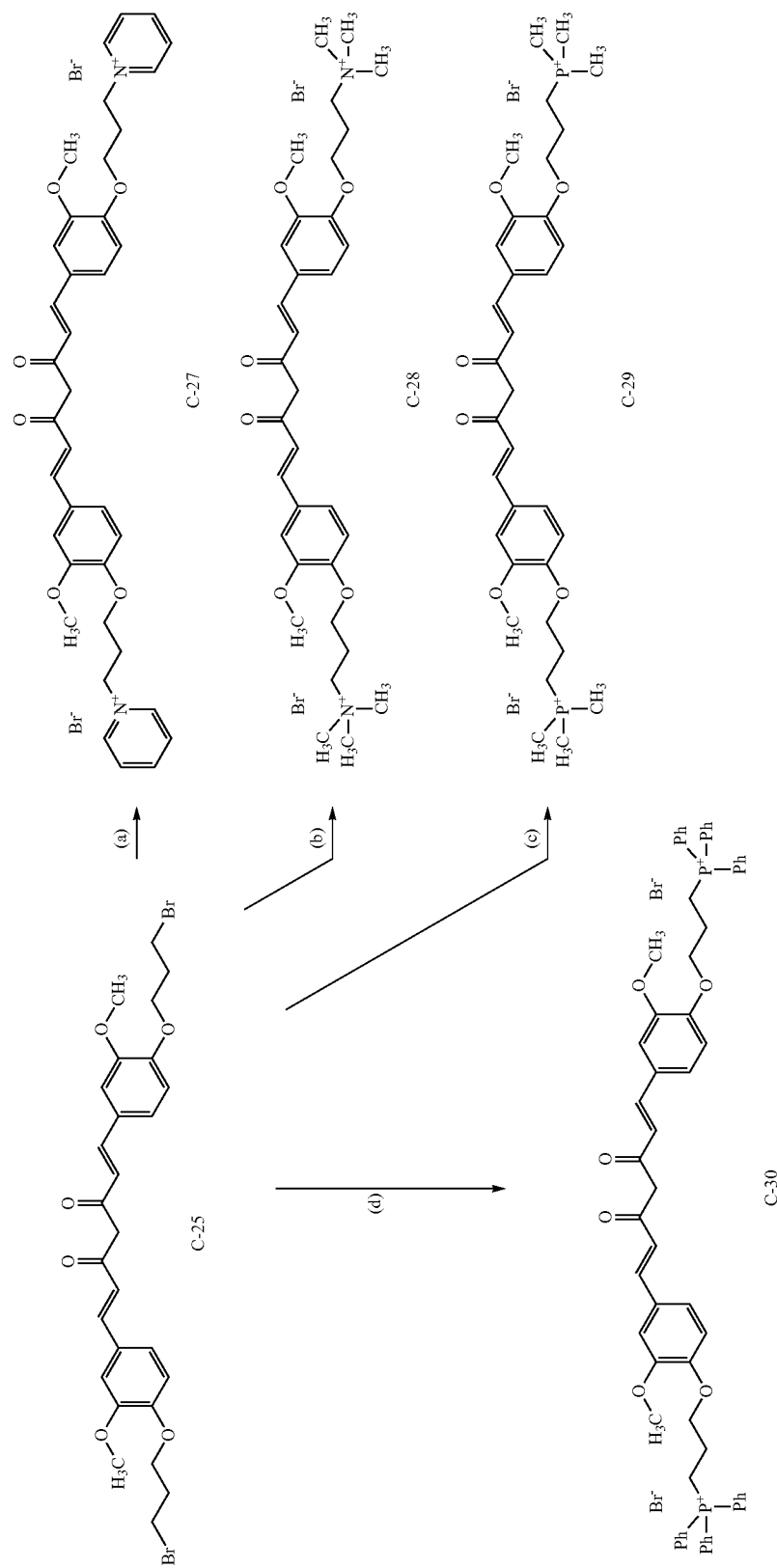

Overview 6: Synthesis of symmetrically substituted curcumins starting from C-25: Conditions: (a) pyridine, DMF, 50° C., overnight; (b) trimethylamine in ethanol, DMF, 50° C., overnight; (c) trimethylphosphine in toluene, DMF, argon, 50° C., overnight; (d) triphenylphosphine, DMF, 50° C., overnight;

2.4 Curcumins with Quaternary Charges

The bis-(3-bromo-propoxy)curcumin (61 mg, 0.1 mmol) C-25 was placed in dry DMF (3 mL). Trimethylamine (2 mL, 5.6 M in ethanol, 11 mmol) or pyridine (790 mg, 0.8 mL, 10 mmol) in DMF (2 mL) was added dropwise through a septum using a syringe over 5 mins and the formulation was stirred overnight in the dark at 50° C. with the exclusion of moisture.

The formulation was poured into a five-fold quantity of diethylether. The precipitate was allowed to settle out and the supernatant solution was carefully decanted off. The residue was washed several times with diethylether and then suspended in 15 mL of chloroform/diethylether 1:1. It was allowed to settle out completely, the supernatant solution was poured away and the precipitate was dried using a high vacuum pump. The product was purified by HPLC.

Ion Exchange Chromatography

A column was loaded with Amberlite 954 and the ion exchange resin was conditioned with 0.1M HCl. After washing with water, it was reconditioned to water/MeOH/MeCN 3:1:1. Next, the TFA salt in a little of the solvent mixture was slowly eluted over the resin and then rinsed with a little solvent. After withdrawing the solvent under reduced pressure, the remaining aqueous solution was freeze-dried.

C-28: 3,3'-(4,4'-((1E,6E)-3,5-dioxohepta-1,6-diene-1,7-diyl)bis(2-methoxy-4,1-phenylene))bis(oxy)bis(N,N,N-trimethylpropan-1-aminium) chloride

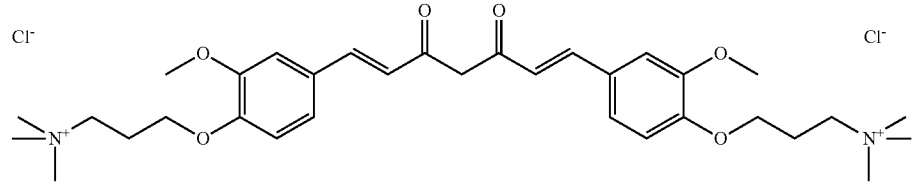

Yield: 30 mg orange solid, 45% of theory

Molecular mass: 568.76+2×35.45=639.66 g/mol; Empirical formula: $C_{33}H_{48}N_2O_6Cl_2$

$^1$H-NMR and MS: see below (SA-CUR-10a).

C-27: 1,1'-(3,3'-(4,4'-((1E,6E)-3,5-dioxohepta-1,6-diene-1,7-diyl)bis(2-methoxy-4,1-phenylene))bis(oxy)bis(propane-3,1-diyl))dipyridinium chloride

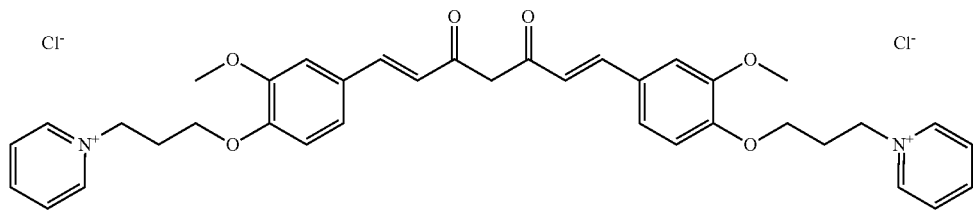 [SMILES: COc1cc(/C=C/C(=O)CC(=O)/C=C/c2ccc(OCCC[n+]3ccccc3)c(OC)c2)ccc1OCCC[n+]1ccccc1 ; [Cl-] ; [Cl-]]

Yield: 36 mg orange solid, 78% of theory
Molecular mass: 608.74+2×35.45=679.64 g/mol; Empirical formula: $C_{37}H_{40}N_2O_6Cl_2$
$^1$H-NMR and MS: see below (SA-CUR-10c).

2.5 Curcumins with Phosphonium Groups

The bis-(3-bromo-propoxy)curcumin C-25 (122 mg, 0.2 mmol) was placed in dry dichloromethane (DCM) (10 mL) and stirred under nitrogen. The phosphine used, in toluene (2 mL, 1 M, 2 mmol), was added dropwise over 5 minutes through a septum using a syringe. The formulation was stirred overnight in a Schlenk tube at 50° C. with the exclusion of moisture, in the dark and in a protective gas atmosphere. All of the volatile components were withdrawn under reduced pressure and the residue was suspended in 30 mL of diethylether with the aid of an ultrasound bath. The precipitate was allowed to settle out and the supernatant solution was carefully decanted. The residue was washed several times with diethylether. After settling of the precipitate, the supernatant solution was poured off and the precipitate was dried using a high vacuum pump.

Ion Exchange Chromatography

A short column was loaded with Amberlite 954 and the ion exchange resin was conditioned with 0.1M HCl. After washing with water, it was reconditioned to water/MeOH/MeCN 3:1:1. Next, the TFA salt in a little of the solvent mixture was slowly eluted over the resin and then rinsed with a little solvent. After withdrawing the solvent under reduced pressure, the remaining aqueous solution was freeze-dried. Quantitative yield.

C-29: 3,3'-(4,4'-((1E,6E)-3,5-dioxohepta-1,6-diene-1,7-diyl)bis(2-methoxy-4,1-phenylene))bis(oxy)bis(trimethylpropan-1-phosphonium) chloride

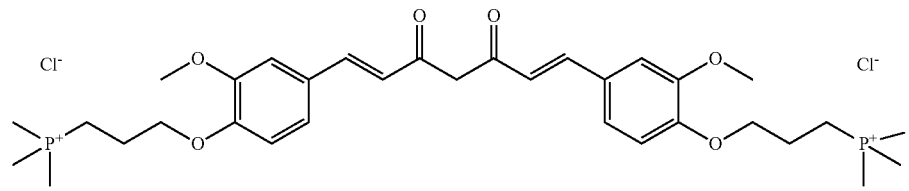

Phosphine used: trimethylphosphine
Yield: 58 mg orange solid, 21% of theory
Molecular mass: 602.69+2×35.45=673.59 g/mol; Empirical formula: $C_{33}H_{48}P_2O_6Cl_2$
$^1$H-NMR and MS: see below SA-CUR-15a.

C-30: 3,3'-(4,4'-((1E,6E)-3,5-dioxohepta-1,6-diene-1,7-diyl)bis(2-methoxy-4,1-phenylene))bis(oxy)bis(triphenylpropan-1-phosphonium) chloride

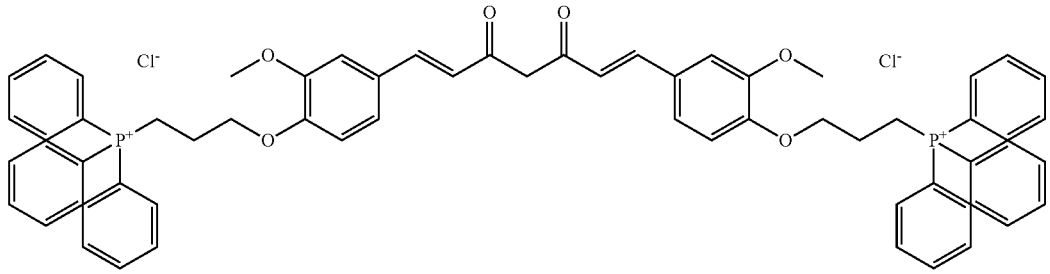

Phosphine used: triphenylphosphine
Yield: 107 mg orange solid, 56% of theory
Molecular mass: 975.12+2×35.45=1046.02 g/mol; Empirical formula: $C_{63}H_{60}P_2O_6Cl_2$
$^1$H-NMR and MS: see below SA-CUR-15b.

2.6 Synthesis of Substituted Curcumins by Alkylation

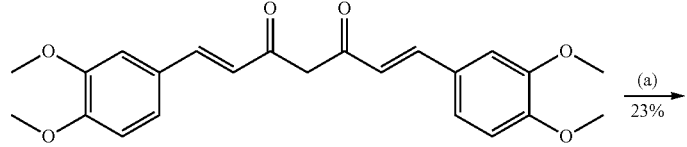

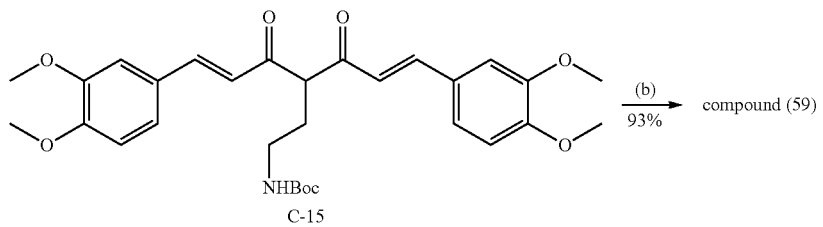

C-15

$\xrightarrow[93\%]{(b)}$ compound (59)

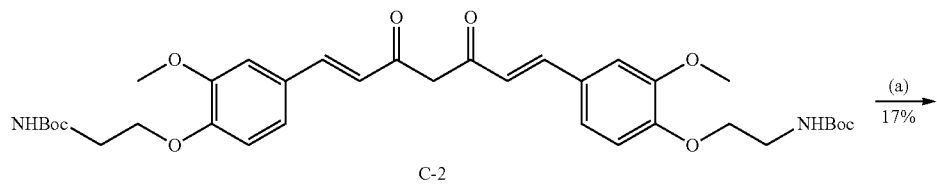

C-2

$\xrightarrow[17\%]{(a)}$

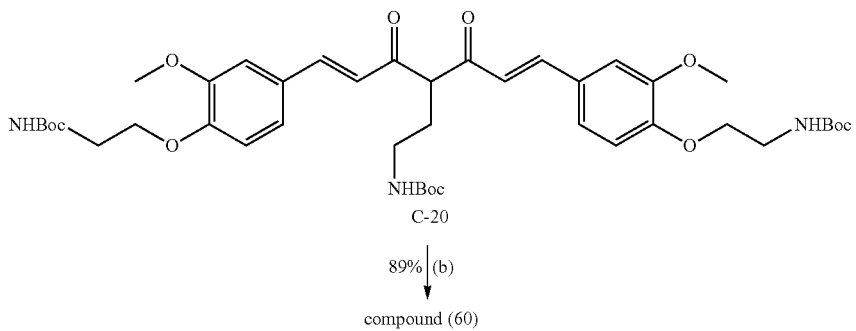

C-20

$\downarrow 89\% \,(b)$ compound (60)

Overview 7: Synthesis of substituted curcumins by alkylation: Conditions: (a) 2-N-tert-butyloxycarbonyl-amino-bromide, DBU, toluene or DCM or THF, 0° C.→RT→60° C.; (b) DCM, TFA, RT, 5 h; then Amberlite IRA-958 ion exchange resin, water Tetramethoxycurcumin (0.4 g, 1 mmol) or curcumin C-2 (0.6 g, 1 mmol) and 2-N-tert-butoxycarbonylaminoethyl bromide (0.34 g, 1.5 mmol) was placed in toluene (4 mL). 1.8-diazabicyclo[5.4.0]undec-7-ene (DBU) (0.15 g, 1 mmol) was added and the mixture was stirred for 15 h at room temperature. The solution was diluted with ethyl acetate (30 mL), and washed with sodium chloride solution (30 mL), potassium hydrogen sulphate solution (5%, 30 mL) and water (30 mL). After drying over MgSO₄, it was rotary evaporated and the residue was purified by column chromatography on silica gel with ethyl acetate/petroleum ether and then by preparative thin layer chromatography.

C-15: 1,7-bis-(3,4-dimethoxyphenyl)-hepta-4-(2-tert-butoxycarbonylamino-ethyl)-1,6-dien-3,5-dione

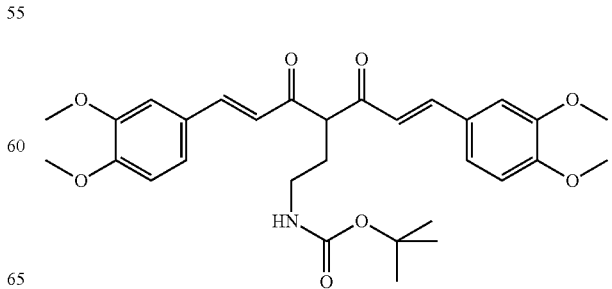

Column chromatography on silica gel with acetone/PE=1:1

Yield: 14% of theory, orange solid or orangey-yellow powder (76 mg)

Molecular mass=539.63 g/mol; Empirical formula=$C_{30}H_{37}NO_8$ $^1$H NMR (300 MHz, CDCl$_3$), δ=7.72-7.53 (m, 2H), 7.22-7.04 (m, 4H), 6.86 (d, J=8.1 Hz, 2H), 6.54 (d, J=15.7 Hz, 2H), 5.11 (s, 1H), 3.88-3.72 (m, 2H), 3.93 (s, 12H), 2.81-2.70 (m, 2H), 1.43 (s, 9H). MS (ESI, CH$_2$Cl$_2$/MeOH+ 10 mmol NH$_4$OAc): 562.3 (MNa$^+$, 13%), 540.3 (MH$^+$, 100%), 484.2 (2%, MH$^+$—C$_4$H$_9$), 440.3 (61%, MH$^+$-boc).

C-20: [2-(4-{7-[4-(2-tert-butoxycarbonylamino-ethoxy)-3-methoxy-phenyl]-3,5-dioxo-hepta-4-(2-tert-butoxycarbonylamino-ethyl)-1,6-dienyl}-2-methoxy-phenoxy)-ethyl]-carbamic acid tert-butyl ester

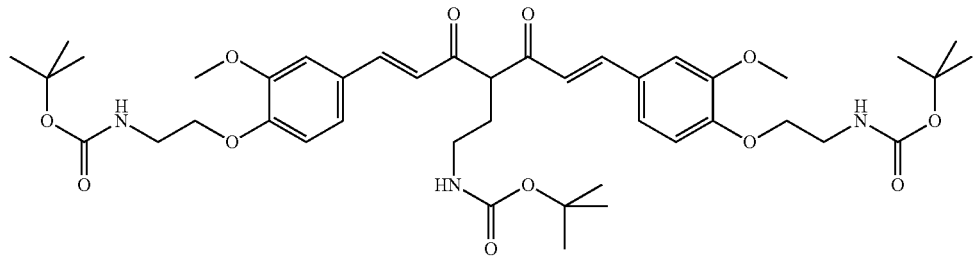 [SMILES: COc1cc(/C=C/C(=O)C(CCNC(=O)OC(C)(C)C)C(=O)/C=C/c2ccc(OCCNC(=O)OC(C)(C)C)c(OC)c2)ccc1OCCNC(=O)OC(C)(C)C]

Column chromatography on silica gel with acetone/PE=1:3→1:1

Yield: 12% of theory, orange, orangey-yellow powder (96 mg).

Molecular mass=797.95 g/mol; Empirical formula=$C_{42}H_{59}N_3O_{12}$ $^1$H NMR (300 MHz, CDCl$_3$), δ=7.64 (d, J=15.7 Hz, 2H), 7.24-7.01 (m, 6H), 6.78 (d, J=15.8 Hz, 2H), 5.16 (s, 2H), 4.12 (dd, J=10.6, 5.4 Hz, 4H), 3.93 (s, 3H), 3.90 (s, 3H), 3.86-3.75 (m, 2H), 3.54 (m, 4H), 2.82-2.71 (m, 2H), 1.45 (s, 9H), 1.44 (s, 9H). MS (ESI, CH$_2$Cl$_2$/MeOH+10 mmol NH$_4$OAc): 820.4 (MNa$^+$, 69%), 798.4 (MH$^+$, 100%), 742.4 (6%, MH$^+$—C$_4$H$_9$), 698.3 (36%, MH$^+$-boc).

Synthesis of Unsymmetrically Substituted Curcumins
General Procedure:
Step 1:

The beta-diketones used were acetyl acetone (1.5 g, 15 mmol) or 3-methyl-2,4-pentanedione (3.42 g, 30 mmol). The corresponding beta-diketone and boron oxide B$_2$O$_3$ (1.5 g, 21 mmol) were suspended in ethyl acetate (20 mL) and stirred for 60 minutes at 70° C. The substituted benzaldehyde E-3 (1.02 g, 3.5 mmol) in ethyl acetate (5 mL) and tributylborate (1.68 g, 7 mmol) was added and the formulation was stirred for half an hour at 85° C. Next, n-butylamine (0.5 mL in 3 mL ethyl acetate) was added dropwise over 10 minutes. After stirring for a further three hours at 80° C., it was cooled to 50° C. and in order to hydrolyse the boron complex, 100 mL of 50% acetic acid was added. After stirring overnight at room temperature, the mixture of solvents, protected from light, was removed and the residue was extracted three times with EE (30 mL each time). The combined organic phases were washed twice with water (50 mL each time), dried over MgSO$_4$ and finally, the solvent was withdrawn under reduced pressure.

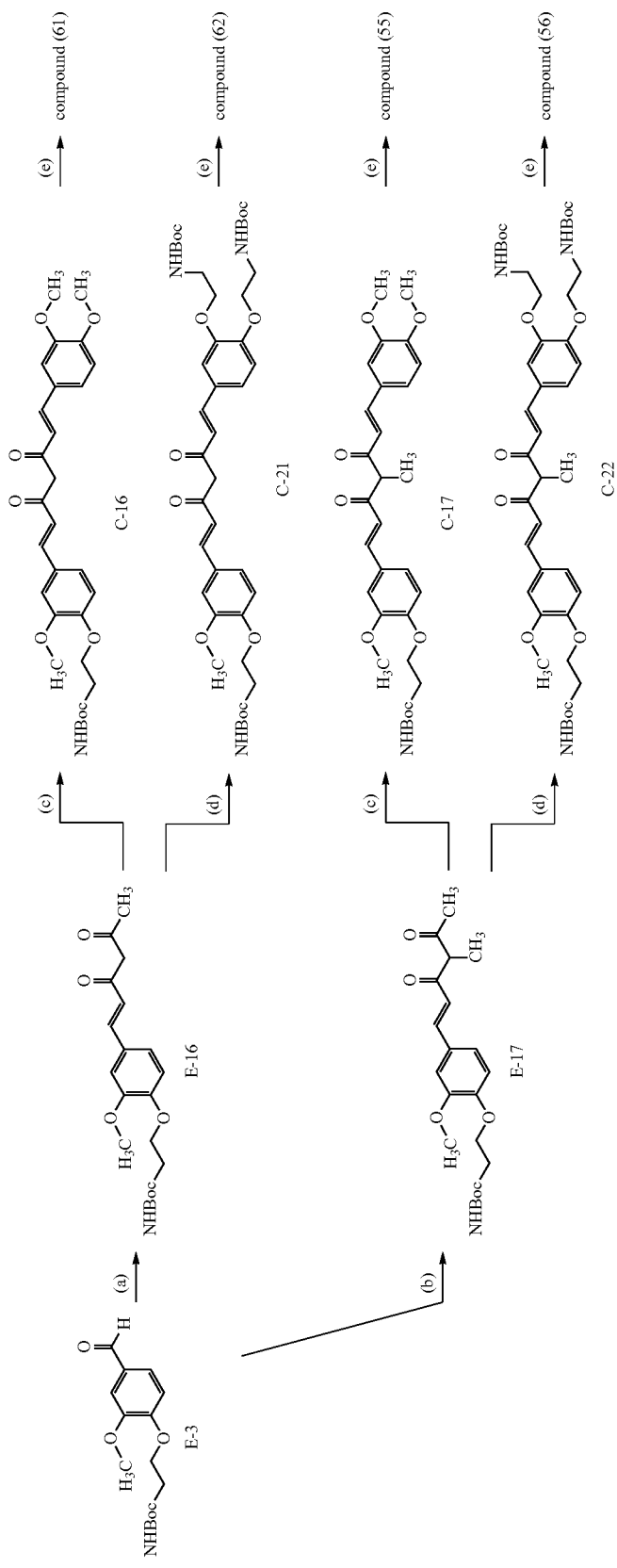

E-16: tert-butyl 2-(4-(3,5-dioxohex-1-enyl)-2-methoxyphenoxy)ethyl carbamate

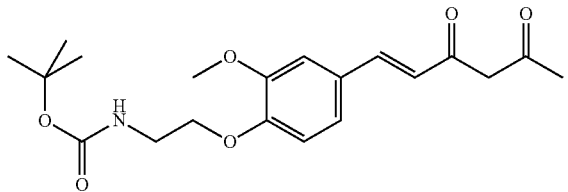 [SMILES: COc1cc(/C=C/C(=O)CC(C)=O)ccc1OCCNC(=O)OC(C)(C)C]

Acetyl acetone was used as the beta-diketone. Purification was carried out using column chromatography on silica gel with acetone/PE=2:5→1:2. The corresponding symmetrically substituted curcumin has poorer solubility in EtOH than the product.

Yield: 687 mg, 52% of theory, yellow solid.

Molecular mass=377.44 g/mol; Empirical formula=$C_{20}H_{27}NO_6$ $^1$H NMR (300 MHz, CDCl$_3$), δ=7.53 (d, J=15.8 Hz, 1H), 7.12-7.00 (m, 2H), 6.88 (d, J=8.3 Hz, 1H), 6.34 (d, J=15.8 Hz, 1H), 5.16 (s, 1H), 4.10 (t, J=5.1 Hz, 2H), 3.90 (s, 3H), 3.56 (d, J=5.3 Hz, 2H), 2.16 (s, 3H), 1.44 (s, 9H). MS (ESI, CH$_2$Cl$_2$/MeOH+10 mmol NH$_4$OAc): 777.4 (46%, 2MNa$^+$), 400.2 (38%, MNa$^+$), 378.2 (12%, MH$^+$), 322.1 (100%, MH$^+$—C$_4$H$_9$), 278.1 (47%, MH$^+$–boc).

E-17: tert-butyl 2-(4-(3,5-dioxo-4-methyl-hex-1-enyl)-2-methoxyphenoxy)-ethyl carbamate

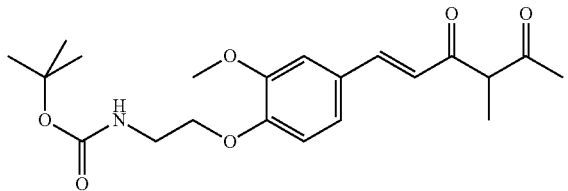 [SMILES: COc1cc(/C=C/C(=O)C(C)C(C)=O)ccc1OCCNC(=O)OC(C)(C)C]

3-methyl-2,4-pentanedione was used as the beta-diketone. Purification was carried out using column chromatography on silica gel with acetone/PE=1:3 and preparative TLC with acetone/PE=1:2.

Yield: 644 mg, 47% of theory, yellow solid.

Molecular mass=391.47 g/mol; Empirical formula=$C_{21}H_{29}NO_6$ $^1$H NMR (300 MHz, CDCl$_3$), δ=7.58 (dd, J=15.7, 6.5 Hz, 1H), 7.13 (d, J=8.3 Hz, 1H), 7.05 (dd, J=4.9, 1.8 Hz, 1H), 6.89 (d, J=8.3 Hz, 1H), 6.74 (dd, J=37.9, 15.7 Hz, 1H), 5.11 (s, 1H), 4.10 (t, J=5.1 Hz, 2H), 3.91 (s, 3H), 3.56 (m, 2H), 2.25+2.18 (s, 3H), 2.02 (s, 3H), 1.44 (s, 10H). MS (ESI, CH$_2$Cl$_2$/MeOH+10 mmol NH$_4$OAc): 805.5 (24%, 2MNa$^+$), 414.3 (53%, MNa$^+$), 392.3 (19%, MH$^+$), 336.2 (100%, MH$^+$—C$_4$H$_9$), 292.2 (34%, MH$^+$–boc).

Step 2:

Tert-butyl-2-(4-(3,5-dioxohex-1-enyl)-2-methoxyphenoxy)ethyl carbamate (185 mg, 0.5 mmol) or tert-butyl-2-(4-(3,5-dioxo-4-methyl-hex-1-enyl)-2-methoxyphenoxy) ethyl carbamate (191 mg, 0.5 mmol) and boron oxide B$_2$O$_3$ (0.07 g, 1 mmol) were suspended in ethyl acetate (3 mL) and stirred for 60 minutes at 80° C. The substituted benzaldehyde (0.6 mmol) in ethyl acetate (3 mL) along with tributylborate (0.24 g, 1 mmol) were added one after the other and the formulation was stirred for half an hour at 80° C. Next, n-butylamine (0.1 mL in 1 mL EE) was added dropwise over 5 minutes. After stirring for a further three hours at 80° C., the slightly cooled solution, still at approximately 50° C., was poured into 40 mL of 50% acetic acid. After stirring overnight at room temperature protected from light, the mixture of solvents was withdrawn under reduced pressure and the residue was extracted three times with EE (20 mL each time). The combined organic phases were washed twice with water (20 mL each time), dried over MgSO$_4$ and finally, the solvent was withdrawn under reduced pressure. Purification was carried out using column chromatography on silica gel.

C-16: tert-butyl 2-(4-((1E,6E)-7-(3,4-dimethoxyphenyl)-3,5-dioxohepta-1,6-dienyl)-2-methoxyphenoxy) ethyl carbamate

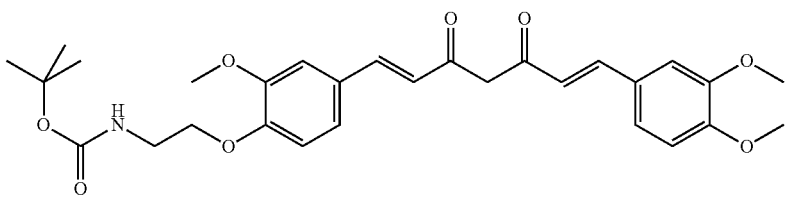 [SMILES: COc1ccc(/C=C/C(=O)CC(=O)/C=C/c2ccc(OCCNC(=O)OC(C)(C)C)c(OC)c2)cc1OC]

Quantity of corresponding aldehyde E-16 used: 100 mg=0.6 mmol

Column chromatography with acetone/PE=1:2→2:3

Yield: 121 mg, 46% of theory, orange, viscous solid or orangey-yellow powder.

Molecular mass=525.60 g/mol; Empirical formula=$C_{29}H_{35}NO_8$ $^1$H NMR (300 MHz, CDCl$_3$), δ=7.60 (dd, J=15.7, 4.5 Hz, 2H), 7.15-7.06 (m, 4H), 6.89 (dd, J=8.3, 3.3 Hz, 2H), 6.50 (d, J=15.8 Hz, 2H), 5.13 (s, 1H), 4.11 (t, J=5.0 Hz, 2H), 3.94 (s, 3H), 3.93 (s, 3H), 3.92 (s, 3H), 3.62-3.52 (m, 2H), 1.45 (s, 9H). MS (ESI, CH$_2$Cl$_2$/MeOH+10 mmol NH$_4$OAc): 1073.5 (19%, 2M+Na$^+$), 526.2 (100%, MH$^+$), 470.2 (21%, MH$^+$—C$_4$H$_9$).

C-21: 2-(4-((1E,6E)-7-(3,4-bis(2-(tert-butoxycarbonylamino)ethoxy)phenyl)-3,5-dioxohepta-1,6-dienyl)-2-methoxyphenoxy)ethyl carbamate

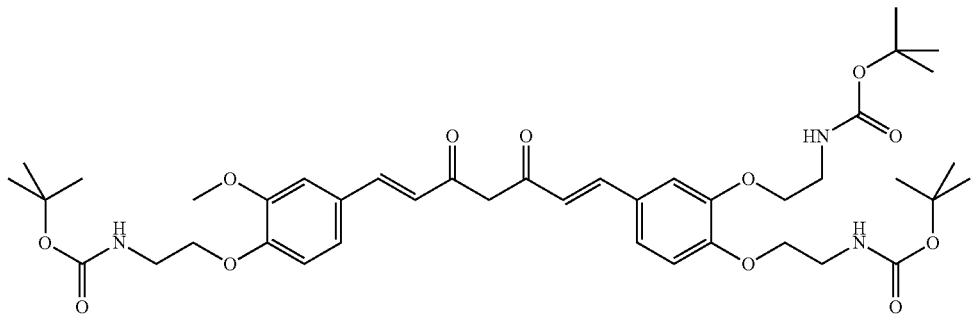 [SMILES: COc1cc(/C=C/C(=O)CC(=O)/C=C/c2ccc(OCCNC(=O)OC(C)(C)C)c(OCCNC(=O)OC(C)(C)C)c2)ccc1OCCNC(=O)OC(C)(C)C]

Quantity of corresponding aldehyde E-16 used: 255 mg=0.6 mmol

Column chromatography with acetone/PE=2:5→1:2

Yield: 172 mg, 44% of theory, orange, very viscous solid.

Molecular mass=783.92 g/mol; Empirical formula=$C_{41}H_{57}N_3O_{12}$ $^1$H NMR (300 MHz, CDCl$_3$), δ=7.57 (dd, J=15.7, 9.3 Hz, 2H), 7.17-7.05 (m, 4H), 6.90 (dd, J=8.2, 6.6 Hz, 2H), 6.49 (d, J=15.7 Hz, 2H), 5.27 (s, 2H), 5.14 (s, 1H), 4.10 (m, 6H), 3.91 (s, 3H), 3.55 (m, 6H), 1.46 (s, 9H), 1.44 (s, 18H). MS (ESI, CH$_2$Cl$_2$/MeOH+10 mmol NH$_4$OAc): 804.6 (73%, MNa$^+$), 784.4 (100%, MH$^+$), 684.3 (71%, MH$^+$-boc).

C-17: tert-butyl-2-(4-((1E,6E)-7-(3,4-dimethoxyphenyl)-3,5-dioxo-4-methyl-hepta-1,6-dienyl)-2-methoxyphenoxy)ethyl carbamate

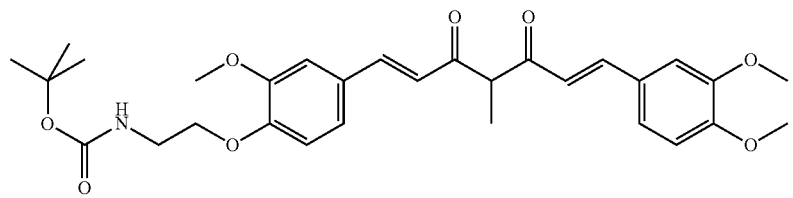 [SMILES: COc1ccc(/C=C/C(=O)C(C)C(=O)/C=C/c2ccc(OCCNC(=O)OC(C)(C)C)c(OC)c2)cc1OC]

Quantity of corresponding aldehyde E-17 used: 100 mg=0.6 mmol
Column chromatography with acetone/PE=1:2→2:3
Yield: 113 mg, 42% of theory, orange, viscous solid
Molecular mass=539.63 g/mol; Empirical formula=$C_{30}H_{37}NO_8$ $^1$H NMR (300 MHz, CDCl$_3$), δ=7.75-7.56 (m, 2H), 7.20-6.82 (m, 7H), 6.70 (d, J=15.9 Hz, 1H), 5.15 (s, 1H), 4.15-4.06 (m, 2H), 3.95 (s, 3H), 3.91 (s, 3H), 3.89 (s, 3H), 3.57 (m, 2H), 2.18 (s, 3H), 1.44 (s, 9H). MS (ESI, CH$_2$Cl$_2$/MeOH+10 mmol NH$_4$OAc): 562.2 (MNa$^+$, 41%), 540.3 (MH$^+$, 100%), 484.2 (MH$^+$—C$_4$H$_9$, 46%), 440.3 (MH$^+$-boc, 3%).

C-22: 2-(4-((1E,6E)-7-(3,4-bis(2-(tert-butoxycarbonylamino)ethoxy)phenyl)-3,5-dioxo-4-methyl-hepta-1,6-dienyl)-2-methoxyphenoxy)ethyl carbamic acid

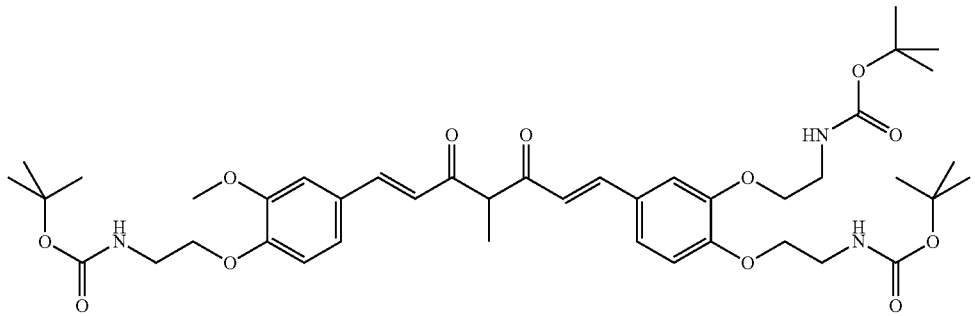 [SMILES: COc1cc(/C=C/C(=O)C(C)C(=O)/C=C/c2ccc(OCCNC(=O)OC(C)(C)C)c(OCCNC(=O)OC(C)(C)C)c2)ccc1OCCNC(=O)OC(C)(C)C]

Quantity of corresponding aldehyde E-17 used: 255 mg=0.6 mmol
Column chromatography with acetone/PE=2:5→1:2
Yield: 160 mg, 40% of theory, orange, very viscous solid.
Molecular mass=797.95 g/mol; Empirical formula=$C_{42}H_{59}N_3O_{12}$ $^1$H NMR (300 MHz, CDCl$_3$), δ=7.74-7.52 (m, 2H), 7.21-6.88 (m, 7H), 6.70 (d, J=15.9 Hz, 1H), 5.29 (s, 2H), 5.16 (s, 1H), 4.10 (t, J=4.8 Hz, 6H), 3.90 (m, 3H), 3.56 (m, 6H), 2.17 (m, 3H), 1.46 (s, 9H), 1.45 (s, 18H). MS (ESI, CH$_2$Cl$_2$/MeOH+10 mmol NH$_4$OAc): 820.4 (100%, MNa$^+$), 798.3 (43%, MH$^+$), 698.4 (67%, MH$^+$-boc).

3. Boc Deprotection of the Curcumins and Ion Exchange Chromatography

The corresponding boc-protected curcumin (0.2 mmol, 120-160 mg) was dissolved in DCM (6 mL). 4 mL of a 10% solution of TFA in DCM (containing 6% TIS) was slowly added dropwise, with stirring. After stirring for 5 h at RT protected from light, the product was precipitated by adding diethylether (10 mL). The precipitate was centrifuged off and then the supernatant was discarded. The solid was suspended in diethylether (30 mL) and centrifuged off once again. The supernatant was also discarded. This washing step was repeated once more and then the product was air dried in darkness.

Ion Exchange Chromatography

A column was loaded with Amberlite 954 and the ion exchange resin was conditioned with 0.1M HCl. After washing with water to a very weak acidic reaction, reconditioning to a water/MeOH/MeCN mixture was carried out as necessary. Next, the TFA salt in as little of the solvent mixture as possible was slowly eluted over the resin and then rinsed several times with a little solvent. After withdrawing the solvent under reduced pressure, the remaining aqueous solution was freeze-dried. Quantitative yield.

Eluent:
Curcumins 12a and 12b: water/MeOH/MeCN 1:1:1
Curcumins 04, 07, 09b, 11 b/c and 14b: water/MeOH/MeCN 9:4:2
All other curcumins: pure water 4. Curcumin Complexes

| Curcumin 01a BF-complex (BF-SA-CUR-1a) | 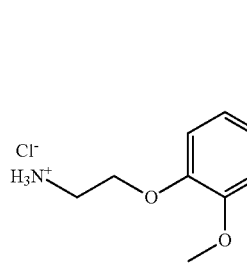 | | (1E,6E)-1,7-bis(4-(2-aminoethoxy)-3-methoxyphenyl) hepta-1,6-diene-3,5-dione hydrochloride BF$_2$ complex | Molecular mass: 504.34 + 2x 35.45 = 527.44 g/mol Empirical formula: $C_{25}H_{31}N_2O_6BF_2Cl_2$ |
|---|---|---|---|---|
| | Cl$^-$ H$_3$N$^+$ | 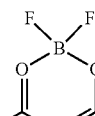 | Cl$^-$ NH | |

-continued

| | | | |
|---|---|---|---|
| Roseo-curcumin 01a hydrochloride (RO-SA-CUR-1a) | 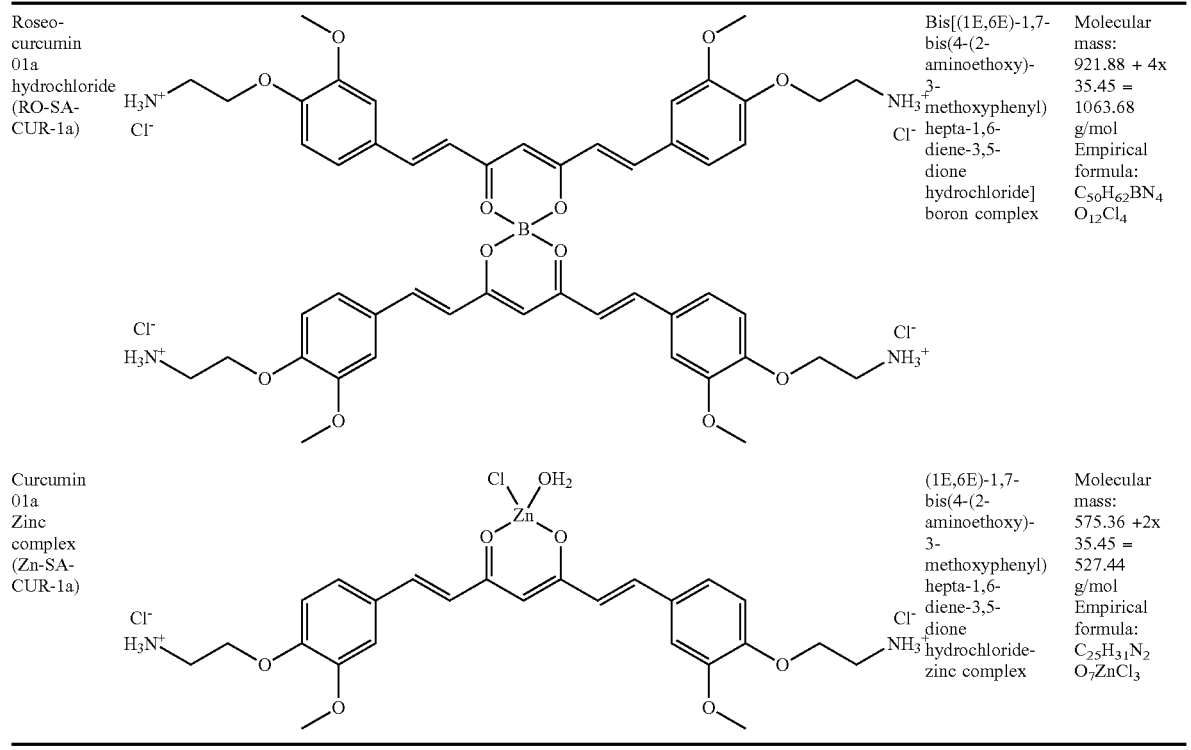 | Bis[(1E,6E)-1,7-bis(4-(2-aminoethoxy)-3-methoxyphenyl) hepta-1,6-diene-3,5-dione hydrochloride] boron complex | Molecular mass: 921.88 + 4x 35.45 = 1063.68 g/mol Empirical formula: $C_{50}H_{62}BN_4O_{12}Cl_4$ |
| Curcumin 01a Zinc complex (Zn-SA-CUR-1a) | | (1E,6E)-1,7-bis(4-(2-aminoethoxy)-3-methoxyphenyl) hepta-1,6-diene-3,5-dione hydrochloride-zinc complex | Molecular mass: 575.36 +2x 35.45 = 527.44 g/mol Empirical formula: $C_{25}H_{31}N_2O_7ZnCl_3$ |

4.a) SA-CUR-01a TEA salt (68 mg, 0.1 mmol) was placed in dry DCM (10 mL). Boron trifluoride etherate (20 µL, 0.12 mmol) was added dropwise and the formulation was stirred overnight. The solution was diluted with diethylether (20 mL), distributed onto two Blue Caps and centrifuged. The pellet was washed several times with diethylether and air dried.

Red powder (TEA salt), quantitative yield.

Ion Exchange Chromatography

A short column was loaded with Amberlite 954 and the ion exchange resin was conditioned with 0.1M HCl. After washing with water to a very weak acidic reaction, the TFA salt was washed in as little water as possible, eluted slowly over the resin and rinsed several times with a little solvent. The aqueous solution was freeze-dried. Quantitative yield.

4.b) SA-CUR-01a chloride (108 mg, 0.2 mmol) and boron trioxide (0.05 mmol) were stirred overnight in aqueous HCl (1 M, 2 mL) at room temperature. The solvent was extracted in a stream of nitrogen and the residue was dried.

Red powder, quantitative yield.

4.c) SA-CUR-01a chloride (54 mg, 0.1 mmol) and zinc acetate dihydrate (0.05 mmol) were refluxed in ethanol/acetic acid/water 3:2:1 (3 mL) for 2 days. The solvent was extracted in a stream of nitrogen and the residue was dried.

Orange powder, quantitative yield.

A summary of the compounds produced is shown in Overview 8.

| Description/Serial number | Structure | Analysis |
|---|---|---|
| Curcumin 0 hydrochloride (SA-CUR-0) compound (40) | 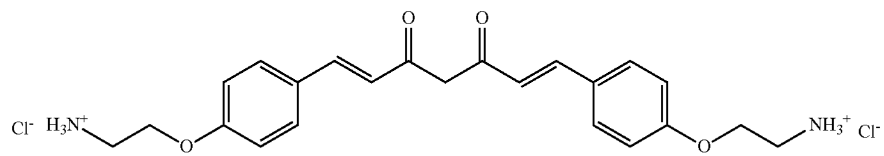 [SMILES: [Cl-] ; [NH3+]CCOc1ccc(/C=C/C(=O)CC(=O)/C=C/c2ccc(OCC[NH3+])cc2)cc1 ; [Cl-]] | ¹H NMR (300 MHz, MeOD), δ = 7.60 (m, 6H), 7.04 (d, J = 6.9 Hz, 4H), 6.67 (d, J = 13.8 Hz, 2H), 4.32-4.17 (m, 4H), 3.46-3.34 (m, 4H). MS (ESI, MeCN/H₂O + 0.06% TFA): 198.1 (100%, (M + 2H⁺)²⁺), 352.2 (9%, MH⁺ —C₂H₅N), 395.2 (2%, MH⁺) |
| Curcumin 01a hydrochloride (SA-CUR-1a) compound (41) | 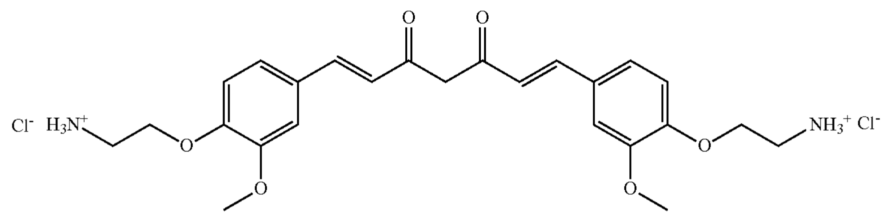 [SMILES: [Cl-] ; COc1cc(/C=C/C(=O)CC(=O)/C=C/c2ccc(OCC[NH3+])c(OC)c2)ccc1OCC[NH3+] ; [Cl-]] | ¹H NMR (300 MHz, MeOD), δ = 7.61 (d, J = 15.7 Hz, 2H), 7.33 (s, 2H), 7.23 (d, J = 8.2 Hz, 2H), 7.06 (d, J = 8.2 Hz, 2H), 6.74 (d, J = 15.7 Hz, 2H), 6.03 (s, 1H), 4.33-4.22 (m, 4H), 3.95 (s, 6H), 3.45-3.34 (m, 4H). MS (ESI, MeCN/H₂O + 0.06% TFA): 228.1 (100%, (M + 2H⁺)²⁺), 412.2 (5%, MH⁺ —C₂H₅N), 455.2 (3%, MH⁺) |
| Curcumin 01d hydrochloride (SA-CUR-1d), HO-SA-CUR-1 compound (71) | 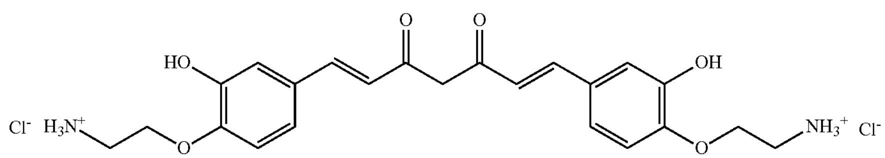 [SMILES: [Cl-] ; [NH3+]CCOc1ccc(/C=C/C(=O)CC(=O)/C=C/c2ccc(OCC[NH3+])c(O)c2)cc1O ; [Cl-]] | ¹H NMR (300 MHz, MeOD), δ = 7.65-6.70 (m, 10H), 4.35-4.24 (m, 4H), 3.46-3.34 (m, 4H). MS (ESI, MeCN/H₂O + 0.06% TFA): 214.1 (100%, (M + 2H⁺)²⁺), 384.2 (7%, MH⁺ —C₂H₅N), 427.2 (5%, MH⁺) |
| Curcumin 01b hydrochloride (SA-CUR-1b), iso-SA-CUR-1 compound (42) | 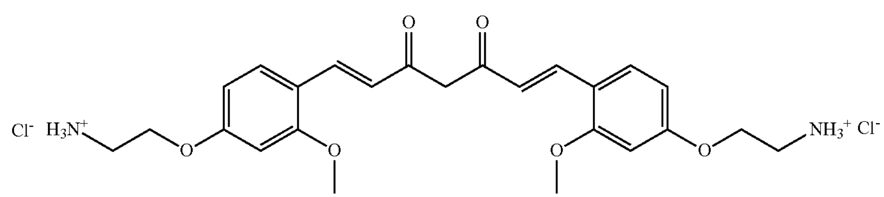 [SMILES: [Cl-] ; COc1cc(OCC[NH3+])ccc1/C=C/C(=O)CC(=O)/C=C/c1ccc(OCC[NH3+])cc1OC ; [Cl-]] | ¹H NMR (300 MHz, MeOD), δ = 7.63 (d, J = 15.8 Hz, 2H), 7.52-7.02 (m, 6H), 6.77 (d, J = 15.7 Hz, 2H), 4.35-4.25 (m, 4H), 3.8 (6H), 3.42-3.32 (m, 4H). MS (ESI, MeCN/H₂O + 0.06% TFA): 228.1 (100%, (M + 2H⁺)²⁺), 412.2 (5%, MH⁺ —C₂H₅N), 455.2 (3%, MH₊) |
| Curcumin 01e hydrochloride (SA-CUR-1e), Me-SA-CUR-1 compound (43) | 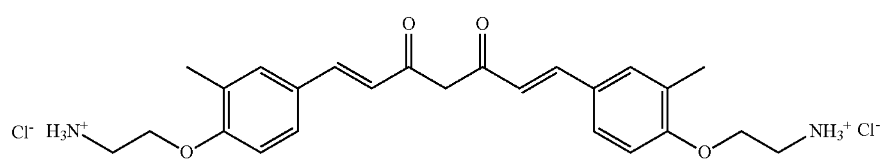 [SMILES: [Cl-] ; Cc1cc(/C=C/C(=O)CC(=O)/C=C/c2ccc(OCC[NH3+])c(C)c2)ccc1OCC[NH3+] ; [Cl-]] | ¹H NMR (300 MHz, MeOD), δ = 7.60 (d, J = 14.3 Hz, 2H), 7.55-7.37 (m, 4H), 6.99 (d, J = 6.8 Hz, 2H), 6.68 (d, J = 14.3 Hz, 2H), 4.28 (m, 4H), 3.48-3.39 (m, 4H), 2.31 (s, 6H). MS (ESI, MeCN/H₂O + 0.06% TFA): 212.1 (100%, (M + 2H⁺)²⁺), 380.2 (6%, MH⁺ —C₂H₅N), 423.2 (2%, MH⁺) |

-continued

| Description/Serial number | Structure | Analysis |
|---|---|---|
| Curcumin 01c hydrochloride (SA-CUR-1e), Iodo-SA-CUR-1 compound (44) | 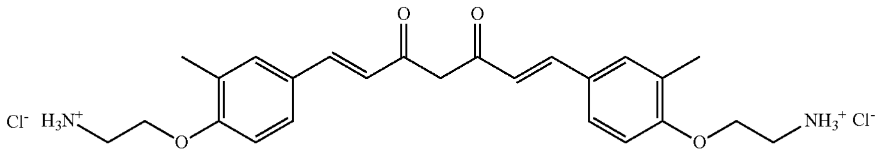 | ¹H NMR (300 MHz, MeOD), δ = 7.68 (s, 2H), 7.56 (d, 14.5 Hz, 2H), 7.35 (s, 2H), 6.81 (d, J = 13.0 Hz, 2H), 6.07 (s, 1H), 4.27-4.15 (m, 4H), 3.95 (s, 6H), 3.42-3.32 (m, 4H). MS (ESI, MeCN/H₂O + 0.06% TFA): 354.0 (100%, (M + 2H⁺)²⁺), 664.0 (4%, MH⁺ —C₂H₅N), 707.1 (1%, MH⁺) |
| Curcumin 02 hydrochloride (SA-CUR-2) compound (45) | 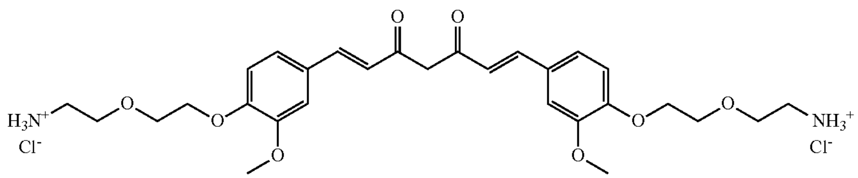 [SMILES: [Cl-] ; COc1cc(/C=C/C(=O)CC(=O)/C=C/c2ccc(OCCOCC[NH3+])c(OC)c2)ccc1OCCOCC[NH3+] ; [Cl-]] | ¹H NMR (300 MHz, MeOD), δ = 7.60 (d, J = 15.7 Hz, 2H), 7.28 (s, 2H), 7.20 (d, J = 8.2 Hz, 2H), 7.01 (d, J = 8.3 Hz, 2H), 6.70 (d, J = 15.8 Hz, 2H), 4.22 (dd, J = 5.2, 3.3 Hz, 4H), 3.91 (s, 6H), 3.94-3.88 (m, 4H), 3.83-3.76 (m, 4H), 3.16 (t, J = 3.2 Hz, 4H). MS (ESI, MeCN/H₂O + 0.06% TFA): 272.1 (100%, (M + 2H⁺)²⁺), 500.2 (3%, MH⁺ —C₂H₅N), 543.3 (3%, MH⁺) |
| Curcumin 08 hydrochloride (SA-CUR-8) compound (46) | 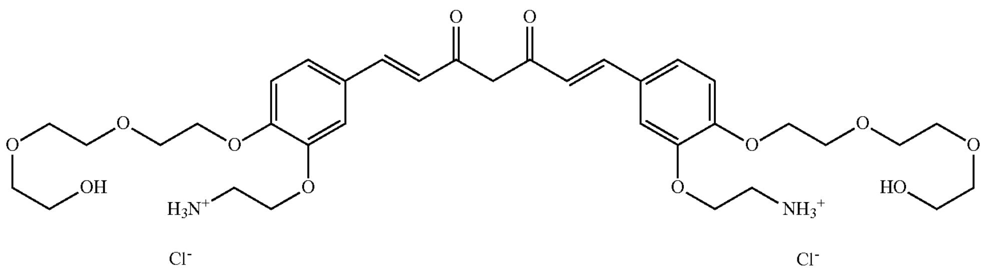 [SMILES: [NH3+]CCOc1cc(/C=C/C(=O)CC(=O)/C=C/c2ccc(OCCOCCOCCO)c(OCC[NH3+])c2)ccc1OCCOCCOCCO ; [Cl-] ; [Cl-]] | ¹H NMR (600 MHz, MeOD), δ = 7.66-6.78 (m, 10H), 4.34-4.17 (m, 6H), 3.89 (m, 4H), 3.81-3.38 (m, 20H), 3.27 (m, 2H). MS (ESI, MeCN/H₂O + 0.06% TFA): 346.2 (100%, (M + 2H⁺)²⁺) |
| Curcumin 04 hydrochloride (SA-CUR-4) compound (51) | 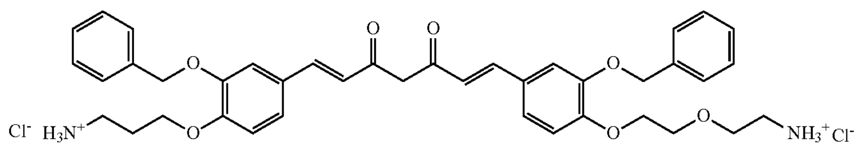 [SMILES: [Cl-] ; [NH3+]CCCOc1ccc(/C=C/C(=O)CC(=O)/C=C/c2ccc(OCCOCC[NH3+])c(OCc3ccccc3)c2)cc1OCc1ccccc1 ; [Cl-]] | ¹H NMR (300 MHz, MeOD), δ = 7.57 (m, 2H), 7.48-7.33 (m, 12H), 7.28 (m, 2H), 7.08 (m, 2H), 6.68 (m, 2H), 5.13 (s, 4H), 4.23 (m, 4H), 3.16 (t, J = 6.4 Hz, 4H), 2.16 (m, 4H). MS (ESI, MeCN/H₂O + 0.06% TFA): 286.1 (100%, (M + 2H⁺)²⁺), 545.3 (4%, MH⁺ —C₂H₅N), 635.3 (1%, MH⁺) |
| Curcumin 07 hydrochloride (SA-CUR-07) compound (48) | 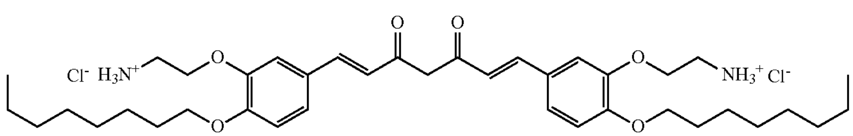 [SMILES: CCCCCCCCOc1ccc(/C=C/C(=O)CC(=O)/C=C/c2ccc(OCCCCCCCC)c(OCC[NH3+])c2)cc1OCC[NH3+] ; [Cl-] ; [Cl-]] | ¹H NMR (300 MHz, DMSO), δ = 8.06 (s, 6H), 7.59 (d, J = 15.8 Hz, 2H), 7.41 (s, 2H), 7.28 (d, J = 8.4 Hz, 2H), 7.09 (d, J = 8.4 Hz, 2H), 6.87 (d, J = 15.9 Hz, 2H), 6.13 (s, 1H), 4.22 (t, J = 5.3 Hz, 4H), 4.06 (t, J = 6.7 Hz, 4H), 3.22 (t, J = 5.2 Hz, 4H), 1.86-1.68 (m, 4H), 1.49-1.22 (m, 20H), 0.87 (t, J = 8.7, 6H). MS (ESI, MeCN/H₂O + 0.06% TFA): 326.2 (100 %, (M + 2H⁺)²⁺), 651.4 (2%, MH⁺) |

| Description/Serial number | Structure | Analysis |
|---|---|---|
| Curcumin 03 hydrochloride (SA-CUR-3) compound (49) | 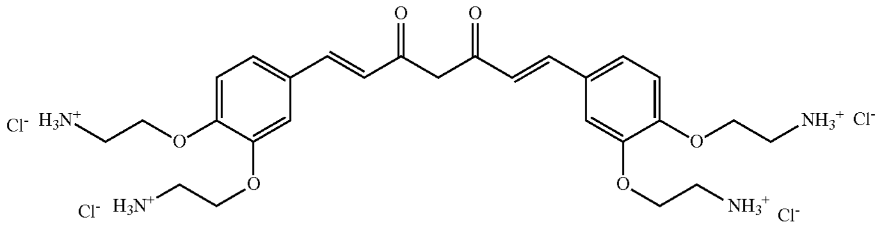 [SMILES: [Cl-] ; [NH3+]CCOc1ccc(/C=C/C(=O)CC(=O)/C=C/c2ccc(OCC[NH3+])c(OCC[NH3+])c2)cc1OCC[NH3+] ; [Cl-] ; [Cl-] ; [Cl-]] | ¹H NMR (300 MHz, MeOD), δ = 7.61 (d, J = 15.8 Hz, 2H), 7.37 (s, 2H), 7.35-7.28 (m, 2H), 7.10 (d, J = 8.4 Hz, 2H), 6.74 (d, J = 15.8 Hz, 2H), 6.02 (s, 1H), 4.32 (dd, J = 9.8, 4.9 Hz, 8H), 3.43 (t, J = 4.8 Hz, 8H). MS (ESI, MeCN/H₂O + 0.06% TFA): 171.8 (100%, (M + 3H⁺)³⁺), 235.6 (43%, (M + 2H⁺)²⁺ —C₂H₅N), 257.1 (44%, (M + 2H⁺)²⁺), 513.3 (15%, MH⁺) |
| Curcumin 05 hydrochloride (SA-CUR-5) compound (50) | 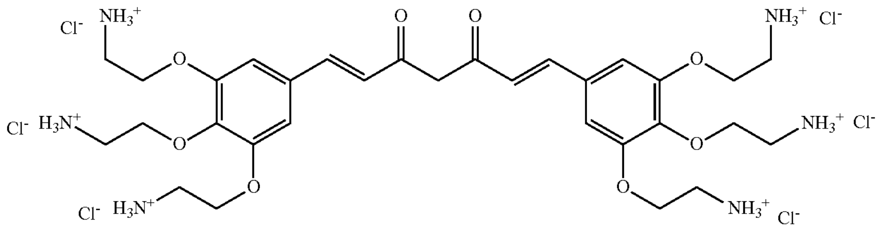 | ¹H NMR (300 MHz, MeOD), δ = 7.62 (d, J = 15.8 Hz, 2H), 7.12 (s, 4H), 6.84 (d, J = 15.9 Hz, 2H), 4.41-4.29 (m, 8H), 4.27-4.20 (m, 4H), 3.50-3.40 (m, 8H), 3.39-3.33 (m, 4H). MS (ESI, MeCN/H₂O + 0.06% TFA): 158.6 (47%, (M + 4H⁺)⁴⁺), 211.1 (100%, (M + 3H⁺)³⁺), 273.1 (6%, (M + 2H⁺)²⁺ —C₂H₅N), 316.2 (24%, (M + 2H⁺)²⁺), 631.3 (12%, MH⁺) |
| Curcumin 01a BF-complex (BF-SA-CUR-1a) compound (68) | 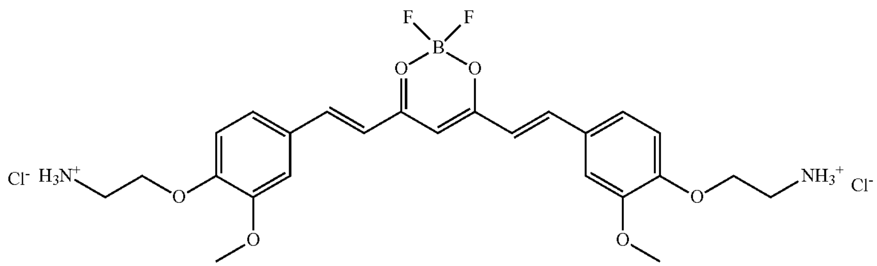 | ¹H NMR (300 MHz, D₂O), δ = 7.32 (m, 2H), 7.72 (m, 4H), 6.31 (m, 2H), 5.84 (s, 1H), 4.11-3.96 (m, 4H), 3.58 (s, 6H), 3.36-3.21 (m, 4H). MS (ESI, MeCN/H₂O + 0.06% TFA): 228.6 (100%, (M + 2H⁺)²⁺-BF₂), 252.1 (3%, (M + 2H⁺)²⁺), 503.2 (7%, MH⁺) |

| Description/Serial number | Structure | Analysis |
|---|---|---|
| Roseo-curcumin 01a hydrochloride (RO-SA-CUR-1a) compound (70) | 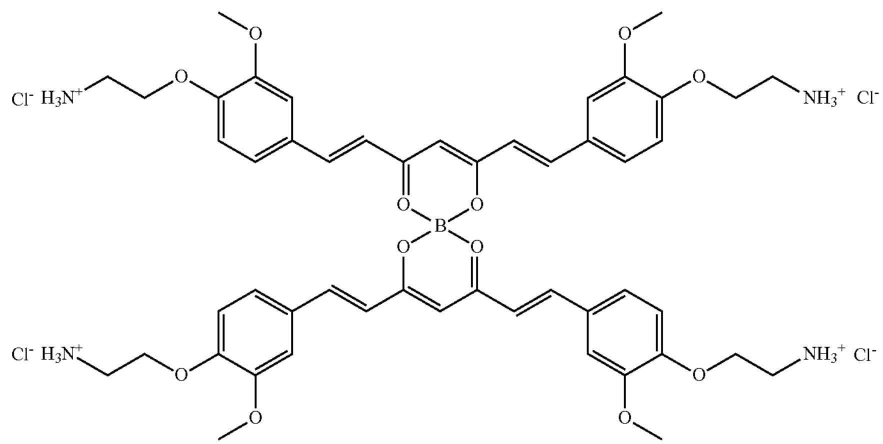 | MS (ESI, MeCN/H$_2$O + 0.06% TFA): 228.6 (100%, (M + 2H$^+$)$^{2+}$-B-ligand), 409.8 (3%, (M + 2H$^+$)$^{2+}$), 918.5 (1%, MH$^+$) |
| Curcumin 01a Zinc complex (Zn-SA-CUR-1a) compound (69a) |  | MS (ESI, MeCN/H$_2$O + 0.06% TFA): 228.6 (100%, (M + 2H$^+$)$^{2+}$-Zn), 553.2 (1%, MH$^+$) |
| Curcumin 09a hydrochloride (Me-SA-CUR-9a) compound (47) | 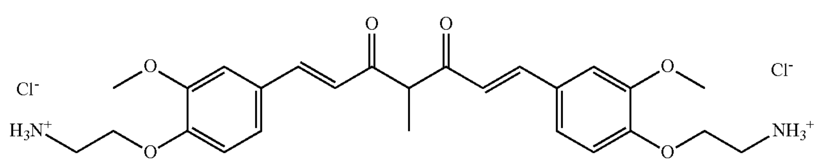 [SMILES: [Cl-] ; COc1cc(/C=C/C(=O)C(C)C(=O)/C=C/c2ccc(OCC[NH3+])c(OC)c2)ccc1OCC[NH3+] ; [Cl-]] | 1H NMR (300 MHz), MeOD), δ = 7.66 (d, J = 15.5 Hz, 2H), 7.35 (s, 2H), 7.29-7.20 (m, 4H), 7.06 (d, J = 8.3 Hz, 2H), 4.32-4.22 (m, 4H), 3.96 (s, 6H), 3.44-3.35 (m, 4H), 2.22 (s, 3H). MS (ESI, MeCN/H$_2$O + 0.06% TFA): 235.1 (100%, (M + 2H$^+$)$^{2+}$), 426.2 (2%, MH$^+$—C$_2$H$_5$N), 469.2 (1%, MH$^+$) |

-continued

| Description/Serial number | Structure | Analysis |
|---|---|---|
| Curcumin 09b hydrochloride (cyclo-SA-CUR-9b) compound (54) | 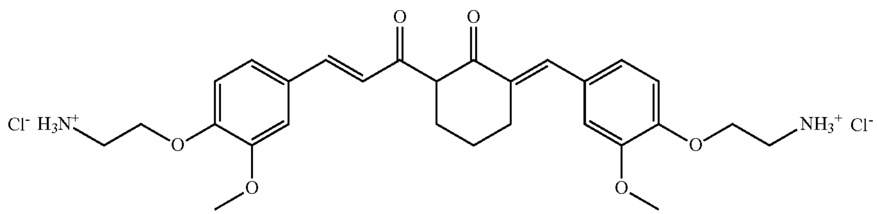 [SMILES: [Cl-] ; COc1cc(/C=C/C(=O)C2CCC/C(=C\c3ccc(OCC[NH3+])c(OC)c3)C2=O)ccc1OCC[NH3+] ; [Cl-]] | $^1$H NMR (400 MHz, MeOD), δ = 7.73-7.56 (m, 2H), 7.19-6.98 (m, 6H), 4.26 (m, 4H), 3.95 (s, 3H), 3.91 (s, 3H), 3.37 (m, 4H), 2.81-2.62 (m, 4H), 1.79 (m, 2H). MS (ESI, MeCN/H$_2$O + 0.06% TFA): 248.1 (100%, (M + 2H$^+$)$^{2+}$), 452.2 (4%, MH$^+$—C$_2$H$_5$N), 495.2 (1%, MH$^+$) |
| Curcumin 10a hydrochloride (SA-CUR-10a) compound (66) | 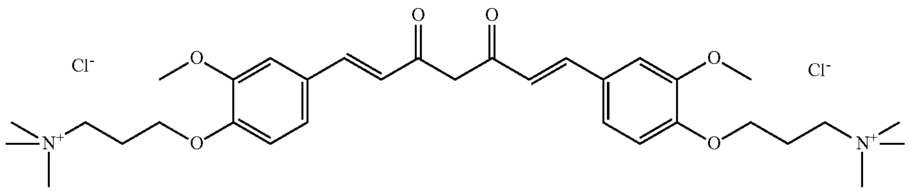 | $^1$H NMR (300 MHz, MeOD), δ = 7.60 (d, J = 15.6 Hz, 2H), 7.28 (s, 2H), 7.20 (d, J = 7.6 Hz, 2H), 7.01 (d, J = 8.1 Hz, 2H), 6.71 (d, J = 15.7 Hz, 2H), 4.17 (t, J = 5.4 Hz, 4H), 3.91 (s, 6H), 3.66-3.53 (m, 4H), 3.20 (s, 18H), 2.38-2.24 (m, 4H). MS (ESI, MeCN/H$_2$O + 0.06% TFA): 284.2 (100%, M$^{2+}$) |
| Curcumin 10b hydrochloride (GUA-SA-CUR-10b) compound (63) | 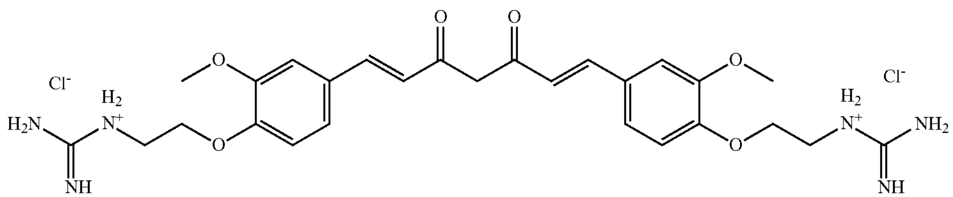 | $^1$H NMR (400 MHz, MeOD), δ = 7.61 (d, J = 13.1 Hz, 2H), 7.34-7.16 (m, 4H), 7.01 (d, J = 7.5 Hz, 2H), 6.74 (m, 4H), 4.18 (t, J = 4 Hz, 4H), 3.92 (d, J = 8.1 Hz, 6H), 3.64 (t, J = 4.3 Hz, 4H). MS (ESI, MeCN/H$_2$O + 0.06% TFA): 270.1 (100%, (M + 2H$^+$)$^{2+}$), 539.3 (2%, MH$^+$) |
| Curcumin 10c hydrochloride (SA-CUR-10c) compound (67) | 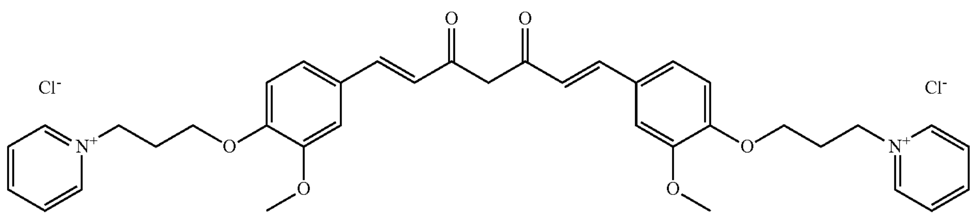 | $^1$H NMR (300 MHz, MeOD), δ = 9.06 (d, J = 5.6 Hz, 4H), 8.61 (t, J = 7.8 Hz, 2H), 8.17-8.02 (m, 4H), 7.58 (d, J = 15.9 Hz, 2H), 7.22 (s, 2H), 7.17 (d, J = 7.6 Hz, 2H), 6.96 (d, J = 8.3 Hz, 2H), 6.69 (d, J = 15.8 Hz, 2H), 4.92-4.83 (m, 4H), 4.19 (t, J = 5.4 Hz, 4H), 3.83 (s, 6H), 2.67-2.48 (m, 4H). MS (ESI, MeCN/H$_2$O + 0.06% TFA): 304.1 (100%, M$^{2+}$) |
| Curcumin 11a hydrochloride (SA-CUR-11a) compound (59) | 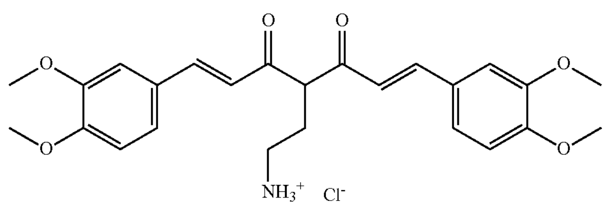 | $^1$H NMR (300 MHz, MeOD), δ = 7.78-6.65 (m, 10H), 4.03-3.85 (m, 2H), 3.90 (s, 12H), 2.97-2.80 (m, 2H). MS (ESI, MeCN/H$_2$O + 0.06% TFA): 440.2 (MH$^+$, 100%) |

| Description/Serial number | Structure | Analysis |
|---|---|---|
| Curcumin 11b hydrochloride (SA-CUR-11b) compound (61) | 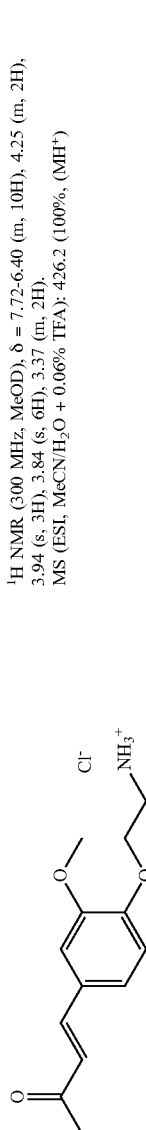 | 1H NMR (300 MHz, MeOD), δ = 7.72-6.40 (m, 10H), 4.25 (m, 2H), 3.94 (s, 3H), 3.84 (s, 6H), 3.37 (m, 2H). MS (ESI, MeCN/H2O + 0.06% TFA): 426.2 (100%, (MH+) |
| Curcumin 11c hydrochloride (SA-CUR-11c) compound (55) | 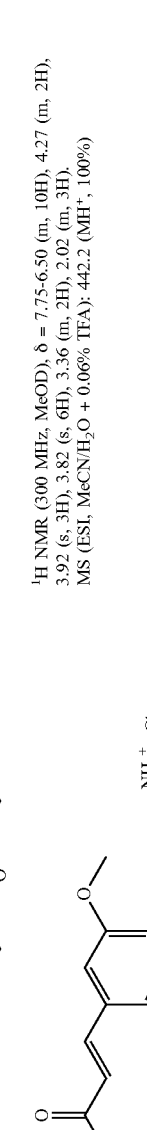 | 1H NMR (300 MHz, MeOD), δ = 7.75-6.50 (m, 10H), 4.27 (m, 2H), 3.92 (s, 3H), 3.82 (s, 6H), 3.36 (m, 2H), 2.02 (m, 3H). MS (ESI, MeCN/H2O + 0.06% TFA): 442.2 (MH+, 100%) |
| Curcumin 12a hydrochloride (SA-CUR-12a) compound (52) | 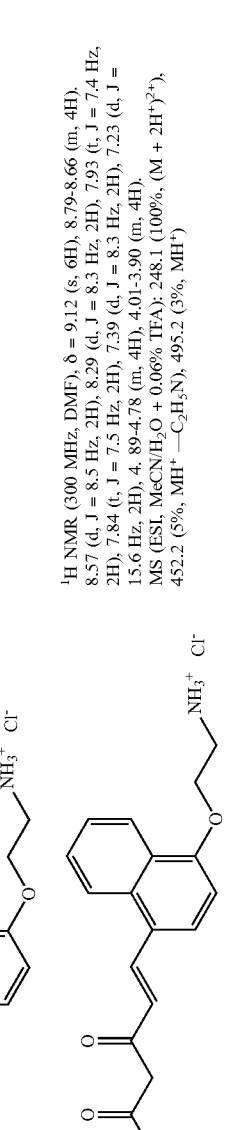 | 1H NMR (300 MHz, DMF), δ = 9.12 (s, 6H), 8.79-8.66 (m, 4H). 8.57 (d, J = 8.5 Hz, 2H), 8.29 (d, J = 8.3 Hz, 2H), 7.93 (t, J = 7.4 Hz, 2H), 7.84 (t, J = 7.5 Hz, 2H), 7.39 (d, J = 8.3 Hz, 2H), 7.23 (d, J = 15.6 Hz, 2H), 4. 89-4.78 (m, 4H), 4.01-3.90 (m, 4H). MS (ESI, MeCN/H2O + 0.06% TFA): 248.1 (100%, (M + 2H+)2+), 452.2 (5%, MH+—C2H5N), 495.2 (3%, MH+) |
| Curcumin 12b hydrochloride (SA-CUR-12b) compound (53) | 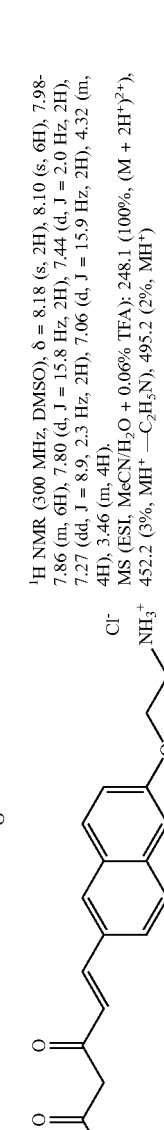 | 1H NMR (300 MHz, DMSO), δ = 8.18 (s, 2H), 8.10 (s, 6H), 7.98-7.86 (m, 6H), 7.80 (d, J = 15.8 Hz, 2H), 7.44 (d, J = 2.0 Hz, 2H), 7.27 (dd, J = 8.9, 2.3 Hz, 2H), 7.06 (d, J = 15.9 Hz, 2H), 4.32 (m, 4H), 3.46 (m, 4H). MS (ESI, MeCN/H2O + 0.06% TFA): 248.1 (100%, (M + 2H+)2+), 452.2 (3%, MH+—C2H5N), 495.2 (2%, MH+) |
| Curcumin 13a hydrochloride (SA-CUR-13a) compound (60) | 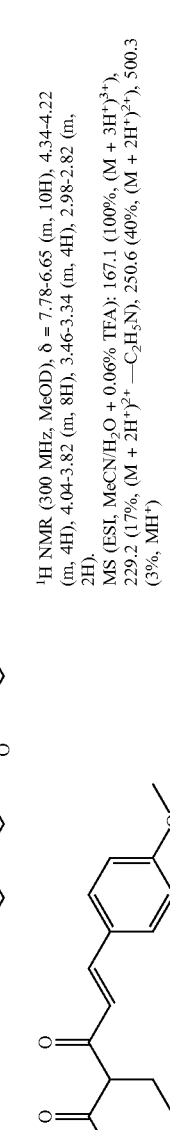 | 1H NMR (300 MHz, MeOD), δ = 7.78-6.65 (m, 10H), 4.34-4.22 (m, 4H), 4.04-3.82 (m, 8H), 3.46-3.34 (m, 4H), 2.98-2.82 (m, 2H). MS (ESI, MeCN/H2O + 0.06% TFA): 167.1 (100%, (M + 3H+)3+), 229.2 (17%, (M + 2H+)2+ —C2H5N), 250.6 (40%, (M + 2H+)2+), 500.3 (3%, MH+) |

| Description/Serial number | Structure | Analysis |
|---|---|---|
| Curcumin 13b hydrochloride (SA-CUR-13b) compound (62) | 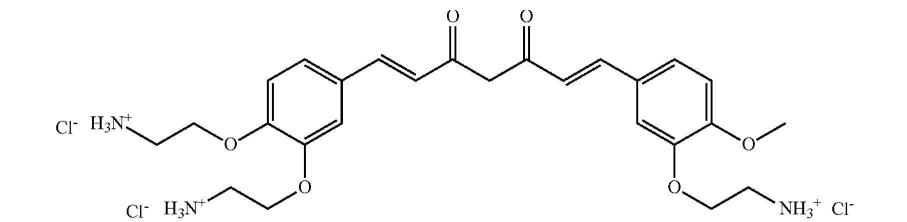 | ¹H NMR (300 MHz, MeOD), δ = 7.60 (d, J = 13.2 Hz, 2H), 7.42-7.17 (m, 4H), 7.12-6.93 (m, 2H), 6.73 (d, J = 12.8 Hz, 2H), 4.40-4.22 (m, 6H), 3.95 (s, 3H), 3.46-3.36 (m, 6H). MS (ESI, MeCN/H₂O + 0.06% TFA): 162.1 (100%, (M + 3H⁺)³⁺), 221.1 (44%, (M + 2H⁺)²⁺ —C₂H₅N), 242.6 (52%, (M + 2H⁺)²⁺), 484.2 (7%, MH⁺). |
| Curcumin 13c hydrochloride (SA-CUR-13c) compound (56) | 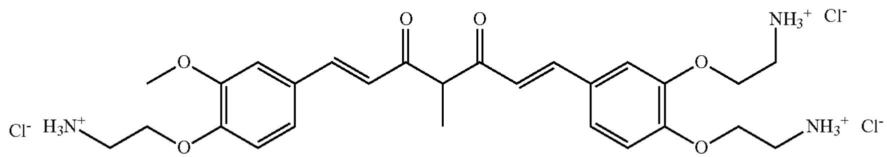 | ¹H NMR (300 MHz, MeOD), δ = 7.80-6.66 (m, 10H), 4.43-4.10 (m, 6H), 3.93 (s, 3H), 3.49-3.24 (m, 6H), 2.11 (m, 3H). MS (ESI, MeCN/H₂O + 0.06% TFA): 166.8 (87%, (M + 3H⁺)³⁺), 249.6 (100%, (M + 2H⁺)²⁺), 498.3 (16%, MH⁺). |
| Curcumin 14a hydrochloride (SA-CUR-14a) compound (57) | 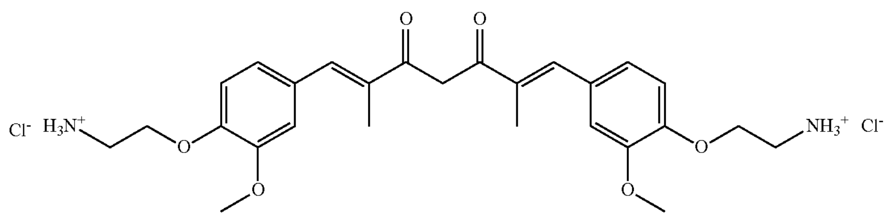 [SMILES: [Cl-] ; COc1cc(/C=C(\C)C(=O)CC(=O)/C(C)=C/c2ccc(OCC[NH3+])c(OC)c2)ccc1OCC[NH3+] ; [Cl-]] | ¹H NMR (400 MHz, MeOD), δ = 7.69-7.58 (m, 2H), 7.23-7.02 (m, 6H), 4.32-4.21 (m, 4H), 3.93 (s, 6H), 3.44-3.35 (m, 4H), 2.20-2.06 (m, 6H). MS (ESI, MeCN/H₂O + 0.06% TFA): 242.1 (100% (M + 2H⁺)²⁺), 440.2 (7%, MH⁺ —C₂H₅N), 483.2 (3%, MH⁺). |
| Curcumin 14b hydrochloride (SA-CUR-14b) compound (58) | 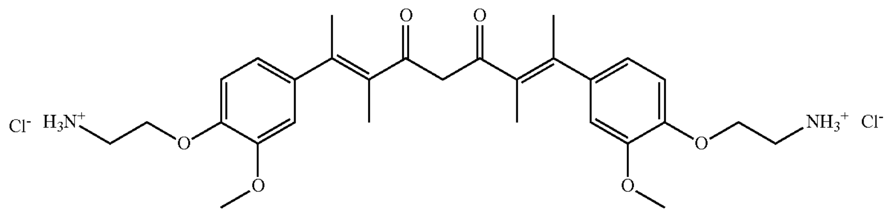 [SMILES: [Cl-] ; COc1cc(/C(C)=C(\C)C(=O)CC(=O)/C(C)=C(\C)c2ccc(OCC[NH3+])c(OC)c2)ccc1OCC[NH3+] ; [Cl-]] | MS (ESI, MeCN/H₂O + 0.06% TFA): 256.1 (100%, (M + 2H⁺)²⁺), 469.3 (7%, MH⁺ —C₂H₅N), 512.3 (4%, MH⁺) |
| Curcumin 15a hydrochloride (SA-CUR-15a) compound (64) | 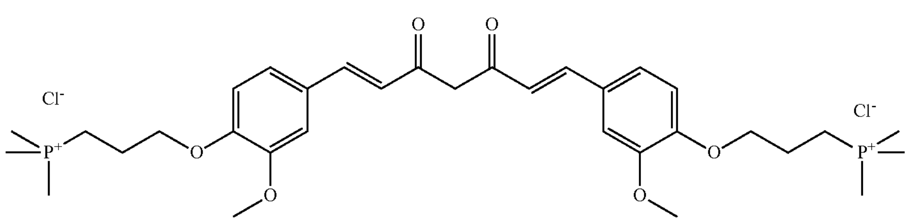 | ¹H NMR (300 MHz, MeOD), δ = 7.58 (d, J = 15.7, 2H), 7.27 (s, 2H), 7.16 (d, J = 8.8 Hz, 2H), 6.98 (d, J = 8.2 Hz, 2H), 6.70 (d, J = 15.8 Hz, 2H), 4.23 (m, 4H), 3.92 (s, 6H), 3.61 (m, 4H), 2.20 (m, 4H), 1.87 (d, J = 14.3, 18H). MS (EDI, MeCN/H₂O + 0.06% TFA): 301.1 (100%, M²⁺) |

| Description/Serial number | Structure | Analysis |
|---|---|---|
| Curcumin 15b hydrochloride (SA-CUR-15b) compound (65) | 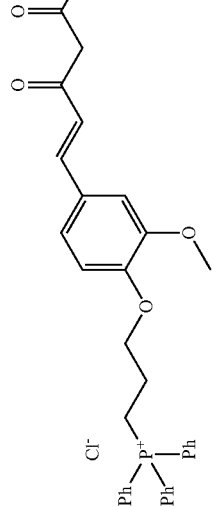 | $^1$H NMR (300 MHz, MeOD), δ = 7.96-7.51 (m, 32H), 7.28 (s, 2H), 7.19 (d, J = 8.8 Hz, 2H), 6.96 (d, J = 8.2Hz, 2H), 6.72 (d, J = 15.8 Hz, 2H), 4.21 (m, 4H), 3.91 (s, 6H), 3.63 (m, 4H), 2.18 (m, 4H). MS (ESI, MeCN/H$_2$O + 0.06% TFA): 487.2 (100%, M$^{2+}$) |

Example 2) Phototoxicity Experiments a) Production of Growing Cultures of Bacterial Strains All of the experiments were carried out under sterile conditions in a safety cabinet (Biosafe 4-130, Ehret, Emmedingen, Germany). After adding the photoactive substances, the work was carried out entirely in darkness.

A sample of the bacterial cell *Staphylococcus. aureus* (ATCC number: 25923) or *Escherichia. coli* (ATCC number: 25922) was removed from a cryo-freeze culture and cultured under aerobic conditions at 37° C. and 175 rpm overnight in an orbital shaker (MAXQ4000, Thermo Scientific, Dubuque, Iowa, USA). Growth was carried out in 20 mL Todd-Hewitt broth (Carl Roth, Karlsruhe, Germany) supplemented with 0.3% of yeast extract (AppliChem, Darmstadt, Germany).

Alternatively, Müller-Hinton media were used for culture:

Müller-Hinton liquid medium (Merck KGaA, Darmstadt, Germany)

2.0 g/L meat extract, 17.5 g/L casein hydrolysate, 1.5 g/L starch, pH: 7.4+0.2.

Müller Hinton agar (Merck KGaA, Darmstadt, Germany)

2.0 g/L meat extract, 17.5 g/L casein hydrolysate, 1.5 g/L starch, 15 g/L Agar, pH: 7.4+0.2.

b) Production of a Culture in the Exponential Growth Phase

Subsequently, dilutions (0, 5, 10, 25 and 20% v/v of the overnight culture) and their absorptions were measured at 600 nm in triplicate for 100 μL (Infinite 200 M Pro, Tecan, Männedorf, Switzerland). A calibration graph (Microsoft Excel) was used to calculate the volume which was required to produce 20 mL of a culture with an absorption of 0.05 at 600 nm. The volume calculated for the overnight culture was topped up with Todd-Hewitt broth (composition as above) to 20 mL and incubated for two hours at 37° C. with constant movement (175 rpm, MAXQ4000). The cultures were then in the exponential growth phase; the absorption at 600 nm was between 0.3 and 0.45.

The subsequent incubation with the photoactive substances as well as irradiation with electromagnetic radiation and determination of the phototoxicity was carried out with two different methods.

c.1) Incubation, Irradiation and Determination of Phototoxicity

A 2-hour culture was divided into 1800 μL aliquots. After centrifuging at 20° C., 830 rcf, 5 min (5417R centrifuge, Eppendorf, Hamburg, Germany), the pellets were re-suspended in phosphate buffer (Dulbeccos' Modified Phosphate Saline, DPBS, Sigma-Aldrich) with either 10 or 50 μM of the corresponding photosensitizer, wherein the final volume was kept at 1800 μL. The solutions obtained were immediately incubated on the orbital shaker (see above for parameters) for 5 or 25 minutes.

Three controls were run at the same time for each photosensitizer. The "light only" control contained DPBS without photosensitizer. The "photosensitizer only" ("PS only") control was incubated like the PDI samples, but not irradiated and kept strictly in darkness. A further control (double negative, "Co−/−"), received neither light nor photosensitizer.

After the incubation, duplicates of the samples (500 μL each) were transferred into a 24-well microtitre plate (Cellstar, Greiner Bio-One, Frickenhausen, Germany). The "PS only" and "Co−/−" samples were placed in their own microtitre plate which was packed in aluminium foil so as to be lightproof.

The irradiation was carried out under constant shaking (MTS4, IKA, Staufen, Germany, ~175 rpm) from below on a LED array with maximum homogeneity of the lighting surface. All of the controls were shaken in the same manner. The technical data for the light source are shown in Table 2; the total dose of light applied was 33.8 J/cm$^2$.

TABLE 2

Technical data for LED Arrays:

| | |
|---|---|
| Diode manufacturer | Roithner Lasertechnik, Wien, Austria |
| Description of diodes | LED 435-12-30 |
| Dominant wavelengths | 430 nm-435 nm |
| Number of diodes in array | 432 |
| Intensity | 9.4 mW/cm$^2$ |

The determination of the colony forming units (CFU) was carried out in accordance with the method published by Miles and Misra (Miles, A A; Misra, S S, Irwin, J O (1938 November). "The estimation of the bactericidal power of the blood" *The Journal of hygiene* 38 (6): 732-49). In this regard, serial dilutions (1:10) of the corresponding bacterial suspension were produced in DPBS. 5×10 μL of each bacterial dilution was then dripped onto Todd-Hewitt plates (with broth, additional 1.5% agar (Agar-Agar, Kobe I, Roth, Karlsruhe, Germany) and incubated at 37° C. for 24 h. Next, the number of surviving colony forming units was determined. All of the tests were carried out four times.

c.2) Incubation, Irradiation and Determination of Phototoxicity

In a second experiment, the photosensitizers (PS) used were dissolved in Millipore water and adjusted to various concentrations. 25 μL of a bacterial suspension grown overnight (~108/mL) was incubated with 25 μL of photosensitizer solution of the various concentrations at room temperature for 10 seconds in darkness in a 96-well plate.

Next, the suspension was irradiated for 5-20 minutes. For the irradiation, the light source BlueV from Waldmann (Villingen-Schwenningen, Germany) was used, which emits light from 380 to 480 nm (emission maximum at approximately 420 nm). The applied energy density was 17.5 mW/cm$^2$.

Each experiment was accompanied by three controls in order to exclude side effect of the irradiation/photosensitizer (PS) on the survival of the bacteria: (i) no PS, only light (=light control), (ii) no light, only PS (=dark control) and (iii) neither light nor PS (=reference control). The determination of the colony forming units (CFU) per mL was also carried out in accordance with the method published by Miles, Misra and Irwin described above in section c.1). All of the tests were carried out four times.

d) Result of Phototoxicity Experiments

Figure 2:
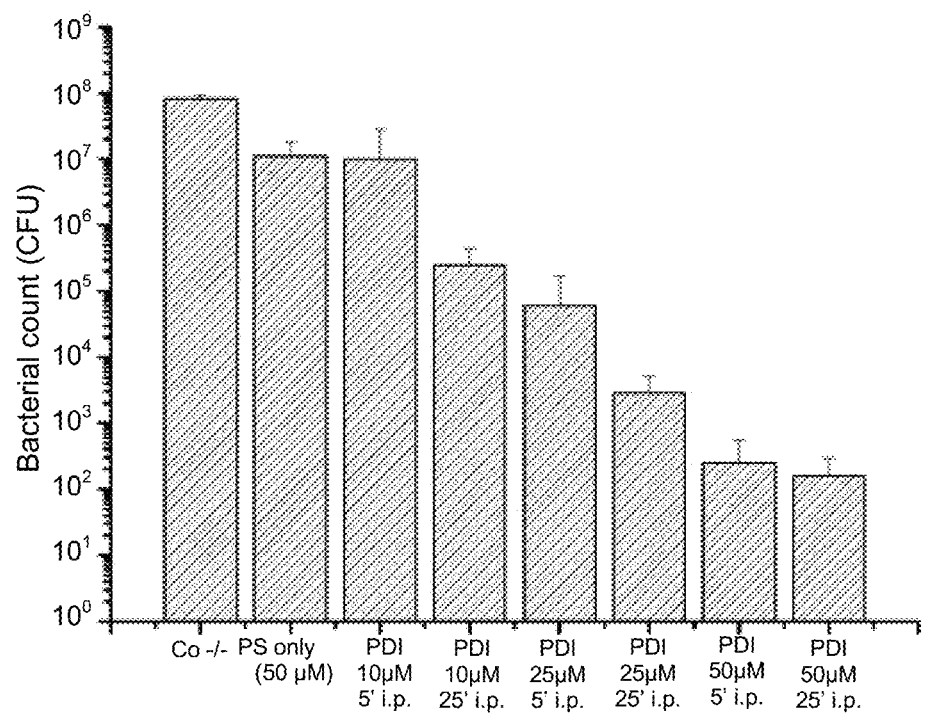
FIG. 2 shows the photodynamic inactivation (PDI) of *E. coli* by SACUR-01a hydrochloride compared with the controls (no light, no PS).
Figure 3:
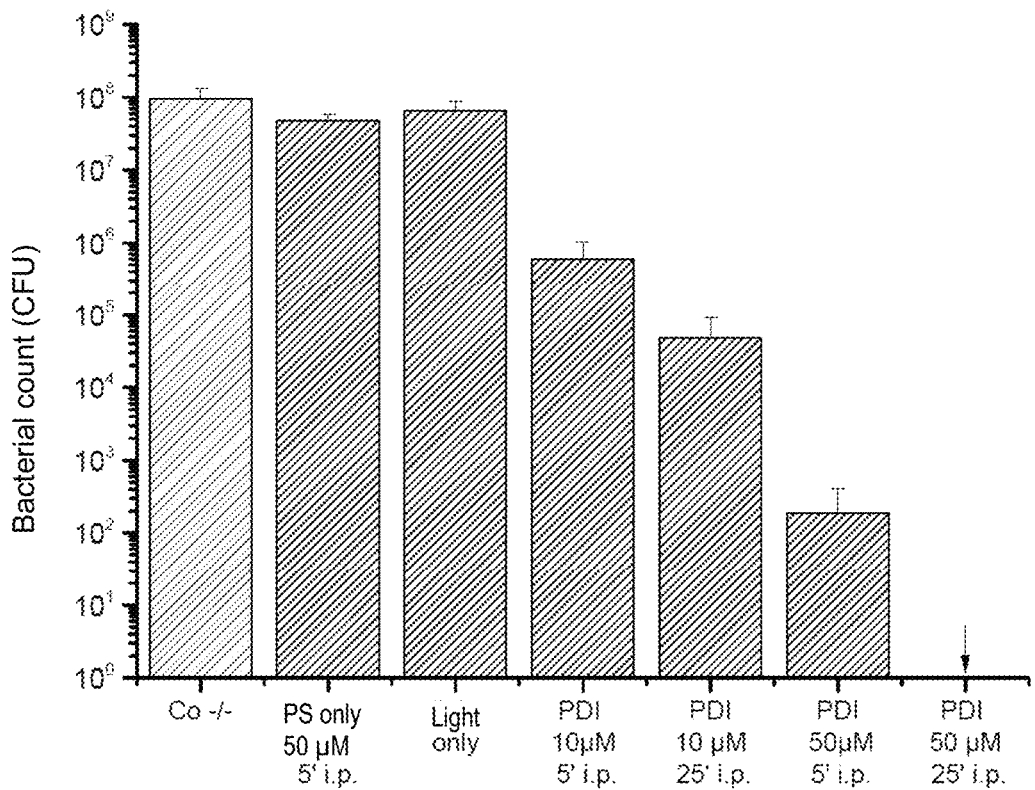
FIG. 3 shows the photodynamic inactivation (PDI) of *E. coli* by SACUR-01 b hydrochloride compared with the controls (no light, no PS).
Figure 4:
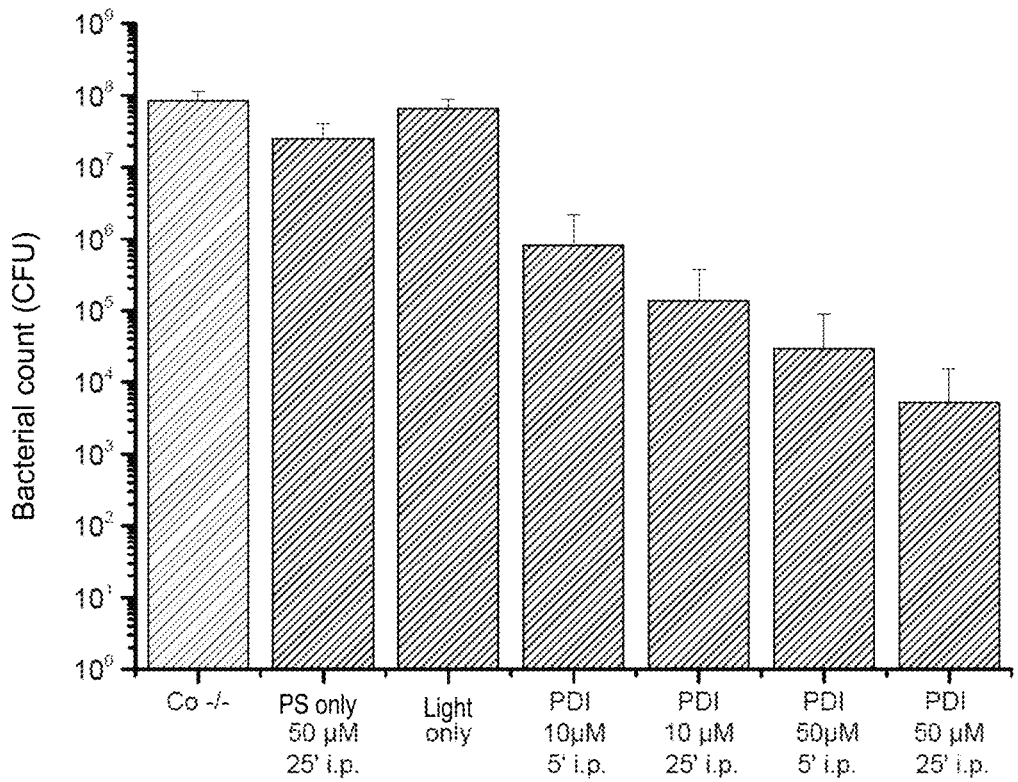
FIG. 4 shows the photodynamic inactivation (PDI) of *E. coli* by SACUR-01c hydrochloride compared with the controls (no light, no PS).
Figure 5:
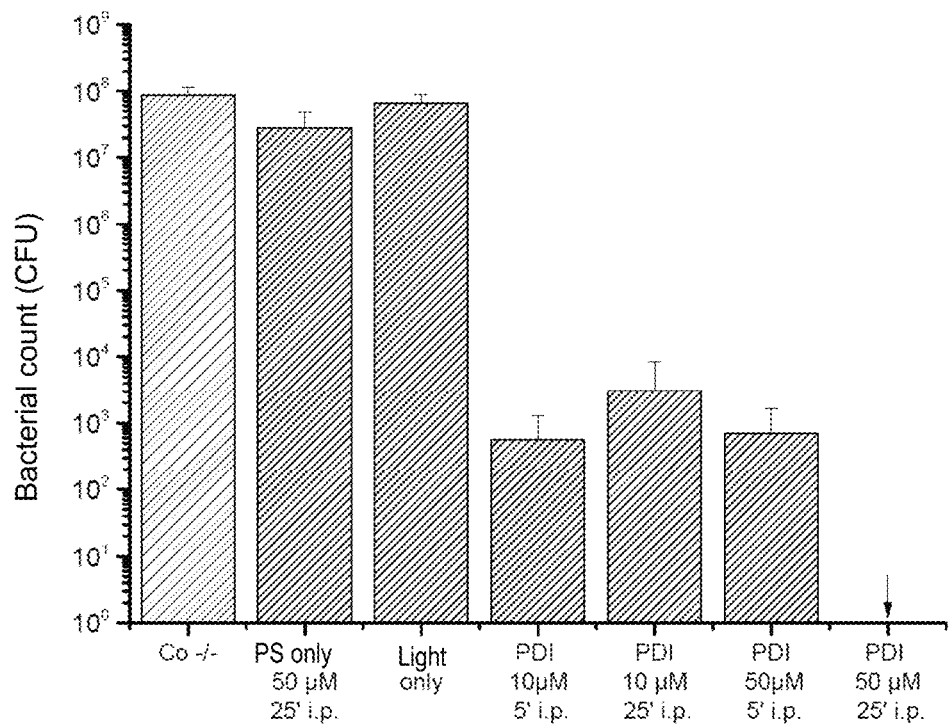
FIG. 5 shows the photodynamic inactivation (PDI) of *E. coli* by SACUR-01e hydrochloride compared with the controls (no light, no PS).
Figure 6:
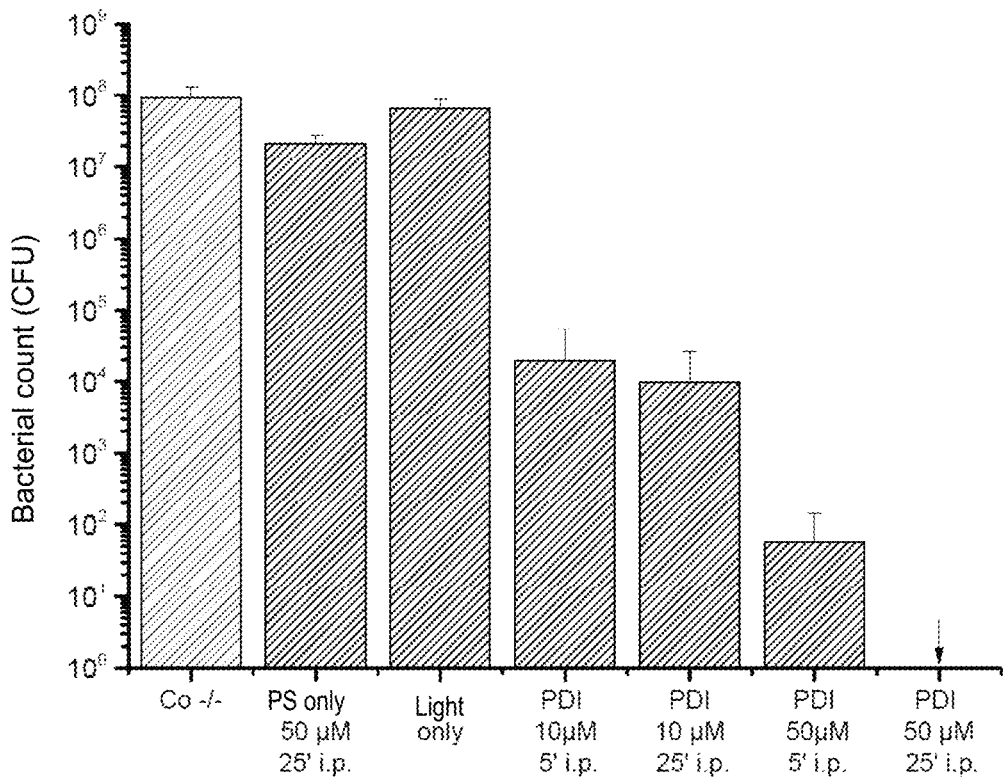
FIG. 6 shows the photodynamic inactivation (PDI) of *E. coli* by SACUR-02 hydrochloride compared with the controls (no light, no PS).
Figure 7A:
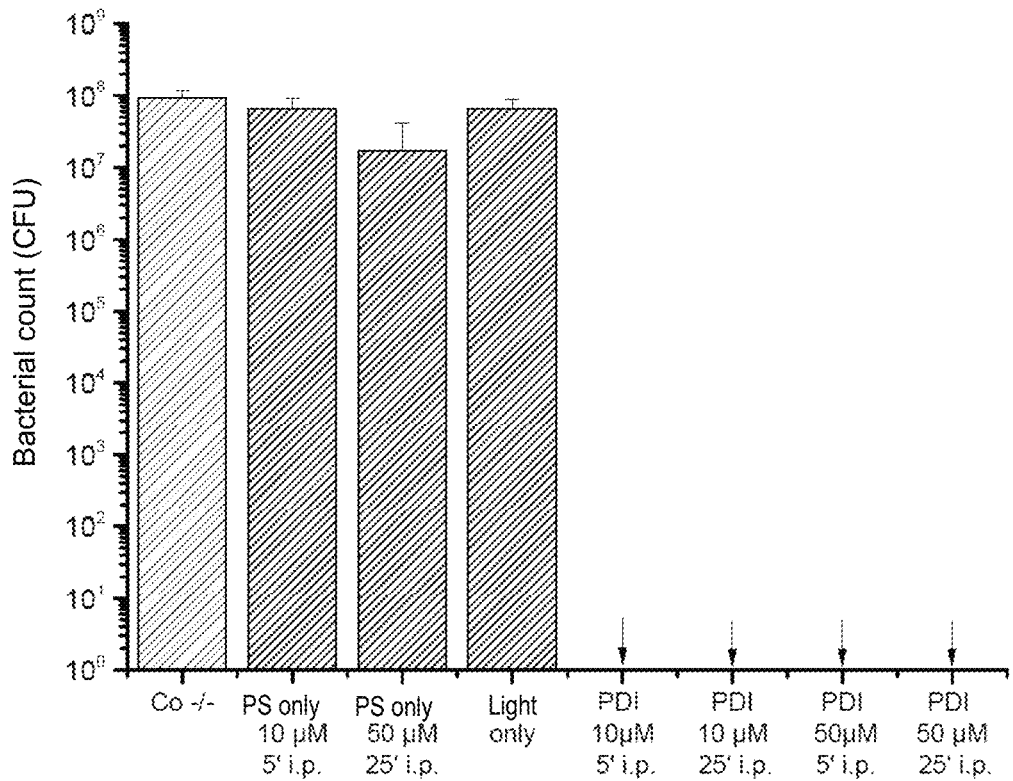
FIGS. 7a and 7b show the photodynamic inactivation (PDI) of *E. coli* by SACUR-03 hydrochloride compared with the controls (no light, no PS).
Figure 7B:
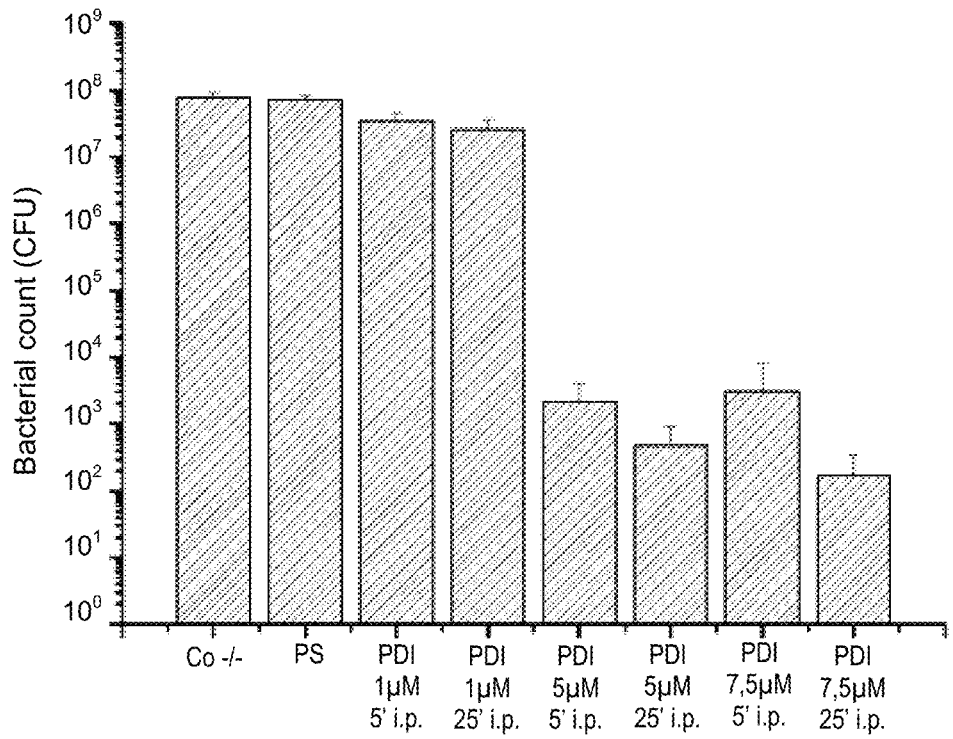
Figure 8:
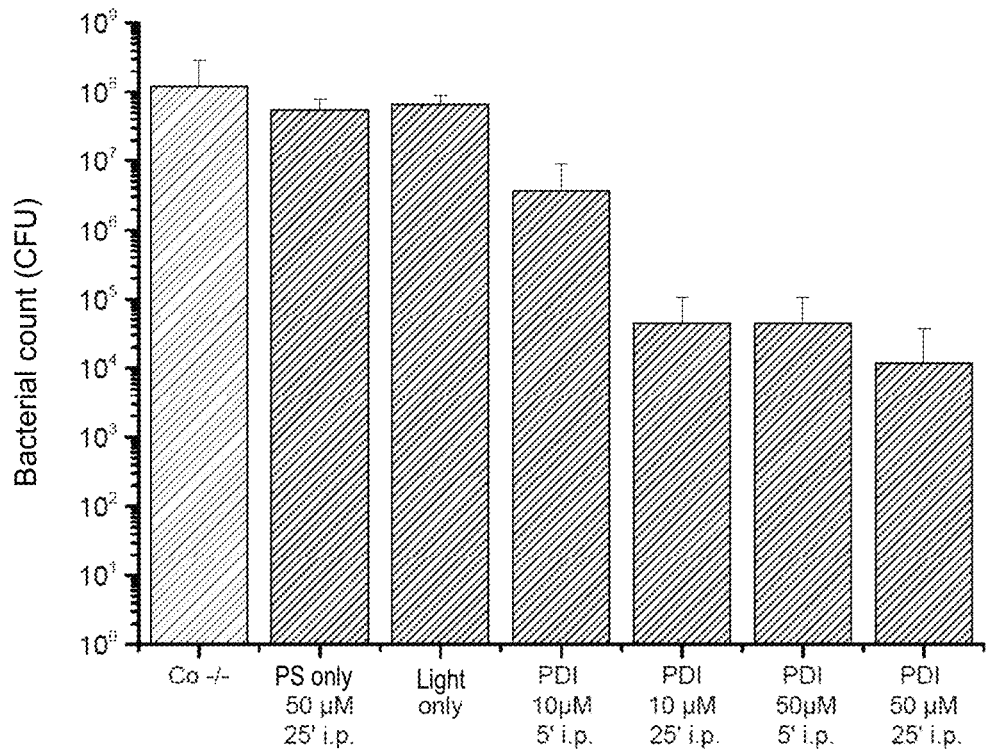
FIG. 8 shows the photodynamic inactivation (PDI) of *E. coli* by SACUR-04 hydrochloride compared with the controls (no light, no PS).
Figure 9:
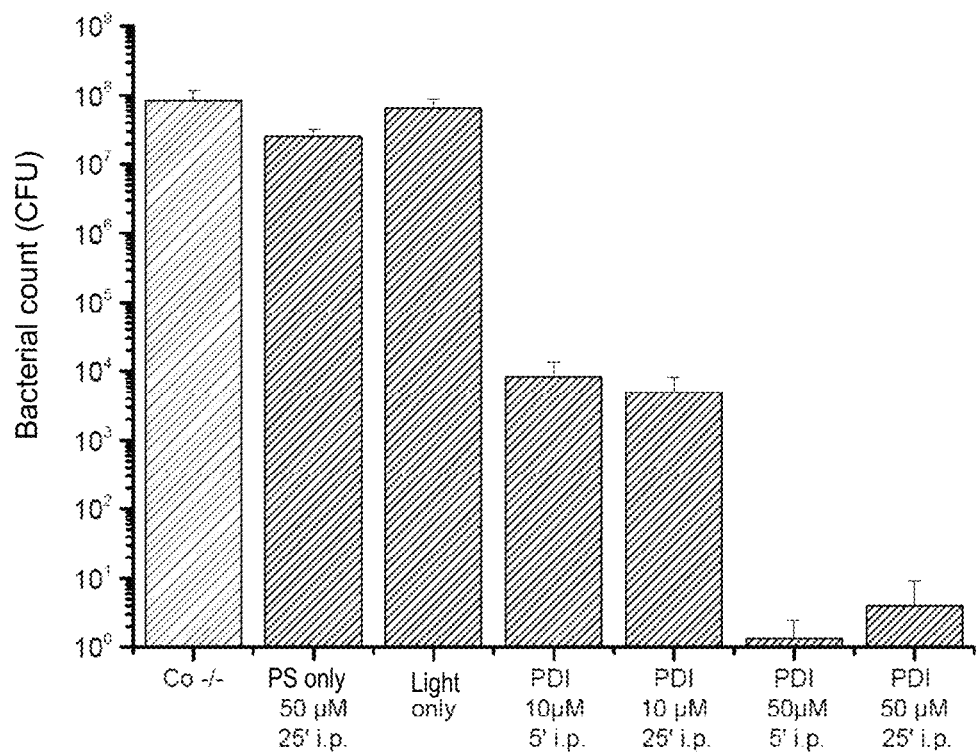
FIG. 9 shows the photodynamic inactivation (PDI) of *E. coli* by SACUR-05 hydrochloride compared with the controls (no light, no PS).
Figure 10:
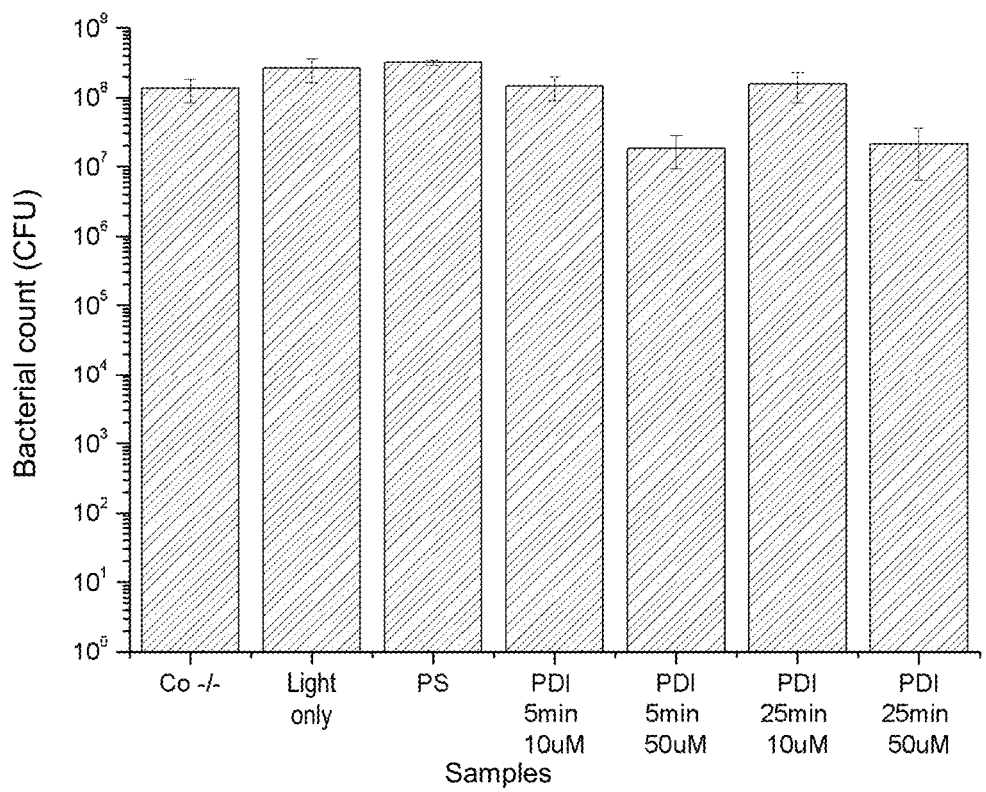
FIG. 10 shows the photodynamic inactivation (PDI) of *E. coli* by SACUR-08 hydrochloride compared with the controls (no light, no PS).
Figure 11:
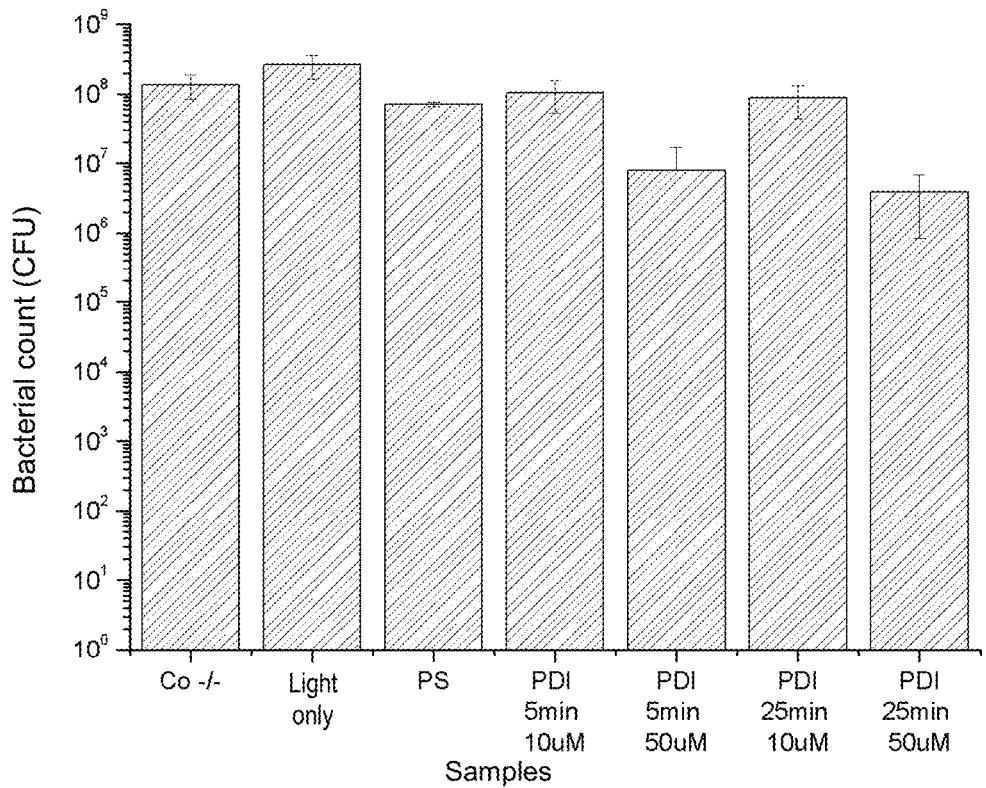
FIG. 11 shows the photodynamic inactivation (PDI) of *E. coli* by SACUR-09b hydrochloride compared with the controls (no light, no PS).
Figure 12:
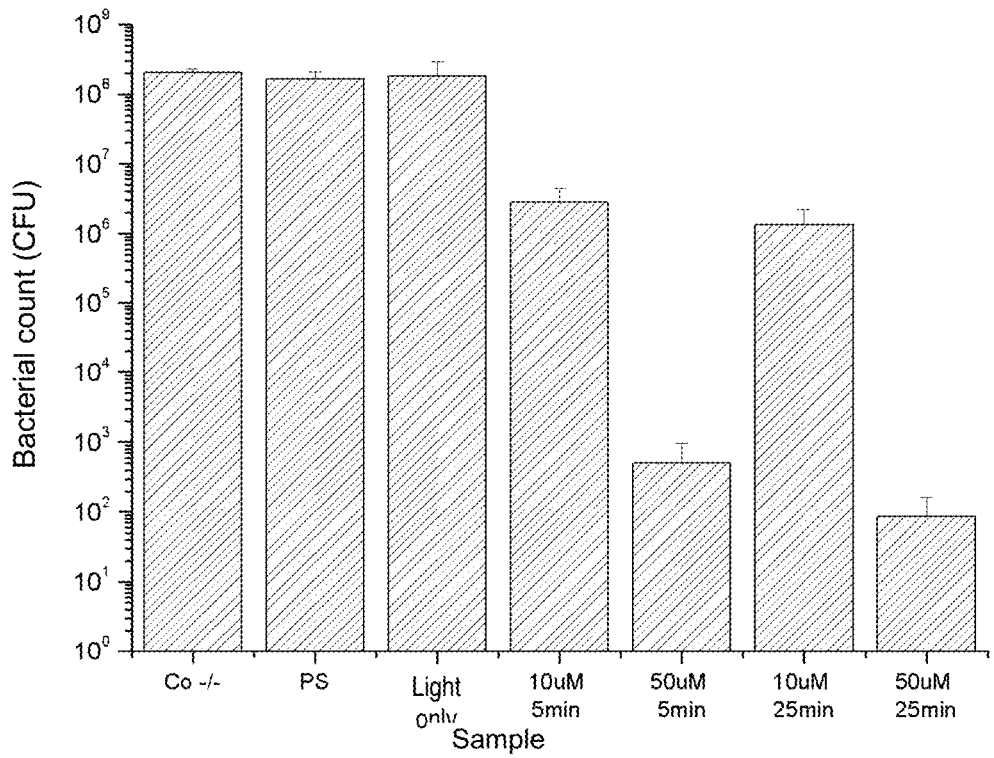
FIG. 12 shows the photodynamic inactivation (PDI) of *E. coli* by SACUR-10a chloride compared with the controls (no light, no PS).
Figure 13:
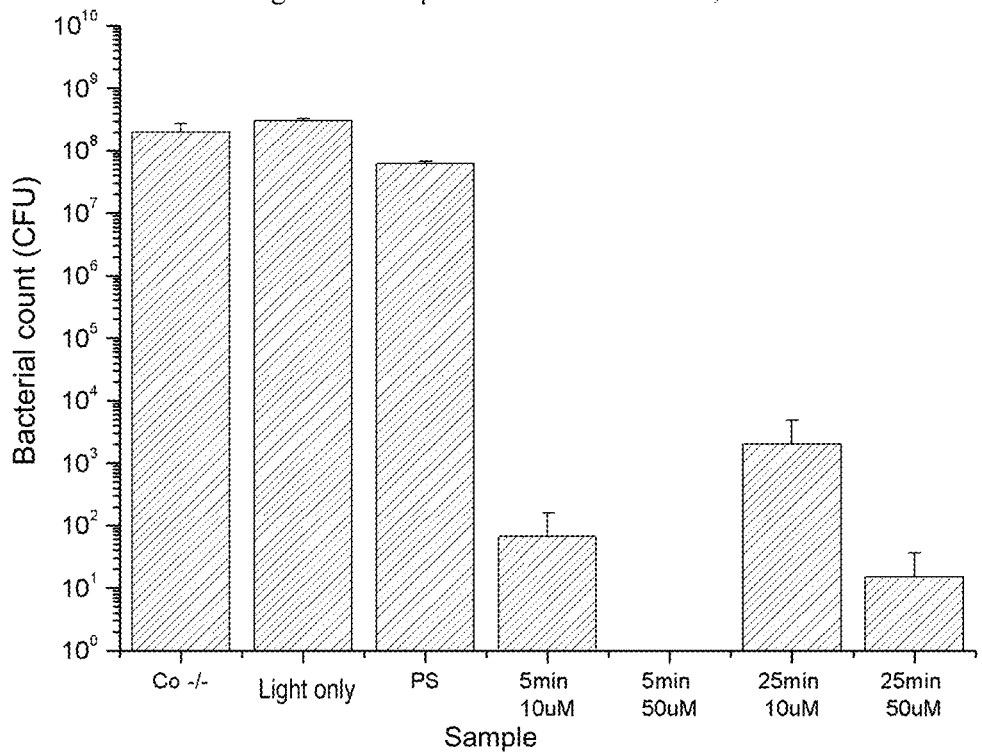
FIG. 13 shows the photodynamic inactivation (PDI) of *E. coli* by SACUR-10b hydrochloride compared with the controls (no light, no PS).
Figure 14:
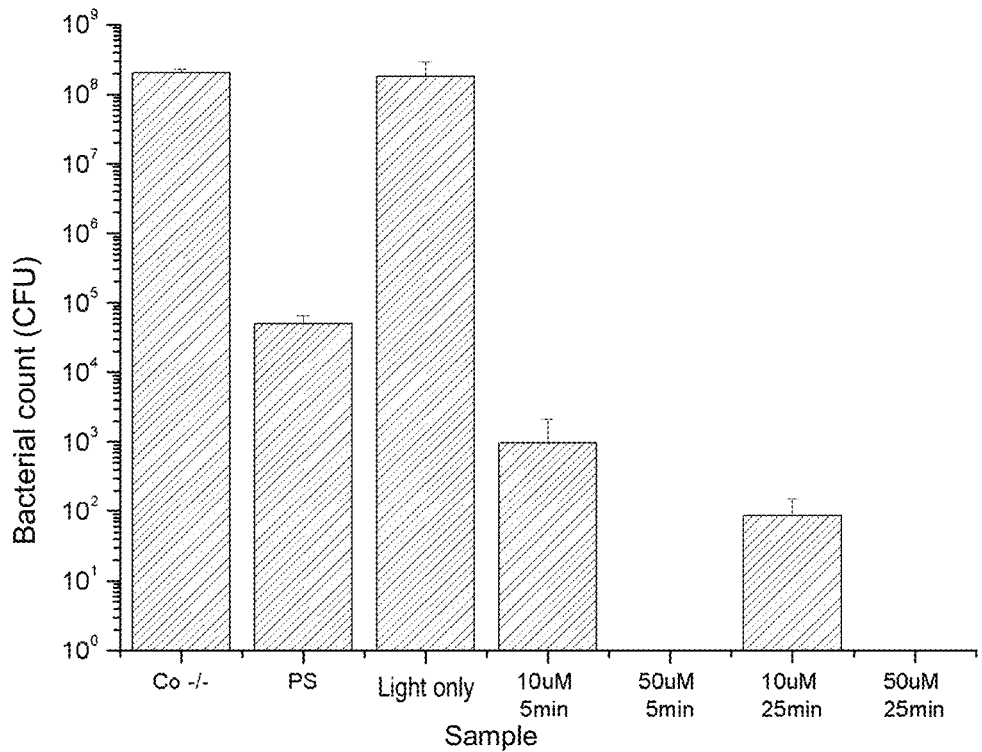
FIG. 14 shows the photodynamic inactivation (PDI) of *E. coli* by SACUR-10c chloride compared with the controls (no light, no PS).
Figure 15:
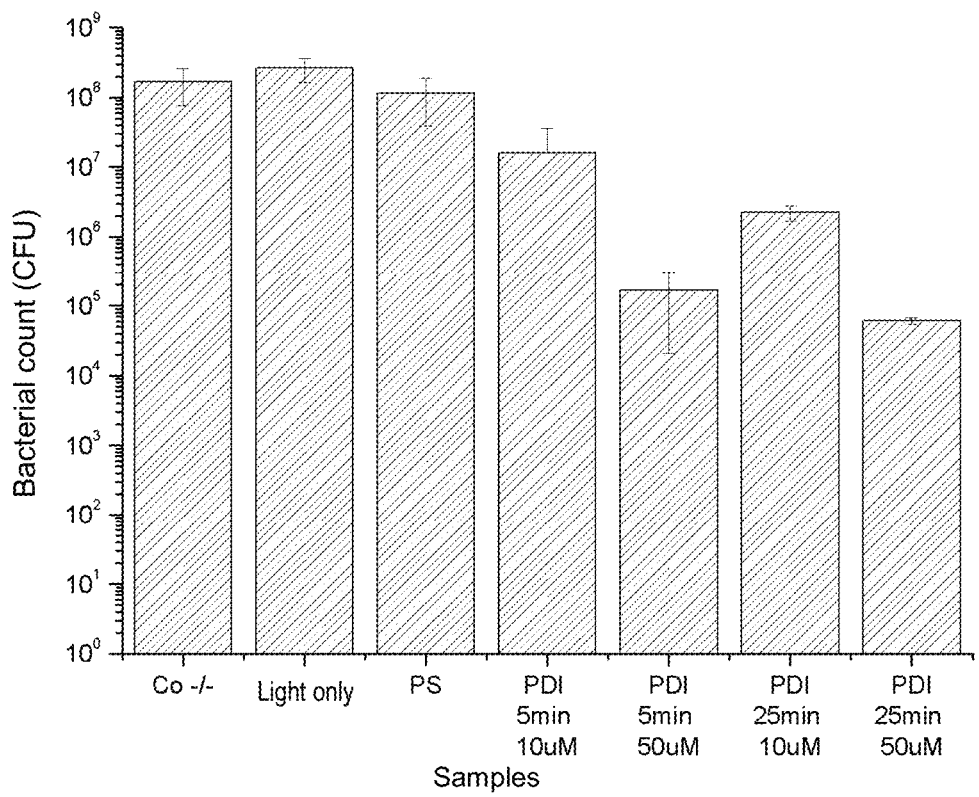
FIG. 15 shows the photodynamic inactivation (PDI) of *E. coli* by SACUR-11 b hydrochloride compared with the controls (no light, no PS).
Figure 16:
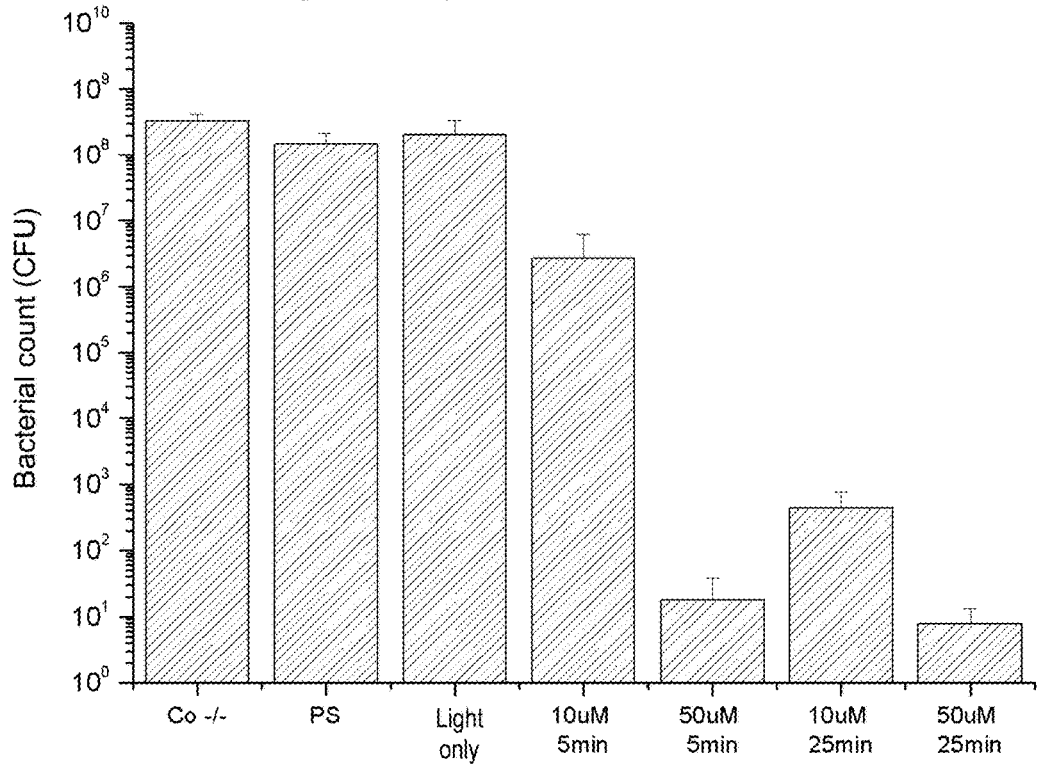
FIG. 16 shows the photodynamic inactivation (PDI) of *E. coli* by SACUR-12a hydrochloride compared with the controls (no light, no PS).
Figure 17:
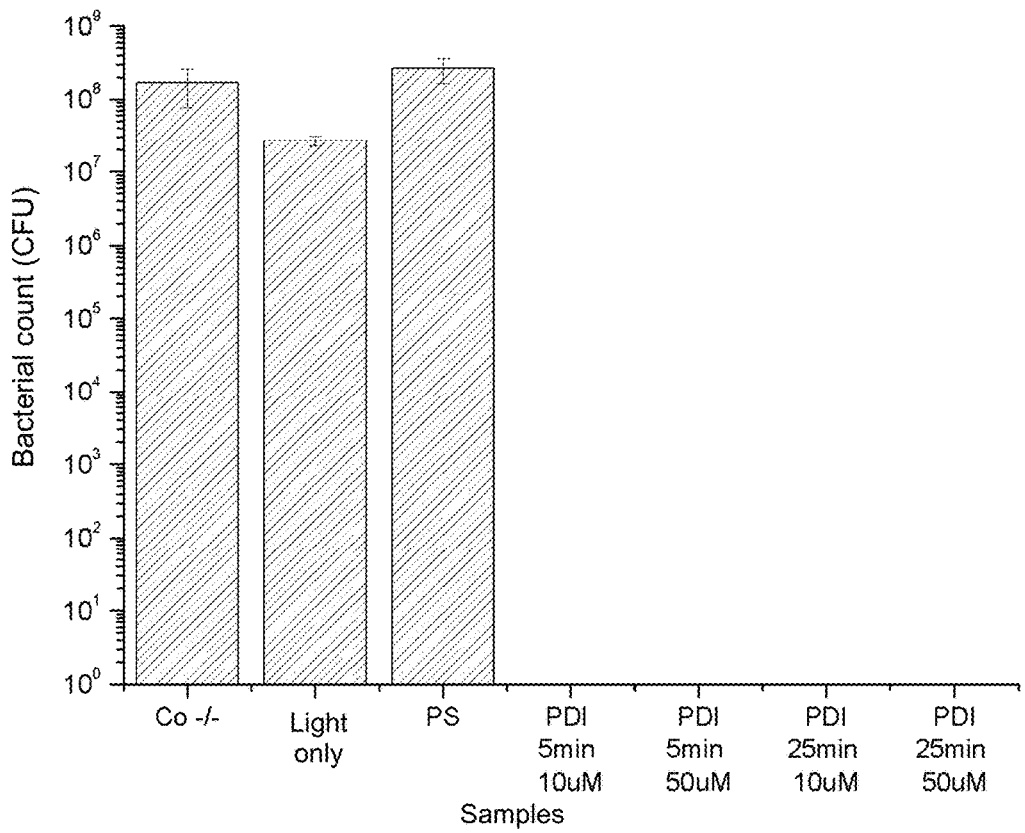
FIG. 17 shows the photodynamic inactivation (PDI) of *E. coli* by SACUR-13b hydrochloride compared with the controls (no light, no PS).
Figure 18:
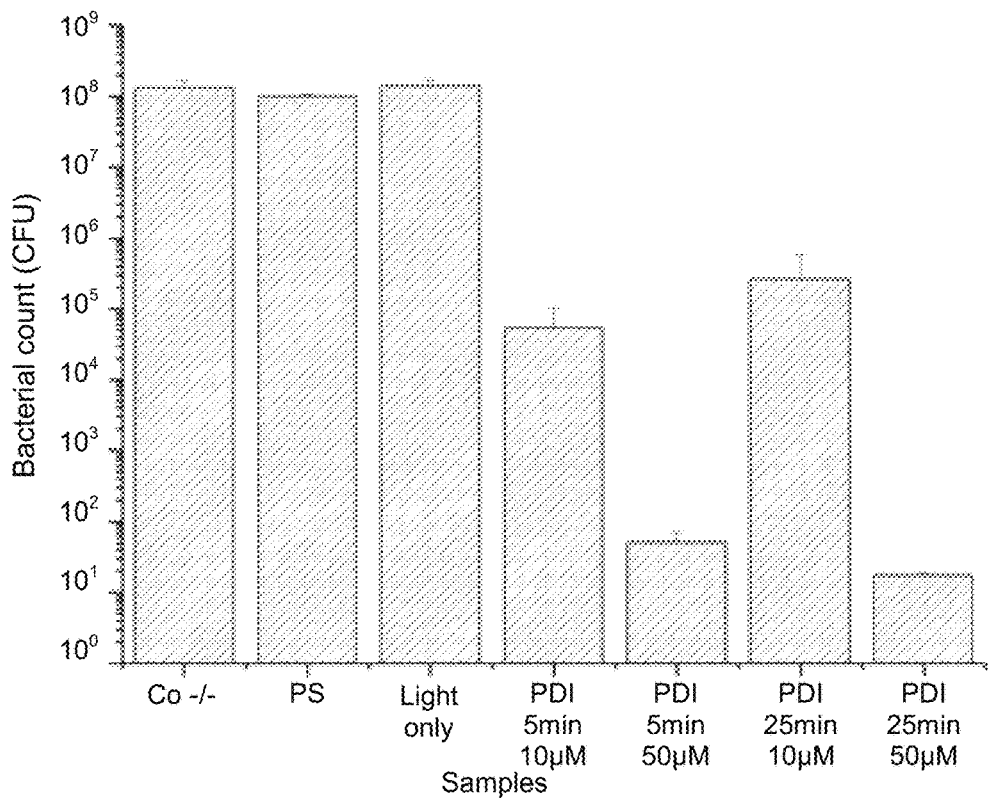
FIG. 18 shows the photodynamic inactivation (PDI) of *E. coli* by Zn-SACUR-1a hydrochloride against *E. coli* compared with the controls (no light, no PS).
Figure 19:
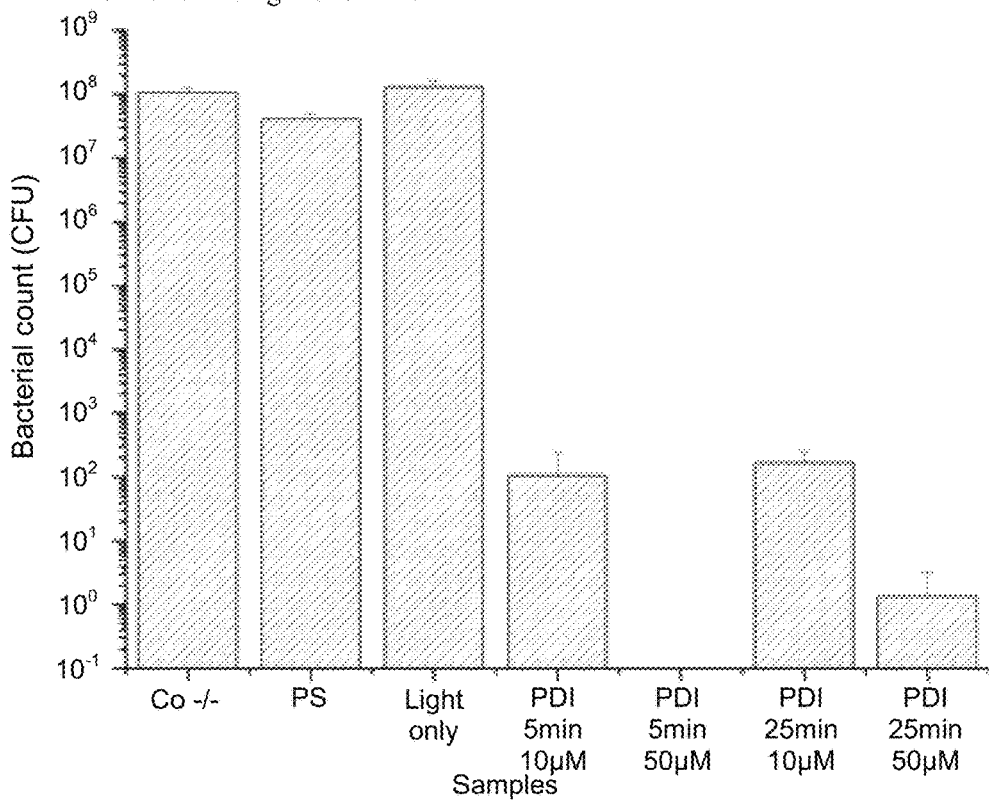
FIG. 19 shows the photodynamic inactivation (PDI) of *E. coli* by RO-SACUR-1a hydrochloride compared with the controls (no light, no PS).
Figure 20:
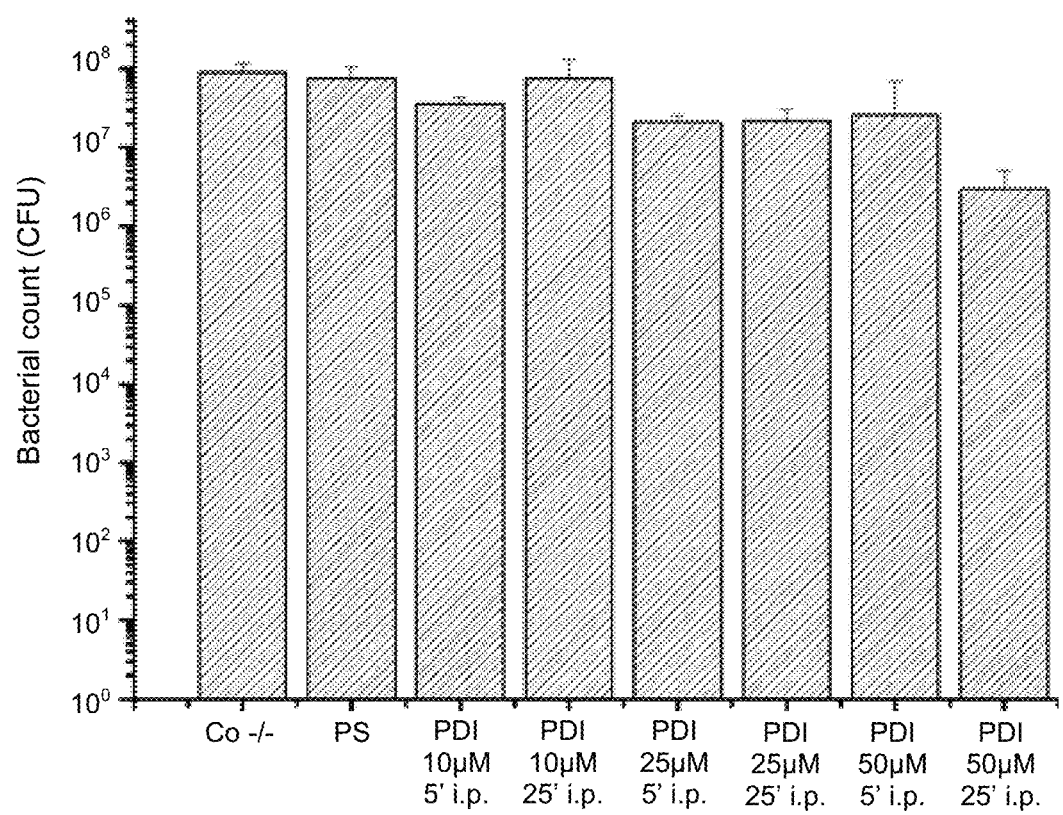
FIG. 20 shows the photodynamic inactivation (PDI) of *E. coli* by SACUR-14b hydrochloride compared with the controls (no light, no PS).

The results of the phototoxicity experiments described above in section c.1) are shown in FIGS. 1 to 20. The photosensitizers were tested against the bacterial strain *E. coli* ATCC 25922. FIGS. 1-20 show the measured surviving colony forming units (CFU).

The results of the phototoxicity experiments described in section c.2) are shown in FIGS. 21 to 33. The photosensitizers (PS) SACUR-01a, SACUR-03 and SACUR-07 were tested against the bacterial strains *S. aureus* ATCC 25923 and *E. coli* ATCC 25922 (FIGS. 21-23). All of the remaining PS were tested against *S. aureus* ATCC 25923 (FIGS. 24-33). FIGS. 21-33 show the logarithmic reduction after illumination with respect to the reference control.

FIG. 21 shows the result of the phototoxicity test using SACUR-01a against *E. coli* ATCC 25922 (left) and against *S. aureus* ATCC 25923 (right). The irradiation period for *E. coli* was 15 minutes; for *S. aureus*, 5 minutes. The average reference control (arithmetic mean with standard deviation) (no light, no PS) was $3.6 \times 10^8$/mL for E. coli and $3.9 \times 10^8$/mL for S. aureus.

FIG. 22 shows the result of the phototoxicity test using SACUR-03 against E. coli ATCC 25922 (left) and against S. aureus ATCC 25923 (right). The irradiation period for E. coli was 15 minutes; for S. aureus, 5 minutes. The average reference control (arithmetic mean with standard deviation) (no light, no PS) was $3.3 \times 10^8$/mL for E. coli and $4.3 \times 10^8$/mL for S. aureus.

FIG. 23 shows the result of the phototoxicity test using SACUR-07 against E. coli ATCC 25922 (left) and against S. aureus ATCC 25923 (right). The irradiation period for E. coli was 45 minutes; for S. aureus, 5 minutes. The average reference control (arithmetic mean with standard deviation) (no light, no PS) was $2.6 \times 10^8$/mL for E. coli and $3.6 \times 10^8$/mL for S. aureus.

FIG. 24 shows the result of the phototoxicity test using SACUR-01a BF2 against S. aureus ATCC 25923. The irradiation period for S. aureus was 5 minutes. The average reference control (arithmetic mean with standard deviation) (no light, no PS) corresponded to ~$3.6 \times 10^8$ bacteria per millilitre.

FIG. 25 shows the result of the phototoxicity test using SACUR-09a against S. aureus ATCC 25923. The irradiation period for S. aureus was 5 minutes. The average reference control (arithmetic mean with standard deviation) (no light, no PS) corresponded to ~$3.3 \times 10^8$ bacteria per millilitre.

FIG. 26 shows the result of the phototoxicity test using SACUR-11a against S. aureus ATCC 25923. The irradiation period for S. aureus was 5 minutes. The average reference control (arithmetic mean with standard deviation) (no light, no PS) corresponded to ~$6.3 \times 10^8$ bacteria per millilitre.

FIG. 27 shows the result of the phototoxicity test using SACUR-11c against S. aureus ATCC 25923. The irradiation period for S. aureus was 5 minutes. The average reference control (arithmetic mean with standard deviation) (no light, no PS) corresponded to ~$5.1 \times 10^8$ bacteria per millilitre.

FIG. 28 shows the result of the phototoxicity test using SACUR-12b against S. aureus ATCC 25923. The irradiation period for S. aureus was 30 minutes. The average reference control (arithmetic mean with standard deviation) (no light, no PS) corresponded to ~$6.2 \times 10^8$ bacteria per millilitre.

FIG. 29 shows the result of the phototoxicity test using SACUR-13a against S. aureus ATCC 25923. The irradiation period for S. aureus was 5 minutes. The average reference control (arithmetic mean with standard deviation) (no light, no PS) corresponded to ~$7.5 \times 10^8$ bacteria per millilitre.

FIG. 30 shows the result of the phototoxicity test using SACUR-13c against S. aureus ATCC 25923. The irradiation period for S. aureus was 5 minutes. The average reference control (arithmetic mean with standard deviation) (no light, no PS) corresponded to ~$5.5 \times 10^8$ bacteria per millilitre.

FIG. 31 shows the result of the phototoxicity test using SACUR-14a against S. aureus ATCC 25923. The irradiation period for S. aureus was 10 minutes. The average reference control (arithmetic mean with standard deviation) (no light, no PS) corresponded to ~$4.2 \times 10^8$ bacteria per millilitre.

FIG. 32 shows the result of the phototoxicity test using SACUR-15a against S. aureus ATCC 25923. The irradiation period for S. aureus was 5 minutes. The average reference control (arithmetic mean with standard deviation) (no light, no PS) corresponded to ~$3.6 \times 10^8$ bacteria per millilitre.

FIG. 33 shows the result of the phototoxicity test using SACUR-15b against S. aureus ATCC 25923. The irradiation period for S. aureus was 5 minutes. The average reference control (arithmetic mean with standard deviation) (no light, no PS) corresponded to ~$6.3 \times 10^8$ bacteria per millilitre.

As can be seen from FIGS. 1-33, irradiation of the microorganisms which were used, Staphylococcus aureus (S. aureus) and Escherichia coli (E. coli), with the light dosage of blue light described (390 nm-500 nm), in the absence of a photosensitizer (0 µM of the respective curcumin) had no influence on the number of surviving microorganisms compared to the non-illuminated control.

Table 3 shows the effect of the tested substances against E. coli ATCC 25922 with an applied light dose of 33.8 J/cm$^2$ for an emission maximum at approximately 435 nm (60 minutes illumination with an intensity of 9.4 mW/cm$^2$). The average reference control (arithmetic mean with standard deviation) (no light, no PS) was $3.6 \times 10^8$/mL. The logarithmic reduction after illumination is shown with respect to the reference control. The respective upper value, indicated by a *, refers to an incubation period of 5 min and the respectively lower value, indicated by a #, refers to an incubation period of 25 min.

TABLE 3

Phototoxicity test for substances against E. coli ATCC 25922.

| | Effectiveness against E. Coli Reduction in CFU in log$_{10}$ at concentration of | | | |
|---|---|---|---|---|
| Description | 10 µM | 50 µM | 100 µM | 250 µM |
| Curcumin 0 hydrochloride (SA-CUR-0) | >4* >5# | >6* >6# | n.d. | n.d. |
| Curcumin 01a hydrochloride (SA-CUR-1a) | >1* >2# | >5* >5# | n.d. | n.d. |
| Curcumin 01b hydrochloride (SA-CUR-1b), | >2* >3# | >5* >7# | n.d. | n.d. |
| Curcumin 01e hydrochloride (SA-CUR-1e), | >5* >5# | >4* >7# | n.d. | n.d. |
| Curcumin 01c hydrochloride (SA-CUR-1c | >2* >2# | >3* >4# | n.d. | n.d. |
| Curcumin 02 hydrochloride (SA-CUR-2) | >2* >4# | >6* >7# | n.d. | n.d. |
| Curcumin 08 hydrochloride (SA-CUR-8) | —* —# | ~1* >1# | n.d. | n.d. |
| Curcumin 04 hydrochloride (SA-CUR-4) | >1* >3# | >3* >4# | n.d. | n.d. |
| Curcumin 03 hydrochloride (SA-CUR-3) | >7* >7# | >7* >7# | n.d. | n.d. |
| Curcumin 05 hydrochloride (SA-CUR-5) | >4* >4# | >7* >6# | n.d. | n.d. |
| Roseo-curcumin 01a hydrochloride (RO-SA-CUR-1a) | >5* >5# | >7* >6# | n.d. | n.d. |
| Curcumin 01a zinc complex (Zn-SA-CUR-1a) | >3* >2# | >5* >5# | n.d. | n.d. |
| Curcumin 09b hydrochloride (cyclo-SA-CUR-9b) | —* —# | >1* >2# | n.d. | n.d. |
| Curcumin 10a hydrochloride (SA-CUR-10a) | >1* >1# | >5* >5# | n.d. | n.d. |
| Curcumin 10b hydrochloride (GUA-SA-CUR-10b) | >5* >4# | >7* >6# | n.d. | n.d. |
| Curcumin 10c hydrochloride (SA-CUR-10c) | >4* >5# | >7* >7# | n.d. | n.d. |
| Curcumin 11b hydrochloride (SA-CUR-11b) | ~1* >1# | ~3* >3# | n.d. | n.d. |
| Curcumin 12a hydrochloride (SA-CUR-12a) | >1* >4# | >6* >6# | n.d. | n.d. |
| Curcumin 13b hydrochloride (SA-CUR-13b) | >7* >7# | >7* >7# | n.d. | n.d. |
| Curcumin 14b hydrochloride (SA-CUR-14b) | —* —# | —* >1# | n.d. | n.d. |

Table 4 shows the action of the tested substances against E. coli ATCC 25922 for an applied light dose of 15.7 J/cm$^2$ with an emission maximum at approximately 420 nm (15 min illumination at an intensity of 17.5 mW/cm$^2$). The average reference control (arithmetic mean with standard deviation) (no light, no PS) was $3.6 \times 10^8$/mL for E. coli. The logarithmic reduction after illumination is shown with respect to the reference control.

TABLE 4

**Phototoxicity test for substances against *E. coli* ATCC 25922**

| Description/serial number | Effectiveness against *E. Coli* Reduction in CFU in $\log_{10}$ at concentration of | | | |
|---|---|---|---|---|
| | 10 µM | 50 µM | 100 µM | 250 µM |
| Curcumin 01a hydrochloride (SA-CUR-1a) | >4 | >5 | n.d. | n.d. |
| Curcumin 07 hydrochloride (SA-CUR-07) | >1 | >4 | n.d. | n.d. |
| Curcumin 03 hydrochloride (SA-CUR-3) | >4 | >5 | n.d. | n.d. |

Table 5 shows the action of the tested substances against *S. aureus* ATCC 25923. The irradiation period was 5 minutes (emission maximum at approximately 420 nm) for an applied intensity of 17.5 mW/cm², i.e. an applied light energy (dosage) of 5.3 J/cm². The average reference control (arithmetic mean with standard deviation) (no light, no PS) was 3.9×10$/mL. The logarithmic reduction after illumination is shown with respect to the reference control.

TABLE 5

**Phototoxicity test against *S. aureus* ATCC 25923.**

| Description/serial number | Effectiveness against *S. aureus* Reduction in CFU in $\log_{10}$ at concentration of | | | |
|---|---|---|---|---|
| | 10 µM | 50 µM | 100 µM | 250 µM |
| Curcumin 01a hydrochloride (SA-CUR-1a) | >3 | >5 | n.d. | n.d. |
| Curcumin 07 hydrochloride (SA-CUR-07) | >2 | >5 | n.d. | n.d. |
| Curcumin 03 hydrochloride (SA-CUR-3) | >4 | >5 | n.d. | n.d. |
| Curcumin 01a BF-complex (BF-SA-CUR-1a) | >5 | >5 | n.d. | n.d. |
| Curcumin 09a hydrochloride (Me-SA-CUR-9a) | >2 | >5 | n.d. | n.d. |
| Curcumin 11a hydrochloride (SA-CUR-11a) | — | >1 | >2 | >5 |
| Curcumin 11c hydrochloride (SA-CUR-11c) | — | >1 | >2 | >5 |
| Curcumin 12b hydrochloride (SA-CUR-12b) | — | >1 | ~2 | >3 |
| Curcumin 13a hydrochloride (SA-CUR-13a) | >1 | >5 | n.d. | n.d. |
| Curcumin 13c hydrochloride (SA-CUR-13c) | >1 | >5 | n.d. | n.d. |
| Curcumin 14a hydrochloride (SA-CUR-14a) | — | >1 | >2 | >3 |
| Curcumin 15a hydrochloride (SA-CUR-15a) | ~1 | >5 | n.d. | n.d. |
| Curcumin 15b hydrochloride (SA-CUR-15b) | >4 | >5 | n.d. | n.d. |

As can clearly be seen from FIGS. 1-33, after incubation of the microorganisms in the presence of the concentrations of the respective photosensitizers employed and subsequent irradiation with the light dosage given above, there was a reduction in the CFU/mL and thus an inactivation of *E. coli* and *S. aureus*.

Comparative Example 3

In a further test, the stability and phototoxicity of the following compounds were tested.

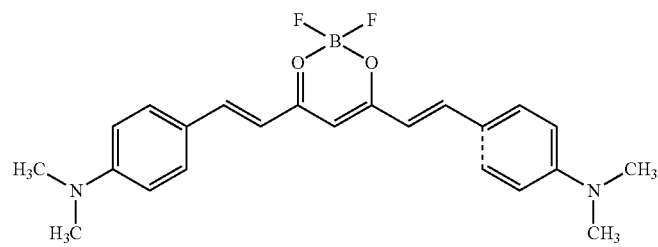

CRANAD-2

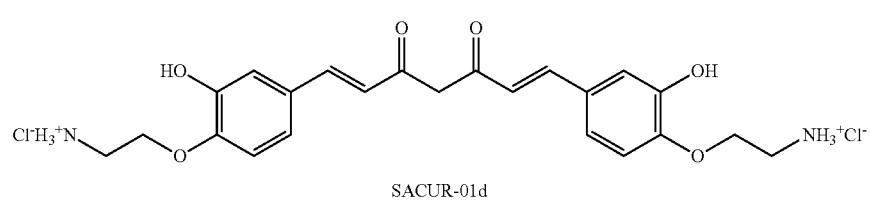

compound (71)

SACUR-01d

The compound CRANAD-2 is a good fluorophore which has a fluorescence quantum yield which is comparable with rhodamine or Cy5 dyes.

Incubation with CRANAD-2 and the bacterial strains *S. aureus* ATCC 25923 and *E. coli* ATCC 25922 employed, as well as irradiation with electromagnetic radiation and determination of the phototoxicity were carried out as described in sections c.1) and c.2) above. An inactivation of the tested bacterial strains *S. aureus* ATCC 25923 and *E. coli* ATCC 25922 upon illumination in the presence of CRANAD-2 could not be ascertained with either of the methods.

Because of the amine substituents directly on the aromatic ring, which can act as electron pair donors, the photophysics are displaced into a singlet process and substantially less energy is available for triplet processes. A good transfer of energy into the triplet level should be the prerequisite for a photodynamic effect which, however, was not observed for the compound CRANAD-2.

Incubation with the compound (71) (SACUR-01d) and the bacterial strains *S. aureus* ATCC 25923 and *E. coli* ATCC 25922 employed as well as irradiation with electromagnetic radiation and determination of the phototoxicity were carried out as described in sections c.1) and c.2) above. Hardly any inactivation of the tested bacterial strains *S. aureus* ATCC 25923 and *E. coli* ATCC 25922 was observed with either of the methods upon illumination in the presence of compound (71) (SACUR-01d), because the decomposition of the compound in the measurement solution meant that no reliable values were obtained. Compound (71) (SACUR-01d) exhibited a low stability in aqueous solution which was comparable with the natural basic substance curcumin. The free OH groups contribute greatly to this photo-instability because due to them, the compound can readily transform into the quinoid mesomer, and thus cleavage of one half of the molecule with the formation of ferulic acids or substituted vanillins is facilitated.

The molar extinction coefficient for compound (71) (SACUR-01d) at 420 nm in the aqueous solutions A-C given below varied between 8000 and 16000 $M^{-1}$ $cm^{-1}$ and thus was significantly smaller than the value known for curcumin ($\varepsilon_{420, H2O}$=23800 $M^{-1}$ $cm^{-1}$) (see Arnaut L G, Formosinho S J. J. Photochem. Photobiol. A: Chem. 75, 1993, pages 1 to 20). These results show that the compound (71) does not have sufficient stability in aqueous solution to establish a photodynamic effect after irradiation.

Aqueous solution A: distilled water.
Aqueous solution B: isotonic sodium chloride solution (0.9% by weight NaCl).
Aqueous solution C: PBS buffer, pH 7.4 (composition: see Sambrook, J.; Maniatis, T.; Russel, D. W.: Molecular cloning: a laboratory manual. Cold Spring Harbor Laboratory Press; 3rd edition (2001)).

What is claimed is:
1. A method for the inactivation of microorganisms, wherein the method comprises the following steps:
(A) bringing the microorganisms into contact with at least one photosensitizer, wherein the photosensitizer is at least one 1,7-diaryl-1,6-heptadiene-3,5-dione derivative with formula (100):

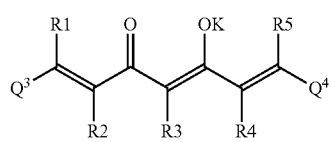

(100)

and/or with formula (101):

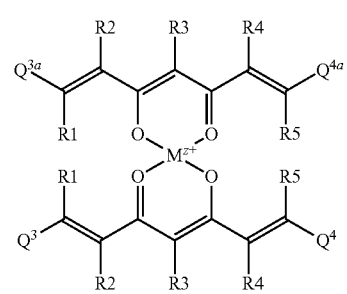

(101)

and/or with formula (102):

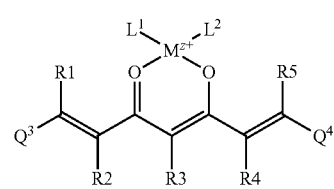

(102)

or respectively a pharmacologically acceptable salt and/or ester and/or complex thereof, wherein the residues $Q^3$, and $Q^{3a}$, respectively independently of each other, represent an aromatic residue with the general formula (11a), (12a) or (13a)

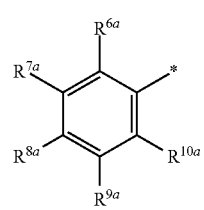

(11a)

(12a)

(13a)

and the residues $Q^4$ and $Q^{4a}$, respectively independently of each other, represent an aromatic residue with the general formula (11b), (12b) or (13b),

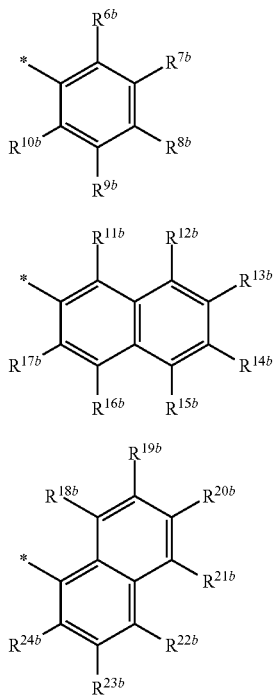

(11b)

(12b)

(13b)

wherein respectively, at least one residue $R^{6a}$ to $R^{10a}$, $R^{11a}$ to $R^{17a}$, $R^{18a}$ to $R^{24a}$, $R^{6b}$ to $R^{10b}$, $R^{11b}$ to $R^{17b}$ or $R^{18b}$ to $R^{24b}$, respectively independently of each other, is an organic residue W1, and wherein none of the residues $R^{6a}$ to $R^{10a}$, $R^{11a}$ to $R^{17a}$, $R^{18a}$ to $R^{24a}$, $R^{6b}$ to $R^{10b}$, $R^{11b}$ to $R^{17b}$ and $R^{18b}$ to $R^{24b}$ is an organic residue W1, wherein the residues $R^{6a}$ to $R^{10a}$, $R^{11a}$ to $R^{17a}$, $R^{18a}$ to $R^{24a}$, $R^{6b}$ to $R^{10b}$, $R^{11b}$ to $R^{17b}$ and $R^{18b}$ to $R^{24b}$, respectively independently of each other, are identical or different and represent hydrogen, halogen, thiol, nitro, carboxylate, aldehyde containing 1 to 8 C atoms, ketone containing 2 to 8 C atoms, O-alkyl containing 1 to 12 C atoms S-alkyl containing 1 to 12 C atoms O-alkenyl containing 2 to 12 C atoms, S-alkenyl containing 2 to 12 C atoms, O-aryl containing 5 to 20 C atoms, S-aryl containing 5 to 20 C atoms, ether containing 2 to 12 C atoms, thioether containing 2- to 12 C atoms, carboxylic acid ester containing 1 to 12 C atoms, carboxylic acid amide containing 1 to 12 C atoms, thioester containing 1 to 12 C atoms, alkyl containing 1 to 12 C atoms, alkenyl containing 2 to 12 C atoms, cycloalkyl containing 3 to 12 C atoms, cycloalkenyl containing 3 to 12 C atoms, alkylaryl containing 1 to 12 C atoms, aryl containing 5 to 20 C atoms, or heteroaryl, which does not contain a nitrogen atoms, containing 4 to 20 C atoms, and wherein in formula (100) K represents hydrogen or a cation, and wherein in formula (101) and (102) $M^{z+}$ is a cation of a metal M or boron, wherein z is the formal oxidation number of the metal M or boron and is a whole number from 1 to 7, and wherein $L^1$ and $L^2$, respectively independently of each other, represent water, halide, cyanide, thiocyanate, phosphate, hydrogen phosphate, or a carboxylate ion of a carboxylic acid containing 1 to 10 carbon atoms and wherein (a) at least one of the residues $Q^3$, $Q^{3a}$, $Q^4$ and $Q^{4a}$, respectively independently of each other, is substituted with at least one organic residue W1, wherein the at least one organic residue W1 has the general formula (4), (5), (6), (7), (8), or (9):

—(C(D)(E))$_h$-X, (4)

-A-(C(D)(E))$_h$-X, (5)

—(C(D)(E))$_k$-aryl-(C(D)(E))$_l$-X, (6)

-A-(C(D)(E))$_k$-aryl-(C(D)(E))$_l$-X, (7)

—((C(D)(E))$_m$-A)$_p$-(C(D)(E))$_n$-X, (8)

-A-((C(D)(E))$_m$-A)$_p$-(C(D)(E))$_n$-X, (9)

wherein h represents a whole number from 1 to 20, wherein k represents a whole number from 0 to 10, wherein l represents a whole number from 0 to 10, and wherein m, n and p, respectively independently of each other, represent a whole number from 1 to 6, and wherein A, respectively independently of each other, represents oxygen or sulphur, wherein D and E, respectively independently of each other, represent hydrogen, halogen, G-R$^{(I)}$, or G-C(=G)-R$^{(II)}$, wherein G, respectively independently of each other, represents oxygen or sulphur, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X, respectively independently of each other, is an organic residue which (i) contains at least one neutral nitrogen atom which can be protonated, or (ii) contains at least one positively charged nitrogen atom, or (iii) contains at least one positively charged phosphorus atom, each having independently at least one counter-ion or a mixture of two or more counter-ions selected from a fluoride, a chloride, a bromide, an iodide, a sulphate, a hydrogen sulphate, a phosphate, a hydrogen phosphate, a dihydrogen phosphate, a tosylate, mesylate, and at least one carboxylate ion of a carboxylic acid containing 1 to 15 carbon atoms, and wherein the residues R1, R2, R3, R4 and R5, respectively independently of each other, represent hydrogen, halogen, alkyl containing 1 to 12 C atoms, cycloalkyl containing 1 to 12 C atoms, alkylaryl containing 1 to 12 C atoms, aryl containing 5 to 20 C atoms, ether containing 2 to 12 C atoms or glycol containing 2 to 12 C atoms, or wherein (b) the residue R3 is an organic residue W2, wherein the one organic residue W2 has the general formula (4), (5), (6), (7), (8), (9), or (10):

—(C(D)(E))$_h$-X, (4)

-A-(C(D)(E))$_h$-X, (5)

—(C(D)(E))$_k$-aryl-(C(D)(E))$_l$-X, (6)

-A-(C(D)(E))$_k$-aryl-(C(D)(E))$_l$-X, (7)

—((C(D)(E))$_m$-A)$_p$-(C(D)(E))$_n$-X, (8)

-A-((C(D)(E))$_m$-A)$_p$-(C(D)(E))$_n$-X, (9),

—(—C(D)=C(E)-)$_r$-X, (10), and wherein, optionally, at least one of the residues $Q^3$, $Q^{3a}$, $Q^4$ and $Q^{4a}$, respectively independently of each other, is substituted with at least one organic residue W1 which has the general formula (4), (5), (6), (7), (8), or (9), wherein h represents a whole number from 1 to 20, wherein k represents a whole number from 0 to 10, wherein l represents a whole number from 0 to 10, and wherein m, n, p, and r, respectively independently of each other, represent a whole number from 1 to 6, and wherein A, respectively independently of each other, represents oxygen or sulphur, wherein D and E, respectively independently of each other, represent hydrogen, halogen, G-R$^{(I)}$, or G-C(=G)-R$^{(II)}$, wherein G, respectively independently of each other, represents oxygen or sulphur, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X, respectively independently of each other, is an organic residue which (i) contains at least one neutral nitrogen atom which can be protonated, or (ii) contains at least one positively charged nitrogen atom, or (iii) contains at least one positively charged phosphorus atom, each having independently at least one counter-ion or a mixture of two or more counter-ions selected from a fluoride, chloride, bromide iodide, sulphate, hydrogen sulphate, phosphate hydrogen phosphate, dihydrogen phosphate, tosylate, mesylate, and at least one carboxylate ion of a carboxylic acid containing 1 to 15 carbon atoms, and wherein the residues R1, R2, R4 and R5, respectively independently of each other, represent hydrogen, halogen, alkyl containing 1 to 12 C atoms, alkylaryl containing 1 to 12 C atoms, aryl containing 5 to 20 C atoms, ether containing 2 to 12 C atoms or glycol containing 2 to 12 C atoms, and (B) irradiating the microorganisms and the at least one photosensitizer with electromagnetic radiation of a suitable wavelength and energy density.

2. The method as claimed in claim 1, wherein, in the compound with formula (100), K is a cation $M^{z+}$ of a metal M or boron, wherein z is the formal oxidation number of the metal M or boron and wherein z represents a whole number from 1 to 7, and wherein the compound has the formula (102):

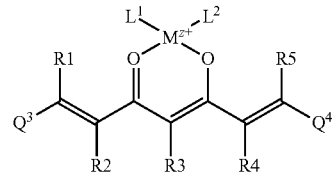

(102)

wherein $L^1$ and $L^2$, respectively independently of each other, represent water, fluoride, chloride, bromide, iodide, phosphate, hydrogen phosphate, dihydrogen phosphate, sulphate, hydrogen sulphate, tosylate, mesylate or at least one carboxylate ion of a carboxylic acid containing 1 to 15 carbon atoms and/or mixtures thereof.

3. The method as claimed in claim 1, wherein the irradiation of the microorganisms and of the at least one photosensitizer with electromagnetic radiation of a suitable wavelength and energy density is carried out in the presence of at least one oxygen-donating compound and/or at least one oxygen-containing gas.

4. The method as claimed in claim 1, wherein the at least one photosensitizer is a compound with formula (1):

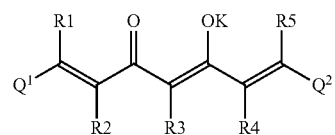

(1)

wherein the residues $Q^1$ represents an aromatic residue with the general formula (11a), (12a) or (13a)

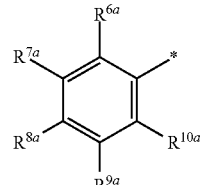

(11a)

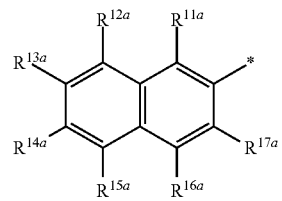

(12a)

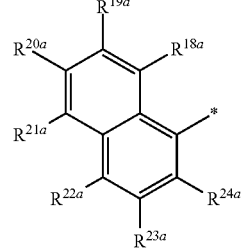

(13a)

and wherein the residue $Q^2$ represents an aromatic residue with the general formula (11b) (12b) or (13b),

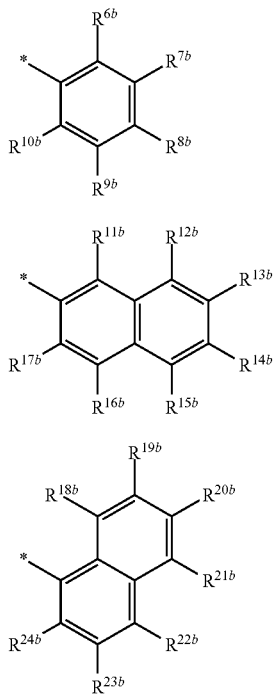

(11b)

(12b)

(13b)

wherein respectively, at least 1 residue $R^{6a}$ to $R^{10a}$, $R^{11a}$ to $R^{17a}$, $R^{18a}$ to $R^{24a}$, $R^{6b}$ to $R^{10b}$, $R^{11b}$ to $R^{17b}$ or $R^{18b}$ to $R^{24b}$, respectively independently of each other, is an organic residue W1a or an organic residue W1b, and wherein none of the residues $R^{6a}$ to $R^{10a}$, $R^{11a}$ to $R^{17a}$, $R^{18a}$ to $R^{24a}$, $R^{6b}$ to $R^{10b}$, $R^{11b}$ to $R^{17b}$ and $R^{18b}$ to $R^{24b}$ is an organic residue W1a or an organic residue W1b, wherein the residues $R^{6a}$ to $R^{10a}$, $R^{11a}$ to $R^{17a}$, $R^{18a}$ to $R^{24a}$, $R^{6b}$ to $R^{10b}$, $R^{11b}$ to $R^{17b}$ and $R^{18b}$ to $R^{24b}$, respectively independently of each other, are identical or different and represent hydrogen, halogen, thiol, nitro, carboxylate, aldehyde containing 1 to 8 C atoms, ketone containing 2 to 8 C atoms, O-alkyl containing 1 to 12 C atoms, S-alkyl containing 1 to 12 C atoms, 0-alkenyl containing 2 to 12 C atoms, S-alkenyl containing 2 to 12 C atoms, O-aryl containing 5 to 20 C atoms, S-aryl containing 5 to 20 C atoms, ether containing 2 to 12 C atoms, thioether containing 2 to 12 C atoms, carboxylic acid ester containing 1 to 12 C atoms, carboxylic acid amide containing 1 to 12 C atoms, thioester containing 1 to 12 C atoms, alkyl containing 1 to 12 C atoms, alkenyl containing 2 to 12 C atoms, cycloalkyl containing 3 to 12 C atoms, cycloalkenyl containing 3 to 12 C atoms, alkylaryl containing 1 to 12 C atoms, aryl containing 5 to 20 C atoms, or heteroaryl, which does not contain a nitrogen atom, containing 4 to 20 C atoms, and wherein the compound with formula (1) does not contain an OH group which is bonded directly to the organic residue $Q^1$ or $Q^2$, and wherein K represents hydrogen or a cation, and wherein
(a) at least one of the residues $Q^1$ and $Q^2$, respectively independently of each other, is substituted with at least one organic residue W1a, and wherein the at least one organic residue W1a has the general formula (5a), (6a), (7a), (8a), or (9a):

-A-(C(D)(E))$_h$-X$^a$, (5a)

—(C(D)(E))$_k$-aryl-(C(D)(E))$_l$-X$^a$, (6a)

-A-(C(D)(E))$_k$-aryl-(C(D)(E))$_l$-X$^a$, (7a)

—((C(D)(E))$_m$-A)$_p$-(C(D)(E))$_n$-X$^a$, (8a)

-A-((C(D)(E))$_m$-A)$_p$-(C(D)(E))$_n$-X$^a$, (9a)

wherein h represents a whole number from 1 to 20, wherein k represents a whole number from 0 to 10, wherein l represents a whole number from 0 to 10, and wherein m, n and p, respectively independently of each other, represent a whole number from 1 to 6, and wherein A, respectively independently of each other, represents oxygen or sulphur, wherein D and E, respectively independently of each other, represent hydrogen, halogen, G-R$^{(I)}$, or G-C(=G)-R$^{(II)}$, wherein G, respectively independently of each other, represents oxygen or sulphur, and wherein the residues R$^{(I)}$ and R$^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X$^a$, respectively independently of each other, represents a residue with formula (20c), (20d), or (21):

(20c)

(20d)

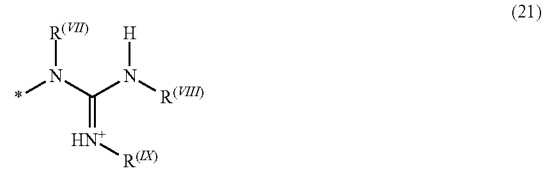
(21)

wherein each of the residues R$^{(VII)}$, R$^{(VIII)}$, and R$^{(IX)}$, respectively independently of each other, represents hydrogen, an aryl residue containing 5 to 12 C atoms, an alkylaryl residue containing 5 to 12 C atoms, an alkyl residue, which may be linear or branched, containing 1 to 8 C atoms, or an ether residue, which may be linear or branched, containing 1 to 8 C atoms, and wherein organic residues with formula (20d) and (21) have independently at least one counter-ion or a mixture of two or more counter-ions selected from a fluoride, a chloride, a bromide, an iodide, a sulphate, a hydrogen sulphate, a phosphate, a hydrogen phosphate, a dihydrogen phosphate, a tosylate, mesylate, and at least one carboxylate ion of a carboxylic acid containing 1 to 15 carbon atoms, and wherein the residues R1, R2, R3, R4 and R5, respectively independently of each other, represent hydrogen, halogen, alkyl containing 1 to 12 C atoms, cycloalkyl containing 1 to 12 C atoms, alkylaryl containing 1 to 12 C atoms, aryl containing 5 to 20 C atoms, ether containing 2 to 12 C atoms or glycol containing 2 to 12 C atoms, or wherein (b) the residue R3 is an organic residue W2a which contains at least one neutral nitrogen atom which can be protonated, and/or at least one positively charged nitrogen atom and/or at least one positively charged phosphorus atom, which have independently at least one counter-ion or a mixture of two or more counter-ions selected from a fluoride, chloride, bromide, iodide, sulphate, hydrogen sulphate, phosphate, hydrogen phosphate, dihydrogen phosphate, tosylate, mesylate, and at least one carboxylate ion of a carboxylic acid containing 1 to 15 carbon atoms, wherein the one organic residue W2a has the general formula (4b), (5b), (6b), (7b), (8b), or (9b):

$$—(C(D)(E))_h\text{-}X^b, \tag{4b}$$

$$\text{-}A\text{-}(C(D)(E))_h\text{-}X^b, \tag{5b}$$

$$—(C(D)(E))_k\text{-aryl-}(C(D)(E))_l\text{-}X^b, \tag{6b}$$

$$\text{-}A\text{-}(C(D)(E))_k\text{-aryl-}(C(D)(E))_l\text{-}X^b, \tag{7b}$$

$$—[(C(D)(E))_m\text{-}A]_p—(C(D)(E))_n\text{-}X^b, \tag{8b}$$

$$\text{-}A\text{-}[(C(D)(E))_m\text{-}A]_p—(C(D)(E))_n\text{-}X^b, \tag{9b}$$

and wherein, optionally, at least one of the residues $Q^1$ and $Q^2$, respectively independently of each other, is substituted with at least one organic residue W1b which has the general formula (4b), (5b), (6b), (7b), (8b), or (9b), wherein h represents a whole number from 1 to 20, wherein k represents a whole number from 0 to 10, wherein l represents a whole number from 0 to 10, and wherein m, n and p, respectively independently of each other, represent a whole number from 1 to 6, and wherein A, respectively independently of each other, represents oxygen or sulphur, wherein D and E, respectively independently of each other, represent hydrogen, halogen, G-$R^{(I)}$, or G-C(=G)-$R^{(II)}$, wherein G, respectively independently of each other, represents oxygen or sulphur, and wherein the residues $R^{(I)}$ and $R^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein $X^b$, respectively independently of each other, is an organic residue which (i) contains at least one neutral nitrogen atom which can be protonated, or (ii) contains at least one positively charged nitrogen atom, or (iii) contains at least one positively charged phosphorus atom, which have independently at least one counter-ion or a mixture of two or more counter-ions selected from a fluoride, a chloride, a bromide, an iodide, a sulphate, a hydrogen sulphate, a phosphate, a hydrogen phosphate, a dihydrogen phosphate, a tosylate, a mesylate, and at least one carboxylate ion of a carboxylic acid containing 1 to 15 carbon atoms, and wherein the residues R1, R2, R4 and R5, respectively independently of each other, represent hydrogen, halogen, alkyl containing 1 to 12 C atoms, alkylaryl containing 1 to 12 C atoms, aryl containing 5 to 20 C atoms, ether containing 2 to 12 C atoms or glycol containing 2 to 12 C atoms, and/or a pharmacologically acceptable salt and/or ester and/or complex thereof.

5. A method for photodynamic inactivation of microorganisms on or within a patient, wherein the method comprises the following steps:

(A) bringing microorganisms on or within a patient into contact with at least one photosensitizer, wherein the photosensitizer is at least one 1,7-diaryl-1,6-heptadiene-3,5-dione derivative with formula (100)

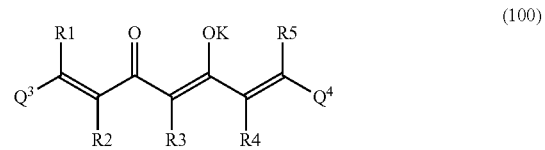

and/or with formula (101): (02862362.1)

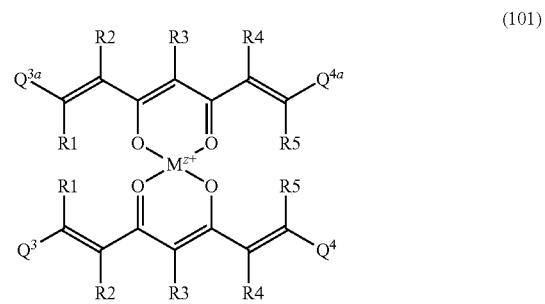

or respectively a pharmacologically acceptable salt and/or ester and/or complex thereof, wherein the residues $Q^3$, and $Q^{3a}$, respectively independently of each other, represent an aromatic residue with the general formula (11a), (12a) or (13a)

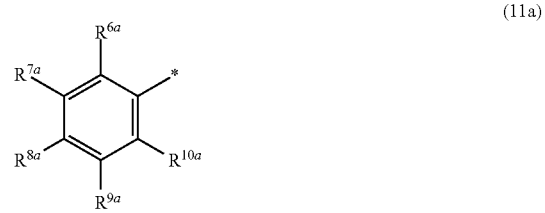

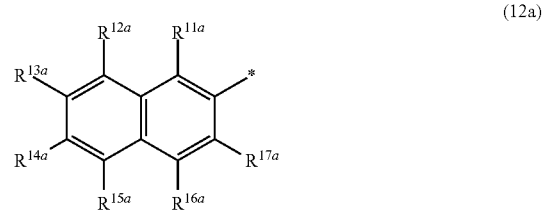

-continued

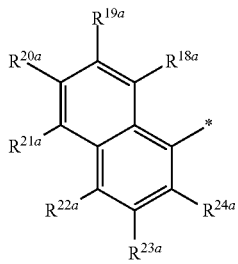
(13a)

and wherein the residues $Q^4$ and $Q^{4a}$, respectively independently of each other, represent an aromatic residue with the general formula (11b), (12b) or (13b),

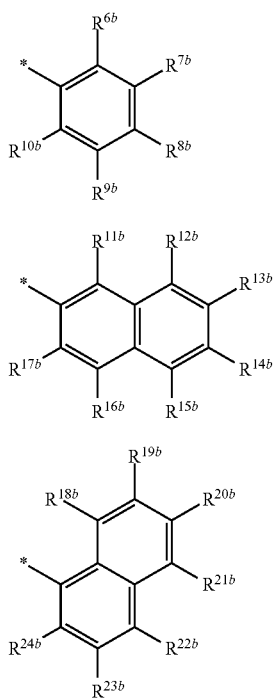

wherein respectively, at least 1 residue $R^{6a}$ to $R^{10a}$, $R^{11a}$ to $R^{17a}$, $R^{18a}$ to $R^{24a}$, $R^{6b}$ to $R^{10b}$, $R^{11b}$ to $R^{17b}$ or $R^{18b}$ to $R^{24b}$, respectively independently of each other, is an organic residue W1, and wherein none of the residues $R^{6a}$ to $R^{10a}$, $R^{11a}$ to $R^{17a}$, $R^{18a}$ to $R^{24a}$, $R^{6b}$ to $R^{10b}$, $R^{11b}$ to $R^{17b}$ and $R^{18b}$ to $R^{24b}$ is an organic residue W1, wherein the residues $R^{6a}$ to $R^{10a}$, $R^{11a}$ to $R^{17a}$, $R^{18a}$ to $R^{24a}$, $R^{6b}$ to $R^{10b}$, $R^{11b}$ to $R^{17b}$ and $R^{18b}$ to $R^{24b}$, respectively independently of each other, are identical or different and represent hydrogen, halogen, thiol, nitro, carboxylate, aldehyde containing 1 to 8 C atoms, ketone containing 2 to 8 C atoms, O-alkyl containing 1 to 12 C atoms, S-alkyl containing 1 to 12 C atoms, O-alkenyl containing 2 to 12 C atoms, S-alkenyl containing 2 to 12 C atoms, O-aryl containing 5 to 20 C atoms, S-aryl containing 5 to 20 C atoms, ether containing 2 to 12 C atoms, thioether containing 2 to 12 C atoms, carboxylic acid ester containing 1 to 12 C atoms, carboxylic acid amide containing 1 to 12 C atoms, thioester containing 1 to 12 C atoms, alkyl containing 1 to 12 C atoms, alkenyl containing 2 to 12 C atoms, cycloalkyl containing 3 to 12 C atoms, cycloalkenyl containing 3 to 12 C atoms, alkylaryl containing 1 to 12 C atoms, aryl containing 5 to 20 C atoms, or heteroaryl, which does not contain a nitrogen atom, containing 4 to 20 C atoms, and wherein K represents hydrogen or a cation, and wherein $M^{z+}$ represents a cation of a metal or boron, wherein z is the formal oxidation number of the metal M or boron and z represents a whole number from 1 to 7, and wherein (a) at least one of the residues $Q^3$, $Q^{3a}$, $Q^4$ and $Q^{4a}$, respectively independently of each other, is substituted with at least one organic residue W1, wherein the at least one organic residue W1 has the general formula (4), (5), (6), (7), (8):

$$—(C(D)(E))_h\text{-}X, \qquad (4)$$

$$\text{-}A\text{-}(C(D)(E))_h\text{-}X, \qquad (5)$$

$$—(C(D)(E))_k\text{-aryl-}(C(D)(E))_l\text{-}X, \qquad (6)$$

$$\text{-}A\text{-}(C(D)(E))_k\text{-aryl-}(C(D)(E))_l\text{-}X, \qquad (7)$$

$$—((C(D)(E))_m\text{-}A)_p\text{-}(C(D)(E))_n\text{-}X, \qquad (8)$$

$$\text{-}A\text{-}((C(D)(E))_m\text{-}A)_p\text{-}(C(D)(E))_n\text{-}X, \qquad (9)$$

wherein h represents a whole number from 1 to 20, wherein k and l, respectively independently of each other, represents a whole number from 0 to 10, and wherein m, n and p, respectively independently of each other, represent a whole number from 1 to 6 and wherein A, respectively independently of each other, represents oxygen or sulphur, wherein D and E, respectively independently of each other, represent hydrogen, halogen, G-$R^{(I)}$, or G-C(=G)-$R^{(II)}$, wherein G, respectively independently of each other, represents oxygen or sulphur, and wherein the residues $R^{(I)}$ and $R^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X, respectively independently of each other, is an organic residue which (i) contains at least one neutral nitrogen atom which can be protonated, or (ii) at least one positively charged nitrogen atom, or (iii) at least one positively charged phosphorus atom, which have independently at least one counter-ion or a mixture of two or more counter-ions selected from a fluoride, a chloride, a bromide, an iodide, a sulphate, a hydrogen sulphate, a phosphate, a hydrogen phosphate, a dihydrogen phosphate, tosylate, a mesylate, and at least one carboxylate ion of a carboxylic acid containing 1 to 15 carbon atoms, and wherein the residues R1, R2, R3, R4 and R5, respectively independently of each other, represent hydrogen, halogen, alkyl containing 1 to 12 C atoms, cycloalkyl containing 1 to 12 C atoms, alkylaryl containing 1 to 12 C atoms, aryl containing 5 to 20 C atoms, ether containing 2 to 12 C atoms or glycol containing 2 to 12 C atoms, or wherein (b) the residue R3 is an organic residue W2, wherein the one organic residue W2 has the general formula (4), (5), (6), (7), (8), (9), or (10):

$$—(C(D)(E))_h-X, \quad (4)$$

$$-A-(C(D)(E))_h-X, \quad (5)$$

$$—(C(D)(E))_k\text{-aryl-}(C(D)(E))_l\text{-}X, \quad (6)$$

$$-A-(C(D)(E))_k\text{-aryl-}(C(D)(E))_l\text{-}X, \quad (7)$$

$$—[(C(D)(E))_m-A]_p-(C(D)(E))_n-X, \quad (8)$$

$$-A-[(C(D)(E))_m-A]_p—(C(D)(E))_n-X, \quad (9)$$

$$—(—C(D)=C(E)-)_r-X, \quad (10)$$

and wherein, optionally, at least one of the residues $Q^3$, $Q^3$, $Q^4$ and $Q^{4a}$, respectively independently of each other, is substituted with at least one organic residue W1 which has the general formula (4), (5), (6), (7), (8), or (9), wherein h represents a whole number from 1 to 20, wherein k and 1, respectively independently of each other, represents a whole number from 0 to 10 and wherein m, n, p, and r, respectively independently of each other, represent a whole number from 1 to 6, and wherein A, respectively independently of each other, represents oxygen or sulphur, wherein D and E, respectively independently of each other, represent hydrogen, halogen, G-$R^{(I)}$, or G-C(=G)-$R^{(II)}$, wherein G, respectively independently of each other, represents oxygen or sulphur, and wherein the residues $R^{(I)}$ and $R^{(II)}$, respectively independently of each other, represent hydrogen, methyl, ethyl, n-propyl, n-butyl, n-pentyl, phenyl or benzyl, wherein phenyl and benzyl may be unsubstituted or substituted, wherein aryl represents a substituted or unsubstituted aromatic group or a substituted or unsubstituted heteroaromatic group which does not contain a nitrogen atom, wherein X, respectively independently of each other, is an organic residue which (i) contains at least one neutral nitrogen atom which can be protonated, or (ii) contains at least one positively charged nitrogen atom, or (iii) contains at least one positively charged phosphorus atom, which have independently at least one counter-ion or mixture of two or more counter-ions selected from a fluoride, a chloride, a bromide, an iodide, a sulphate, a hydrogen sulphate, a phosphate, a hydrogen phosphate, a dihydrogen phosphate, a tosylate, a mesylate, and at least one carboxylate ion of a carboxylic acid containing 1 to 15 carbon atoms, and wherein the residues R1, R2, R4 and R5, respectively independently of each other, represent hydrogen, halogen, alkyl containing 1 to 12 C atoms, alkylaryl containing 1 to 12 C atoms, aryl containing 5 to 20 C atoms, ether containing 2 to 12 C atoms or glycol containing 2 to 12 C atoms; and (B) irradiating the microorganisms and the at least one photosensitizer with electromagnetic radiation of a suitable wavelength and energy density to inactivate said microorganisms.

6. The method according to claim 5, wherein said microorganisms are selected from the group consisting of viruses, archaea, bacteria, bacterial spores, fungi, fungal spores, protozoa, algae and blood-transmissible parasites.

7. The method according to claim 5, wherein the microorganisms on or within the patient are brought into contact with the at least one photosensitizer in at least one selected from the group consisting of cleaning of teeth, dental prostheses and dental braces, treatment of a disease of the dental tissue and of the periodontium.

8. The method according to claim 5, wherein the microorganisms on or within the patient are brought into contact with the at least one photosensitizer for treatment of an infectious skin disease.

9. The method according to claim 5, wherein the microorganisms on or within the patient are brought into contact with the at least one photosensitizer for reduction of the bacterial count in a wound.

\* \* \* \* \*